US012753440B2

(12) United States Patent
Nickolas et al.

(10) Patent No.: US 12,753,440 B2
(45) Date of Patent: Oct. 6, 2026

(54) BIOMARKERS OF RENAL OSTEODYSTROPHY TYPE

(71) Applicants: The Trustees of Columbia University in the City of New York, New York, NY (US); The Trustees of Indiana University, Bloomington, IN (US)

(72) Inventors: Thomas L. Nickolas, New York, NY (US); Sharon Moe, Indianapolis, IN (US); Neal X. Chen, Carmel, IN (US)

(73) Assignees: The Trustees of Columbia University in the City of New York, New York, NY (US); The Trustees of Indiana University, Bloomington, IN (US)

( * ) Notice: Subject to any disclaimer, the term of this patent is extended or adjusted under 35 U.S.C. 154(b) by 1328 days.

(21) Appl. No.: 17/103,638

(22) Filed: Nov. 24, 2020

(65) Prior Publication Data

US 2021/0079476 A1 Mar. 18, 2021

Related U.S. Application Data

(63) Continuation-in-part of application No. PCT/US2019/034073, filed on May 24, 2019.

(60) Provisional application No. 62/750,670, filed on Oct. 25, 2018, provisional application No. 62/676,547, filed on May 25, 2018.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/112* (2013.01); *C12Q 2600/158* (2013.01); *C12Q 2600/178* (2013.01)

(58) Field of Classification Search
CPC ........ C12Q 2600/112; C12Q 2600/158; C12Q 2600/178; A61P 13/12; A61P 19/10
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 4,675,189 | A | 6/1987 | Kent et al. |
| 5,133,974 | A | 7/1992 | Paradissis et al. |
| 5,407,686 | A | 4/1995 | Patel et al. |
| 5,736,152 | A | 4/1998 | Dunn |

FOREIGN PATENT DOCUMENTS

| | | | |
|---|---|---|---|
| WO | WO-2014118705 A1 | 8/2014 | |
| WO | WO-2015189345 A2 * | 12/2015 | ............ A61K 45/00 |

OTHER PUBLICATIONS

Gennari L, Bianciardi S, Merlotti D. MicroRNAs in bone diseases. Osteoporos Int. Apr. 2017;28(4):1191-1213. doi: 10.1007/s00198-016-3847-5. Epub Nov. 30, 2016. PMID: 27904930. (Year: 2017).*

Improved assessment of bone turnover by the PTH-(1-84)/large C-PTH fragments ratio in ESRD patients Monier-Faugere, Marie-Claude et al. Kidney International, vol. 60, Issue 4, 1460-1468 (Year: 2001).*

Swathi K. Sista, Seth M. Arum, Management of adynamic bone disease in chronic kidney disease: A brief review, Journal of Clinical & Translational Endocrinology, vol. 5, 2016, pp. 32-35, ISSN 2214-6237, https://doi.org/10.1016/j.jcte.2016.07.002. (Year: 2016).*

Osteoporosis in chronic kidney disease Cunningham, John et al. American Journal of Kidney Diseases, vol. 43, Issue 3, 566-571 (Year: 2004).*

Banzhaf-Strathmann, J., Edbauer, D. Good guy or bad guy: the opposing roles of microRNA 125b in cancer. Cell Commun Signal 12, 30 (2014). https://doi.org/10.1186/1478-811X-12-30 (Year: 2014).*

Ha M, Pang M, Agarwal V, Chen ZJ. Interspecies regulation of microRNAs and their targets. Biochim Biophys Acta. Nov. 2008;1779 (11):735-42. doi: 10.1016/j.bbagrm.2008.03.004. Epub Mar. 25, 2008. PMID: 18407843; PMCID: PMC2586835. (Year: 2008).*

Kelsey & Samelson .Variation in Risk Factors for Fractures at Different Sites. Curr Osteoporos Rep. Dec. 2009 ; 7(4): 127-133. (Year: 2009).*

Schipper et al. Treatment of osteoporosis in renal insufficiency. Clin Rheumatol (2015) 34:1341-1345. (Year: 2015).*

Seibel .Biochemical Markers of Bone Turnover Part I: Biochemistry and Variability. Clin Biochem Rev. Nov. 2005;26(4):97-122.). ( Year: 2005).*

Kim et al. Identification of differentially expressed miRNAs associated with chronic kidney disease-mineral bone disorder. Front. Med. 2017, 11(3): 378-385.) (Year: 2017).*

Kocijan et al. Circulating microRNA Signatures in Patients With Idiopathic and Postmenopausal Osteoporosis and Fragility Fractures. The Journal of Clinical Endocrinology & Metabolism, vol. 101, Issue 11, Nov. 1, 2016, pp. 4125-4134. (Year: 2016).*

Toussaint & Damsiewicz. Do the benefits of using calcitriol and other vitamin D receptor activators in patients with chronic kidney disease outweigh the harms? Nephrology 22, Suppl. 2 (2017) 51-56. (Year: 2017).*

(Continued)

*Primary Examiner* — Brian Whiteman
*Assistant Examiner* — Amanda M Zahorik
(74) *Attorney, Agent, or Firm* — Wilmer Cutler Pickering Hale and Dorr LLP

(57) ABSTRACT

Provided herein is a method of treating low turnover renal osteodystrophy in a subject being administered an agent that reduces bone turnover comprising measuring a level of one or more miRNAs in a sample from the subject. The miRNA being measured can include miRNA-30b, miRNA-30c, miRNA-125b and miRNA-155. Administration of the agent that reduces bone turnover can be stopped if the level of the one or more miRNAs measured is lower than a level of the one or more miRNAs measured in a control subject. Administration of the agent that reduces bone turnover can be continued if the level of the one or more miRNAs measured is not lower than a level of the one or more miRNAs measured in a control subject.

11 Claims, 62 Drawing Sheets

Specification includes a Sequence Listing.

(56) References Cited

OTHER PUBLICATIONS

Hanley et al. Denosumab: mechanism of action and clinical outcomes. Int J Clin Pract. Sep. 12, 2012;66(12):1139-1146. (Year: 2012).*
Mehvar & Brocks. Stereospecific Pharmacokinetics and Pharmacodynamics of Beta-Adrenergic Blockers in Humans. J Pharm Pharmaceut Sci (www.ualberta.ca/~csps) 4(2):185-200, 2001. (Year: 2001).*
"KDIGO Clinical Practice Guideline for Acute Kidney Injury", Kidney International, vol. 2, Issue Supplement 1, Mar. 2012 (141 pages).
"KDIGO Clinical Practice Guideline for the Diagnosis, Evaluation, Prevention, and Treatment of Chronic Kidney Disease-Mineral and Bone Disorder (CKD-MBD)", Kidney International, 76(Suppl 113):S1-S130, Aug. 2009 (134 pages).
Adragao, T. et al., "Low Bone Volume—A Risk Factor for Coronary Calcifications in Hemodialysis Patients", Clin J Am Soc Nephrol, 4:450-455, 2009 (6 pages).
Adragao, T. et al., "Femoral bone mineral density reflects histologically determined cortical bone volume in hemodialysis patients", Osteoporos Int, 21:619-625, 2010, published online Jun. 25, 2009 (7 pages).
Alem, A.M. et al., "Increased risk of hip fracture among patients with end-stage renal disease", Kidney International, 58:396-399, 2000 (4 pages).
Allen, M.R. et al., "Adverse Mandibular Bone Effects Associated with Kidney Disease Are Only Partially Corrected with Bisphosphonate and/or Calcium Treatment", Am J Nephrol, 38:458-464, published online Nov. 22, 2013 (7 pages).
Allen, M.R. et al., "Changes in skeletal collagen cross-links and matrix hydration in high- and low-turnover chronic kidney disease", Osteoporos Int, 26:977-985, 2015, published online Dec. 3, 2014 (9 pages).
Allen, M.R. et al. "Skeletal effects of zoledronic acid in an animal model of chronic kidney disease", Osteoporos Int, 24:1471-1481, published online Aug. 21, 2012 (11 pages).
An, J.H. et al., "Changes of MicroRNA Profile and MicroRNA-mRNA Regulatory Network in Bones of Ovariectomized Mice", Journal of Bone and Mineral Research, 29(3):644-656, Mar. 2014 (13 pages).
Anastasilakis, A.D. et al., "Changes of Circulating MicroRNAs in Response to Treatment With Teriparatide or Denosumab in Postmenopausal Osteoporosis", J Clin Endocrinol Metab, 103:1206-1213, Mar. 2018, published online Dec. 22, 2017 (8 pages).
Bakhshandeh, B. et al., "MicroRNA signature associated with osteogenic lineage commitment", Mol Biol Rep, 39:7569-7581, 2012 (13 pages).
Bala, Y. et al., "Role of cortical bone in bone fragility", Curr Opin Rheumatol, 27(4):406-413, Jul. 2015 (8 pages).
Balderman, J. A. F. et al., "Bone Morphogenetic Protein-2 Decreases MicroRNA-30b and MicroRNA-30c to Promote Vascular Smooth Muscle Cell Calcification", Journal of the American Heart Association, 1: e003905, 2012 (11 pages).
Ball, A.M. et al., "Risk of Hip Fracture Among Dialysis and Renal Transplant Recipients", JAMA, 288(23):3014-3018, Dec. 18, 2002 (5 pages).
Barreto, D. et al., "Association of Changes in Bone Remodeling and Coronary Calcification in Hemodialysis Patients: A Prospective Study", American Journal of Kidney Diseases, 52(6):1139-1150, Dec. 2008 (12 pages).
Behets, G.J. et al., "Bone histomorphometry before and after long-term treatment with cinacalcet in dialysis patients with secondary hyperparathyroidism", Kidney International, 87:846-856, 2015, published online Oct. 22, 2014 (11 pages).
Bervoets, An R.J., et al., "Useful Biochemical Markers for Diagnosing Renal Osteodystrophy in Predialysis End-Stage Renal Failure Patients", American Journal of Kidney Diseases, 41(5) pp. 997-1007 May 2003 (11 pages).
Biggerstaff, B.J., "Comparing diagnostic tests: a simple graphic using likelihood ratios", Statistics in Medicine, 19:649-663, Apr. 13, 1999 (19 pages).
Bloch, D.A., "Comparing Two Diagnostic Tests Against the Same "Gold Standard" in the Same Sample", Biometrics 53:73-85, Mar. 1997 (15 pages).
Block, G.A. et al., "A Single-Dose Study of Denosumab in Patients With Various Degrees of Renal Impairment", Journal of Bone and Mineral Research, 27(7):1471-1479, Jul. 2012, published online Mar. 28, 2012 (9 pages).
Brandenburg, V.M. et al., "Adynamic bone disease—bone and beyond", NDT Plus, 3:135-147, 2008 (13 pages).
Carvalho, C. et al., "Cortical bone analysis in a predialysis population: a comparison with a dialysis population", J Bone Miner Metab, 35(5):513-521, 2017, published online Nov. 9, 2016 (9 pages).
Cejka, D. et al., "Effect of Teriparatide on Early Bone Loss After Kidney Transplantation", American Journal of Transplantation, 8:1864-1870, 2008 (7 pages).
Cejka, D. et al., "Treatment of Hemodialysis-Associated Adynamic Bone Disease with Teriparatide ($PTH_{1-34}$): A Pilot Study", Kidney & Blood Pressure Research, 33:221-226, published online Jun. 24, 2010 (6 pages).
Chan, H. W.-H. et al., "Prospective study on dialysis patients after total parathyroidectomy without autoimplant", Nephrology, 15:441-447, 2009 (7 pages).
Chaturvedi, P. et al., "Differential miRNA Expression in Cells and Matrix Vesicles in Vascular Smooth Muscle Cells from Rats with Kidney Disease", PLoS One, 10(6):e0131589, DOI:10.1371/journal.pone.0131589, Jun. 26, 2015 (16 pages).
Chen, N.X. et al., "Decreased MicroRNA Is Involved in the Vascular Remodeling Abnormalities in Chronic Kidney Disease (CKD)", PLoS One, 8(5):e64558, May 22, 2013 (10 pages).
Chen, N.X. et al., "Low Bone Turnover in Chronic Kidney Disease Is Associated with Decreased VEGF-A Expression and Osteoblast Differentiation", Am J Nephrol 41:464-473, published online Jul. 25, 2015 (10 pages).
Chiang, C., "The use of bone turnover markers in chronic kidney disease-mineral and bone disorders", Nephrology, 22(Suppl. 2): 11-13, 2017 (3 pages).
Coco, M. et al., "Effect of Risedronate on Bone in Renal Transplant Recipients", J Am Soc Nephrol, 23:1426-1437, 2012 (12 pages).
Coco, M. et al., "Increased Incidence of Hip Fractures in Dialysis Patients With Low Serum Parathyroid Hormone", American Journal of Kidney Diseases, 36(6):1115-1121, Dec. 2000 (7 pages).
Coco, M. et al., "Prevention of Bone Loss in Renal Transplant Recipients: A Prospective, Randomized Trial of Intravenous Pamidronate", J Am Soc Nephrol, 14:2669-2676, 2003 (8 pages).
Coen, G. et al., "Bone GLA protein in predialysis chronic renal failure. Effects of $1,25(OH)_2D_3$ administration in a long-term follow-up", Kidney International, 28:783-790, 1985 (8 pages).
Cooper, D.M.L. et al., "Cortical Bone Porosity: What Is It, Why Is It Important, and How Can We Detect It?", Curr Osteoporos Rep, 14:187-198, 2016 (12 pages).
Coresh, J. et al., "Calibration and Random Variation of the Serum Creatinine Assay as Critical Elements of Using Equations to Estimate Glomerular Filtration Rate", American Journal of Kidney Diseases, 39(5):920-929, May 2002 (10 pages).
Coresh, J. et al., "Prevalence of Chronic Kidney Disease in the United States", JAMA, 298(17):2038-2047, Nov. 7, 2007 (10 pages).
Cowley, B.D., Jr. et al., "Autosomal-dominant polycystic kidney disease in the rat", Kidney International, 43:522-534, 1993 (13 pages).
Davies, M.R. et al., "Low Turnover Osteodystrophy and Vascular Calcification Are Amenable to Skeletal Anabolism in an Animal Model of Chronic Kidney Disease and the Metabolic Syndrome", J Am Soc Nephrol, 16:917-928, 2005 (12 pages).
Delong, E.R. et al., "Comparing the Areas Under Two or More Correlated Receiver Operating Characteristic Curves: A Nonparametric Approach", Biometrics, 44:837-845, Sep. 1988 (9 pages).
Dempster, D.W. al., "Standardized Nomenclature, Symbols, and Units for Bone Histomorphometry: A 2012 Update of the Report of the ASBMR Histomorphometry Nomenclature Committee", Journal of Bone and Mineral Research, 28(1):1-16, Jan. 2013 (16 pages).

(56) References Cited

OTHER PUBLICATIONS

Denburg, M. et al., "Declining Hip Fracture Rates in Dialysis Patients: Is This Winning the War?", AJKD, 71(2):154-156, Feb. 2018 (3 pages).
Dooley, A.C. et al., "Increased Risk of Hip Fracture Among Men With CKD", American Journal of Kidney Diseases, 51(1):38-44, Jan. 2008 (7 pages).
Eguchi, T. et al., "OstemiR: A Novel Panel of MicroRNA Biomarkers in Osteoblastic and Osteocytic Differentiation from Mesencymal Stem Cells", PLoS One, 8(3):e58796, Mar. 22, 2013 (18 pages).
El-Kishawi, A. M.W. et al., "Renal Osteodystrophy: Review of the Disease and its Treatment", Saudi J Kidney Dis Transplant, 17(3):373-382, 2006 (10 pages).
Feichtinger, X. et al., "Bone-related Circulating MicroRNAs miR-29b-3p, miR-550a-3p, and miR-324-3p and their Association to Bone Microstructure and Histomorphometry", Scientific Reports, 8:4867, Mar. 20, 2018 (11 pages).
Ferreira, A. et al., "Effects of Sevelamer Hydrochloride and Calcium Carbonate on Renal Osteodystrophy in Hemodialysis Patients", J Am Soc Nephrol, 19:405-412, 2008 (8 pages).
Feurer, E. et al., "Lack of Association Between Select Circulating miRNAs and Bone Mass, Turnover, and Fractures: Data From the OFELY Cohort", Journal of Bone and Mineral Research, 34(6):1074-1085, Jun. 2019 (12 pages).
Fried, L.F. et al., "Association of Kidney Function with Incident Hip Fracture in Older Adults", J Am Soc Nephrol, 18:282-286, 2007 (5 pages).
Fusaro, M. et al., "High Prevalence of Vertebral Fractures Assessed by Quantitative Morphometry in Hemodialysis Patients, Strongly Associated with Vascular Calcifications", Calcif Tissue Int, 93:39-47, published online Mar. 14, 2013 (9 pages).
Garmilla-Ezquerra, P. et al., "Analysis of the Bone MicroRNome in Osteoporotic Fractures", Calcif Tissue Int, 96:30-37, 2015, published online Nov. 29, 2014 (9 pages).
Go, A.S. et al., "Chronic Kidney Disease and the Risks of Death, Cardiovascular Events, and Hospitalization", N Engl J Med, 351:1296-1305, Sep. 23, 2004 (10 pages).
Griffiths-Jones, S. et al., "miRBase: tools for microRNA genomics", Nucleic Acids Research, 36(Database issue):D154-D158, published online Nov. 8, 2007 (5 pages).
Hajian-Tilaki, K. "Sample size estimation in diagnostic test studies of biomedical informatics", Journal of Biomedical Informatics, 48:193-204, published online Feb. 26, 2014 (12 pages).
Hamdy, N. A.T. et al., "Effect of alfacalcidol on natural course of renal bone disease in mild to moderate renal failure", BMJ, 310: 358-363, Feb. 11, 1995 (6 pages).
Heilmeier, U. et al., "Serum miRNA Signatures Are Indicative of Skeletal Fractures in Postmenopausal Women With and Without Type 2 Diabetes and Influence Osteogenic and Adipogenic Differentiation of Adipose Tissue-Derived Mesenchymal Stem Cells In Vitro", Journal of Bone and Mineral Research, 31(12): 2173-2192, Dec. 2016 (20 pages).
Hu, R. et al., "A Runx2/miR-3960/miR-2861 Regulatory Feedback Loop during Mouse Osteoblast Differentiation", The Journal of Biological Chemistry, 286(14):12328-12339, Apr. 8, 2011 (12 pages).
International Search Report and Written Opinion as issued by the U.S. Patent and Trademark Office as International Searching Authority, in International Application No. PCT/US19/34073, dated Dec. 2, 2019 (19 pages).
Isakova, T. et al., "Change in estimated glomerular filtration rate and fracture risk in the Action to Control Cardiovascular Risk in Diabetes Trial", Bone, 78:23-27, published online Apr. 30, 2015 (5 pages).
Ishani, A. et al., "The Effect of Raloxifene Treatment in Postmenopausal Women with CKD", J Am Soc Nephrol, 19(7):1430-1438, doi:10.1681/ASN.2007050555 Jul. 2008 (9 pages).
Iyer, S.P. et al., "Kidney Transplantation with Early Corticosteroid Withdrawal: Paradoxical Effects at the Central and Peripheral Skeleton", J Am Soc Nephrol, 25:1331-1341, 2014 (11 pages).
Jamal, S.A. et al., "Alendronate Treatment in Women With Normal to Severely Impaired Renal Function: An Analysis of the Fracture Intervention Trial", Journal of Bone and Mineral Research, 22(4):503-508, published online Jan. 22, 2007 (6 pages).
Jamal, S.A. et al., "Effects of Denosumab on Fracture and Bone Mineral Density by Level of Kidney Function", Journal of Bone and Mineral Research, 26(8):1829-1835, Aug. 2011 (7 pages).
Jeong, S. et al., "Differentially expressed miR-3680-5p is associated with parathyroid hormone regulation in peritoneal dialysis patients", PLoS One, 12(2):e0170535, Feb. 2, 2017 (14 pages).
Kagiya, T. et al., "Expression profiling of microRNAs in RAW264.7 cells treated with a combination of tumor necrosis factor alpha and RANKL during osteoclast differentiation", J Periodont Res, 48:373-385, 2013 (13 pages).
KDIGO Working Group, "Chapter 1: Introduction and definition of CKD-MBD and the development of the guideline statements", Kidney International, 79(Supp 113): S3-S8, 2009 (6 pages).
Kent, K. et al., "Abstract MO0034: Feasibility and Reproducibility using HRpQCTII in Children and Adolescents", American Society for Bone and Mineral Research Annual Meeting, Atlanta, GA, 2016 (1 page).
Ketteler, M. et al., "Executive summary of the 2017 KDIGO Chronic Kidney Disease-Mineral and Bone Disorder (CKD-MBD) Guideline Update: what's changed and why it matters", Kidney International, 92:26-36, 2017 (11 pages).
Khairallah, P. et al., "Management of Osteoporosis in CKD", Clin J Am Soc Nephrol, 13:962-969, 2018 (8 pages).
Kim, S.M. et al., "Hip Fracture in Patients with Non-Dialysis-Requiring Chronic Kidney Disease", Journal of Bone and Mineral Research, 31(10):1803-1809, Oct. 2016 (7 pages).
Kurz, P. et al., "Evidence for abnormal calcium homeostasis in patients with adynamic bone disease", Kidney International, 46:855-861, 1994 (7 pages).
Langer, R., "New Methods of Drug Delivery", Science, 249:1527-1533, Sep. 28, 1990 (8 pages).
Lehmann, G. et al., "Bone histomorphometry and biochemical markers of bone turnover in patients with chronic kidney disease Stages 3-5", Clinical Nephrology, 70(4):296-305, 2008 (10 pages).
Lehmann, G. et al., "Specific measurement of PTH (1-84) in various forms of renal osteodystrophy (ROD) as assessed by bone histomorphometry", Kidney International 68:1206-1214, 2005 (9 pages).
Leopold, J.A., "MicroRNAs Regulate Vascular Medial Calcification", Cells, 3:963-980, Oct. 14, 2014 (18 pages).
Lewis, B. et al., "Prediction of Mammalian MicroRNA Targets", Cell. 115:787-798, Dec. 26, 2003 (12 pages).
Lian, J. et al., "MicroRNA control of bone formation and homeostasis", Nature Reviews Endocrinology, 8:212-227, Apr. 2012, published online Jan. 31, 2012 (16 pages).
Lin, X.-J. et al., "A serum microRNA classifier for early detection of hepatocellular carcinoma: a multicentre, retrospective, longitudinal biomarker identification study with a nested case-control study", Lancet Oncol, 16:804-815, Jul. 2015, published online Jun. 16, 2015 (12 pages).
Lindsay, R. et al., "A Novel Tetracycline Labeling Schedule for Longitudinal Evaluation of the Short-Term Effects of Anabolic Therapy With a Single Iliac Crest Bone Biopsy: Early Actions of Teriparatide", Journal of Bone and Mineral Research, 21(3):366-373, published online Nov. 21, 2005 (8 pages).
London, G.M. et al., "Arterial Calcifications and Bone Histomorphometry in End-Stage Renal Disease", J Am Soc Nephrol, 15:1943-1951, 2004 (9 pages).
London, G.M. et al., "Arteriosclerosis, vascular calcifications and cardiovascular disease in uremia", Curr Opin Nephrol Hypertens, 14:525-531, 2005 (7 pages).
London, G.M. et al., "Association of Bone Activity, Calcium Load, Aortic Stiffness, and Calcifications in ESRD", J Am Soc Nephrol, 19(9):1827-1835, 2008 (9 pages).
London, G. et al., "The new kidney disease: improving global outcomes (KDIGO) guidelines—expert clinical focus on bone and vascular calcification", Clinical Nephrology, 74(6):423-432, 2010 (12 pages).

(56) References Cited

OTHER PUBLICATIONS

Luckman, M. et al., "Spine Trabecular Bone Score as an Indicator of Bone Microarchitecture at the Peripheral Skeleton in Kidney Transplant Recipients", Clin J Am Soc Nephrol, 12:644-652, Apr. 2017 (9 pages).
M'baya-Moutoula, E. et al., "High inorganic phosphate concentration inhibits osteoclastogenesis by modulating miR-223", Biochimica et Biophysica Acta, 1852:2202-2212, published online Aug. 6, 2015 (11 pages).
Macneil, J.A. et al., "Bone strength at the distal radius can be estimated from high-resolution peripheral quantitative computed tomography and the finite element method", Bone, 42:1203-1213, available online Feb. 13, 2008 (11 pages).
Malluche, H.H. et al., "An assessment of cinacalcet HCI effects on bone histology in dialysis patients with secondary hyperparathyroidism", Clinical Nephrology, 69(4):269-278, Apr. 2008 (14 pages).
Malluche, H.H. et al., "Renal Osteodystrophy in the First Decade of the New Millennium: Analysis of 630 Bone Biopsies in Black and White Patients", Journal of Bone and Mineral Research, 26(6):1368-1376, Jun. 2011, published online Dec. 6, 2010 (9 pages).
Miller, P.D. et al., "Safety and Efficacy of Risedronate in Patients With Age-Related Reduced Renal Function as Estimated by the Cockcroft and Gault Method: A Pooled Analysis of Nine Clinical Trials", Journal of Bone and Mineral Research, 20(12):2105-2115, published online Aug. 22, 2005 (11 pages).
Miller, P.D. et al., "Teriparatide in postmenopausal women with osteoporosis and mild or moderate renal impairment", Osteoporos Int, 18:59-68, 2007 (10 pages).
Mizuno, Y. et al., "miR-125b inhibits osteoblastic differentiation by down-regulation of cell proliferation", Biochemical and Biophysical Research Communications, 368:267-272, published online Jan. 28, 2008 (6 pages).
Moe, S.M. et al. "A rat model of chronic kidney disease-mineral bone disorder", Kidney International, 75:176-84, 2009 published online Sep. 17, 2008 (9 pages).
Moe, S.M. et al. "R-568 reduces ectopic calcification in a rat model of chronic kidney disease- mineral bone disorder (CKD-MBD)", Nephrol Dial Transplant, 24:2371-2377, Mar. 3, 2009 (7 pages).
Moe, S.M. et al., "A Comparison of Calcium to Zoledronic Acid for Improvement of Cortical Bone in an Animal Model of CKD", Journal of Bone and Mineral Research, 29(4):902-910 Apr. 2014 (9 pages).
Moe, S.M. et al., "Anti-Sclerostin Antibody Treatment in a Rat Model of Progressive Renal Osteodystrophy", Journal of Bone and Mineral Research, 30(3):499-509, Mar. 2015 (11 pages).
Moe, S. et al., "Definition, evaluation, and classification of renal osteodystrophy: A position statement from Kidney Disease: Improving Global Outcomes (KDIGO)", Kidney International, 69:1945-1953, Apr. 26, 2006 (9 pages).
Moe, S.M. et al., "The Pathophysiology of Early-Stage Chronic Kidney Disease-Mineral Bone Disorder (CKD-MBD) and Response to Phosphate Binders in the Rat", Journal of Bone and Mineral Research, 26(11):2672-2681, Nov. 2011 (10 pages).
Monier-Faugere, M.-C. et al., "High Prevalence of Low Bone Turnover and Occurrence of Osteomalacia after Kidney Transplantation", J Am Soc Nephrol, 11(6):1093-1099, 2000 (7 pages).
Mueller, T.L. et al., "Computational finite element bone mechanics accurately predicts mechanical competence in the human radius of an elderly population", Bone, 48:1232-1238, published online Mar. 2, 2011 (7 pages).
National Institutes of Health, "Kidney Disease Research Funding and Priority Setting", GAO—United States Government Accountability Office: Report to Congressional Requesters, GAO-17-121, Dec. 19, 2016 (33 pages).
Naylor, K.L. et al., "The three-year incidence of fracture in chronic kidney disease", Kidney International, 86:810-818, published online Jan. 15, 2014 (9 pages).
Newman, C.L. et al., "Calcitriol Suppression of Parathyroid Hormone Fails to Improve Skeletal Properties in an Animal Model of Chronic Kidney Disease", Am J Nephrol, 43:20-31, published online Feb. 17, 2016 (12 pages).
Newman, C.L. et al., "Cortical Bone Mechanical Properties Are Altered in an Animal Model of Progressive Chronic Kidney Disease", PLOS One, 9(6):e99262, Jun. 9, 2014 (8 pages).
Nickolas, T., "Serologic test to diagnose and manage low turnover renal osteodystrophy", Columbia Technology Ventures, http://innovation.columbia.edu/technologies/CU18256, Feb. 8, 2018 (2 pages).
Nickolas, T.L. et al. "Relationship between Moderate to Severe Kidney Disease and Hip Fracture in the United States", J Am Soc Nephrol, 17: 3223-3232, 2006 (10 pages).
Nickolas, T.L. et al., "A microRNA Approach to Discriminate Cortical Low Bone Turnover in Renal Osteodystrophy", JBMR® Plus (WOA), 4(5):e10353, May 2020 (10 pages).
Nickolas, T.L. et al., "Bone Mass and Microarchitecture in CKD Patients with Fracture", J Am Soc Nephrol, 21: 1371-1380, 2010 (10 pages).
Nickolas, T.L. et al., "Discriminants of Prevalent Fractures in Chronic Kidney Disease", J Am Soc Nephrol, 22: 1560-1572, 2011 (13 pages).
Nickolas, T.L. et al., "Rapid Cortical Bone Loss in Patients With Chronic Kidney Disease", Journal of Bone and Mineral Research, 28(8):1811-1820, Aug. 2013 (10 pages).
Nishiyama, K. K. et al., "Longitudinal HR-pQCT and Image Registration Detects Endocortical Bone Loss in Kidney Transplantation Patients", Journal of Bone and Mineral Research, 30(3):554-561, Mar. 2015 (8 pages).
Paccou, J. et al., "Lower leg arterial calcification assessed by high-resolution peripheral quantitative computed tomography is associated with bone microstructure abnormalities in women", Osteoporos Int, 27:3279-3287, published online Jun. 21, 2016 (9 pages).
Palcu, P. et al., "Teriparatide and Bone Turnover and Formation in a Hemodialysis Patient With Low-Turnover Bone Disease: A Case Report", Am J Kidney Dis, 65(6):933-936, 2015 (4 pages).
Parfitt, A.M., "Perspective: A Structural Approach to Renal Bone Disease", Journal of Bone and Mineral Research, 13(8):1213-1220, 1998 (8 pages).
Parfitt, A.M. et al., "Relationships between Surface, Volume and Thickness of Iliac Trabecular Bone in Aging and in Osteoporosis: Implications for the Microanatomic and Cellular Mechanisms of Bone Loss", The Journal of Clinical Investigation, 72:1396-1409, Oct. 1983 (14 pages).
Patsch, J. M. et al., "Quantification of lower leg arterial calcifications by high-resolution peripheral quantitative computed tomography", Bone, 58:42-47, 2014, published online Aug. 14, 2013 (6 pages).
Pialat, JB. et al., "Visual grading of motion induced image degradation in high resolution peripheral computed tomography: Impact of image quality on measures of bone density and micro-architecture", Bone, 50:111-118, 2012, available online Oct. 13, 2011 (8 pages).
Pistoia, W. et al., "Mechanical consequences of different scenarios for simulated bone atrophy and recovery in the distal radius", Bone, 33:937-945, 2003 (9 pages).
Rhee, Y. et al., "PTH Receptor Signaling in Osteocytes Governs Periosteal Bone Formation and Intracortical Remodeling", Journal of Bone and Mineral Research, 26(5):1035-1046, May 2011 (12 pages).
Rubin, M. et al., "PTH(1-84) Administration Reverses Abnormal Bone-Remodeling Dynamics and Structure in Hypoparathyroidism", Journal of Bone and Mineral Research, 26(11), pp. 2727-2736, Nov. 2011 (10 pages).
Sato, M. et al., "Circulating osteocyte-derived exosomes contain miRNAs which are enriched in exosomes from MLO-Y4 cells", Biomedical Reports, 6:223-231, 2017 (9 pages).
Schafer, H., "Efficient Confidence Bounds for Roc Curves", Statistics in Medicine, 13:1551-1561 (1994) (11 pages).

(56) References Cited

OTHER PUBLICATIONS

Seeliger, C. et al., "Five Freely Circulating miRNAs and Bone Tissue miRNAs Are Associated With Osteoporotic Fractures", Journal of Bone and Mineral Research, 29(8):1718-1728, Aug. 2014 (11 pages).
Sethupathy, P. et al., "TarBase: A comprehensive database of experimentally supported animal microRNA targets", RNA, 12(2):192-197, 2006 (7 pages).
Sharma, A.K. et al., "Deterioration of Cortical Bone Microarchitecture: Critical Component of Renal Osteodystrophy Evaluation", Am J Nephrol, 47:376-384, published May 23, 2018 (10 pages).
Shilo, V. et al., "Let-7 and MicroRNA-148 Regulate Parathyroid Hormone Levels in Secondary Hyperparathyroidism", J Am Soc Nephrol, 28:2353-2363, 2017 (26 pages).
Silva, B.C. et al., "Parathyroid hormone: anabolic and catabolic actions on the skeleton", Current Opinion in Pharmacology, 22:41-50, available online Apr. 5, 2015 (10 pages).
Slatopolsky, E. et al., "Chapter 39: Bone Disease in Chronic Renal Failure and After Renal Transplantation", Disorders of Bone and Mineral Metabolism, Coe, et al., Editors, Raven Press, Ltd., New York: Raven Press, pp. 905-934, 1992 (31 pages).
Spasovski, G.B. et al., "Spectrum of renal bone disease in end-stage renal failure patients not yet on dialysis", Nephrol Dial Transplant, 18:1159-1166, 2003 (8 pages).
Sprague, S.M. et al., "Diagnostic Accuracy of Bone Turnover Markers and Bone Histology in Patients With CKD Treated by Dialysis", Am J Kidney Dis, 67(4):559-566, 2016 (8 pages).
Subramanian, A. et al., "Gene set enrichment analysis: A knowledge-based approach for interpreting genome-wide expression profiles", PNAS, 102(43):15545-15550, Oct. 25, 2005 (6 pages).
Subramanian, A. et al., "GSEA-P: a desktop application for Gene Set Enrichment Analysis", Bioinformatics, 23(23):3251-3253, published online Jul. 20, 2007 (3 pages).
Sumida, K. et al., "Once-weekly teriparatide in hemodialysis patients with hypoparathyroidism and low bone mass: a prospective study", Osteoporosis Int, 27:1441-1450, 2016, published online Nov. 2, 2015 (10 pages).
Tekindal, M.A. et al., "The Performances of Two Diagnostics Tests: Mcnemar and Newcombe Graphical Approach", Pak. J. Statist., 33(4):301-314, 2017 (14 pages).
Toussaint, N.D. et al., "Associations between vascular calcification, arterial stiffness and bone mineral density in chronic kidney disease", Nephrol Dial Transplant, 23:586-593, 2008, published online Oct. 12, 2017 (8 pages).
United States Renal Data System, "2018 USRDS Annual Data Report: Executive Summary", 2018 (14 pages).
Vaira, V., et al., "MicroRNAs in parathyroid physiopathology", Molecular and Cellular Endocrinology, http://dx.doi.org/10.1016/i.mce.2016.10.035, 2016 (7 pages).
Van Wijnen, A.J. et al., "MicroRNA Functions in Osteogenesis and Dysfunctions in Osteoporosis", Curr Osteoporos Rep, 11:72-82, published online Apr. 23, 2013 (11 pages).
Wagner, J. et al., "Increased bone fractures among elderly United States hemodialysis patients", Nephrol Dial Transplant, 29:146-151, 2014, published online Sep. 26, 2013 (6 pages).
Wang, H. et al., "MIR-125b Regulates the Osteogenic Differentiation of Human Mesenchymal Stem Cells by Targeting BMPR1b", Cell Physiol Biochem, 41:530-542, published online Jan. 31, 2017 (13 pages).
Weilner, S. et al., "Differentially circulating miRNAs after recent osteoporotic fractures can influence osteogenic differentiation", Bone, 79:43-51, available online May 28, 2015 (9 pages).
Zhang, Y. et al., "A program of microRNAs controls osteogenic lineage progression by targeting transcription factor Runx2", PNAS, 108(24):9863-9868, Jun. 14, 2011 (6 pages).
Zhang, J. et al., "Interferon-ß-induced miR-155 inhibits osteoclast differentiation by targeting SOCS1 and MITF", FEBS Letters, 586:3255-3262, available online Jul. 4, 2012 (8 pages).
Zhao, H. et al., "Transforming Growth Factor ß1/Smad4 Signaling Affects Osteoclast Differentiation via Regulation of miR-155 Expression", Mol. Cells, 40(3):211-221, published online Mar. 29, 2017 (11 pages).
Zhou, B. et al., "High-resolution peripheral quantitative computed tomography (HR-pQCT) can assess microstructural and biomechanical properties of both human distal radius and tibia: Ex vivo computational and experimental validations", Bone, 86:58-67, published online Feb. 26, 2016 (10 pages).

* cited by examiner

| FIG. 1: Cohort Characteristics by tertile of bone formation rate (BFR) | | | |
|---|---|---|---|
| N=24 | | | |
| | Bone Turnover Group | | |
| | Lowest Tertile BFR (n=8) | Middle Tertile BFR (n=8) | Highest Tertile BFR (n=8) |
| Histomorphometry | | | |
| Bone formation rate - mean $mm^2/mm/year$ (SD) | 0.005 (0.005) | 0.012 (0.006) | 0.065 (0.036) |
| Adjusted apposition rate - mean µm/day (SD) | 0.089 (0.070) | 0.336 (0.219) | 0.913 (0.656) |
| Demographics | | | |
| Age - mean years (SD) | 72 (8) | 64 (15) | 61 (14) |
| Female - N (%) | 4 (57%) | 6 (67%) | 5 (71%) |
| White - N (%) | 4 (57%) | 5 (56%) | 5 (71%) |
| Comorbids - N (%) | | | |
| Prevalent fracture | 2 (29%) | 6 (67%) | 5 (71%) |
| Dialysis | 1 (14%) | 2 (22%) | 3 (43%) |
| History of transplant | 0 (0%) | 1 (11%) | 1 (14%) |
| Biochemical - median (IQR) | | | |
| GFR - mL/min/1.74 | 21 (14; 57) | 33 (18; 36) | 29 (18; 50) |
| Parathyroid hormone - pg/mL | 83 (54; 305) | 78 (37; 97) | 166 (60; 438) |
| Bone Specific Alkaline Phosphatase - U/L | 36 (27; 39) † | 30 (27; 36) ζ | 68 (50; 83) |
| miRNA - median (IQR) | | | |
| miR-30b | 0.940 (0.511; 1.372) *† | 3.469 (1.304; 4.223) | 2.341 (1.553; 2.791) |
| miR-30c | 1.052 (0.622; 1.556) * | 3.278 (1.400; 4.057) | 2.036 (1.470; 2.545) |
| miR-125b | 3.028 (2.514; 4.402) | 9.077 (4.169; 11.668) | 9.352 (5.332; 12.390) |
| miR-155 | 0.794 (0.693; 1.022) * | 1.506 (1.294; 2.480) ζ | 0.959 (0.861; 1.218) |
| p <0.05: * low vs. middle; † low vs. high; ζ middle vs. high | | | |

FIG. 1

| FIG. 2: Spearman Correlations between miRNAs and Biomarkers of CKD-MBD | | | | | | | |
|---|---|---|---|---|---|---|---|
| | miRNA-30c | miRNA-125b | miRNA-155 | Calcium | Phosphorus | intact PTH | BSAP |
| miRNA-30b<br>p-value | 0.98<br><.0001 | 0.80<br><.0001 | 0.49<br>0.01 | -0.41<br>0.04 | -0.54<br>0.006 | -0.06<br>0.8 | 0.33<br>0.2 |
| miRNA-30c<br>p-value | | 0.76<br><.0001 | 0.56<br>0.005 | -0.44<br>0.03 | -0.54<br>0.006 | -0.09<br>0.7 | 0.28<br>0.2 |
| miRNA-125b<br>p-value | | | 0.39<br>0.059 | -0.26<br>0.2 | -0.49<br>0.02 | 0.06<br>0.8 | 0.44<br>0.054 |
| miRNA-155<br>p-value | | | | -0.26<br>0.2 | -0.19<br>0.4 | -0.43<br>0.057 | -0.09<br>0.7 |

FIG. 2

FIG. 3: Spearman correlations between miRNAs, PTH, BSAP and Dynamic Measures from Bone Histomorphometry

| | MS/BS | MAR | BFR/BS | OS/BS | AjAR | ES/BS | OMT | MLT |
|---|---|---|---|---|---|---|---|---|
| | **Trabecular Bone** | | | | | | | |
| miRNA-30b | 0.19 | 0.06 | 0.21 | -0.02 | 0.33 | -0.33 | 0.21 | -0.08 |
| p-value | 0.4 | 0.8 | 0.3 | 0.9 | 0.1 | 0.1 | 0.4 | 0.8 |
| miRNA-30c | 0.13 | 0.09 | 0.16 | -0.04 | 0.26 | -0.33 | 0.16 | -0.02 |
| p-value | 0.5 | 0.7 | 0.5 | 0.9 | 0.2 | 0.1 | 0.5 | 0.9 |
| miRNA-125b | 0.19 | -0.17 | 0.15 | 0.01 | 0.23 | -0.24 | 0.30 | -0.03 |
| p-value | 0.4 | 0.4 | 0.5 | 1.0 | 0.3 | 0.3 | 0.2 | 0.9 |
| miRNA-155 | -0.12 | 0.05 | -0.15 | -0.05 | -0.15 | -0.32 | -0.17 | 0.32 |
| p-value | 0.6 | 0.8 | 0.5 | 0.8 | 0.5 | 0.1 | 0.5 | 0.2 |
| Intact PTH | **0.63** | 0.27 | **0.49** | **0.51** | 0.19 | **0.62** | 0.13 | -0.11 |
| p-value | **0.002** | 0.2 | **0.02** | **0.01** | 0.4 | **0.002** | 0.6 | 0.7 |
| BSAP | **0.65** | 0.25 | **0.67** | 0.42 | **0.65** | 0.10 | 0.24 | -0.46 |
| p-value | **0.001** | 0.3 | **0.0008** | 0.058 | **0.0015** | 0.7 | 0.4 | 0.066 |
| | **Endocortical Bone** | | | | | | | |
| miRNA-30b | 0.31 | 0.04 | 0.29 | -0.17 | **0.44** | -0.23 | 0.32 | **-0.52** |
| p-value | 0.1 | 0.9 | 0.2 | 0.4 | **0.03** | 0.3 | 0.2 | **0.03** |
| miRNA-30c | 0.22 | 0.01 | 0.19 | -0.17 | 0.39 | -0.30 | 0.22 | **-0.50** |
| p-value | 0.3 | 1.0 | 0.4 | 0.4 | 0.1 | 0.2 | 0.4 | **0.04** |
| miRNA-125b | 0.18 | -0.12 | 0.11 | -0.04 | 0.17 | 0.01 | 0.22 | -0.38 |
| p-value | 0.4 | 0.6 | 0.6 | 0.9 | 0.4 | 1.0 | 0.4 | 0.1 |
| miRNA-155 | -0.03 | 0.07 | -0.10 | -0.10 | 0.05 | -0.15 | -0.25 | -0.06 |
| p-value | 0.9 | 0.7 | 0.7 | 0.6 | 0.8 | 0.5 | 0.3 | 0.8 |
| Intact PTH | 0.25 | 0.16 | 0.28 | **0.49** | -0.06 | 0.35 | 0.39 | 0.20 |
| p-value | 0.3 | 0.5 | 0.2 | **0.02** | 0.8 | 0.1 | 0.2 | 0.5 |
| BSAP | **0.55** | 0.26 | **0.49** | 0.23 | 0.37 | -0.03 | 0.30 | -0.39 |
| p-value | **0.01** | 0.2 | **0.03** | 0.3 | 0.1 | 0.9 | 0.3 | 0.2 |
| | **Cortical Bone** | | | | | | | |
| miRNA-30b | 0.39 | 0.32 | **0.43** | -0.12 | **0.50** | 0.10 | 0.23 | -0.16 |
| p-value | 0.069 | 0.1 | **0.04** | 0.6 | **0.01** | 0.7 | 0.4 | 0.5 |
| miRNA-30c | 0.30 | 0.27 | 0.36 | -0.15 | **0.42** | 0.07 | 0.23 | -0.13 |
| p-value | 0.2 | 0.2 | 0.095 | 0.5 | **0.0484** | 0.7 | 0.4 | 0.6 |
| miRNA-125b | **0.43** | 0.27 | 0.38 | 0.02 | **0.49** | 0.18 | 0.13 | -0.39 |
| p-value | **0.04** | 0.2 | 0.1 | 0.9 | **0.02** | 0.4 | 0.6 | 0.1 |
| miRNA-155 | -0.05 | 0.07 | 0.09 | -0.21 | 0.12 | -0.30 | 0.08 | 0.30 |
| p-value | 0.8 | 0.8 | 0.7 | 0.3 | 0.6 | 0.2 | 0.8 | 0.3 |
| Intact PTH | 0.33 | 0.21 | 0.14 | 0.05 | 0.18 | **0.50** | 0.03 | -0.17 |
| p-value | 0.1 | 0.4 | 0.5 | 0.8 | 0.4 | **0.02** | 0.9 | 0.6 |
| BSAP | **0.81** | **0.54** | **0.67** | **0.67** | **0.59** | 0.40 | 0.09 | **-0.73** |
| p-value | **<.0001** | **0.01** | **0.001** | **0.001** | **0.006** | 0.077 | 0.8 | **0.005** |

FIG. 3

FIG. 4: Area under the curve (AUCs): miRNAs for the diagnosis of turnover

| | Low vs Non-Low | | High vs. Non-High | |
|---|---|---|---|---|
| | AUC | 95% CI | AUC | 95% CI |
| PTH | 0.479 | 0.209-0.753 | 0.593 | 0.296-0.901 |
| BSAP | 0.781 | 0.571-0.991 | 0.956 | 0.862-1.000 |
| miR-30b | 0.875 | 0.733-1.000 | 0.650 | 0.408-0.892 |
| miR-30c | 0.825 | 0.645-1.000 | 0.608 | 0.362-0.855 |
| miR-125b | 0.800 | 0.613-0.987 | 0.658 | 0.365-0.951 |
| miR-155 | 0.767 | 0.559-0.974 | 0.558 | 0.310-0.807 |
| miR Panel | 0.983 | 0.944-1.000 | 0.800 | 0.576-1.000 |

FIG. 4

FIG. 5: Area under the curve (AUCs): Parathyroid Hormone (PTH), Bone Specific Alkaline Phosphatase (BSAP) and miRNAs for the diagnosis of turnover

| | Low vs Non-Low | | High vs. Non-High | |
|---|---|---|---|---|
| | AUC | 95% CI | AUC | 95% CI |
| PTH | 0.479 | 0.209-0.753 | 0.593 | 0.296-0.901 |
| BSAP | 0.781 | 0.571-0.991 | 0.956 | 0.862-1.000 |
| miR-30b | 0.875 | 0.733-1.000 | 0.650 | 0.408-0.892 |
| miR-30c | 0.825 | 0.645-1.000 | 0.608 | 0.362-0.855 |
| miR-125b | 0.800 | 0.613-0.987 | 0.658 | 0.365-0.951 |
| miR-155 | 0.767 | 0.559-0.974 | 0.558 | 0.310-0.807 |
| miR Panel | 0.983 | 0.944-1.000 | 0.800 | 0.576-1.000 |

FIG. 5

| Table 1: AUCs for PTH and BSAP for Diagnosis of Turnover by Bone Formation Rate and Adjusted Apposition Rate from Bone Biopsy | | | | |
|---|---|---|---|---|
| | Low vs. Non-Low | | High vs. Non-High | |
| | AUC | 95% CI | AUC | 95% CI |
| PTH | 0.479 | 0.206-0.753 | 0.593 | 0.296-0.901 |
| BSAP | 0.781 | 0.571-0.991 | 0.956 | 0.862-1.000 |

FIG. 7

| FIG. 10: AUCs for miRNAs for Diagnosis of Turnover by Bone Formation Rate and Adjusted Apposition Rate from Bone Biopsy | | | | |
|---|---|---|---|---|
| | Low vs. Non-Low | | High vs. Non-High | |
| | AUC | 95% CI | AUC | 95% CI |
| miRNA 30b | 0.875 | 0.733-1.000 | 0.650 | 0.408-0.892 |
| miRNA 30c | 0.825 | 0.645-1.000 | 0.608 | 0.362-0.855 |
| miRNA 125b | 0.800 | 0.613-0.987 | 0.658 | 0.365-0.951 |
| miRNA 155 | 0.767 | 0.559-0.974 | 0.558 | 0.310-0.807 |

FIG. 10

| FIG. 11: Existing Cohort Characteristics by tertile of bone formation rate (BFR) | | | |
|---|---|---|---|
| N=24 | | | |
| Demographics | Bone Turnover Group | | |
| | Lowest Tertile BFR | Middle Tertile BFR | Highest Tertile BFR |
| Age - mean years (SD) | 72 (8) | 64 (15) | 61 (14) |
| Female - N (%) | 4 (57%) | 6 (67%) | 5 (71%) |
| White - N (%) | 4 (57%) | 5 (56%) | 5 (71%) |
| Comorbids - N (%) | | | |
| Prevalent fracture | 2 (29%) | 6 (67%) | 5 (71%) |
| GFR mL/min/1.74 (median - IQR) | 21 (14; 57) | 33 (18; 36) | 29 (18; 50) |
| Dialysis | 1 (14%) | 2 (22%) | 3 (43%) |
| History of transplant | 0 (0%) | 1 (11%) | 1 (14%) |

FIG. 11

| FIG. 12: Data Collection | | | |
|---|---|---|---|
| | Visit 1 | Visit 2 | Visit 3 |
| Time period | 1-month be-fore treatment | 3-months after treatment | 5-days after completion of second label |
| Medical History | x | x | |
| Medication Review | x | x | |
| Physical Exam | x | x | |
| Creatinine, CKD-EPI eGFR | x | x | |
| Blood for miRNAs | x | x | |
| Label 1: Sumycin | x | | |
| Label 2: Demeclocycline | | x | |
| Bone Biopsy | | | X |

FIG. 12

| | Lowest Tertile BFR (n=8) | Middle Tertile BFR (n=7) | Highest Tertile BFR (n=8) |
|---|---|---|---|
| Demographics | | | |
| Age - mean years (SD) | 71 (8) | 64 (17) | 62 (13) |
| Female - N (%) | 5 (63%) | 4 (57%) | 6 (75%) |
| White - N (%) | 4 (50%) | 4 (57%) | 6 (75%) |
| Comorbidities - N (%) | | | |
| Prevalent fracture | 2 (25%) | 5 (71%) | 6 (75%) |
| MDRD GFR – mL/minute (min; max) | 18 (9; 62) | 33 (32; 43) | 22 (13; 63) |
| Dialysis | 1 (13%) | 2 (29%) | 3 (38%) |
| History of transplant | 0 (0%) | 1 (11%) | 1 (14%) |

FIG. 16A

PTH 0.590 (0.296-0.901)
BSAP 0.960(0.862-1.000)

| | |
|---|---|
| miR-30b | 0.650 (0.408-0.892) |
| miR-30c | 0.610 (0.362-0.855) |
| miR-125b | 0.660 (0.365-0.951) |
| miR-155 | 0.560 (0.310-0.807) |

miR-30b 0.880 (0.733-1.000)
miR-30c 0.830 (0.645-1.000)
miR-125b 0.800 (0.613-0.987)
miR-155 0.770 (0.559-0.974)

| | AUC | 95% CI | p-value vs. miR Panel |
|---|---|---|---|
| PTH | 0.509 | 0.251-0.766 | 0.006 |
| BSAP | 0.589 | 0.349-0.830 | 0.02 |
| miR-30b | 0.866 | 0.709-1.000 | 0.4 |
| miR-30c | 0.813 | 0.610-1.000 | 0.2 |
| miR-125b | 0.813 | 0.635-0.990 | 0.2 |
| miR-155 | 0.723 | 0.499-0.948 | 0.06 |
| miR Panel | 0.929 | 0.821-1.000 | - |

FIG. 26

| | Low (n=30) | Normal (n=30) | High (n=30) |
|---|---|---|---|
| *NYC - %* | 48 | 100 | 44 |
| *Brazil - %* | 52 | 0 | 56 |
| *Age - years ± SD* | 53 ± 14 | 60 ± 11 | 57 ± 16 |
| *Sex - % Female* | 59 | 69 | 44 |
| *Race - % White* | 66 | 50 | 56 |
| *CKD 3 - %* | 27 | 46 | 26 |
| *CKD 4 - %* | 17 | 8 | 7 |
| *CKD 5 (no dialysis) - %* | 7 | 31 | 4 |
| *CKD-5D (dialysis) - %* | 48 | 15 | 63 |
| *History of Kidney Transplant - %* | 14 | 12 | 0 |
| *History of Fracture - %* | 17 | 27 | 26 |

FIG. 30

| ASSAY | Manufacturer | Assay Type | Inter-assay Precision | Intra-assay Precision |
|---|---|---|---|---|
| Intact PTH | Scantibodies Laboratory (Santee, CA) | RIA | 5.81% | 4.00% |
| $25OHD_2$<br>$25OHD_3$<br>$1,25D_2$<br>$1,25D_3$ | NA (CUIMC Bone Biomarker Lab) | LCMS | 8.1%<br>5.5%<br>15.6%<br>9.9% | 2.4%<br>3.5%<br>15.1%<br>9.9% |
| BSAP | Quidel (San Diego, CA) | ELISA | 5.90% | 5.00% |
| Osteocalcin | Immunodiagnostic Systems (Scottsdale, AZ) | ELISA | 4.00% | 1.77% |
| P1NP | Orion Diagnostica (Espoo, Finland) | RIA | 8.00% | 5.90% |
| C-Telopeptide | Immunodiagnostic Systems (Scottsdale, AZ) | ELISA | 7.70% | 2.17% |
| TRAP-5b | Immunodiagnostic Systems (Scottsdale, AZ) | ELISA | 7.70% | 9.00% |
| FGF-23 (C-terminal) | Immunodiagnostic Systems (Scottsdale, AZ) | ELISA | 3.55% | 1.90% |
| Sclerostin | Teco Medical (Switzerland) | ELISA | 3.50% | 3.10% |
| DKK-1 | Biomedica (ALPCO) | ELISA | 10.5% | 7.50% |
| IGF-1 | Siemens Healthcare Diagnostics (Deerfield, IL) | IMM | 3.70% | 2.95% |

FIG. 31

| | Low | Normal | High |
|---|---|---|---|
| *miRNA-30b* | ↓ | ↔ | ↑ |
| *miRNA-30c* | ↓ | ↔ | ↑ |
| *miRNA-125b* | ↓ | ↔ | ↑ |
| *miRNA-155* | ↓ | ↔ | ↑ |

FIG. 32

| *Table 5: Data Collection at each study visit for human study* | Recruitment | Visit 1 (Pre-Treatment) | Visit 2 (3-months) | Visit 3 (9-months treatment) | Visit 4 (10-months: bone biopsy) |
|---|---|---|---|---|---|
| Informed Consent & Screening | X | | | | |
| Clinical history, Physical Activity Assessment, Dietary Questionnaire | | X | | | |
| Blood Samples: miRNA, PTH, bone formation and resorption markers, bone metabolism markers | | X | X | | X |
| HR-pQCT imaging of the radius and tibia (For Aim 3) | | X | | X | |
| Bone biopsy label #1 | | X | | | |
| Bone biopsy label #2 | | | | X | |
| Pre-bone biopsy assessment (BMP, CBC, PT/PTT) | | | | X | |
| Iliac bone biopsy (2 cores) | | | | | X |

FIG. 33

| | High turnover prior to treatment | Low turnover after treatment |
|---|---|---|
| *miRNA-30b* | ↑ | ↓ |
| *miRNA-30c* | ↑ | ↓ |
| *miRNA-125b* | ↑ | ↓ |
| *miRNA-155* | ↑ | ↓ |

FIG. 34

*Table 7: Bone turnover groups for the rat models of ROD (all groups have n=14 animals)*

| Group | Condition | Treatment | Intervention | Age at sacrifice |
|---|---|---|---|---|
| 1 | Moderate hyperparathyroidism: high turnover | CKD, no treatment | None | 23 weeks (n = 14) |
| 2 | Severe hyperparathyroidism: high turnover | CKD, no treatment | None | 28 weeks (n = 14) |
| 3 | High to Low turnover | CKD, calcium | Calcium 3% in the drinking water 18 to 28 weeks | 28 weeks (n = 14) |
| 4 | High to Low turnover | CKD, calcimimetic | KP2326 (0.6 mg/kg tiw) 18 to 28 weeks | 28 weeks (n = 14) |
| 5 | Low to High turnover | CKD, calcium to no calcium | Calcium 18 to 23 weeks, and then no treatment 23 to 28 weeks | half (n = 14) at 23 weeks and half (n = 14) at 28 weeks |
| 6 | Low to High turnover | CKD, calcimimetic to no calcimimetic | KP2326 18 to 23 weeks, and then no treatment 23 to 28 weeks | half (n = 14) at 23 weeks and half (n = 14) at 28 weeks |

FIG. 35

*Table 8: Rat bone tissue preparation at sacrifice and analysis plans*

| *Specimen* | *Fixed/Storage Methods* | *Analyses and previous publications by our group demonstrating capabilities* |
|---|---|---|
| Left Femur and Tibia | Marrow rinsed as above and snap frozen. Later vortexed to collect remaining marrow and surface celll, and then remaining bone for bone cell RNA. | miRNA analyses comparing bone marrow, bone vortex (surface cells), and bone tissue for Aim 3a (see preliminary data below). |
| Right Femur | Frozen in saline-soaked gauze at -20°C | Mechanical testing (4 pt monotonic testing to determine measured structural and estimate material properties) [62,63,65] |
| Right Tibia | Fixed in NBF/stored in 70% EtOH | Micro/CT (midshaft for geometry and cortical porosity) [63,65] and Histomorphometry (Aims 1 and 2) |

FIG. 36

*Table 9: Hypothesized direction of correlation & regression coefficients for Aims 3a (cross sectional) and 3b/c (prospective)*

| | |
|---|---|
| **Aim 3a (cross sectional)** | |
| **Primary Measure** | **Circulating miRNA (post-treatment)** |
| Bone-Tissue | + |
| Bone Marrow | Not Significant |
| Bone Vortex | Not Significant |
| **Aim 3b (humans; prospective)** | |
| **Primary Measure** | **Change in Circulating miRNA with 9 months treatment** |
| **Microarchitecture (HR-pQCT)** | |
| Cortical density | + |
| Cortical porosity | - |
| Trabecular bone volume | + |
| **Biomechanics (FEA)** | |
| Estimated Stiffness & Failure Load | + |
| **Aim 3c (rats; prospective)** | |
| **Primary Measure** | **Change in Circulating miRNA with 4 to 8 weeks of various treatments (Table 7)** |
| **Biomechanics** | |
| Work to Failure (energy under curve) | + |
| Stiffness & Failure Load | + |
| **Microarchitecture (microCT)** | |
| Cortical density | + |
| Cortical porosity | - |
| Trabecular bone volume | + |

FIG. 39

| Cohort Characteristics by adynamic bone disease status | | | |
|---|---|---|---|
| N=23 | | | |
| | Bone Turnover Group | | |
| | Low Bone Turnover (n=7) | Non-Low Bone Turnover (n=16) | p-value |
| Histomorphometry - median (IQR) | | | |
| Bone formation rate / Bone surface - mm$^2$/mm/year | 0.0017 (0.0005; 0.0063) | 0.0181 (0.0133; 0.0460) | |
| Demographics | | | |
| Age - mean years (SD) | 71 (9) | 63 (14) | NS |
| Female - N (%) | 4 (57%) | 11 (69%) | NS |
| White - N (%) | 4 (57%) | 10 (63%) | NS |
| Comorbids - N (%) | | | |
| Prevalent fracture | 1 (14%) | 12 (75%) | NS |
| Dialysis | 1 (14%) | 5 (31%) | NS |
| History of transplant | 0 (0%) | 1 (11%) | NS |
| Biochemical - median (IQR) | | | |
| GFR - mL/min/1.74 | 22 (17; 57) | 33 (14; 36) | NS |
| Calcium mg/dL | 9.6 (9.5; 10.0) | 9.3 (9.0; 10.1) | NS |
| Phosphorus mg/dL | 3.9 (3.5; 6.0) | 3.8 (3.2; 4.3) | NS |
| 25-hydroxyvitamin D ng/mL | 38.5 (24.8; 46.1) | 25.8 (15.0; 44.5) | NS |
| Parathyroid hormone - pg/mL | 84 (54; 149) | 78 (34; 224) | NS |
| Bone Specific Alkaline Phosphatase - U/L | 29 (23; 38) | 36 (23; 56) | NS |
| Osteocalcin | 45 (26; 155) | 71 (33; 171) | NS |
| P1NP µl/L | 76 (47; 233) | 138 (79; 213) | NS |
| C-Telopeptide ng/mL | 0.723 (0.428; 1.570) | 0.847 (0.563; 1.345) | NS |
| Trap-5b U/L | 2.839 (2.549; 3.336) | 4.275 (2.906; 5.860) | NS |
| Sclerostin | 1.592 (0.933; 1.991) | 1.545 (1.083; 1.973) | NS |
| FGF-23 | 163 (95; 362) | 162 (128; 515) | NS |
| miRNA - median (IQR) | | | |
| miR-30b | 0.774 (0.421; 1.447) * | 2.341 (1.205; 3.562) | 0.007 |
| miR-30c | 0.848 (0.500; 1.636) * | 2.036 (1.328; 3.409) | 0.02 |
| miR-125b | 2.989 (2.407; 4.202) * | 9.188 (3.386; 11.416) | 0.02 |
| miR-155 | 0.802 (0.673; 1.159) | 1.218 (0.861; 1.457) | 0.1 |
| * $p < 0.05$ low vs. non-low | | | |

FIG. 40

Table : nan Correlations between miRNAs and Biomarkers of CKD-MBD and Bone Turnover

| | miRNA-30c | miRNA-125b | miRNA-155 | Calcium | Phosphorus | 25(OH)D | intact PTH | BSAP | Osteocalcin | P1NP | C-Telopeptide | Trap-5b | Sclerostin | FGF-23 |
|---|---|---|---|---|---|---|---|---|---|---|---|---|---|---|
| miRNA-30b | 0.98 | 0.80 | 0.49 | -0.41 | -0.54 | -0.01 | -0.06 | 0.33 | -0.07 | 0.03 | 0.08 | 0.03 | -0.27 | -0.15 |
| p-value | <.0001 | <.0001 | 0.01 | 0.04 | 0.006 | 1.0 | 0.8 | 0.2 | 0.8 | 0.9 | 0.8 | 0.9 | 0.3 | 0.6 |
| miRNA-30c | | 0.76 | 0.56 | -0.44 | -0.54 | 0.02 | -0.09 | 0.28 | -0.11 | -0.01 | 0.01 | 0.00 | -0.27 | -0.15 |
| p-value | | <.0001 | 0.005 | 0.03 | 0.006 | 0.9 | 0.7 | 0.2 | 0.6 | 1.0 | 1.0 | 1.0 | 0.3 | 0.6 |
| miRNA-125b | | | 0.39 | -0.26 | -0.49 | -0.02 | 0.06 | 0.44 | 0.09 | 0.10 | 0.23 | 0.22 | -0.34 | -0.19 |
| p-value | | | 0.059 | 0.2 | 0.02 | 0.9 | 0.8 | 0.054 | 0.7 | 0.7 | 0.3 | 0.4 | 0.1 | 0.5 |
| miRNA-155 | | | | -0.26 | -0.19 | -0.02 | -0.43 | -0.09 | -0.28 | 0.01 | -0.28 | 0.02 | -0.03 | 0.23 |
| p-value | | | | 0.2 | 0.4 | 0.9 | 0.057 | 0.7 | 0.2 | 1.0 | 0.2 | 0.9 | 0.9 | 0.4 |

FIG. 41

| Spearman correlations between miRNAs, PTH, BSAP and Dynamic Measures from Bone Histomorphometry<br>* p< 0.05 | | | |
|---|---|---|---|
| | BFR/BS | Aj.A.R. | MLT |
| **Trabecular Bone** | | | |
| miRNA-30b | 0.21 | 0.33 | -0.08 |
| miRNA-30c | 0.16 | 0.26 | -0.02 |
| miRNA-125b | 0.15 | 0.23 | -0.03 |
| miRNA-155 | -0.15 | -0.15 | 0.32 |
| Intact PTH | **0.49*** | 0.19 | -0.11 |
| 25(OH)D | **-0.49*** | -0.37 | 0.29 |
| BSAP | **0.76*** | **0.59*** | -0.39 |
| Osteocalcin | **0.53*** | 0.26 | -0.14 |
| P1NP | **0.47*** | 0.36 | -0.33 |
| C-Telopeptide | **0.63*** | 0.39 | -0.30 |
| Trab-5b | **0.45*** | 0.23 | -0.15 |
| Sclerostin | 0.02 | -0.20 | 0.15 |
| FGF-23 | 0.01 | -0.28 | 0.34 |
| **Endocortical Bone** | | | |
| miRNA-30b | 0.29 | **0.44*** | **-0.52*** |
| miRNA-30c | 0.19 | 0.39 | **-0.50*** |
| miRNA-125b | 0.11 | 0.17 | -0.38 |
| miRNA-155 | -0.10 | 0.05 | -0.06 |
| Intact PTH | 0.28 | -0.06 | 0.20 |
| 25(OH)D | **-0.45*** | -0.20 | 0.17 |
| BSAP | **0.51*** | 0.25 | -0.28 |
| Osteocalcin | **0.53*** | 0.11 | -0.08 |
| P1NP | **0.53*** | 0.34 | -0.32 |
| C-Telopeptide | **0.60*** | 0.20 | -0.04 |
| Trab-5b | 0.33 | 0.05 | 0.07 |
| Sclerostin | 0.25 | 0.00 | -0.02 |
| FGF-23 | 0.06 | -0.17 | 0.04 |
| **Cortical Bone** | | | |
| miRNA-30b | **0.43*** | **0.50*** | -0.16 |
| miRNA-30c | 0.36 | **0.42*** | -0.13 |
| miRNA-125b | 0.38 | **0.49*** | -0.39 |
| miRNA-155 | 0.09 | 0.12 | 0.30 |
| Intact PTH | 0.14 | 0.18 | -0.17 |
| 25(OH)D | -0.45 | -0.24 | 0.15 |
| BSAP | **0.71*** | **0.57*** | **-0.66*** |
| Osteocalcin | **0.49*** | 0.29 | -0.29 |
| P1NP | 0.43 | 0.19 | -0.20 |
| C-Telopeptide | **0.56*** | 0.40 | -0.31 |
| Trab-5b | 0.43 | 0.30 | -0.26 |
| Sclerostin | -0.06 | -0.15 | 0.15 |
| FGF-23 | -0.07 | -0.21 | 0.18 |

FIG. 42

*Area under the curve (AUCs) for Discrimination of Low Turnover ROD by PTH, BSAP and miRNAs (miRs). Combining the 4 miRs into a single biomarker panel had discrimination that was superior to PTH and BSAP.*

| | AUC | 95% CI | p-value vs. miR Panel |
|---|---|---|---|
| **PTH** | 0.509 | 0.251-0.766 | 0.006 |
| **BSAP** | 0.589 | 0.349-0.830 | 0.02 |
| **miR-30b** | 0.866 | 0.709-1.000 | 0.4 |
| **miR-30c** | 0.813 | 0.610-1.000 | 0.2 |
| **miR-125b** | 0.813 | 0.635-0.990 | 0.2 |
| **miR-155** | 0.723 | 0.499-0.948 | 0.06 |
| **miR Panel** | 0.929 | 0.821-1.000 | - |

FIG. 43

| N = 23 | Bone turnover group: Low bone turnover (n = 7) | Bone turnover group: Non-low bone turnover (n = 16) | p Value |
|---|---|---|---|
| Histomorphometry–median (IQR) | | | |
| Intracortical bone formation rate / bone surface ($mm^3/mm^2/year$) | 0.0017 (0.0005; 0.0063) | 0.0181 (0.0133; 0.0460) | 0.0005 |
| Intracortical mineral apposition rate (μm/d) | 0.3000 (0.3000; 0.3000) | 0.6637 (0.5248; 0.7240) | 0.0008 |
| Intracortical mineralization lag time (days) | 48.2 (34.2; 165.9) | 18.8 (12.8; 31.1) | 0.02 |
| Trabecular bone formation rate / bone surface ($mm^3/mm^2/year$) | 0.0024 (0.0001; 0.0060) | 0.0101 (0.0059; 0.0209) | 0.02 |
| Trabecular mineral apposition rate (μm/d) | 0.3000 (0.3000; 0.6699) | 0.5296 (0.5087; 0.6494) | NS |
| Trabecular mineralization lag time (days) | 47.0 (18.5; 1067.8) | 33.4 (22.9; 61.0) | NS |
| Endocortical bone formation rate / bone surface ($mm^3/mm^2/year$) | 0.0051 (0.0006; 0.0115) | 0.0156 (0.0099; 0.0249) | 0.02 |
| Endocortical mineral apposition rate (μm/d) | 0.3000 (0.3000; 0.6021) | 0.5323 (0.4224; 0.5694) | NS |
| Endocortical mineralization lag time (days) | 32.7 (3.9; 106.3) | 26.0 (16.0; 84.7) | NS |
| Demographics | | | |
| Age–mean years (SD) | 71 (9) | 63 (14) | NS |
| Female–N (%) | 4 (57%) | 11 (69%) | NS |
| White–N (%) | 4 (57%) | 10 (63%) | NS |
| Comorbids–N (%) | | | |
| Prevalent fracture | 1 (14%) | 12 (75%) | NS |
| Dialysis | 1 (14%) | 5 (31%) | NS |
| History of transplant | 0 (0%) | 1 (11%) | NS |

FIG. 46

| | Bone turnover group | | |
|---|---|---|---|
| N = 23 | Low bone turnover (n = 7) | Non-low bone turnover (n = 16) | p Value |
| Biochemical–median (IQR) | | | |
| GFR (mL/min/1.74) | 22 (17; 57) | 33 (14; 36) | NS |
| Calcium (mg/dL) | 9.6 (9.5; 10.0) | 9.3 (9.0; 10.1) | NS |
| Phosphorus (mg/dL) | 3.9 (3.5; 6.0) | 3.8 (3.2; 4.3) | NS |
| 25-hydroxyvitamin D (ng/mL) | 38.5 (24.8; 46.1) | 25.8 (15.0; 44.5) | NS |
| PTH (pg/mL) | 84 (54; 149) | 78 (34; 224) | NS |
| Bone-specific alkaline phosphatase (U/L) | 29 (23; 38) | 36 (23; 56) | NS |
| Osteocalcin (ng/mL) | 45 (26; 155) | 71 (33; 171) | NS |
| P1NP (μL/L) | 76 (47; 233) | 138 (79; 213) | NS |
| C-Telopeptide (ng/mL) | 0.723 (0.428; 1.570) | 0.847 (0.563; 1.345) | NS |
| TRAP-5b (U/L) | 2.839 (2.549; 3.336) | 4.275 (2.906; 5.860) | NS |
| Sclerostin (ng/mL) | 1.592 (0.933; 1.991) | 1.545 (1.083; 1.973) | NS |
| Fibroblast growth factor 23 (RU/mL) | 163 (95; 362) | 162 (128; 515) | NS |
| miRNA–median (IQR) | | | |
| miR-30b | 0.774 (0.421; 1.447)* | 2.341 (1.205; 3.562) | 0.007 |
| miR-30c | 0.848 (0.500; 1.636)* | 2.036 (1.328; 3.409) | 0.02 |
| miR-125b | 2.989 (2.407; 4.202)* | 9.188 (3.386; 11.416) | 0.02 |
| miR-155 | 0.802 (0.673; 1.159) | 1.218 (0.861; 1.457) | 0.1 |

GFR = glomerular filtration rate; IQR = interquartile range; NS = not significant; TRAP-5b = tartrate-resistant acid phosphatase 5b.

*$p < 0.05$ low versus non-low.

FIG. 46 cont.

| | miRNA-30c | miRNA-125b | miRNA-155 | Kidney function | Calcium | Phosphorus | 25 (OH)D | Intact PTH | BSAP | Osteocalcin | P1NP | C-Telopeptide | TRAP-5b | Sclerostin | FGF-23 |
|---|---|---|---|---|---|---|---|---|---|---|---|---|---|---|---|
| miRNA-30b | **0.98** | **0.77** | **0.51** | 0.28 | **−0.41** | **−0.54** | −0.15 | −0.12 | −0.05 | −0.06 | 0.02 | −0.09 | 0.05 | −0.25 | −0.15 |
| p Value | **<.0001** | **<.0001** | **.01** | .2 | **.05** | **.007** | .5 | .6 | .8 | .8 | .9 | .7 | .8 | .3 | .6 |
| miRNA-30c | | **0.75** | **0.57** | 0.32 | **−0.44** | **−0.54** | −0.15 | −0.12 | −0.03 | −0.11 | −0.01 | −0.13 | 0.01 | −0.25 | −0.15 |
| p Value | | **<.0001** | **0.005** | 0.1 | **0.03** | **0.007** | 0.5 | 0.6 | 0.9 | 0.7 | 1.0 | 0.5 | 1.0 | 0.3 | 0.6 |
| miRNA-125b | | | **0.39** | 0.21 | −0.25 | **−0.49** | −0.04 | −0.08 | −0.01 | 0.11 | 0.11 | 0.04 | 0.24 | −0.32 | −0.19 |
| p Value | | | **0.066** | 0.3 | 0.3 | **0.02** | 0.8 | 0.7 | 0.9 | 0.6 | 0.6 | 0.9 | 0.3 | 0.2 | 0.5 |
| miRNA-155 | | | | 0.17 | −0.29 | −0.17 | −0.35 | −0.14 | −0.30 | −0.23 | 0.06 | −0.32 | 0.04 | 0.06 | 0.23 |
| p Value | | | | 0.4 | 0.2 | 0.4 | 0.1 | 0.5 | 0.2 | 0.3 | 0.8 | 0.1 | 0.9 | 0.8 | 0.4 |

BSAP = bone-specific alkaline phosphatase; CKD-MBD = chronic kidney disease-mineral and bone disorder; FGF-23 = fibroblast growth factor 23; miRNA = microRNA; TRAP-5b = tartrate-resistant acid phosphatase 5b. Boldface indicates significant correlations.

FIG. 47

| | BFR/BS | AjAR | MLT |
|---|---|---|---|
| Trabecular bone | | | |
| Endocortical bone | **0.85**[c] | 0.34 | **0.57**[b] |
| Cortical bone | **0.77**[c] | **0.70**[c] | 0.33 |
| miRNA-30b | 0.16 | 0.25 | −0.20 |
| miRNA-30c | 0.09 | 0.20 | −0.17 |
| miRNA-125b | 0.09 | 0.18 | −0.14 |
| miRNA-155 | −0.18 | −0.15 | 0.06 |
| Intact PTH | **0.54**[b] | 0.08 | 0.11 |
| 25(OH)D | **−0.45**[a] | −0.21 | 0.10 |
| BSAP | **0.64**[c] | 0.36 | −0.21 |
| Osteocalcin | **0.55**[b] | 0.27 | −0.11 |
| P1NP | **0.49**[a] | 0.37 | −0.32 |
| C-Telopeptide | **0.66**[c] | 0.27 | −0.13 |
| TRAP-5b | **0.44**[a] | 0.25 | −0.15 |
| Sclerostin | 0.05 | −0.22 | 0.20 |
| Fibroblast growth factor 23 | 0.01 | −0.28 | 0.34 |
| Endocortical bone | | | |
| Cortical bone | **0.74**[c] | **0.60**[b] | **0.48**[a] |
| miRNA-30b | 0.27 | **0.44**[a] | −0.23 |
| miRNA-30c | 0.15 | 0.40 | −0.22 |
| miRNA-125b | 0.12 | 0.16 | −0.10 |
| miRNA-155 | −0.02 | 0.15 | −0.05 |
| Intact PTH | 0.23 | −0.32 | 0.35 |
| 25(OH)D | −0.38 | −0.13 | 0.09 |
| BSAP | 0.34 | 0.00 | −0.07 |
| Osteocalcin | **0.47**[a] | 0.06 | −0.01 |
| P1NP | **0.49**[a] | 0.32 | −0.22 |
| C-Telopeptide | **0.44**[a] | −0.09 | 0.29 |
| TRAP-5b | 0.32 | 0.08 | 0.12 |
| Sclerostin | 0.19 | −0.07 | −0.02 |
| Fibroblast growth factor 23 | 0.06 | −0.17 | −0.08 |
| Cortical bone | | | |
| miRNA-30b | 0.35 | **0.51**[b] | −0.31 |
| miRNA-30c | 0.27 | **0.42**[a] | −0.24 |
| miRNA-125b | 0.34 | **0.52**[b] | **−0.50**[a] |
| miRNA-155 | 0.01 | 0.13 | 0.01 |
| Intact PTH | 0.20 | 0.03 | 0.03 |
| 25(OH) D | −0.22 | −0.12 | −0.03 |
| BSAP | **0.48**[a] | 0.24 | −0.30 |
| Osteocalcin | **0.49**[a] | 0.29 | −0.24 |
| P1NP | 0.43 | 0.19 | −0.13 |
| C-Telopeptide | **0.42**[a] | 0.20 | −0.04 |
| TRAP-5b | 0.43 | 0.30 | −0.15 |
| Sclerostin | −0.06 | −0.15 | 0.09 |
| Fibroblast growth factor 23 | −0.07 | −0.21 | 0.03 |

AjAR = adjusted apposition rate; BFR/BS = bone formation rate / bone surface; BSAP = bone-specific alkaline phosphatase; CKD-MBD = chronic kidney disease-mineral and bone disorder; miRNA = microRNA; MLT = mineralization lag time; TRAP-5b = tartrate-resistant acid phosphatase 5b. Boldface indicates significant correlations.

[a] $p < 0.05$.

[b] $p < 0.01$.

[c] $p < 0.001$.

FIG. 48

| Trabecular[a] | | | | |
|---|---|---|---|---|
| | AUC | 95% CI | *p* Value versus BTM panel | *p* Value versus miRNA panel |
| PTH | 0.843 | 0.666 to 1.000 | 0.7 | 0.2 |
| BSAP | 0.779 | 0.570 to 1.000 | 0.3 | 0.4 |
| CTx | 0.873 | 0.714 to 1.000 | 0.7 | 0.1 |
| miR-30b | 0.539 | 0.264 to 0.814 | 0.02 | 0.6 |
| miR-30c | 0.569 | 0.301 to 0.836 | 0.03 | 0.7 |
| miR-125b | 0.490 | 0.250 to 0.731 | 0.01 | 0.4 |
| miR-155 | 0.520 | 0.241 to 0.798 | 0.01 | 0.5 |
| BTM panel | 0.882 | 0.731 to 1.000 | — | 0.1 |
| miRNA panel | 0.673 | 0.339 to 1.000 | 0.1 | — |

| Endocortical[a] | | | | |
|---|---|---|---|---|
| | AUC | 95% CI | *p* Value versus BTM panel | *p* Value versus miRNA panel |
| PTH | 0.554 | 0.289 to 0.817 | 0.2 | 0.002 |
| BSAP | 0.553 | 0.311 to 0.797 | 0.3 | 0.0004 |
| CTx | 0.661 | 0.400 to 0.922 | 0.5 | 0.02 |
| miR-30b | 0.625 | 0.388 to 0.863 | 0.8 | 0.004 |
| miR-30c | 0.554 | 0.297 to 0.810 | 0.5 | 0.001 |
| miR-125b | 0.527 | 0.278 to 0.775 | 0.4 | 0.0003 |
| miR-155 | 0.580 | 0.295 to 0.865 | 0.6 | 0.004 |
| BTM panel | 0.670 | 0.411 to 0.928 | — | 0.03 |
| miRNA panel | 0.982 | 0.940 to 1.000 | 0.03 | — |

FIG. 49

| | Intracortical[a] | | | |
|---|---|---|---|---|
| | AUC | 95% CI | $p$ Value versus BTM panel | $p$ Value versus miRNA panel |
| PTH | 0.509 | 0.251 to 0.766 | 0.5 | 0.006 |
| BSAP | 0.589 | 0.349 to 0.830 | 0.5 | 0.02 |
| CTx | 0.576 | 0.289 to 0.863 | 0.9 | 0.04 |
| miR-30b | 0.866 | 0.709 to 1.000 | 0.1 | 0.4 |
| miR-30c | 0.813 | 0.610 to 1.000 | 0.3 | 0.2 |
| miR-125b | 0.813 | 0.635 to 0.990 | 0.2 | 0.2 |
| miR-155 | 0.723 | 0.499 to 0.948 | 0.5 | 0.06 |
| BTM panel | 0.598 | 0.359 to 0.837 | - | 0.02 |
| miRNA panel | 0.929 | 0.821 to 1.000 | 0.02 | - |

AUC = area under the curve; BSAP = bone-specific alkaline phosphatase; BTM = bone turnover marker; CKD-MBD = chronic kidney disease-mineral and bone disorder; miRNA = microRNA.

[a]Low turnover in each compartment was based on the lowest compartmental tertile of bone formation rate / bone surface.

FIG. 49 cont.

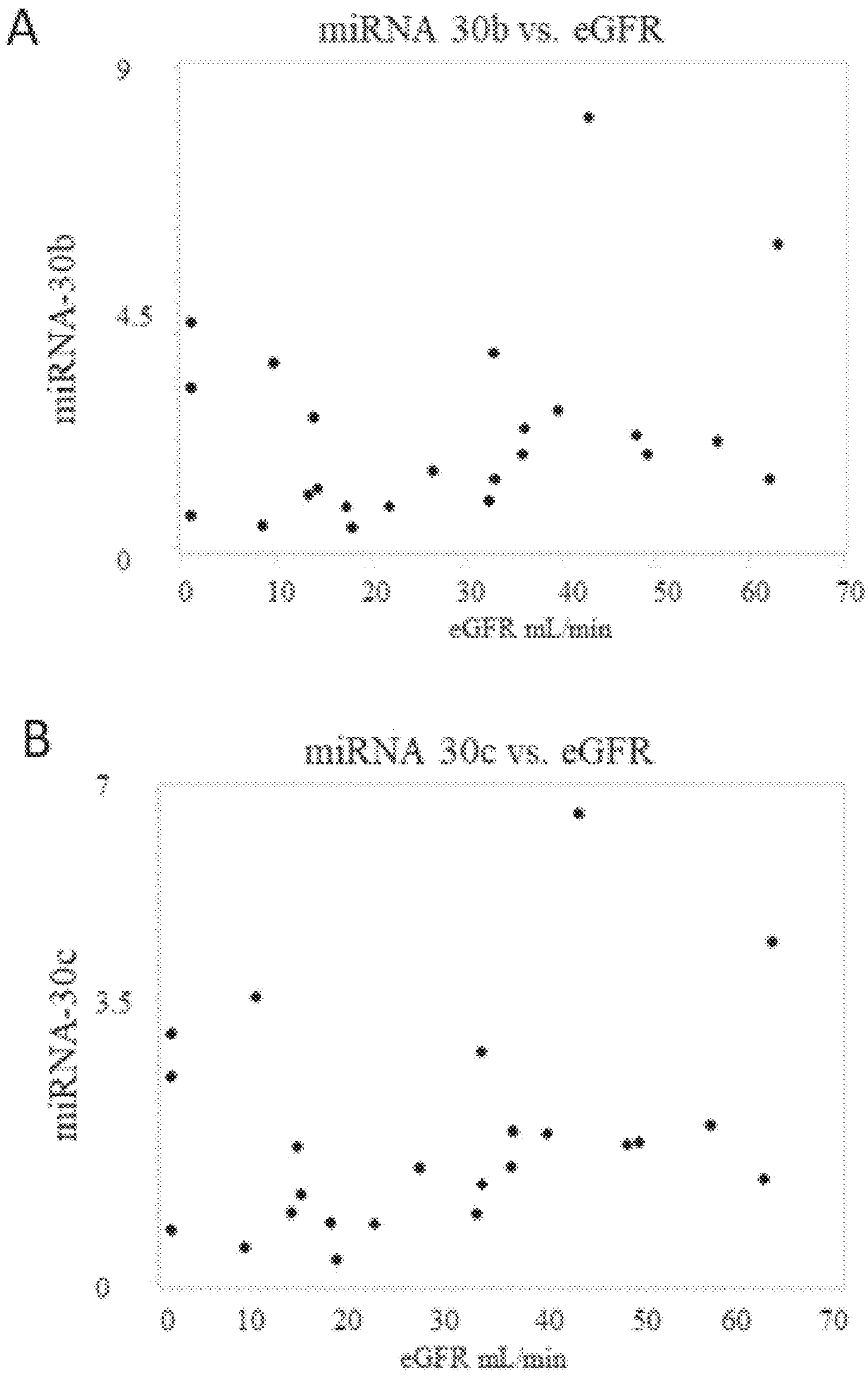
FIGS. 52A-B

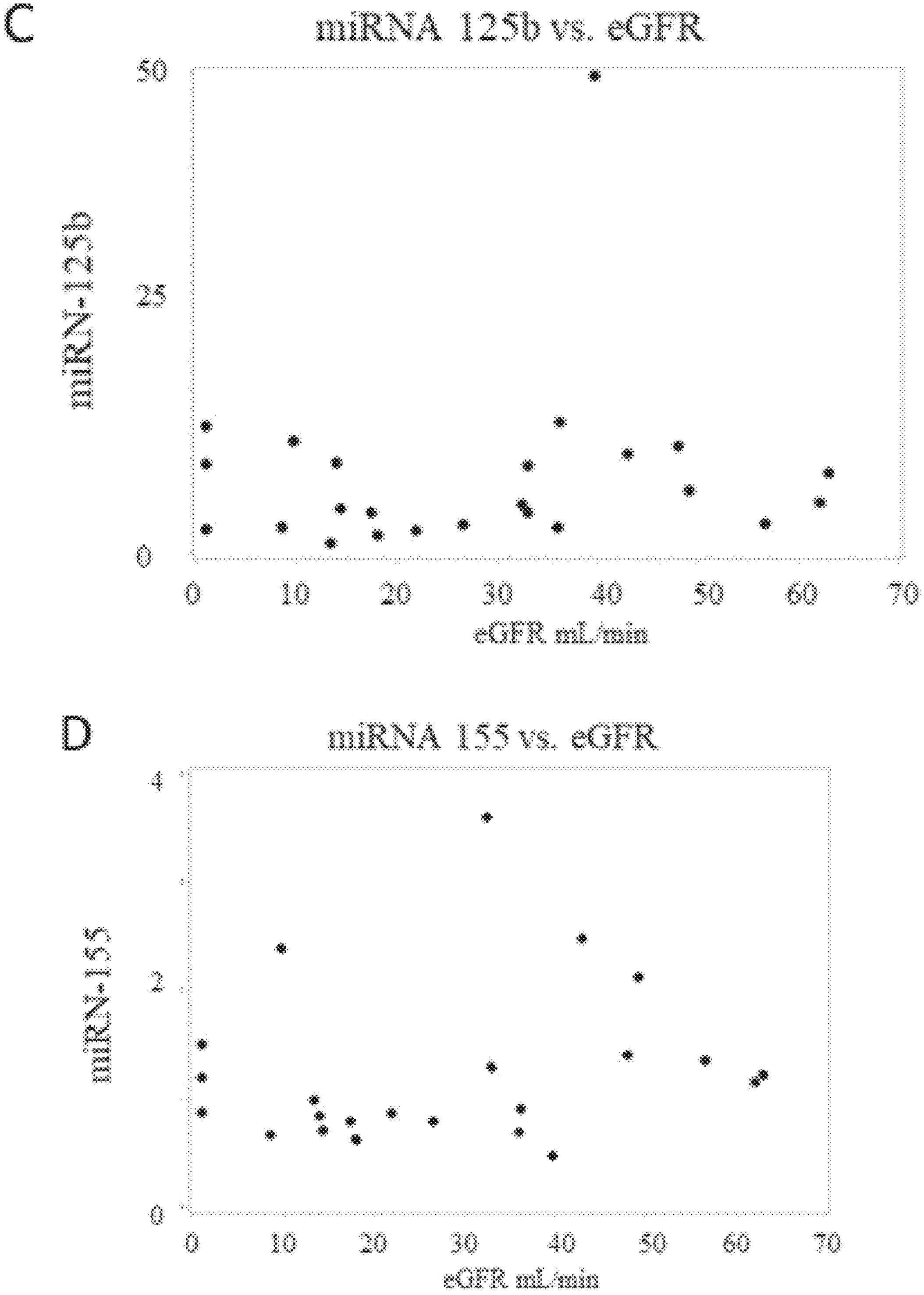
FIGS. 52C-D

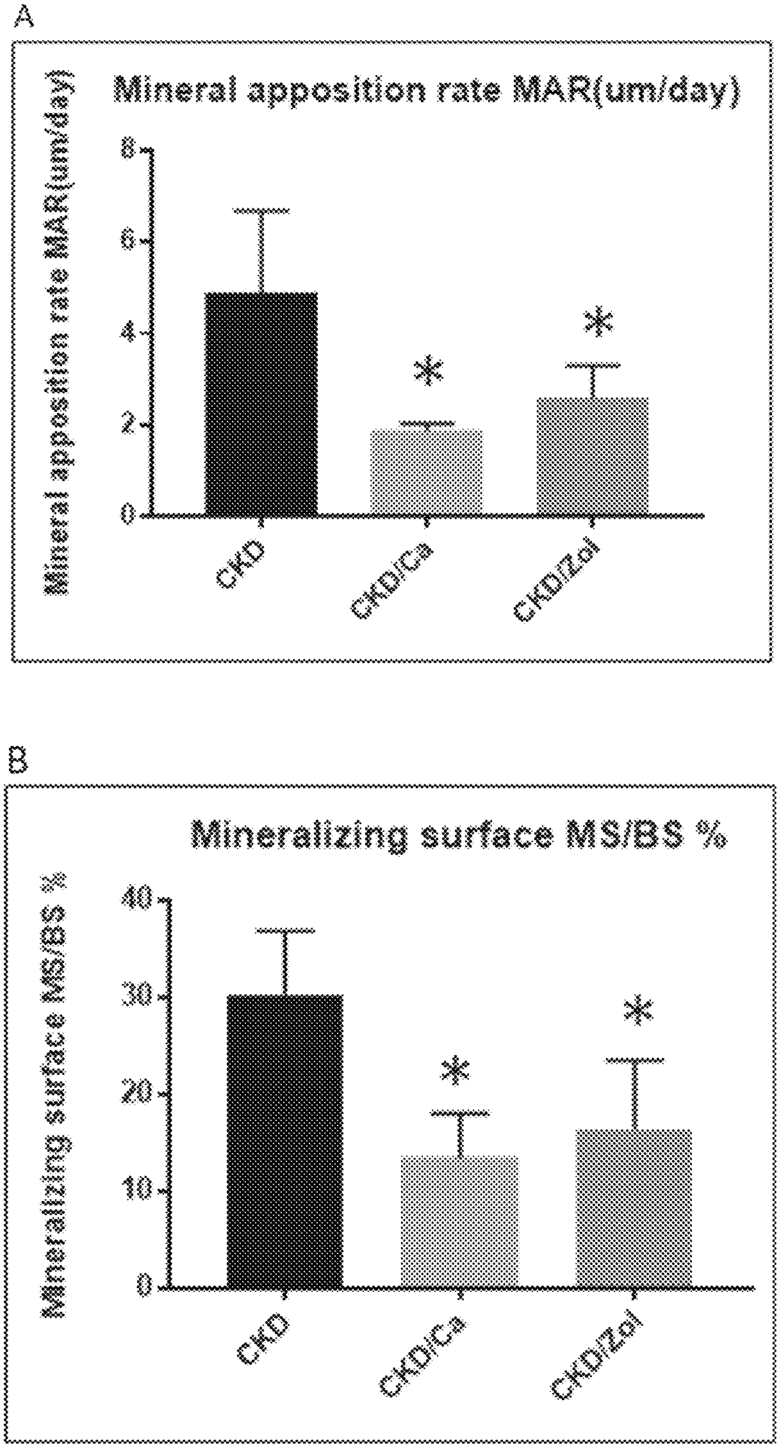
FIGS. 53A-B

BIOMARKERS OF RENAL OSTEODYSTROPHY TYPE

This application is a continuation-in-part of International Application No. PCT/US19/34073, filed on May 24, 2019, which claims the benefit of and priority under 35 U.S.C. § 119(e) to U.S. Ser. No. 62/676,547 filed May 25, 2018, and U.S. Ser. No. 62/750,670 filed Oct. 25, 2018, the contents of each of which is hereby incorporated by reference in its entirety.

This application claims the benefit of and priority All patents, patent applications and publications cited herein are hereby incorporated by reference in their entirety. The disclosures of these publications in their entireties are hereby incorporated by reference into this application.

GOVERNMENT SUPPORT

This invention was made with government support under DK080139 awarded by National Institutes of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Jul. 18, 2019, is named 0019240_01147WO1_SL.txt and is 1,297 bytes in size.

BACKGROUND OF THE INVENTION

Renal osteodystrophy is a bone metabolic disease associated with abnormal bone turnover. It affects nearly all patients with chronic kidney disease. Proper treatment of renal osteodystrophy requires an accurate estimate of bone turnover, as excess treatment of high-turnover disease can induce low bone turnover. However, current biomarkers of bone turnover do not provide estimates accurate enough for guiding treatment of renal osteodystrophy, and bone biopsies are invasive, expensive, and require up to three months for results.

SUMMARY OF THE INVENTION

In certain aspects, the invention provides a method of treating low turnover renal osteodystrophy in a subject being administered an agent that reduces bone turnover comprising: a) measuring a level of one or more miRNAs in a sample from the subject; and b) i) stopping administration of the agent that reduces bone turnover if the level of the one or more miRNAs measured in step a) is lower than a level of the one or more miRNAs measured in one or more control subjects; or ii) continuing administration of the agent that reduces bone turnover if the level of the one or more miRNAs measured in step a) is not lower than a level of the one or more miRNAs measured in the one or more control subjects.

In some embodiments, i), administration of the agent that reduces bone turnover is stopped if the level of the one or more miRNAs measured in step a) is at least about 3-fold lower than a level of the one or more miRNAs measured in the one or more control subjects; or ii), administration of the agent that reduces bone turnover is continued if the level of the one or more miRNAs measured in step a) is not at least about 3-fold lower than a level of the one or more miRNAs measured in the one or more control subjects. In some embodiments, the sample is blood. In some embodiments, the sample is serum. In some embodiments, the sample is bone. In some embodiments, the sample is bone marrow.

In some embodiments, the one or more miRNA sequences is miRNA-30b, miRNA-30c, miRNA-125b, miRNA-155, or any combination thereof.

In some embodiments, the subject has chronic kidney disease. In some embodiments, the subject has stage 3 to 5D chronic kidney disease.

In some embodiments, the level of the one or more miRNAs is the expression level of the miRNA. In some embodiments, the agent that reduces bone turnover is a vitamin D analog, calcitrol and analogs thereof, a calcimimetic, or an anti-resorptive agent selected from alendronate, risedronate, or denosumab.

In some embodiments, the method of treating low turnover renal osteodystrophy further comprises measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step a) is lower than a level of the one or more miRNAs measured in the one or more control subjects and the level of PTH is lower than about 100 pg/mL, 70 pg/mL, 50 pg/mL, 40 pg/mL, 30 pg/mL, 20 pg/mL, 10 pg/mL or 5 pg/mL and/or BSAP is lower than about 100 international units (IU)/L, 90 IU/ml, 80 IU/ml, 70 IU/ml, 60 IU/ml, 50 IU/ml, 44 IU/ml, 40 IU/ml, 30 IU/ml, or 20 IU/ml. In some embodiments, the administration of the agent that reduces bone turnover is stopped if the level of the one or more miRNAs measured in step a) is at least about 3-fold lower than a level of the one or more miRNAs measured in the one or more control subjects and the level of PTH is lower than about 100 pg/mL, 70 pg/mL, 50 pg/mL, 40 pg/mL, 30 pg/mL, 20 pg/mL, 10 pg/mL or 5 pg/mL and/or BSAP is lower than about 100 international units (IU)/L, 90 IU/ml, 80 IU/ml, 70 IU/ml, 60 IU/ml, 50 IU/ml, 44 IU/ml, 40 IU/ml, 30 IU/ml, or 20 IU/ml. In some embodiments, if the level of the one or more miRNAs measured in step a) is lower than a level of the one or more miRNAs measured in the one or more control subjects the subject is administered an anabolic agent. In some embodiments, the anabolic agent is teriparatide or abaloparatide. In some embodiments, if the level of the one or more miRNAs measured in step a) is at least about 3-fold lower than a level of the one or more miRNAs measured in the one or more control subjects the subject is administered an anabolic agent. In some embodiments, the anabolic agent is teriparatide or abaloparatide.

In some embodiments, the level of the one or more miRNA is measured by real time PCR. In some embodiments, the level of the one or more miRNA is measured periodically. In some embodiments, the measuring of the level of the one or more miRNA is periodically repeated about every 3, 4, 5, 6, 7, 8, 9, 10, 11, or 12 months.

In certain aspects, the invention provides a method of treating high turnover renal osteodystrophy in a subject being administered an agent that increases bone turnover comprising: a) measuring a level of one or more miRNAs in a sample from the subject; and b) i) stopping administration of the agent that increases bone turnover if the level of the one or more miRNAs measured in step a) is higher than a level of the one or more miRNAs measured in one or more control subjects; or ii) continuing administration of the agent that increases bone turnover if the level of the one or more miRNAs measured in step a) is not higher than a level of the one or more miRNAs measured in the one or more control subjects.

In some embodiments, i) administration of the agent that increases bone turnover is stopped if the level of the one or more miRNAs measured in step a) is at least about 3-fold higher than a level of the one or more miRNAs measured in the one or more control subjects; or ii) administration of the agent that increases bone turnover is continued if the level of the one or more miRNAs measured in step a) is not at least about 3-fold higher than a level of the one or more miRNAs measured in one or more control subjects. In some embodiments, the sample is blood. In some embodiments, the sample is serum. In some embodiments, the sample is blood plasma. In some embodiments, the sample is bone. In some embodiments, the sample is bone marrow.

In some embodiments, the one or more miRNAs is miRNA-30b, miRNA-30c, miRNA-125b, miRNA-155, or any combination thereof. In some embodiments, the subject has chronic kidney disease. In some embodiments, the subject has stage 3 to 5D chronic kidney disease.

In some embodiments, the agent that increases bone turnover is an anabolic agent. In some embodiments, the anabolic agent is teriparatide, or abaloparatide. In some embodiments, the level of the one or more miRNAs is the expression level of the miRNA. In some embodiments, the method further comprises measuring a level of parathyroid hormone (PTH), and/or bone specific alkaline phosphatase (BSAP) in a sample from the subject. In some embodiments, if the level of the one or more miRNAs measured in step a) is higher than a level of the one or more miRNAs measured in the one or more control subjects, the subject is administered an agent that reduces bone turnover. In some embodiments, the agent that reduces bone turnover is a vitamin D analog, calcitrol and analogs thereof, a calcimimetic, or an anti-resorptive agent selected from alendronate, risedronate, or denosumab. In some embodiments, if the level of the one or more miRNAs measured in step a) is at least about 3-fold higher than a level of the one or more miRNAs measured in the one or more control subjects, the subject is administered an agent that reduces bone turnover.

In some embodiments, the level of the one or more miRNA is measured by real time PCR. In some embodiments, measurement of the level of the one or more miRNAs is periodically repeated. In some embodiments, the measuring is periodically repeated about every 3, 4, 5, 6, 7, 8, 9, 10, 11, or 12 months.

In certain aspects, the invention provides a method of treating abnormal bone turnover in a subject comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a) and/or lower than a level of the one or more miRNAs measured in the one or more control subjects or ii) continuing administration of the agent that reduces bone turnover if the level of the one or more miRNAs measured in step c) is not lower than a level of the one or more miRNAs measured in step a).

In some embodiments, in i), administration of the agent that reduces bone turnover is stopped if the level of the one or more miRNAs measured in step c) is at least about 3-fold lower than the level of the one or more miRNAs measured in step a) and/or at least about 3-fold lower than a level of the one or more miRNAs measured in one or more control subjects or in ii), administration of the agent that reduces bone turnover continued if the level of the one or more miRNAs measured in step c) is not at least about 3-fold lower than a level of the one or more miRNAs measured in step a) and/or is not at least about 3-fold lower than a level of the one or more miRNAs measured in one or more control subjects.

In some embodiments, if administration of the agent that reduces bone turnover is not stopped, the measuring of step c) is periodically repeated. In some embodiment, the measuring of step c) is periodically repeated about every 3, 4, 5, 6, 7, 8, 9, 10, 11, or 12 months.

In some embodiments, the sample is blood. In some embodiments, the sample is serum.

In some embodiments, said one or more miRNA is miRNA-30b, miRNA-30c, miRNA-125b, miRNA-155, or any combination thereof. In some embodiments, the abnormal bone turnover is renal osteodystrophy, osteoporosis, or Gaucher disease. In some embodiments, the abnormal bone turnover is renal osteodystrophy.

In some embodiments, the subject has chronic kidney disease. In some embodiments, the level of the one or more miRNAs is the expression level of the miRNA. In some embodiments, the agent that reduces bone turnover is a vitamin D analog, calcitrol and analogs thereof, a calcimimetic, or an anti-resorptive agent. In some embodiments, the anti-resorptive agent is alendronate, risedronate, or denosumab.

In some embodiments, the measuring steps a) and/or c) further comprise measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step c) is lower than the level of the one or more miRNAs measured in step a) and/or lower than the level of the one or more miRNAs measured in one or more control subjects, and the level of PTH and/or BSAP measured in step c) is lower than a level of PTH and/or BSAP measured in step a) and/or lower than a level of about 100 pg/mL, 70 pg/mL, 50 pg/mL, 40 pg/mL, 30 pg/mL, 20 pg/mL, 10 pg/mL or 5 pg/mL for PTH and/or lower than a level of about 100 international units (IU)/L, 90 IU/ml, 80 IU/ml, 70 IU/ml, 60 IU/ml, 50 IU/ml, 44 IU/ml, 40 IU/ml, 30 IU/ml, or 20 IU/ml for BSAP. In some embodiments, the administration of the agent that reduces bone turnover is stopped if the level of the one or more miRNAs measured in step c) is at least about 3-fold lower than the level of the one or more miRNAs measured in step a) and/or at least 3-fold lower than the level of the one or more miRNAs measured in a control subject, and the level of PTH and/or BSAP measured in step c) is lower than a level of PTH and/or BSAP measured in step a) and/or lower than a level of about 100 pg/mL, 70 pg/mL, 50 pg/mL, 40 pg/mL, 30 pg/mL, 20 pg/mL, 10 pg/mL or 5 pg/mL for PTH and/or lower than a level of about 100 international units (IU)/L, 90 IU/ml, 80 IU/ml, 70 IU/ml, 60 IU/ml, 50 IU/ml, 44 IU/ml, 40 IU/ml, 30 IU/ml, or 20 IU/ml for BSAP.

In some embodiments, the level of the one or more miRNA is measured by real time PCR.

In certain aspects, the invention provides a method of reducing the risk of fractures in a subject in need thereof being administered an agent that reduces bone turnover comprising: a) measuring a level of one or more miRNAs in a sample from the subject; and b) i) stopping administration of the agent that reduces bone turnover if the level of the one or more miRNAs measured in step a) is lower than a level of the one or more miRNAs measured in one or more control subjects; or ii) continuing administration of the agent that reduces bone turnover if the level of the one or more miRNAs measured in step a) is not lower than a level of the one or more miRNAs measured in one or more control subjects.

In some embodiments, in i), administration of the agent that reduces bone turnover is stopped if the level of the one or more miRNAs measured in step a) is at least about 3-fold lower than a level of the one or more miRNAs measured in one or more control subjects; or in ii), administration of the agent that reduces bone turnover is continued if the level of the one or more miRNAs measured in step a) is not at least about 3-fold lower than a level of the one or more miRNAs measured in one or more control subjects.

In certain aspects, the invention provides a method of reducing the risk of fractures in a subject in need thereof comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a) and/or lower than a level of the one or more miRNAs measured in one or more control subjects or ii) continuing administration of the agent that reduces bone turnover if the level of the one or more miRNAs measured in step c) is not lower than a level of the one or more miRNAs measured in step a) and/or lower than a level of the one or more miRNAs measured in one or more control subjects.

In some embodiments, in i), administration of the agent that reduces bone turnover is stopped if the level of the one or more miRNAs measured in step c) is at least about 3-fold lower than the level of the one or more miRNAs measured in step a) and/or is at least about 3-fold lower than a level of the one or more miRNAs measured in one or more control subjects or in ii), administration of the agent that reduces bone turnover is continued if the level of the one or more miRNAs measured in step c) is not at least about 3-fold lower than a level of the one or more miRNAs measured in step a) and/or is not at least 3-fold lower than a level of the one or more miRNAs measured in one or more control subjects.

In certain aspects, the invention provides a method of quantitatively determining a level of miRNA-30b, miRNA-30c, miRNA-125b and miRNA-155, the method comprising performing teal time PCR using miRNA-30b, miRNA-30c, miRNA-125b and miRNA-155 present in or isolated from a sample as a template for amplification.

In certain aspects, the invention provides a diagnostic kit comprising reagents capable of quantifying the level of miRNA-30b, miRNA-30c, miRNA-125b and miRNA-155 in a sample from a subject.

In some embodiments, the reagents comprise at least one oligonucleotide probe capable of binding to at least a portion of miRNA-30b, miRNA-30c, miRNA-125b and miRNA-155. In some embodiments, the at least one oligonucleotide probe is selected from

```
                                    (SEQ ID NO: 1)
UGUAAACAUCCUACACUCAGCU,

                                    (SEQ ID NO: 2)
UGUAAACAUCCUACACUCUCAGC,

                                    (SEQ ID NO: 3)
UCCCUGAGACCCUAACUUGUGA, or

                                    (SEQ ID NO: 4)
UUAAUGCUAAUCGUGAUAGGGGU.
```

In some embodiments, the sample is blood. In some embodiments, the sample is serum.

In certain aspects, the invention provides a method of diagnosing bone turnover type in a subject in need thereof comprising: a) measuring a level of one or more miRNAs in a sample from the subject; and b) i) diagnosing the subject with low bone turnover if the level of the one or more miRNAs measured in step a) is lower than a level of the one or more miRNAs measured in one or more control subjects; or ii) diagnosing the subject with normal or high bone turnover if the level of the one or more miRNAs measured in step a) is not lower than a level of the one or more miRNAs measured in one or more control subjects.

In some embodiments, in i), the subject is diagnosed with low bone turnover if the level of the one or more miRNAs measured in step a) is at least about 3-fold lower than a level of the one or more miRNAs measured in one or more control subjects; or in ii), the subject is diagnosed with normal or high bone turnover if the level of the one or more miRNAs measured in step a) is not at least about 3-fold lower than a level of the one or more miRNAs measured in one or more control subjects. In some embodiments, said sample is blood. In some embodiments, said sample is serum.

In some embodiments, said one or more miRNA sequences is miRNA-30b, miRNA-30c, miRNA-125b, miRNA-155, or any combination thereof. In some embodiments, the subject has chronic kidney disease. In some embodiments, the subject has stage 3 to 5D chronic kidney disease. In some embodiments, the level of the one or more miRNAs is the expression level of the miRNA. In some embodiments, the method further comprises measuring a level of parathyroid hormone (PTH), and/or bone specific alkaline phosphatase (BSAP) is measured in a sample from the subject.

In some embodiments, the level of the one or more miRNA is measured by real time PCR.

In some embodiments, the abnormal bone turnover is in cortical bone. In some embodiments, the abnormal bone turnover is in endocortical bone. In some embodiments, the abnormal bone turnover is in intracortical bone. In some embodiments, markers of CKD-MBD and BTMs discriminate low bone turnover in trabecular bone. In some embodiments, markers of CKD-MBD and BTMs do not discriminate low bone turnover in cortical bone (e.g., endocortical bone, intracortical bone). In some embodiments, the level of one or more miRNAs discriminate low bone turnover in cortical bone (e.g. endocortical bone or intracortical bone). In some embodiments, the level of one or more miRNAs do not discriminate low bone turnover in trabecular bone (e.g. endocortical bone or intracortical bone).

BRIEF DESCRIPTION OF FIGURES

The figures presented herein are black and white representations of images originally created in color.

FIG. 1 shows cohort characteristics by tertile of bone formation rate (BFR).

FIG. 2 shows spearman correlations between miRNAs and biomarkers of CKD-MBD.

FIG. 3 shows spearman correlations between miRNAs, PTH, BSAP and dynamic measures from bone histomorphometry.

FIG. 4 shows area under the curve (AUCs): miRNAs for the diagnosis of turnover.

FIG. 5 shows area under the curve (AUCs): Parathyroid Hormone (PM), Bone Specific Alkaline Phosphatase (BSAP) and miRNAs for the diagnosis of turnover.

FIG. 7 shows area under the curve (AUCs) for PTH and BSAP for diagnosis of turnover by bone formation rate and adjusted apposition rate from bone biopsy.

FIG. 10 shows area under the curve (AUCs) for miRNAs for diagnosis of turnover by bone formation rate and adjusted apposition rate from bone biopsy.

FIG. 11 shows existing cohort characteristics by tertile of bone formation rate (BFR).

FIG. 12 shows data collection as described in Example 3.

FIGS. 16A-B show cohort characteristics and bone turnover. Cohort characteristics are described in FIG. 16A. Bone turnover is described in FIG. 16B.

FIG. 17A shows a scatter plot of Adj.A.R. and PTH. FIG. 17B shows a scatter plot of Adj.A.R. and BSAP.

FIG. 18A shows a scatter plot of Adj.A.R. and P1NP. FIG. 18B shows a scatter plot of Adj.A.R. and osteocalcin.

FIG. 19A show a scatter plot of Adj.A.R. and Serum CTX. FIG. 19B shows a scatter plot of Adj.A.R. and Trab5B.

FIG. 20A shows a scatter plot of Adj.A.R. and miR-30b. FIG. 20B shows a scatter plot of Adj.A.R. and miR-30c. FIG. 20C shows a scatter plot of Adj.A.R. and miR-125b.

FIG. 22A shows BSAP and PTH. To conform to the requirements for PCT patent applications, color lines have been marked up with arrows and labels. FIG. 22B shows different miRs. Color lines have been marked up with arrows and labels. FIG. 22C shows a miR panel including all four miRs.

FIG. 23A shows BSAP and PTH. To conform to the requirements for PCT patent applications, color lines have been marked up with arrows and labels. FIG. 23B shows different miRs. Color lines have been marked up with arrows and labels. FIG. 23C shows a miR panel including all four miRs.

FIG. 26 shows area under the curve (AUCs) for discrimination of low turnover ROD by PTH, BSAP and miRNAs (miRs). Combining the 4 miRs into a single biomarker panel had discrimination that was superior to PTH and BSAP.

FIG. 30 shows cohort characteristics of 90 CKD patients with low, normal or high turnover ROD (30/group)

FIG. 31 shows information regarding assays and precision.

FIG. 32 shows possible direction of miRNAs based on bone biopsy derived turnover.

FIG. 33 shows data collection at each study visit for the human study.

FIG. 34 shows possible direction of miRNAs in the CKD human cohorts based on bone biopsy derived turnover before and after treatment.

FIG. 35 shows bone turnover groups for the rat models of ROD.

FIG. 36 shows rat bone tissue preparation at sacrifice and analysis plans.

FIG. 37A shows mesenchymal and blood cells. FIG. 37B the remaining sample reflected bone, mostly the osteocyte fraction.

FIG. 38A shows the expression levels of 4 miRNAs in three fractions of bone from CKD rats. FIG. 38B shows the expression levels of bone markers in three fractions of bones from CKD rats.

FIG. 39 show possible direction of correlation and regression coefficients.

FIG. 40 shows cohort characteristics by adynamic bone disease status.

FIG. 41 shows spearman correlations between miRNAs and biomarkers of CKD-MBD and bone turnover.

FIG. 42 shows spearman correlations between miRNAs, PTH, BSAP and dynamic measures from bone histomorphometry.

FIG. 43 shows area under the curve (AUCs) for discrimination of low turnover ROD by PTH, BSAP and miRNAs (miRs).

FIG. 44A shows mineral apposition rate.

FIG. 44B shows mineralizing surface. FIG. 44C shows bone formation rate.

FIG. 46 shows cohort characteristics by bone turnover level status.

FIG. 47 shows spearman correlations between miRNAs and biomarkers of CKD-MBD and bone turnover.

FIG. 48 shows spearman correlations between dynamic histomorphometry, miRNAs, PTH, BSAP, and markers of bone turnover.

FIG. 49 shows discrimination of low turnover at the trabecular, endocortical, and cortical bone compartments for biomarkers of CKD-MBD, bone turnover, and miRNAs.

FIGS. 52A-D show scatter plots between miRNA-30b (FIG. 52A), 30c (FIG. 52B), 125b (FIG. 52C), and 155 (FIG. 52D) and kidney function. Patients on hemodialysis are indicated at the extreme left of the scatter plots. There was no relationships between the miRNAs and kidney function.

FIGS. 53A-C show histomorphometric analysis for mineral apposition rate (FIG. 53A), mineralizing surface (FIG. 53B) and bone formation rate (FIG. 53C) of bone from CKD rats fed a calcium deficient or calcium containing diet, and rats given zoledronic acid and a calcium deficient diet. Data are shown as mean±SD (n=8-10 rats each group). *p<0.05 CKD vs. CKD/Ca or CKD/Zol

DETAILED DESCRIPTION OF THE INVENTION

Figure 6:
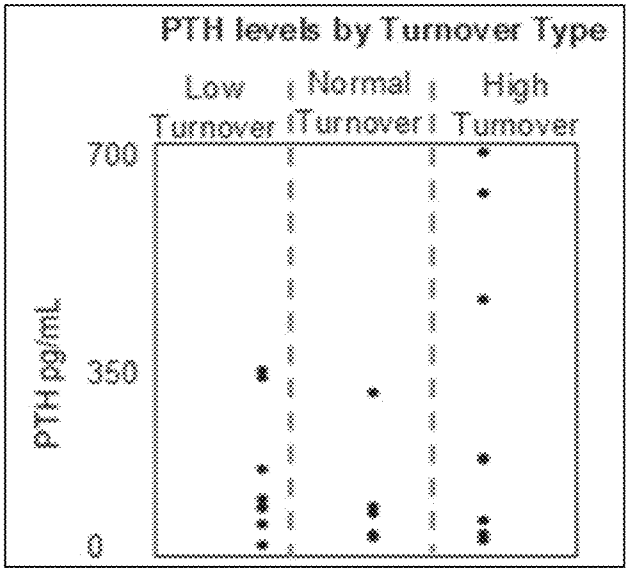
FIG. 6 shows PTN levels by turnover type.

The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference.

The singular forms “a”, “an” and “the” include plural reference unless the context clearly dictates otherwise. The use of the word “a” or “an” when used in conjunction with the term “comprising” in the claims and/or the specification may mean “one,” but it is also consistent with the meaning of “one or more,” “at least one,” and “one or more than one.”

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

The terms “animal,” “subject” and “patient” as used herein includes all members of the animal kingdom including, but not limited to, mammals, animals (e.g., cats, dogs, horses, swine, etc.) and humans.

The term “control subject” as used herein refers to one or more subjects or who is used to provide a basis for comparison. In some embodiments, the control subject is a healthy individual. In some embodiments, the control subject has chronic kidney disease without renal osteodystrophy. In some embodiments, the control subject has renal osteodystrophy and does not receive treatment for it. In some embodiments, the control subject has low turnover renal osteodystrophy and does not receive treatment for it. In some embodiments, the control subject has a bone disorder and does not receive a treatment for it. In some embodiments, the control subject has a bone disorder and receives a treatment for it, wherein the treatment is different than the treatment of the subject. In some embodiments, the control subject is age and/or sex matched to the subject.

The term “lower” as used herein refers to the statistically significant or meaningful difference between two values, wherein the lower value is less than the other value. The term “higher” as used herein refers to the statistically significant or meaningful difference between two values, wherein the higher value is more than the other value.

The serologic test described herein is a miRNA panel that provides discrimination of low turnover osteodystrophy from non-low turnover osteodystrophy. The clinical use for this biomarker panel is to guide therapeutic managements of renal osteodystrophy, for example, with vitamin D analogs, calcimimetics and anti-osteoporotic agents.

Patients suffering from chronic kidney disease (CKD) often present with mineral and bone disorders (CKD-MBD) that result in detrimental bone loss and fracture. Heterogeneity in the underlying root cause complicates effective treatment strategies, thereby creating a need for accurate diagnosis in order to instruct successful therapeutic programs. Described herein is a serologic assay that uses a miRNA panel to discriminate low turnover renal osteodystrophy from non-low turnover renal osteodystrophy. Also described herein is a serologic assay that uses a miRNA panel to discriminate high turnover renal osteodystrophy from non-high turnover renal osteodystrophy. This non-invasive approach offers superior accuracy to other serum biomarkers and minimizes the need for intrusive bone biopsies in order to guide therapy. As such, described herein is an assay that may be used as a diagnostic to inform the course of treatment in patients with CKD, and may also be used to identify responders after drug administration.

Described herein is the use of a set of circulating microRNAs (miRNAs) that are associated with the inhibition of osteoblast (miRNA-30b, 30c, and 125b) and osteoclast (miRNA-155) development and/or function. As osteoblast and osteoclast development are necessary for bone homeostasis, their inhibition is suggestive of low bone turnover. In addition to identifying these miRNAs, described herein is their incorporation into a miRNA panel that can serve as a serologic test for biomarkers of bone turnover. An accurate serologic test can help guide therapeutic treatment for renal osteodystrophy in patients with chronic kidney disease.

Chronic kidney disease affects more than 1 in 10 Americans (Coresh J, Selvin E, Stevens L A, Manzi J, Kusek J W, Eggers P, Van Lente F, Levey A S. Prevalence of chronic kidney disease in the United States. JAMA. 2007 November; 298(17): 2038-47.). Nearly all patients with advanced chronic kidney disease are affected by renal osteodystrophy, a bone metabolic disorder that causes abnormal bone turnover rates (El-Kishawi A M, El-Nahas, A M. Renal osteodystrophy: review of the disease and its treatment. Saudi J Kidney Dis Transpl. 2006 September: 17(3): 373-82.). Treatment of renal osteodystrophy depends on determining bone turnover rate, as excessive use of some therapeutic agents can induce low bone turnover (Brandenburg V M and Floege J. Adynamic bone disease—bone and beyond. NDT Plus. 2008 June: 1(3):135-147.). Current serologic tests for bone turnover rely on parathyroid hormone levels, and are not accurate enough to guide treatment (Brandenburg V M and Floege J. A dynamic bone disease—bone and beyond. NDT Plus. 2008 June: 1(3):135-147.). Bone biopsies are thus the recommended method of defining turnover and guiding treatment in international clinical practice guidelines (Kidney Disease Improving Global Outcomes; www.KDIGO.org), but are invasive, expensive, and time-consuming (Chiang C. The use of bone turnover markers in chronic kidney disease-mineral and bone disorders. Nephrology. 2017 March: 22 Suppl. 2: 11-13).

Described herein is the identification of circulating miRNA markers of osteoblast (miRNA-30b, 30c, and 125b) and osteoclast (miRNA-155) inhibition. Described herein is the application of these miRNAs into a miRNA panel that can be used as a serological test to identify low-turnover renal osteodystrophy. Described herein is a potential accurate and rapid method of diagnosing low bone turnover in renal osteodystrophy, which can help guide treatment for chronic kidney disease patients.

Abnormalities in Bone Turnover

A main obstacle to the diagnosis and management of renal osteodystrophy (ROD) is the inability to accurately identify bone turnover by non-invasive methods. The gold standard, transiliac crest bone biopsy, is impractical to obtain in most patients. Parathyroid hormone and circulating protein biomarkers of bone turnover are currently used but have insufficient sensitivity or specificity to differentiate low from high turnover, an important criterion to safely and confidently guide ROD treatment. Described herein is an approach to identify low turnover ROD through the use of microRNA analysis. In twenty-four patients with CKD Stage 3-5D, diagnostic test characteristics for discrimination of turnover-type were determined by four circulating microRNAs that regulate osteoblast and osteoclast development. These biomarkers provide superior discrimination of low turnover ROD than biomarkers in current use.

CKD mineral and bone disorder (CKD-MBD) is a common complication of kidney disease, and it affects the majority of patients with moderate to severe CKD. Recently, prospective studies have shown that measurement of bone mineral density by dual energy x-ray absorptiometry predicts incident fracture, providing nephrologists the ability to risk classify patients for skeletal fragility and targeted anti-fracture strategies for the first time. Furthermore, an expanding body of literature and anecdotal evidence suggest that pharmacologic agents used to treat osteoporosis in the general population can be safely used in patients with CKD. The effects of the Kidney Disease Improving Global Outcomes (KDIGO) clinical guideline updates in 2017 on the management of CKD-associated osteoporosis, recent investigations on the effects of antiosteoporotic agents in patients with CKD, and an overview of novel antiosteoporosis agents and the potential challenges related their use in CKD are described in Khairallah, P. and Nickolas, T L., *Management of Osteoporosis in CKD* published in the Clinical Journal of the American Society of Nephrology, Vol. 13, (2018) the entire contents of which is hereby incorporated by reference in its entirety.

Methods of Treatment

In some embodiments, the method described herein includes guiding therapy for renal osteodystrophy in subjects with chronic kidney disease. In some embodiment, the method described herein includes establishing bone turnover type in subjects with renal osteodystrophy. In some embodiment, the method described herein includes monitoring turnover rate in bone disease, including but not limited to osteoporosis, renal osteodystrophy, and other metabolic bone diseases.

The methods described herein can provide a method of treating renal osteodystrophy by resulting in less bone loss, less fractures or risk of fractures, lower vascular calcifications, less cardiovascular events, increased biomechanical bone competence, improved bone microarchitecture, improved bone quality, such as increased cortical density or decreases in cortical porosity, and improved bone collagen.

The methods described herein can also be used to examine bone turnover in interventions that result in dramatic changes in bone turnover such as parathyroidectomy and administration of anti-resorptives.

Methods of Treating Low Turnover Renal Osteodystrophy

In certain aspects, the invention provides a method of treating low turnover renal osteodystrophy in a subject being administered an agent that reduces bone turnover comprising: a) measuring a level of one or more miRNAs in a sample from the subject; and b) i) stopping administration of the agent that reduces bone turnover if the level of the one or more miRNAs measured in step a) is lower than a level of the one or more miRNAs measured in one or more control subjects; or ii) continuing administration of the agent that reduces bone turnover if the level of the one or more miRNAs measured in step a) is not lower than a level of the one or more miRNAs measured in the one or more control subjects.

In some embodiments, i) administration of the agent that reduces bone turnover is stopped if the level of the one or more miRNAs measured in step a) is at least about 3-fold lower than a level of the one or more miRNAs measured in the one or more control subjects; or ii) administration of the agent that reduces bone turnover is continued if the level of the one or more miRNAs measured in step a) is not at least about 3-fold lower than a level of the one or more miRNAs measured in one or more control subjects.

In some embodiments, the sample is blood. In some embodiments, the sample is serum. In some embodiments, the sample is blood plasma. In some embodiments, the sample is bone. In some embodiments, the sample is bone marrow.

In some embodiments, the one or more miRNAs is miRNA-30b, miRNA-30c, miRNA-125b, miRNA-155, or any combination thereof.

In some embodiments, the subject has chronic kidney disease. In some embodiments, the subject has stage 3 to 5D chronic kidney disease.

In some embodiments, the level of the one or more miRNAs is the expression level of the miRNA.

In some embodiments, the agent that reduces bone turnover is a vitamin D analog, calcitrol and analogs thereof, a calcimimetic, or an anti-resorptive agent selected from alendronate, risedronate, or denosumab.

In some embodiments, the method further comprises measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step a) is lower than a level of the one or more miRNAs measured in the one or more control subjects and the level of PTH is lower than about 100 pg/mL, 70 pg/mL, 50 pg/mL, 40 pg/mL 30 pg/mL, 20 pg/mL, 10 pg/mL, or 5 pg/mL and/or BSAP is lower than about 100 international units (IU)/L, 90 IU/L, 80 IU/L, 70 IU/L, 60 IU/L, 50 IU/L, 44 IU/L, 40 IU/L, 30 IU/L, or 20 IU/L. In some embodiments, the administration of the agent that reduces bone turnover is stopped if the level of the one or more miRNAs measured in step a) is at least about 3-fold lower than a level of the one or more miRNAs measured in the one or more control subjects and the level of PTH is lower than about 100 pg/mL, 70 pg/mL, 50 pg/mL, 40 pg/mL 30 pg/mL, 20 pg/mL, 10 pg/mL, or 5 pg/mL and/or BSAP is lower than about 100 international units (IU)/L, 90 IU/L, 80 IU/L, 70 IU/L, 60 IU/L, 50 IU/L, 44 IU/L, 40 IU/L, 30 IU/L, or 20 IU/L.

In some embodiments, if the level of the one or more miRNAs measured in step a) is lower than a level of the one or more miRNAs measured in the one or more control subjects, the subject is administered an anabolic agent. In some embodiments, the anabolic agent is teriparatide, or abaloparatide. In some embodiments, if the level of the one or more miRNAs measured in step a) is at least about 3-fold lower than a level of the one or more miRNAs measured in the one or more control subjects, the subject is administered an anabolic agent. In some embodiments, the anabolic agent is teriparatide or abaloparatide.

In some embodiments, the level of the one or more miRNA is measured by real time PCR.

In some embodiments, measurement of the level of the one or more miRNAs is periodically repeated. In some embodiments, the measuring is periodically repeated about every 3, 4, 5, 6, 7, 8, 9, 10, 11, or 12 months.

Methods of Treating High Turnover Renal Osteodystrophy

In certain aspects, the invention provides a method of treating high turnover renal osteodystrophy in a subject being administered an agent that increases bone turnover comprising: a) measuring a level of one or more miRNAs in a sample from the subject; and b) i) stopping administration of the agent that increases bone turnover if the level of the one or more miRNAs measured in step a) is higher than a level of the one or more miRNAs measured in one or more control subjects; or ii) continuing administration of the agent that increases bone turnover if the level of the one or more miRNAs measured in step a) is not higher than a level of the one or more miRNAs measured in the one or more control subjects.

In some embodiments, i) administration of the agent that increases bone turnover is stopped if the level of the one or more miRNAs measured in step a) is at least about 3-fold higher than a level of the one or more miRNAs measured in the one or more control subjects; or ii) administration of the agent that increases bone turnover is continued if the level of the one or more miRNAs measured in step a) is not at least about 3-fold higher than a level of the one or more miRNAs measured in one or more control subjects.

In some embodiments, the sample is blood. In some embodiments, the sample is serum. In some embodiments, the sample is blood plasma. In some embodiments, the sample is bone. In some embodiments, the sample is bone marrow.

In some embodiments, the one or more miRNAs is miRNA-30b, miRNA-30c, miRNA-125b, miRNA-155, or any combination thereof.

In some embodiments, the subject has chronic kidney disease. In some embodiments, the subject has stage 3 to 5D chronic kidney disease.

In some embodiments, the level of the one or more miRNAs is the expression level of the miRNA.

In some embodiments, the agent that increases bone turnover is an anabolic agent. In some embodiments, the anabolic agent is teriparatide, or abaloparatide.

In some embodiments, the method further comprises measuring a level of parathyroid hormone (PTH), and/or bone specific alkaline phosphatase (BSAP) in a sample from the subject.

In some embodiments, if the level of the one or more miRNAs measured in step a) is higher than a level of the one or more miRNAs measured in the one or more control subjects, the subject is administered an agent that reduces bone turnover. In some embodiments, the agent that reduces bone turnover is a vitamin D analog, calcitrol and analogs thereof, a calcimimetic, or an anti-resorptive agent selected from alendronate, risedronate, or denosumab. In some embodiments, if the level of the one or more miRNAs measured in step a) is at least about 3-fold higher than a level of the one or more miRNAs measured in the one or more control subjects, the subject is administered an agent that reduces bone turnover.

In some embodiments, the level of the one or more miRNA is measured by real time PCR.

In some embodiments, measurement of the level of the one or more miRNAs is periodically repeated. In some embodiments, the measuring is periodically repeated about every 3, 4, 5, 6, 7, 8, 9, 10, 11, or 12 months.

Methods of Treating Abnormal Bone Turnover

In certain aspects, the invention provides a method of treating abnormal bone turnover in a subject comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a) and/or lower than a level of the one or more miRNAs measured in one or more control subjects, or ii) continuing administration of the agent that reduces bone turnover if the level of the one or more miRNAs measured in step c) is not lower than a level of the one or more miRNAs measured in step a) and/or is not lower than a level of the one or more miRNAs measured in one or more control subjects.

In certain aspects, the invention provides a method of treating abnormal bone turnover in a subject comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a), or ii) continuing administration of the agent that reduces bone turnover if the level of the one or more miRNAs measured in step c) is not lower than a level of the one or more miRNAs measured in step a).

In certain aspects, the invention provides a method of treating abnormal bone turnover in a subject comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than a level of the one or more miRNAs measured in one or more control subjects, or ii) continuing administration of the agent that reduces bone turnover if the level of the one or more miRNAs measured in step c) is not lower than a level of the one or more miRNAs measured in one or more control subjects.

In some embodiments, in i) administration of the agent that reduces bone turnover is stopped if the level of the one or more miRNAs measured in step c) is at least about 3-fold lower than the level of the one or more miRNAs measured in step a) and/or at least about 3-folder lower than a level of the one or more miRNAs measured in one or more control subjects, or in ii) administration of the agent that reduces bone turnover continued if the level of the one or more miRNAs measured in step c) is not at least about 3-fold lower than a level of the one or more miRNAs measured in step a) and/or is not at least about 3-fold lower than a level of the one or more miRNAs measured in one or more control subjects.

In some embodiments, in i) administration of the agent that reduces bone turnover is stopped if the level of the one or more miRNAs measured in step c) is at least about 3-fold lower than the level of the one or more miRNAs measured in step a), or in ii) administration of the agent that reduces bone turnover continued if the level of the one or more miRNAs measured in step c) is not at least about 3-fold lower than a level of the one or more miRNAs measured in step a).

In some embodiments, if administration of the agent that reduces bone turnover is not stopped, the measuring of step c) is periodically repeated. In some embodiment, the measuring of step c) is periodically repeated about every 3, 4, 5, 6, 7, 8, 9, 10, 11, or 12 months.

In some embodiments, the sample is blood. In some embodiments, the sample is serum. In some embodiments, the sample is blood plasma. In some embodiments, the sample is bone. In some embodiments, the sample is bone marrow.

In some embodiments, said one or more miRNAs is miRNA-30b, miRNA-30c, miRNA-125b, miRNA-155, or any combination thereof.

In some embodiments, the abnormal bone turnover is renal osteodystrophy, osteoporosis, or Gaucher disease. In some embodiments, the abnormal bone turnover is renal osteodystrophy. In some embodiments, the subject had low bone turnover. In some embodiments, the subject has chronic kidney disease.

In some embodiments, the level of the one or more miRNAs is the expression level of the miRNA.

In some embodiments, the agent that reduces bone turnover is a vitamin D analog, calcitrol and analogs thereof, a calcimimetic, or an anti-resorptive agent. In some embodiments, the anti-resorptive agent is alendronate, risedronate, or denosumab.

In some embodiments, the measuring steps a) and c) further comprise measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step c) is lower than the level of the one or more miRNAs measured in step a) and/or the level of the one or more miRNAs measured in a control subject, and the level of PTH and/or BSAP measured in step c) is lower than a level of PTH and/or BSAP measured in step a) and/or lower than a level of about 100 pg/mL, 70 pg/mL, 50 pg/mL, 40 pg/mL 30 pg/mL, 20 pg/mL, 10 pg/mL, or 5 pg/mL for PTH and/or lower than a level of about 100 international units (IU)/L, 90 IU/L, 80 IU/L, 70 IU/L, 60 IU/L, 50 IU/L, 44 IU/L, 40 IU/L, 30 IU/L, or 20 IU/L for BSAP. In some embodiments, the administration of the agent that reduces bone turnover is stopped if the level of the one or more miRNAs measured in step c) is at least about 3-fold lower than the level of the one or more miRNAs measured in step a) and/or the level of the one or more miRNAs measured in a control subject, and the level of PTH and/or BSAP measured in step c) is lower than a level of PTH and/or BSAP measured in step a) and/or lower than a level of about 100 pg/mL, 70 pg/mL, 50 pg/mL, 40 pg/mL 30 pg/mL, 20 pg/mL, 10 pg/mL, or 5 pg/mL for PTH and/or lower than a level of about 100 international units (IU)/L, 90 IU/L, 80 IU/L, 70 IU/L, 60 IU/L, 50 IU/L, 44 IU/L, 40 IU/L, 30 IU/L, or 20 IU/L for BSAP.

In some embodiments, the measuring steps a) and c) further comprise measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step c) is lower than the level of the one or more miRNAs measured in step a), and the level of PTH and/or BSAP measured in step c) is lower than a level of PTH and/or BSAP measured in step a) and/or lower than a level of 100 pg/mL, 70 pg/mL, 50 pg/mL, 40 pg/mL 30 pg/mL, 20 pg/mL, 10 pg/mL, or 5 pg/mL for PTH and/or lower than a level of about 100 international units (IU)/L, 90 IU/L, 80 IU/L, 70 IU/L, 60 IU/L, 50 IU/L, 44 IU/L, 40 IU/L, 30 IU/L, or 20 IU/L for BSAP. In some embodiments, the administration of the agent that reduces bone turnover is stopped if the level of the one or more miRNAs measured in step c) is at least about 3-fold lower than the level of the one or more miRNAs measured in step a), and the level of PTH and/or BSAP measured in step c) is lower than a level of PTH and/or BSAP measured in step a) and/or lower than a level of about 100 pg/mL, 70 pg/mL, 50 pg/mL, 40 pg/mL 30 pg/mL, 20 pg/mL, 10 pg/mL, or 5 pg/mL for PTH and/or lower than a level of about 100 international units (IU)/L, 90 IU/L, 80 IU/L, 70 IU/L, 60 IU/L, 50 IU/L, 44 IU/L, 40 IU/L, 30 IU/L, or 20 IU/L for BSAP.

In some embodiments, the level of the one or more miRNA is measured by real time PCR.

In certain aspects, the invention provides a method of treating abnormal bone turnover in a subject comprising: a) measuring a first level of one or more miRNAs in a sample from the subject; b) administering to the subject an agent that increases bone turnover; c) measuring a second level of one or more miRNAs in a sample from the subject; and d) i) stopping administration of the agent that increases bone turnover if the level of the one or more miRNAs measured in step c) is higher than the level of the one or more miRNAs measured in step a) and/or higher than a level of the one or more miRNAs measured in one or more control subjects, or ii) continuing administration of the agent that increases bone turnover if the level of the one or more miRNAs measured in step c) is not higher than a level of the one or more miRNAs measured in step a) and/or is not higher than a level of the one or more miRNAs measured in one or more control subjects.

In certain aspects, the invention provides a method of treating abnormal bone turnover in a subject comprising: a) measuring a first level of one or more miRNAs in a sample from the subject; b) administering to the subject an agent that increases bone turnover; c) measuring a second level of one or more miRNAs in a sample from the subject; and d) i) stopping administration of the agent that increases bone turnover if the level of the one or more miRNAs measured in step c) is higher than the level of the one or more miRNAs measured in step a), or ii) continuing administration of the agent that increases bone turnover if the level of the one or more miRNAs measured in step c) is not higher than a level of the one or more miRNAs measured in step a).

In certain aspects, the invention provides a method of treating abnormal bone turnover in a subject comprising: a) measuring a first level of one or more miRNAs in a sample from the subject; b) administering to the subject an agent that increases bone turnover; c) measuring a second level of one or more miRNAs in a sample from the subject; and d) i) stopping administration of the agent that increases bone turnover if the level of the one or more miRNAs measured in step c) is higher than a level of the one or more miRNAs measured in one or more control subjects, or ii) continuing administration of the agent that increases bone turnover if the level of the one or more miRNAs measured in step c) is not higher than a level of the one or more miRNAs measured in one or more control subjects.

In some embodiments, in i) administration of the agent that increases bone turnover is stopped if the level of the one or more miRNAs measured in step c) is at least about 3-fold higher than the level of the one or more miRNAs measured in step a) and/or at least about 3-folder higher than a level of the one or more miRNAs measured in one or more control subjects, or in ii) administration of the agent that increases bone turnover continued if the level of the one or more miRNAs measured in step c) is not at least about 3-fold higher than a level of the one or more miRNAs measured in step a) and/or is not at least about 3-fold higher than a level of the one or more miRNAs measured in one or more control subjects.

In some embodiments, in i) administration of the agent that increases bone turnover is stopped if the level of the one or more miRNAs measured in step c) is at least about 3-fold higher than the level of the one or more miRNAs measured in step a), or in ii) administration of the agent that increases bone turnover continued if the level of the one or more miRNAs measured in step c) is not at least about 3-fold higher than a level of the one or more miRNAs measured in step a).

In some embodiments, if administration of the agent that increases bone turnover is not stopped, the measuring of step c) is periodically repeated. In some embodiment, the measuring of step c) is periodically repeated about every 3, 4, 5, 6, 7, 8, 9, 10, 11, or 12 months.

In some embodiments, the subject had low bone turnover. is renal osteodystrophy, osteoporosis, or Gaucher disease. In some embodiments, the abnormal bone turnover is renal osteodystrophy. In some embodiments, the subject has chronic kidney disease. In some embodiments, the subject had high bone turnover.

In some embodiments, the agent that increases bone turnover is an anabolic agent. In some embodiments, the anabolic agent is teriparatide, or abaloparatide.

In some embodiments, the measuring steps a) and c) further comprise measuring a level of parathyroid hormone (PTH), and/or bone specific alkaline phosphatase (BSAP) in a sample from the subject.

In some embodiments, the level of the one or more miRNA is measured by real time PCR.

In some embodiments, the abnormal bone turnover is in cortical bone. In some embodiments, the abnormal bone turnover is in endocortical bone. In some embodiments, the abnormal bone turnover is in intracortical bone. In some embodiments, markers of CKD-MBD and BTMs discriminate low bone turnover in trabecular bone. In some embodiments, markers of CKD-MBD and BTMs do not discriminate low bone turnover in cortical bone (e.g., endocortical bone, intracortical bone). In some embodiments, the level of one or more miRNAs discriminate low bone turnover in cortical bone (e.g. endocortical bone or intracortical bone). In some embodiments, the level of one or more miRNAs do not discriminate low bone turnover in trabecular bone (e.g. endocortical bone or intracortical bone).

Methods of Reducing the Risk of Fractures

In certain aspects, the invention provides a method of reducing the risk of fractures in a subject in need thereof being administered an agent that reduces bone turnover comprising: a) measuring a level of one or more miRNAs in a sample from the subject; and b) i) stopping administration of the agent that reduces bone turnover if the level of the one or more miRNAs measured in step a) is lower than a level of the one or more miRNAs measured in one or more control subjects; or ii) continuing administration of the agent that reduces bone turnover if the level of the one or more miRNAs measured in step a) is not lower than a level of the one or more miRNAs measured in one or more control subjects.

In some embodiments, in i), administration of the agent that reduces bone turnover is stopped if the level of the one or more miRNAs measured in step a) is at least about 3-fold lower than a level of the one or more miRNAs measured in one or more control subjects; or in ii), administration of the agent that reduces bone turnover is continued if the level of the one or more miRNAs measured in step a) is not at least about 3-fold lower than a level of the one or more miRNAs measured in one or more control subjects.

In certain aspects, the invention provides a method of reducing the risk of fractures in a subject in need thereof comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a) and/or lower than a level of the one or more miRNAs measured in one or more control subjects or ii) continuing administration of the agent that reduces bone turnover if the level of the one or more miRNAs measured in step c) is not lower than a level of the one or more miRNAs measured in step a) and/or lower than a level of the one or more miRNAs measured in one or more control subjects.

In certain aspects, the invention provides a method of reducing the risk of fractures in a subject in need thereof comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than the level of the one or more miRNAs measured in step a), or ii) continuing administration of the agent that reduces bone turnover if the level of the one or more miRNAs measured in step c) is not lower than a level of the one or more miRNAs measured in step a).

In certain aspects, the invention provides a method of reducing the risk of fractures in a subject in need thereof comprising: a) measuring a first level of one or more miRNAs in a sample from the subject; b) administering to the subject an agent that reduces bone turnover; c) measuring a second level of one or more miRNAs in a sample from the subject; and d) i) stopping administration of the agent that reduces bone turnover if the level of the one or more miRNAs measured in step c) is lower than a level of the one or more miRNAs measured in one or more control subjects or ii) continuing administration of the agent that reduces bone turnover if the level of the one or more miRNAs measured in step c) is not lower than a level of the one or more miRNAs measured in one or more control subjects.

In some embodiments, in i) administration of the agent that reduces bone turnover is stopped if the level of the one or more miRNAs measured in step c) is at least about 3-fold lower than the level of the one or more miRNAs measured in step a) and/or is at least about 3-fold lower than a level of the one or more miRNAs measured in one or more control subjects or in ii) administration of the agent that reduces bone turnover is continued if the level of the one or more miRNAs measured in step c) is not at least about 3-fold lower than a level of the one or more miRNAs measured in step a) and/or is not at least about 3-fold lower than a level of the one or more miRNAs measured in one or more control subjects.

In some embodiments, in i) administration of the agent that reduces bone turnover is stopped if the level of the one or more miRNAs measured in step c) is at least about 3-fold lower than the level of the one or more miRNAs measured in step a), or in ii) administration of the agent that reduces bone turnover is continued if the level of the one or more miRNAs measured in step c) is not at least about 3-fold lower than a level of the one or more miRNAs measured in step a).

In some embodiments, in i) administration of the agent that reduces bone turnover is stopped if the level of the one or more miRNAs measured in step c) is at least about 3-fold lower than a level of the one or more miRNAs measured in one or more control subjects, or in ii) administration of the agent that reduces bone turnover is continued if the level of the one or more miRNAs measured in step c) is not at least about 3-fold lower than a level of the one or more miRNAs measured in one or more control subjects.

In some embodiments, the sample is blood. In some embodiments, the sample is serum. In some embodiments, the sample is blood plasma. In some embodiments, the sample is bone. In some embodiments, the sample is bone marrow.

In some embodiments, the one or more miRNAs is miRNA-30b, miRNA-30c, miRNA-125b, miRNA-155, or any combination thereof.

In some embodiments, the subject has chronic kidney disease. In some embodiments, the subject has stage 3 to 5D chronic kidney disease.

In some embodiments, the level of the one or more miRNAs is the expression level of the miRNA.

In some embodiments, the agent that reduces bone turnover is a vitamin D analog, calcitrol and analogs thereof, a calcimimetic, or an anti-resorptive agent selected from alendronate, risedronate, or denosumab.

In some embodiments, the method further comprises measuring a level of parathyroid hormone (PTH), and/or bone specific alkaline phosphatase (BSAP) in a sample from the subject. In some embodiments, the administration of the agent that reduces bone turnover is stopped if the level of the one or more miRNAs measured in step a) is lower than a level of the one or more miRNAs measured in the one or more control subjects and the level of PTH is lower than about 100 pg/mL, 70 pg/mL, 50 pg/mL, 40 pg/mL 30 pg/mL, 20 pg/mL, 10 pg/mL, or 5 pg/mL and/or BSAP is lower than about 100 international units (IU)/L, 90 IU/L, 80 IU/L, 70 IU/L, 60 IU/L, 50 IU/L, 44 IU/L, 40 IU/L, 30 IU/L, or 20 IU/L. In some embodiments, the administration of the agent that reduces bone turnover is stopped if the level of the one or more miRNAs measured in step a) is at least about 3-fold lower than a level of the one or more miRNAs measured in the one or more control subjects and the level of PTH is lower than about 100 pg/mL, 70 pg/mL, 50 pg/mL, 40 pg/mL 30 pg/mL, 20 pg/mL, 10 pg/mL, or 5 pg/mL and/or BSAP is lower than about 100 international units (IU)/L, 90 IU/L, 80 IU/L, 70 IU/L, 60 IU/L, 50 IU/L, 44 IU/L, 40 IU/L, 30 IU/L, or 20 IU/L.

In some embodiments, if the level of the one or more miRNAs measured in step a) is lower than a level of the one or more miRNAs measured in the one or more control subjects, the subject is administered an anabolic agent. In some embodiments, the anabolic agent is teriparatide, or abaloparatide. In some embodiments, if the level of the one or more miRNAs measured in step a) is at least about 3-fold lower than a level of the one or more miRNAs measured in the one or more control subjects, the subject is administered an anabolic agent. In some embodiments, the anabolic agent is teriparatide or abaloparatide.

In some embodiments, the level of the one or more miRNA is measured by real time PCR.

In some embodiments, measurement of the level of the one or more miRNAs is periodically repeated. In some embodiments, the measuring is periodically repeated about every 3, 4, 5, 6, 7, 8, 9, 10, 11, or 12 months.

Methods of Diagnosis

Methods of Diagnosing Bone Turnover in Renal Osteodystrophy

In some embodiments, the method described herein includes a method of diagnosing low turnover renal osteodystrophy in a subject with chronic kidney disease. In some embodiments, the method described herein includes a method of diagnosing high turnover renal osteodystrophy in a subject with chronic kidney disease. In some embodiments, the method described herein includes a method of diagnosing a bone metabolic disorder. In some embodiments, the method described herein includes a method of diagnosing disease associated with abnormal bone turnover rate. In some embodiments, the method described herein includes a method of distinguishing between low turnover renal osteodystrophy and non-low turnover renal osteodystrophy (i.e., normal and high turnover) in a subject with chronic kidney disease. In some embodiments, the method described herein includes a method of distinguishing between high turnover renal osteodystrophy and non-high turnover renal osteodystrophy (i.e., normal and low turnover) in a subject with chronic kidney disease.

In some embodiment, the method described herein includes diagnosing disease associated with abnormalities in bone turnover, including osteoporosis, renal osteodystrophy, and abnormalities of bone due to other systemic metabolic diseases (for example Gaucher disease).

In certain aspects, the invention provides a method of diagnosing bone turnover type in a subject in need thereof comprising: a) measuring a level of one or more miRNAs in a sample from the subject; and b) i) diagnosing the subject with low bone turnover if the level of the one or more miRNAs measured in step a) is lower than a level of the one or more miRNAs measured in one or more control subjects; or ii) diagnosing the subject with normal or high bone turnover if the level of the one or more miRNAs measured in step a) is not lower than a level of the one or more miRNAs measured in one or more control subjects.

In some embodiments, in i) the subject is diagnosed with low bone turnover if the level of the one or more miRNAs measured in step a) is at least about 3-fold lower than a level of the one or more miRNAs measured in one or more control subject; or in ii) the subject is diagnosed with normal or high bone turnover if the level of the one or more miRNAs measured in step a) is not at least about 3-fold lower than a level of the one or more miRNAs measured in one or more control subjects.

In certain aspects, the invention provides a method of diagnosing bone turnover type in a subject in need thereof comprising: a) measuring a level of one or more miRNAs in a sample from the subject; and b) i) diagnosing the subject with high bone turnover if the level of the one or more miRNAs measured in step a) is higher than a level of the one or more miRNAs measured in one or more control subjects; or ii) diagnosing the subject with normal or low bone turnover if the level of the one or more miRNAs measured in step a) is not higher than a level of the one or more miRNAs measured in one or more control subjects.

In some embodiments, in i) the subject is diagnosed with high bone turnover if the level of the one or more miRNAs measured in step a) is at least about 3-fold higher than a level of the one or more miRNAs measured in one or more control subject; or in ii) the subject is diagnosed with normal or low bone turnover if the level of the one or more miRNAs measured in step a) is not at least about 3-fold higher than a level of the one or more miRNAs measured in one or more control subjects.

In some embodiments, said sample is blood. In some embodiments, said sample is serum. In some embodiments, the sample is blood plasma. In some embodiments, the sample is bone. In some embodiments, the sample is bone marrow.

In some embodiments, the one or more miRNAs is miRNA-30b, miRNA-30c, miRNA-125b, miRNA-155, or any combination thereof.

In some embodiments, the subject has chronic kidney disease. In some embodiments, the subject has stage 3 to 5D chronic kidney disease.

In some embodiments, the level of the one or more miRNAs is the expression level of the miRNA.

In some embodiments, the level of the one or more miRNA is measured by real time PCR.

microRNAs, Use as Markers, and Diagnostic Kits of the Invention

MicroRNAs (miRNAs) are a class of small, noncoding RNA molecules, approximately 18 to 28 nucleotides long. 940 members of the family have so far been identified in humans. The major role of miRNAs is in the posttranscriptional regulation of protein expression. They are involved in regulating normal as well as pathological cellular processes. Sometimes one miRNA can target multiple genes, thus regulating the expression of several proteins.

miRNAs may undergo multiple processing events to reach their functional nucleotide sequence. Most miRNAs are generated from protein-coding transcriptional units. These miRNA are called "canonical". However, some miRNAs are generated from nonprotein-coding transcriptional units. These miRNA are called "non-canonical". In both cases, the miRNAs can be located either within intronic or exonic regions. Canonical intronic miRNAs are Drosha dependent and are thus processed cotranscriptionally with protein-coding transcripts in the nucleus. The pre-miRNA then enters the miRNA pathway, whereas the rest of the transcript undergoes pre-mRNA splicing to produce mature mRNA which will then direct protein synthesis. Noncanonical intronic small RNAs can derive from small introns that resemble pre-miRNAs. These can bypass the Drosha-processing step.

miRNAs can be organized in a cluster of related miRNAs, targeting multiple mRNA transcripts within a common cellular response pathway. This thematic organization provides miRNAs clusters with the capacity to coordinate regulation of multiple steps within a single pathway. Therefore, miRNAs are capable of complex and adaptive regulatory control of entire pathways.

Putative miRNAs can be identified using bioinformatics approaches, which are then experimentally verified. A range of techniques have been developed for miRNA profiling in laboratory conditions. These include but are not limited to quantitative PCR, miRNA arrays, RNA-seq, multiplex miRNA profiling. In one embodiment, miRNA expression is determined by real-time polymerase chain reaction (PCR). A real-time PCR, also known, as quantitative PCR, monitors amplification of the target nucleotide sequence in real time and not only at the end of the amplification process. Methods for the detection of PCR products in real-time PCR include but are not limited to: non-specific fluorescent dyes that intercalate with any nucleotides and sequence-specific probes consisting of oligonucleotides that are labelled with a fluorescent reporter which permits detection only after hybridization of the probe with its complementary sequence. 5' 6-FAM (Fluorescein) is the most commonly used fluorescent dye attachment for oligonucleotides.

TaqMan PCR, which is a type of real-time PCR, utilizes a nucleic-acid probe complementary to a segment of the target nucleotide sequence. The probe is labeled with two fluorescent moieties. The emission spectrum of one overlaps the excitation spectrum of the other, resulting in "quenching" of the first fluorophore by the second. The probe is present during the PCR and if product is made, the probe is degraded via the 5'-nuclease activity of Taq polymerase that is specific for nucleotide sequences hybridized to template. The degradation of the probe allows the two fluorophores to separate, which reduces quenching and increases intensity of the emitted light.

RNA sequencing (RNA-seq) uses high-throughput, or next-generation, sequencing to detect the presence and quantity RNA in a given sample. These technologies allow for rapid DNA and RNA sequencing. For example, Illumina sequencing works by simultaneously identifying DNA bases, as each base emits a unique fluorescent signal, and adding them to a nucleic acid chain. Roche 454 sequencing is based on pyrosequencing, a technique which detects pyrophosphate release, using fluorescence, after nucleotides are incorporated by polymerase to a new strand of nucleotides. Ion Torrent sequencing measures the direct release of protons from incorporated bases.

In some embodiments, the nucleotide sequence of miRNA-30b is UGUAAACAUCCUACACUCAGCU (SEQ ID NO: 1). In some embodiments, the nucleotide sequence of miRNA-30c is UGUAAACAUCCUACACUCUCAGC (SEQ ID NO: 2). In some embodiments, the nucleotide sequence of miRNA-125b is UCCCUGAGACCCUAACUUGUGA (SEQ ID NO:3). In some embodiments, the nucleotide sequence of miRNA-155 is UUAAUGCUAAUCGUGAUAGGGGU (SEQ ID NO:4).

Samples can be collected from subjects for processing of miRNAs. In some embodiments, the sample is blood. In some embodiments, the sample is serum. In some embodiments, the sample is blood plasma. In some embodiment, the sample is bone marrow. In some embodiments, the sample is bone. In some embodiments, the samples is any biological tissues in which levels of miRNA-30b, 30c, 125b and 155 can be measured. Samples can include, for example, a bodily fluid from a subject, including, blood plasma, lymph, mucus (including snot and phlegm), saliva, serum, urine, feces, internal body fluids, including cerebrospinal fluid surrounding the brain and the spinal cord. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL.

In some embodiments, measurements of miRNAs in samples from subjects are performed periodically. In some embodiments, samples are taken periodically every 3, 4, 5, 6, 7, 8, 9, 10, 11, or 12 months and measurements of miRNAs in samples are performed. In some embodiments, samples are taken periodically for measurement of miRNA levels when deemed necessary by a medical professional.

In certain aspects, the invention provides a method of quantitatively determining a level of miRNA-30b, miRNA-30c, miRNA-125b and miRNA-155, the method comprising performing real time PCR using miRNA-30b, miRNA-30c, miRNA-125b and miRNA-155 present in or isolated from a sample as a template for amplification.

In some embodiment, the subject matter described herein also provides a kit for diagnosing low turnover renal osteodystrophy. In some embodiment, the subject matter described herein also provides a kit for diagnosing high turnover renal osteodystrophy. In some embodiment, the subject matter described herein also provides a kit for distinguishing between low turnover renal osteodystrophy and non-low turnover renal osteodystrophy (i.e., normal or high turnover renal osteodystrophy). In some embodiment, the subject matter described herein also provides a kit for distinguishing between high turnover renal osteodystrophy and non-high turnover renal osteodystrophy (i.e., normal or low turnover renal osteodystrophy).

In some embodiments, the kits of the invention comprises reagents capable of quantifying the level of miRNA-30b, miRNA-30c, miRNA-125b and miRNA-155 in a sample from a subject. In some embodiments, the reagents of a kits of the invention comprise at least one oligonucleotide probe capable of binding to at least a portion of miRNA-30b, miRNA-30c, miRNA-125b and miRNA-155. In some embodiments, a kits of the invention comprise at least one oligonucleotide probe selected from

```
                                 (SEQ ID NO: 1)
UGUAAACAUCCUACACUCAGCU,

                                 (SEQ ID NO: 2)
UGUAAACAUCCUACACUCUCAGC,

                                 (SEQ ID NO: 3)
UCCCUGAGACCCUAACUUGUGA, or

                                 (SEQ ID NO: 4)
UUAAUGCUAAUCGUGAUAGGGGU.
```

In one embodiment, the kits of the invention comprise only one oligonucleotide probe. In another embodiment, the kits of the invention comprise a plurality of nucleic acid molecules, each nucleic acid molecule encoding at least one microRNA sequence, wherein the plurality of nucleic acid molecules comprises a panel of four nucleic acid molecules encoding miRNA-30b, miRNA-30c, miRNA-125b and miRNA-155. In some embodiments the kit is used for diagnosing low turnover renal osteodystrophy. In some embodiments the kit is used for diagnosing high turnover renal osteodystrophy. In another embodiment, the kits of the invention consists of a panel of four nucleic acid molecules encoding miRNA-30b, miRNA-30c, miRNA-125b and miRNA-155. In another embodiment, the kits of the invention consists of a panel of four nucleic acid molecules wherein the four nucleic acid molecules are probes for miRNA-30b, miRNA-30c, miRNA-125b and miRNA-155.

In certain aspects, the invention provides a diagnostic kit comprising reagents capable of quantifying the level of miRNA-30b, miRNA-30c, miRNA-125b and miRNA-155 in a sample from a subject.

In some embodiments, the reagents comprise at least one oligonucleotide probe capable of binding to at least a portion of miRNA-30b, miRNA-30c, miRNA-125b and miRNA-155. In some embodiments, the at least one oligonucleotide probe is selected from

```
                                 (SEQ ID NO: 1)
UGUAAACAUCCUACACUCAGCU,

                                 (SEQ ID NO: 2)
UGUAAACAUCCUACACUCUCAGC,

                                  (SEQ ID NO: 3
UCCCUGAGACCCUAACUUGUGA,
or

                                 (SEQ ID NO: 4)
UUAAUGCUAAUCGUGAUAGGGGU.
```

In some embodiments, said one or more miRNA sequences is miRNA-30b, miRNA-30c, miRNA-125b, miRNA-155, or any combination thereof. In some embodiments, the subject has chronic kidney disease. In some embodiments, the subject has stage 3 to 5D chronic kidney disease. In some embodiments, the level of the one or more miRNAs is the expression level of the miRNA. In some embodiments, a level of parathyroid hormone (PTH), and/or bone specific alkaline phosphatase (BSAP) is measured in a sample from the subject.

In some embodiments, the level of the one or more miRNA is measured by real time PCR.

The nucleic acid moles of the invention can be any type of nucleic acid, such as DNA, including synthetic or semi-synthetic DNA, as well as any form of corresponding RNA. The nucleic acid can be a non-naturally occurring nucleic acid created artificially (such as by assembling, cutting, ligating or amplifying sequences). It can be double-stranded or single-stranded. The invention further provides for nucleic acids that are complementary to miRNA sequences miRNA-30b, miRNA-30c, miRNA-125b, and miRNA-155. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC. The invention also contemplates minor variation in nucleic acid sequences which do not affect the ability of the nucleic acid to be used in the kits of the invention to detect miRNA-30b, miRNA-30c, miRNA-125b, and miRNA-155.

Combination Methods

The methods and diagnostic kits and panels of the invention can be used in combination with other known markers of renal osteodystrophy. Non-limiting examples of biochemical assays are shown in FIG. 31. Non-limiting examples of dynamic measures from bone histomorphometry which can be used in combination with the methods and diagnostic kits and panels of the invention are shown in FIG. 42. For example, the methods of the invention can further comprise performing histomorphometry and/or measuring other bone turnover markers. Non-limiting examples of markers include PTH, BSAP, 25(OH)D, P1NP, Osteocalcin, CTX, and Trab5b.

PTH/BSAP

Parathyroid hormone (PTH) is secreted from four parathyroid glands, which are small glands in the neck, located behind the thyroid gland. Parathyroid hormone regulates calcium levels in the blood, by increasing the levels when they are too low. PTH works through its actions on the kidneys, bones and intestine. PTH stimulates the release of calcium from large calcium stores in the bones into the bloodstream. This increases bone destruction and decreases the formation of new bone.

Bone-specific alkaline phosphatase (BSAP) is an enzyme produced by activated osteoblasts that appears to have a role in calcium hydroxyapatite deposition on bone. Osteocalcin is a bone matrix protein manufactured by osteoblasts but also released from bone during bone resorption, and thus reflects both osteoblastic activation and bone resorption activity.

Intact PTH and serum BSAP can be measured by an immunoassay system. An immunoassay is a biochemical test that measures the presence and/or concentration of a macromolecule or a small molecule in a solution through the use of a specific antibody, which recognizes and binds the molecule of interest in what might be a complex mixture of molecule. In some embodiments, PTH and BSAP can be measured by an automated immunoassay system.

Agents of the Invention

In some embodiments, the invention provides for the administration or cessation or pausing of administration of various agents.

Agents that Reduce Bone Turnover

In some embodiments, an agent that reduces bone turnover is a vitamin D analog, calcitrol and analogs thereof, a calcimimetic, or an anti-resorptive agent.

In some embodiments, the agent that reduces bone turnover is a vitamin D receptor activator (VDRA). In some embodiments the agent that reduces bone turnover is calcitrol, paricalcitol, or doxercalciferol.

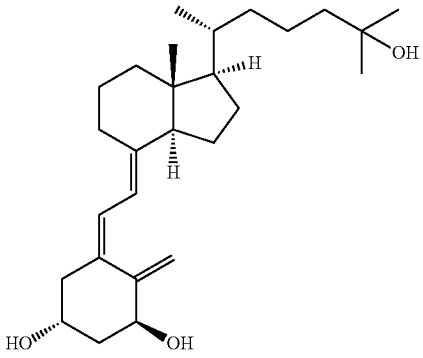

Calcitrol

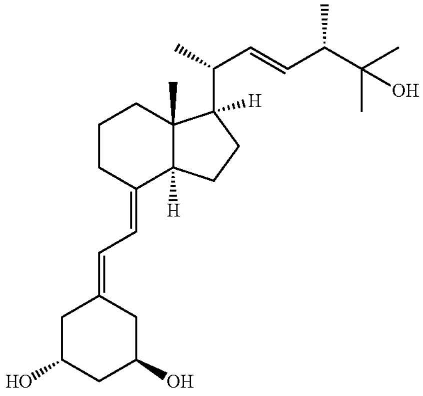

Paricalcitrol

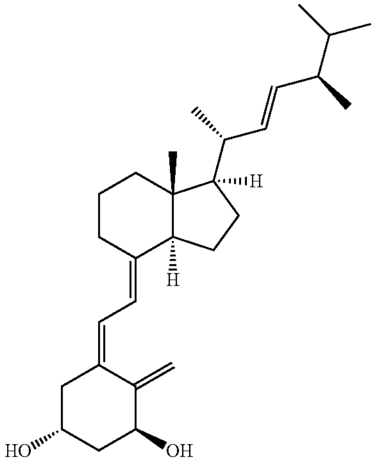

Doxercalciferol

In some embodiments, the agent that reduces bone turnover is cinacalcet or etelcalcetide.

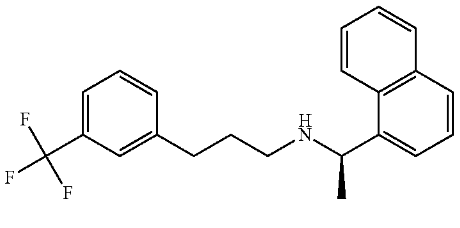

Cinacalcet

-continued

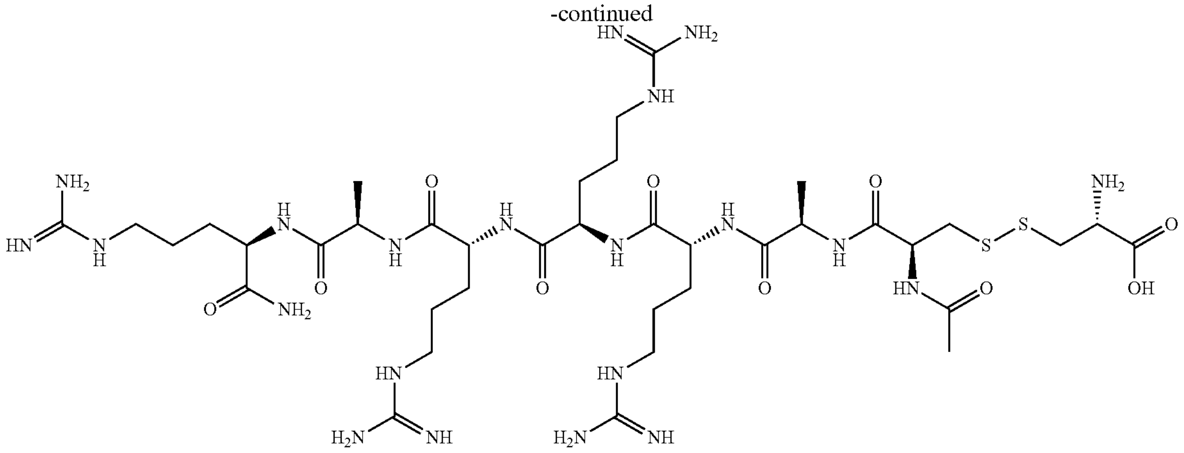

Etelcalcetide

In some embodiments, the anti-resorptive agent is alendronate. In some embodiments, the anti-resorptive agent is risedronate. In some embodiments, the anti-resorptive agent is denosumab.

In one embodiment, alendronate can be formulated as an oral tablet, wherein the table contains 5 mg, 10 mg, 35 mg, 40 mg, 70 mg of active ingredient. In one embodiment, risedronate can be formulated as an oral tablet, wherein the table contains 5 mg, 30 mg, 35 mg, or 150 mg of active ingredient. In one embodiment, denosumab is a human monoclonal anti-body, which can be formulated as a subcutaneous injection.

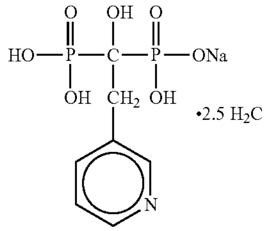

Risedronate Sodium

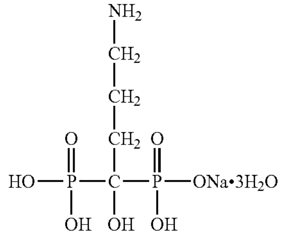

Alendronate Sodium

Anabolic Agents

In one embodiment, a subject in need thereof is administered an anabolic agent. An anabolic agent is any of a class of steroid hormones resembling testosterone. These agents stimulate the growth or manufacture of body tissues. By directly stimulating bone formation, anabolic agents reduce fracture incidence by improving other bone qualities in addition to increasing bone mass. In some embodiments, the anabolic agent is teriparatide or abaloparatide. Abaloparatide is a parathyroid hormone-related protein (PTHrP) analog drug to treat osteoporosis. In some embodiments, the recommended dose of abaloparatide is 80 mcg subcutaneous injection once a day, administered in the periumbilical area using a prefilled pen device containing 30 doses. In some embodiments, the anabolic agent is teriparatide. Teriparatide is a recombinant protein form of parathyroid hormone consisting of the first (N-terminus) 34 amino acids, which is the bioactive portion of the hormone. Teriparatide can increase bone mineral density and bone turnover, improve bone microarchitecture, and change bone size. Furthermore, teriparatide can reduce the incidence of vertebral and non-vertebral fractures. In one embodiment, teriparatide is administered by injection once a day in the thigh or abdomen.

Administration

Administration of an agent can occur once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12, 13, 14, 15, 16, 17, 18, 19, or 20 years, or a combination thereof. Furthermore, an agent can be co-administrated with another therapeutic.

Some aspects of the subject matter disclosed herein involve administering an effective amount of a pharmaceutical composition also referred to as agent to a subject to achieve a specific outcome.

For use in therapy, an effective amount of the agent or compound can be administered to a subject by any mode allowing the compound to be taken up by the appropriate target cells. "Administering" the pharmaceutical composition of the subject matter described herein can be accomplished by any means known to the skilled artisan. Specific routes of administration include, but are not limited to, oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example the pharmaceutical compositions according to the subject matter disclosed herein can be administered by intravenous, intramuscular, or other parenteral means. They can also be administered by intranasal application, inhalation, topically, orally, or as implants; even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops, or preparations with protracted release of active compounds in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, See Langer R (1990) Science 249:1527-33, which is incorporated herein by reference in its entirety.

The pharmaceutical compositions disclosed herein can be prepared and administered in dose units. Liquid dose units are vials or ampoules for injection or other parenteral administration. Solid dose units are tablets, capsules, powders, and suppositories. For treatment of a patient, different doses may be necessary depending on activity of the compound, manner of administration, purpose of the administration (i.e., prophylactic or therapeutic), nature and severity of the disorder, age and body weight of the patient. The administration of a given dose can be carried out both by single administration in the form of an individual dose unit or else several smaller dose units. Repeated and multiple administration of doses at specific intervals of days, weeks, or months apart are also contemplated by the subject matter described herein.

The pharmaceutical compositions described herein can be administered per se (neat) or in the form of a pharmaceutically-acceptable salt. When used in medicine the salts should be pharmaceutically acceptable, but non-pharmaceutically-acceptable salts can conveniently be used to prepare pharmaceutically-acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose, any bland fixed mineral or non-mineral oil may be employed including synthetic mono or diglycerides. In addition, fatty acids such as oleic acid find use in the preparation of injectables. Carrier formulations suitable for subcutaneous, intramuscular, intraperitoneal, intravenous, etc. administrations can be found in Remington's Pharmaceutical Sciences, Mack Publishing Company, Easton, PA.

The compounds useful in the subject matter disclosed herein can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of the subject matter described herein, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time release, delayed release, or sustained-release delivery systems. Such systems can avoid repeated administrations of the compounds, increasing convenience to the subject and the physician. Many types of release delivery systems are available and known to those of ordinary skill in the art. They include polymer base systems such as poly(lactide glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non polymer systems that are: lipids including sterols such as cholesterol, cholesterol esters and fatty acids, or neutral fats such as mono di and tri glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the subject matter described herein is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump based hardware delivery systems can be used, some of which are adapted for implantation.

The formulations, both for human medical use and veterinary use, of compounds according to the subject matter described herein typically include such compounds in association with a pharmaceutically acceptable carrier.

As used herein, the phrase "pharmaceutically-acceptable carrier" includes but is not limited to a pharmaceutically-acceptable material, composition or vehicle, such as a liquid or solid filler, diluent, excipient, solvent, or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as butylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present subject matter, and with each other, in a manner such that there is no interaction which would substantially impair the desired pharmaceutical efficiency.

The carrier should be "acceptable" in the sense of being compatible with compounds of the subject matter described herein and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the subject matter disclosed herein and/or known in the art) also can be incorporated into the compositions. The formulations can conveniently be presented in dosage unit form and can be prepared by any of the methods well known in the art of pharmacy. In general, some formulations are prepared by bringing the compound into association with a liquid carrier or a finely divided solid carrier or both, and then, if necessary, shaping the product into the desired formulation. A pharmaceutical composition of the subject matter disclosed herein should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral administration can be prepared by any of the methods well known in the pharmaceutical art, described, for example, in Remington's Pharmaceutical Sciences, 18th ed. (Mack Publishing Company, 1990). Formulations of the subject matter described herein suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste, or a topical composition comprising, e.g., a cream or gel. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Oral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the subject matter disclosed herein are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Topical compositions can be formulated as creams, ointments, jellies, solutions or suspensions, etc.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—A microRNA Approach to Diagnosing Renal Osteodystrophy

A main obstacle to diagnosis and management of renal osteodystrophy (ROD) is the identification of underlying bone turnover-type (low, normal or high). Four microRNAs (miRNAs) that regulate osteoblast (miRNA-30b, 30c, 125b) and osteoclast development (miRNA-155) can provide superior discrimination of low turnover from normal or high turnover than biomarkers in current clinical use.

In twenty-four patients with CKD Stages 3-5D, tetracycline double-labeled transiliac crest bone biopsy were obtained and levels of the current standard of care monitoring tests parathyroid hormone (PTH), bone specific alkaline phosphatase (BSAP) and circulating levels of miRNA-30b, 30c, 125b and 155 were measured. Spearman correlations assessed relationships between miRNAs and dynamic parameters of histomorphometry and PTH and BSAP. Diagnostic test characteristics for discriminating low or high turnover were determined by receiver operator curve analysis; areas under curve (AUC) were compared by $\chi^2$-test. miRNAs moderately correlated with bone formation rate/bone surface and adjusted apposition rate at the endo- and intra-cortical envelops (p 0.43-0.51; p<0.05). Discrimination of low vs. non-low turnover was 0.875, 0.825, 0.800 and 0.767 for miRNA-30b, 30c, 125b and 155 respectively, and 0.479 and 0.781 for PTH and BSAP respectively. For all four miRNAs combined, the AUC was 0.983, which was superior to that of BSAP alone (p<0.05). These data suggest that circulating miRNAs provide accurate non-invasive identification of bone turnover. Additional miRNA biomarkers of turnover can be discovered and validated and their impact on clinical decision making and outcomes can be determined.

INTRODUCTION

Renal osteodystrophy (ROD) is a complex disorder of bone metabolism that affects nearly all patients with CKD[1-5]. ROD results in bone loss[6] and fractures[7-12] and has been linked to increased risk of vascular calcification, cardiovascular (CV) events[13-17] and increased healthcare costs[18]. For CKD patients, compared to the general population, fractures and CV risk are more than 17-[7, 11, 19] and 1.4-fold[20] greater respectively, mortality rates after fracture and CV events are more than 3-[18] and 10-fold greater[20], respectively, and in 2010 healthcare associated costs after fracture exceeded $600 million[18].

ROD is defined by the Kidney Disease Improving Global Outcomes (KDIGO) classification of bone Turnover, Mineralization and Volume (TMV)[21]. ROD TMV class can change over time or the initial bone abnormality can worsen as kidney function declines. The primary goal of ROD treatment is reducing high bone turnover with calcitriol and its analogues and/or calcimimetics, at the same time as avoiding the development of low turnover through excessive use of these same agents or phosphate binders. In addition, emerging data and clinical experience suggest that ROD with bone loss or fractures may be safely managed with treatments that are used for osteoporosis (anti-resorptives for high turnover ROD; anabolics for low turnover ROD)[22-32], as long as low turnover ROD can be identified. The primary concern in identifying and preventing the development of low turnover ROD is that it has been associated with risk of fractures[33] and vascular calcification that may increase CV risk[14, 34, 35]. Guidelines and clinical experience recommend that diagnosis of turnover should be obtained prior to starting ROD treatment, and turnover should be monitored during the course of therapy because turnover may change, thus requiring treatment adjustments. Tetracycline double-labeled transiliac crest bone biopsy with histomorphometry is the gold standard method to define turnover; however, its widespread use in the clinic for either diagnosis or treatment monitoring is impractical. Therefore, the KDIGO best evidence guidelines recommend that clinical use (i.e., starting/stopping) of these agents is guided by the biomarkers parathyroid hormone (PTH) and bone specific alkaline phosphatase (BSAP)[36]. However, bone biopsy studies in CKD patients demonstrated that PTH and BSAP are poor guides for ROD treatment[37]. Thus, there is an unmet clinical need to identify non-invasive biomarkers with better diagnostic accuracy than PTH and BSAP for the identification of turnover to guide ROD treatment decisions and for use in clinical trials.

MicroRNAs (miRNA) are small noncoding sequences of ~22 nucleotides that bind to the 3'-untranslated regions of mRNAs to silence gene expression by inhibiting translation or promoting degradation of target mRNAs. miRNA expression during osteoblast and osteoclast development has been studied[38-40], bone cell phenotypic effects of miRNA substitutions and knockdowns have been described[41, 42] the impact of hormones and RANK[43] on miRNA expression signatures and relationships between miRNAs and histomorphometry in osteoporosis[44] have been reported, and dysregulation in levels of circulating miRNA expression has been noted in patients with osteoporosis[45-47] and fractures[48, 49]. In CKD patients, levels of miRNAs and PTH have been correlated[50] and in cell culture inorganic phosphate was shown to modulate osteoclastogenesis by miRNA-233[51]. miRNAs have not been tested as biomarkers of turnover in CKD. Circulating miRNAs reported in previous investigations to regulate osteoblast (miRNA-30b, 30c, 125b) and osteoclast (miRNA-155) development could be associated with low turnover[39, 52, 53].

Methods

Cohort

The study design has been previously described[6, 54, 55]. In brief, twenty-four patients with CKD stages 3-5D were recruited from the general nephrology clinics. Estimated glomerular filtration rate (eGFR) was determined by the Modification of Diet in Renal Disease (MDRD) short formula for CKD patients not on dialysis[56]. Patients were excluded if they had a history of malignancy, bilateral lower extremity amputations, non-ambulatory, institutionalized, or used bisphosphonates, Teriparatide, gonadal steroids, aromatase inhibitors or anticonvulsants that induce cytochrome-P450. All CKD etiologies were eligible.

Laboratory Measurements and microRNA Isolation and Analysis

Blood was obtained morning and fasting. Routine laboratories were measured by Quest diagnostics. PTH and BSAP were measured in a specialized research laboratory. Intact PTH and serum BSAP were measured by Roche Elecsys 2010 analyzer (Roche Diagnostics, Indianapolis, IN). Intra- and inter-assay precisions are 1.0% and 4.4% and 6.0% and 8.0% for intact PTH and BSAP respectively. Total RNA were isolated from plasma and miRNA expression determined by real time PCR using TaqMan miRNA assay (Applied Biosystem, Foster City, CA) normalized by spiking with *C. elegans* miRNA-39[57].

Transiliac Bone Biopsy and Histomorphometry

After double-labeling with tetracycline in a 3:12:3-day sequence, transiliac bone biopsy was performed using a 7.5 mm Bordier-type trephine. Specimens were fixed and dehydrated in ethanol and were embedded in polymethylmethacrylate. Histomorphometry was performed with a morphometric program (OsteoMeasure, Version 4.000, OsteoMetrics, Inc., Atlanta, GA, USA). All variables were expressed and calculated according to the recommendations of the American Society for Bone and Mineral Research[58]. Classification of ROD was assessed by interpreting of histology and histomorphometry indexes according to the TMV (turnover, mineralization, volume) system[59]. Low, normal and high turnover were defined as the lowest, middle and highest tertile of the bone formation rate/bone surface (BFR/BS) and the adjusted apposition rate (AjAR).

Statistical Methods

Statistical analyses were conducted using SAS (version 9.4, SAS Institute, Cary, NC). Continuous data were evaluated for normality before statistical testing and log-transformed when appropriate. Group differences were determined by t-test for unequal variances or ANOVA. Relationships between miRNAs, PTH and BSAP and histomorphometry were determined by Spearman correlation. Standard receiver operator characteristic (ROC) curve analysis was performed to determine the ability of miRNAs to discriminate low and high turnover.

Results

Cohort characteristics, stratified by turnover-type, are presented in FIG. 1. Bone turnover groups did not differ by demographics, kidney function or comorbid status. Levels of BSAP were lower in subjects with low or normal versus high turnover, circulating miRNA-30b, 30c and 155 were lower in subjects with low versus normal turnover and miRNA-30b were lower in subjects with low versus high turnover. In correlation analyses between miRNAs and markers of CKD-MBD: (1) miRNA-30b, 30c and 125b were directly and strongly related to each other and were positively and moderately related to miRNA-155; (2) miRNA-30b, 30c and 125b were indirectly related to phosphorus levels and miRNA-30b and 30c were indirectly related to calcium; and (3) none of the miRNAs were related to PTH or BSAP (FIG. 2). In correlation analyses between miRNAs, PTH and BSAP and histomorphometry: (1) miRNA-30b and 30c were directly related to BFR/BS and AjAR at the cortical and endocortical envelops and inversely related to mineralization lag time at the endocortical envelope, and (2) PTH and BSAP were related to dynamic parameters at all three bone envelopes (FIG. 3). In discrimination analyses, BSAP and all miRNAs moderately discriminated low turnover and BSAP highly discriminated high turnover. A panel of all four miRNAs had highest discrimination for low turnover (AUC 0.983; 95% CI 0.944-1.000), which was significantly greater than that for BSAP alone ($p<0.05$, respectively) (FIG. 4).

DISCUSSION

These novel data suggest that miRNAs provide accurate non-invasive diagnosis of low turnover type. The goal of the subject matter disclosed herein was to test whether a priori defined miRNAs that regulate osteoblast and osteoclast development are associated with low bone turnover. Circulating miR-30b, 30c, 125b, 155 and BSAP were found to have similar diagnostic accuracy for low turnover, PTH did not discriminate turnover type, and a panel of all four miRNAs had significantly better diagnostic accuracy for low turnover than BSAP alone. Furthermore, all miRNAs discriminated low turnover ROD with greater diagnostic accuracy than that reported for PTH and BSAP in the largest ROD biomarker studies to date (0.701 and 0.757, respectively)[4, 37].

Two large bone biopsy studies characterized contemporary trends in ROD and diagnostic accuracy of PTH and BSAP for turnover-type[4, 37]. In 630 dialysis patients, Malluche et al.[4] reported that low turnover ROD was prevalent in the majority of patients (58%). Levels of PTH were lower in patients with low compared to high turnover ROD and total alkaline phosphatase did not differ between turnover-types. A second study of 492 patients was led by a KDIGO consortium and assessed the diagnostic accuracy of PTH and BSAP for turnover-type[37]. Similar to Malluche et al.[4] the prevalence of low turnover ROD predominated (59%). PTH and BSAP insufficiently identified low or high turnover to guide confidently ROD treatment: for PTH and BSAP the AUC for discriminating low vs. non-low turnover was 0.701 and 0.757 respectively and for discriminating high vs. non-high turnover ROD was 0.724 and 0.711 respectively. Combining PTH with BSAP did not improve accuracy for identifying either low or high turnover ROD.

The data disclosed herein are the first to use state-of-the art personalized medicine approaches to identify novel non-invasive biomarkers of ROD turnover-type. The lack of correlation between miRNAs and PTH, despite their excellent discrimination of bone turnover, may reflect their relationships to cellular processes occurring at the bone-tissue level. In contrast, levels of calciotropic hormones, such as PTH, are regulated by phosphorus and calcium rather than bone cellular activity. Furthermore, the finding that a panel of miRNAs more accurately discriminated a disease than a single miRNA is consistent with data in hepatocellular cancer[60]. Studies with large cohorts of patients can confirm the data disclosed herein, with bone-tissue level confirmation of miRNA expression patterns, and with studies demonstrating that the miRNA profile changes in response to bone-tissue level changes in turnover. Finally, miRNA biomarkers with high diagnostic accuracy for high turnover can be identified.

In conclusion, four circulating miRNA biomarkers of low bone turnover were identified. Diagnostic test characteristics of the four circulating miRNA biomarkers can be validated, other miRNA biomarkers of low and high turnover can be identified, and it can be demonstrated that the four circulating miRNA biomarkers inform clinical management and improve clinical outcomes in CKD.

REFERENCES FOR EXAMPLE 1

1. Spasovski, G B, Bervoets, A R, Behets, G J, Ivanovski, N, Sikole, A, Dams, G, Couttenye, M M, De Broe, M E, D'Haese, P C: Spectrum of renal bone disease in end-stage renal failure patients not yet on dialysis. *Nephrol Dial Transplant,* 18: 1159-1166, 2003.
2. Hamdy, N A, Kanis, J A, Beneton, M N, Brown, C B, Juttmann, J R, Jordans, J G, Josse, S, Meyrier, A, Lins, R L, Fairey, I T: Effect of alfacalcidol on natural course of renal bone disease in mild to moderate renal failure. *BMJ,* 310: 358-363, 1995.
3. Coen, G, Mazzaferro, S, Bonucci, E, Taggi, F, Ballanti, P, Bianchi, A R, Donato, G, Massimetti, C, Smacchi, A, Cinotti, G A: Bone GLA protein in predialysis chronic renal failure. Effects of 1,25(OH)2D3 administration in a long-term follow-up. *Kidney Int,* 28: 783-790, 1985.
4. Malluche, H H, Mawad, H W, Monier-Faugere, M C: Renal osteodystrophy in the first decade of the new millennium: analysis of 630 bone biopsies in black and white patients. *J Bone Miner Res,* 26: 1368-1376, 2011.
5. Behets, G J, Spasovski, G, Sterling, L R, Goodman, W G, Spiegel, D M, De Broe, M E, D'Haese, P C: Bone histomorphometry before and after long-term treatment with cinacalcet in dialysis patients with secondary hyperparathyroidism. *Kidney Int,* 87: 846-856, 2015.
6. Nickolas, T L, Stein, E M, Dworakowski, E, Nishiyama, K K, Komandah-Kosseh, M, Zhang, C A, McMahon, D J, Liu, X S, Boutroy, S, Cremers, S, Shane, E: Rapid cortical bone loss in patients with chronic kidney disease. *J Bone Miner Res,* 28: 1811-1820, 2013.
7. Nickolas, T L, McMahon, D J, Shane, E: Relationship between Moderate to Severe Kidney Disease and Hip Fracture in the United States. *J Am Soc Nephrol,* 17: 3223-3232, 2006.
8. Fried, L F, Biggs, M L, Shlipak, M G, Seliger, S, Kestenbaum, B, Stehman-Breen, C, Sarnak, M, Siscovick, D, Harris, T, Cauley, J, Newman, A B, Robbins, J: Association of kidney function with incident hip fracture in older adults. *J Am Soc Nephrol,* 18: 282-286, 2007.
9. Ball, A M, Gillen, D L, Sherrard, D, Weiss, N S, Emerson, S S, Seliger, S L, Kestenbaum, B R, Stehman-Breen, C: Risk of Hip Fracture Among Dialysis and Renal Transplant Recipients. *JAMA: The Journal of the American Medical Association,* 288: 3014-3018, 2002.
10. Dooley, A C, Weiss, N S, Kestenbaum, B: Increased risk of hip fracture among men with CKD. *Am J Kidney Dis,* 51: 38-44, 2008.
11. Naylor, K L, McArthur, E, Leslie, W D, Fraser, L A, Jamal, S A, Cadarette, S M, Pouget, J G, Lok, C E, Hodsman, A B, Adachi, J D, Garg, A X: The three-year incidence of fracture in chronic kidney disease. *Kidney Int,* 2014.
12. Isakova, T, Craven, T E, Scialla, J J, Nickolas, T L, Schnall, A, Barzilay, J, Schwartz, A V, Action to Control Cardiovascular Risk in Diabetes, T: Change in estimated glomerular filtration rate and fracture risk in the Action to Control Cardiovascular Risk in Diabetes Trial. *Bone,* 78: 23-27, 2015.
13. Toussaint, N D, Lau, K K, Strauss, B J, Polkinghorne, K R, Kerr, P G: Associations between vascular calcification, arterial stiffness and bone mineral density in chronic kidney disease. *Nephrol Dial Transplant,* 23: 586-593, 2008.
14. London, G M, Marty, C, Marchais, S J, Guerin, A P, Metivier, F, de Vernejoul, M C: Arterial calcifications and bone histomorphometry in end-stage renal disease. *J Am Soc Nephrol,* 15: 1943-1951, 2004.
15. London, G M, Marchais, S J, Guerin, A P, Boutouyrie, P, Metivier, F, de Vernejoul, M C: Association of bone activity, calcium load, aortic stiffness, and calcifications in ESRD. *J Am Soc Nephrol,* 19: 1827-1835, 2008.
16. Adragao, T, Herberth, J, Monier-Faugere, M C, Branscum, A J, Ferreira, A, Frazao, J M, Dias Curto, J, Malluche, H H: Low bone volume—a risk factor for coronary calcifications in hemodialysis patients. *Clin J Am Soc Nephrol,* 4: 450-455, 2009.
17. Kurz, P, Monier-Faugere, M C, Bognar, B, Werner, E, Roth, P, Vlachojannis, J, Malluche, H H: Evidence for abnormal calcium homeostasis in patients with adynamic bone disease. *Kidney Int,* 46: 855-861, 1994.
18. Kim, S M, Long, J, Montez-Rath, M, Leonard, M, Chertow, G M: Hip Fracture in Patients with Non-Dialysis-Requiring Chronic Kidney Disease. *J Bone Miner Res,* 2016.
19. Alem, A M, Sherrard, D J, Gillen, D L, Weiss, N S, Beresford, S A, Heckbert, S R, Wong, C, Stehman-Breen, C: Increased risk of hip fracture among patients with end-stage renal disease. *Kidney Int,* 58: 396-399, 2000.
20. Go, A S, Chertow, G M, Fan, D, McCulloch, C E, Hsu, C Y: Chronic kidney disease and the risks of death, cardiovascular events, and hospitalization. *N Engl J Med,* 351: 1296-1305, 2004.
21. Moe, S, Drueke, T, Cunningham, J, Goodman, W, Martin, K, Olgaard, K, Ott, S, Sprague, S, Lameire, N, Eknoyan, G, Kidney Disease: Improving Global, O: Definition, evaluation, and classification of renal osteodystrophy: a position statement from Kidney Disease: Improving Global Outcomes (KDIGO). *Kidney Int,* 69: 1945-1953, 2006.
22. Jamal, S A, Ljunggren, O, Stehman-Breen, C, Cummings, S R, McClung, M R, Goemaere, S, Ebeling, P R, Franek, E, Yang, Y C, Egbuna, O I, Boonen, S, Miller, P D: Effects of denosumab on fracture and bone mineral density by level of kidney function. *J Bone Miner Res,* 26: 1829-1835, 2011.
23. Ishani, A, Blackwell, T, Jamal, S A, Cummings, S R, Ensrud, K E, Investigators, M: The effect of raloxifene treatment in postmenopausal women with CKD. *J Am Soc Nephrol,* 19: 1430-1438, 2008.
24. Jamal, S A, Bauer, D C, Ensrud, K E, Cauley, J A, Hochberg, M, Ishani, A, Cummings, S R: Alendronate Treatment in Women with Normal to Severely Impaired Renal Function: An Analysis of the Fracture Intervention Trial*. *J Bone Miner Res,* 2007.
25. Miller, P D, Schwartz, E N, Chen, P, Misurski, D A, Krege, J H: Teriparatide in postmenopausal women with osteoporosis and mild or moderate renal impairment. *Osteoporos Int,* 18: 59-68, 2007.
26. Miller, P D, Roux, C, Boonen, S, Barton, I P, Dunlap, L E, Burgio, D E: Safety and efficacy of risedronate in patients with age-related reduced renal function as estimated by the cockcroft and gault method: a pooled analysis of nine clinical trials. *J Bone Miner Res,* 20: 2105-2115, 2005.
27. Cejka, D, Benesch, T, Krestan, C, Roschger, P, Klaushofer, K, Pietschmann, P, Haas, M: Effect of teriparatide on early bone loss after kidney transplantation. *Am J Transplant,* 8: 1864-1870, 2008.
28. Cejka, D, Kodras, K, Bader, T, Haas, M: Treatment of Hemodialysis-Associated Adynamic Bone Disease with Teriparatide (PTH1-34): A Pilot Study. *Kidney & blood pressure research,* 33: 221-226, 2010.
29. Palcu, P, Dion, N, Ste-Marie, L G, Goltzman, D, Radziunas, I, Miller, P D, Jamal, S A: Teriparatide and bone turnover and formation in a hemodialysis patient with low-turnover bone disease: a case report. *Am J Kidney Dis,* 65: 933-936, 2015.
30. Sumida, K, Ubara, Y, Hoshino, J, Mise, K, Hayami, N, Suwabe, T, Kawada, M, Imafuku, A, Hiramatsu, R, Hasegawa, E, Yamanouchi, M, Sawa, N, Takaichi, K: Once-weekly teriparatide in hemodialysis patients with hypoparathyroidism and low bone mass: a prospective study. *Osteoporosis International,* 27: 1441-1450, 2016.
31. Block, G A, Bone, H G, Fang, L, Lee, E, Padhi, D: A single-dose study of denosumab in patients with various degrees of renal impairment. *J Bone Miner Res,* 27: 1471-1479, 2012.
32. Khairallah, P, Nickolas, T L: Management of Osteoporosis in CKD. *Clin J Am Soc Nephrol,* 2018.
33. Coco, M, Rush, H: Increased incidence of hip fractures in dialysis patients with low serum parathyroid hormone. *Am J Kidney Dis,* 36: 1115-1121, 2000.
34. Davies, M R, Lund, R J, Mathew, S, Hruska, K A: Low turnover osteodystrophy and vascular calcification are amenable to skeletal anabolism in an animal model of chronic kidney disease and the metabolic syndrome. *J Am Soc Nephrol,* 16: 917-928, 2005.
35. Barreto, D V, Barreto Fde, C, Carvalho, A B, Cuppari, L, Draibe, S A, Dalboni, M A, Moyses, R M, Neves, K R, Jorgetti, V, Miname, M, Santos, R D, Canziani, M E: Association of changes in bone remodeling and coronary calcification in hemodialysis patients: a prospective study. *Am J Kidney Dis,* 52: 1139-1150, 2008.
36. Chapter 1: Introduction and definition of CKD-MBD and the development of the guideline statements. *Kidney Int,* 76: S3-S8, 2009.
37. Sprague, S M, Bellorin-Font, E, Jorgetti, V, Carvalho, A B, Malluche, H H, Ferreira, A, D'Haese, P C, Drueke, T B, Du, H, Manley, T, Rojas, E, Moe, S M: Diagnostic Accuracy of Bone Turnover Markers and Bone Histology in Patients With CKD Treated by Dialysis. *Am J Kidney Dis,* 2015.
38. Bakhshandeh, B, Soleimani, M, Hafizi, M, Paylakhi, S H, Ghaemi, N: MicroRNA signature associated with osteogenic lineage commitment. *Molecular Biology Reports,* 39: 7569-7581, 2012.
39. Eguchi, T, Watanabe, K, Hara, E S, Ono, M, Kuboki, T, Calderwood, S K: OstemiR: A Novel Panel of MicroRNA Biomarkers in Osteoblastic and Osteocytic Differentiation from Mesencymal Stem Cells. *PLoS ONE,* 8: e58796, 2013.
40. Hu, R, Liu, W, Li, H, Yang, L, Chen, C, Xia, Z-Y, Guo, L-J, Xie, H, Zhou, H-D, Wu, X-P, Luo, X-H: A Runx2/miR-3960/miR-2861 Regulatory Feedback Loop during Mouse Osteoblast Differentiation. *Journal of Biological Chemistry,* 286: 12328-12339, 2011.
41. Lian, J B, Stein, G S, van Wijnen, A J, Stein, J L, Hassan, M Q, Gaur, T, Zhang, Y: MicroRNA control of bone formation and homeostasis. *Nat Rev Endocrinol,* 8: 212-227, 2012.
42. van Wijnen, A J, van de Peppel, J, van Leeuwen, J P, Lian, J B, Stein, G S, Westendorf, J J, Oursler, M-J, Im, H-J, Taipaleenmaki, H, Hesse, E, Riester, S, Kakar, S: MicroRNA Functions in Osteogenesis and Dysfunctions in Osteoporosis. *Current Osteoporosis Reports,* 11: 72-82, 2013.
43. Kagiya, T, Nakamura, S: Expression profiling of microRNAs in RAW264.7 cells treated with a combination of tumor necrosis factor alpha and RANKL during osteoclast differentiation. *J Periodontal Res,* 48: 373-385, 2013.
44. Feichtinger, X, Muschitz, C, Heimel, P, Baierl, A, Fahrleitner-Pammer, A, Redl, H, Resch, H, Geiger, E, Skalicky, S, Dormann, R, Plachel, F, Pietschmann, P, Grillari, J, Hackl, M, Kocijan, R: Bone-related Circulating MicroRNAs miR-29b-3p, miR-550a-3p, and miR-324-3p and their Association to Bone Microstructure and Histomorphometry. *Scientific reports,* 8: 4867, 2018.
45. An, J H, Ohn, J H, Song, J A, Yang, J Y, Park, H, Choi, H J, Kim, S W, Kim, S Y, Park, W Y, Shin, C S: Changes of microRNA profile and microRNA-mRNA regulatory network in bones of ovariectomized mice. *J Bone Miner Res,* 29: 644-656, 2014.
46. Garmilla-Ezquerra, P, Sañudo, C, Delgado-Calle, J, Pérez-Nuñez, M I, Sumillera, M, Riancho, J A: Analysis of the Bone MicroRNome in Osteoporotic Fractures. *Calcified tissue international,* 96: 30-37, 2015.
47. Seeliger, C, Karpinski, K, Haug, A T, Vester, H, Schmitt, A, Bauer, J S, van Griensven, M: Five freely circulating miRNAs and bone tissue miRNAs are associated with osteoporotic fractures. *J Bone Miner Res,* 29: 1718-1728, 2014.
48. Heilmeier, U, Hackl, M, Skalicky, S, Weilner, S, Schroeder, F, Vierlinger, K, Patsch, J M, Baum, T, Oberbauer, E, Lobach, I, Burghardt, A J, Schwartz, A V, Grillari, J, Link, T M: Serum miRNA Signatures Are Indicative of Skeletal Fractures in Postmenopausal Women With and Without Type 2 Diabetes and Influence Osteogenic and Adipogenic Differentiation of Adipose Tissue-Derived Mesenchymal Stem Cells In Vitro. *J Bone Miner Res,* 31: 2173-2192, 2016.
49. Weilner, S, Skalicky, S, Salzer, B, Keider, V, Wagner, M, Hildner, F, Gabriel, C, Dovjak, P, Pietschmann, P, Grillari-Voglauer, R, Grillari, J, Hackl, M: Differentially circulating miRNAs after recent osteoporotic fractures can influence osteogenic differentiation. *Bone,* 79: 43-51, 2015.
50. Jeong, S, Oh, J M, Oh, K H, Kim, I W: Differentially expressed miR-3680-5p is associated with parathyroid hormone regulation in peritoneal dialysis patients. *PLoS One,* 12: e0170535, 2017.
51. M'Baya-Moutoula, E, Louvet, L, Metzinger-Le Meuth, V, Massy, Z A, Metzinger, L: High inorganic phosphate concentration inhibits osteoclastogenesis by modulating miR-223. *Biochimica et biophysica acta,* 1852: 2202-2212, 2015.
52. Balderman, J A, Lee, H Y, Mahoney, C E, Handy, D E, White, K, Annis, S, Lebeche, D, Hajjar, R J, Loscalzo, J, Leopold, J A: Bone morphogenetic protein-2 decreases microRNA-30b and microRNA-30c to promote vascular smooth muscle cell calcification. *Journal of the American Heart Association,* 1: e003905, 2012.
53. Zhao, H, Zhang, J, Shao, H, Liu, J, Jin, M, Chen, J, Huang, Y: Transforming Growth Factor beta1/Smad4 Signaling Affects Osteoclast Differentiation via Regulation of miR-155 Expression. *Molecules and cells,* 40: 211-221, 2017.
54. Nickolas, T L, Cremers, S, Zhang, A, Thomas, V, Stein, E, Cohen, A, Chauncey, R, Nikkel, L, Yin, M T, Liu, X S, Boutroy, S, Staron, R B, Leonard, M B, McMahon, D J, Dworakowski, E, Shane, E: Discriminants of prevalent fractures in chronic kidney disease. *J Am Soc Nephrol,* 22: 1560-1572, 2011.

55. Nickolas, T L, Stein, E, Cohen, A, Thomas, V, Staron, R B, McMahon, D J, Leonard, M B, Shane, E: Bone mass and microarchitecture in CKD patients with fracture. *J Am Soc Nephrol,* 21: 1371-1380, 2010.
56. Coresh, J, Astor, B, McQuillan, G, Kusek, J, Greene, T, Van Lente, F, Levey, A: Calibration and random variation of the serum creatinine assay as critical elements of using equations to estimate glomerular filtration rate. *American Journal of Kidney Diseases,* 39: 920-929, 2002.
57. Chen, N X, Kiattisunthorn, K, O'Neill, K D, Chen, X, Moorthi, R N, Gattone, V H, 2nd, Allen, M R, Moe, S M: Decreased microRNA is involved in the vascular remodeling abnormalities in chronic kidney disease (CKD). *PLoS One,* 8: e64558, 2013.
58. Parfitt, A M, Mathews, C H, Villanueva, A R, Kleerekoper, M, Frame, B, Rao, D S: Relationships between surface, volume, and thickness of iliac trabecular bone in aging and in osteoporosis. Implications for the microanatomic and cellular mechanisms of bone loss. *The Journal of clinical investigation,* 72: 1396-1409, 1983.
59. KDIGO clinical practice guideline for the diagnosis, evaluation, prevention, and treatment of Chronic Kidney Disease-Mineral and Bone Disorder (CKD-MBD). *Kidney Int Suppl: S*1-130, 2009.
60. Lin, X J, Chong, Y, Guo, Z W, Xie, C, Yang, X J, Zhang, Q, Li, S P, Xiong, Y, Yuan, Y, Min, J, Jia, W H, Jie, Y, Chen, M S, Chen, M X, Fang, J H, Zeng, C, Zhang, Y, Guo, R P, Wu, Y, Lin, G, Zheng, L, Zhuang, S M: A serum microRNA classifier for early detection of hepatocellular carcinoma: a multicentre, retrospective, longitudinal biomarker identification study with a nested case-control study. *Lancet Oncol,* 16: 804-815, 2015.

Example 2

A main impediment to diagnosis and management of renal osteodystrophy (ROD) is the identification of underlying bone turnover-type (low, normal or high). Four microRNAs (miRNAs) that regulate osteoblast (miRNA-30b, 30c, 125b) and osteoclast development (miRNA-155) could provide superior discrimination of low turnover from normal or high turnover than biomarkers in clinical use. In twenty-four patients with chronic kidney disease (CKD) Stages 3-5D, double-labeled transiliac crest bone biopsy was obtained and levels of parathyroid hormone (PTH), bone specific alkaline phosphatase (BSAP) and circulating levels of miRNA-30b, 30c, 125b and 155 were measured. Spearman correlations assessed relationships between miRNAs and dynamic parameters of histomorphometry and PTH and BSAP. Diagnostic test characteristics for discriminating low or high turnover were determined by receiver operator curve analysis; areas under curve (AUC) were compared by $\chi^2$-test. miRNAs moderately correlated with bone formation rate/bone surface and adjusted apposition rate at the endo- and intra-cortical envelops (p 0.43-0.51; $p<0.05$). The AUCs and 95% confidence intervals for discrimination of low versus non-low and high versus non-high turnover for miRNAs, PTH and BSAP are presented in FIG. 5. Discrimination of low versus non-low turnover was 0.875, 0.825, 0.800 and 0.767 for miRNA-30b, 30c, 125b and 155 respectively, and 0.479 and 0.781 for PTH and BSAP respectively. For all four miRNAs combined, the AUC was 0.983, which was superior to that of BSAP alone ($p<0.05$). BSAP but neither the miRNAs nor PTH discriminated high versus non-high turnover. These data suggest that circulating miRNAs provide accurate non-invasive identification of bone turnover. Additional miRNA biomarkers of both high and low turnover can be discovered and validated and their impact on clinical decision making and outcomes can be determined.

Example 3

More than one in ten Americans has chronic kidney disease (CKD)[1]. Renal osteodystrophy (ROD) is a complex disorder of bone metabolism that affects nearly all patients with advanced CKD over their lifetimes[2-6]. ROD is associated with adverse clinical outcomes including bone loss[7], fractures[8-13], cardiovascular events[14-16] and death[17]. ROD is defined by the Kidney Disease Improving Global Outcomes (KDIGO) classification of bone Turnover, Mineralization, and Volume (TMV)[18]. ROD TMV class can change over time or the initial bone abnormality can worsen as kidney function declines. The primary goal of ROD treatment is reducing high turnover with active vitamin D and/or calcimimetics, at the same time as avoiding the development of low turnover through excessive use of these same therapeutic agents. The KDIGO best evidence guidelines recommend that clinical use (i.e., starting/stopping) of these agents is guided by the biomarker parathyroid hormone (PTH)[19]. However, bone biopsy studies in CKD patients demonstrate that PTH is a poor guide to starting or stopping ROD treatment, with areas under the curve (AUC) of 0.724 and 0.701 for differentiating high and low turnover ROD respectively[20]. Therefore, KDIGO recommends tetracycline double-labeled transiliac crest bone biopsy with histomorphometry to define turnover and guide treatment strategies[18]. A major limitation of bone biopsy is that it is invasive, expensive, not widely available, and requires ~3-months to obtain results. Thus, there is an unmet clinical need to identify biomarkers with better diagnostic accuracy for the prediction of underlying turnover assessed by bone histomorphometry to guide treatment decisions in the clinic and for use in clinical trials.

Analyses described herein (see e.g. Examples 1 and 2) from an a priori defined subset of circulating microRNAs (miRNA) that are associated with inhibition of osteoblast (miRNA-30b, 30c, 125b) and osteoclast (miRNA-155) development suggest they are accurate biomarkers of low turnover[21, 22]. In twenty-four CKD patients with bone biopsies, areas under the curve for discrimination of low from non-low turnover ROD were 0.875, 0.825, 0.800, and 0.767 for miRNA-30b, 30c, 125b, and 155 respectively, while PTH did not discriminate in this population. Based on these findings, it is proposed, without being bound by theory, that circulating miRNAs discriminate turnover in ROD. Changes in levels of miRNAs could also reflect changes in turnover. Bone biopsies (n=60) can be used to further expand the studies described herein. In a discovery cohort of 24 CKD patients, miRNA-sequence (seq) can be used to identify additional novel circulating miRNA expression signatures that are specific to low and high turnover ROD, and in a validation cohort of 36 CKD patients the accuracy of the miRNA expression signatures for turnover identified in the discovery cohort can be tested. The subject matter disclosed herein has the potential to result in a paradigm shift in the diagnosis and management of ROD.

Circulating miRNA expression signatures that serve as better diagnostic biomarkers of bone turnover than those in current clinical use can be identified. Without being bound by theory, low and high turnover ROD can have unique circulating miRNA expression signatures.

Circulating miRNA expression signatures that discriminate low and high turnover and/or high turnover versus normal or low turnover ROD can be identified. Both of these discrimination scenarios are important clinically in determining optimal treatment of ROD. miRNA-seq can be used to identify miRNA expression signatures that may or may not include the miRNA in Examples 1 associated with turnover discrimination in a discovery cohort (K23-DK080139) of 24 CKD patients (stages 3-5D) with known prevalence of low and high turnover ROD. The AUC can be assessed, specificity, sensitivity, positive and negative predictive values, and net reclassification index for miRNAs described herein and for additional miRNAs identified from miRNA-seq analyses. Diagnostic test characteristics will be analyzed with and without PTH and clinically used markers of bone turnover to identify the best circulating signature/model of underlying bone turnover.

The accuracy of miRNA expression signatures can be validated. In a cross-sectional study of 36 patients with CKD stages 3-5 with bone biopsies and stored blood done, the diagnostic test characteristics of the miRNA expression signatures can be validated, using Real-Time PCR, with and without PTH and markers of boneturnover.

miRNA expression signatures that serve as biomarkers for bone turnover changes due to treatment interventions can be tested. Without being bound by theory, changes in bone turnover are reflected by changes in circulating miRNA expression signatures.

Transiliac crest bone biopsy can be obtained in 22 patients using a quadruple label single-biopsy protocol to measure turnover before and 3 months after parathyroidectomy or administration of medications that dramatically decrease turnover (anti-resorptives such as bisphosphonates or denosumab) and determine if the miRNA expression signatures identified undergo a directional change from a signature of high to low turnover.

Renal osteodystrophy (ROD) is a significant disease. ROD is a complex heterogeneous disorder of bone that results from abnormal calcium and phosphate metabolism, decreased calcitriol synthesis, increased para-thyroid hormone (PTH) levels, metabolic acidosis, and defective bone mineralization[23]. Specifically, ROD is the bone component of CKD-Mineral and Bone Disease (CKD-MBD), a disorder of bone, mineral metabolism, and soft tissue calcifications. More than one in ten Americans has CKD[1] and CKD-MBD occurs in nearly 100% of CKD patients[2-6]. ROD results in bone loss[7] and fractures[8-13] and has been linked to increased risk of vascular calcifications and CV events[16, 24-27] For CKD patients, compared to the general population, fractures and cardiovascular (CV) risk are more than 17-[8, 12, 28] and 1.4-fold[14] greater respectively, and mortality rates after fracture and CV events are more than 3-[17] and 10-fold greater[14], respectively. In 2010, healthcare associated costs after fracture exceeded $600 million[17]. Thus, improvements in the diagnosis and clinical management of ROD is a critical first step in the long-term goal of reducing morbidity and mortality in patients with CKD-MBD[29].

Diagnosis of turnover is an impediment to ROD treatment. The 2005 KDIGO committee shifted the historical nomenclature of ROD-type (e.g., osteitis fibrosa cystica) to a unified classification system based on bone Turnover, Mineralization, and Volume (TMV)[18], and ROD-turnover is now classified as low, normal, or high turnover ROD. Current treatment of ROD is focused on suppressing high turnover with active vitamin D (calcitriol and analogs) and/or calcimimetics, while simultaneously avoiding the development of low turnover ROD through excessive use of these same agents. In addition, emerging data and clinical experience suggest that ROD with bone loss or fractures may be safely managed with treatments that are used for osteoporosis (anti-resorptives for high turnover ROD; anabolics for low turnover ROD)[30-39], as long as low turnover ROD can be identified and avoided. The primary concern in identifying and preventing the development of low turnover ROD is that it has been associated with risk of fractures[40] and vascular calcifications that may increase CV risk[25, 41, 42]. Guidelines and clinical experience recommend that diagnosis of turnover should be obtained prior to starting ROD treatment, and turnover should be monitored during the course of therapy because turnover may change, thus requiring an alteration to the treatment (discontinuing calcitriol or calcimimetics for over suppression of turnover). The gold standard method to define turnover is double labeled tetracycline transiliac crest bone biopsy with quantitative histomorphometry. However, bone biopsy is invasive, expensive, requires ~3-months for results, cannot be used for rapid decision making, is not easily implemented as a disease and treatment monitoring tool, and is available at only several centers worldwide. In addition, it assumes that iliac crest remodeling is representative of systemic turnover. Since these limitations render bone biopsy impractical and in the vast majority of cases impossible to use for either diagnosis or treatment monitoring, KDIGO recommends that circulating levels of PTH can be used in the clinic to diagnose and guide management of ROD[19].

PTH and has poor accuracy for turnover. Two large bone biopsy studies recently characterized contemporary trends in ROD and diagnostic accuracy of PTH for turnover type[5, 20]. In 630 dialysis patients, Malluche et al.[5] reported that low turnover ROD was prevalent in the majority of patients (58%) while only a minority of patients (3%) had a defect in mineralization. Levels of PTH were lower in patients with low compared to high turnover ROD, but diagnostic accuracy of PTH for turnover was not assessed. Total alkaline phosphatase, a formation marker that is commonly measured in dialysis patients, did not differ between turnover types. A second study was led by a KDIGO consortium, it included 492 patients from 4 countries and assessed the diagnostic accuracy of PTH for turnover type[20]. Similar to Malluche et al.[5] the prevalence of low turnover ROD predominated (59%). PTH insufficiently identified low or high turnover to confidently guide ROD treatment: the area under the curve (AUC), sensitivity, and specificity for discriminating low vs. non-low turnover ROD was 0.701, 65%, and 67% respectively, and for discriminating high vs. non-high turnover ROD was 0.724, 37%, and 86% respectively. Combining PTH with the bone formation marker bone specific alkaline phosphatase (BSAP) did not improve accuracy, with AUCs of 0.718 for identifying both low and high turnover ROD.

Figure 8:
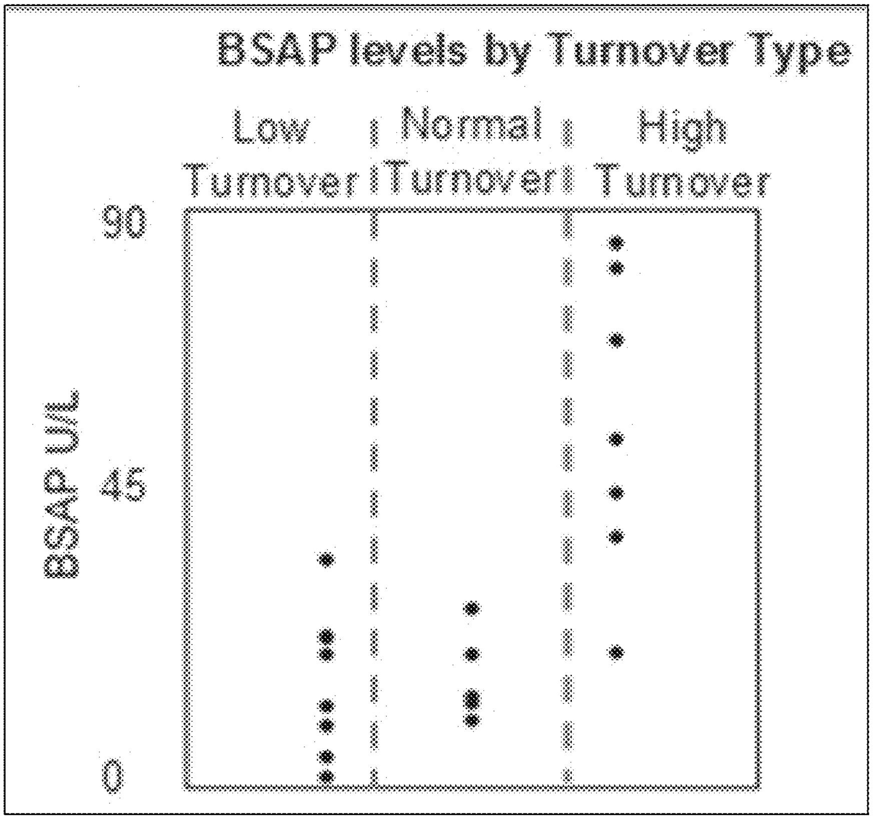
FIG. 8 shows BSAP levels by turnover type.

24 patients with CKD Stages 3-5D underwent bone biopsy. Low, normal, and high turnover ROD were defined as the lowest, middle, and highest tertiles of BFR/BS and Adjusted Apposition Rate. PTH levels did not differ by turnover-type (FIG. 6; mean±SD pg/mL: 138±113; 101±102; 276±269 for low, normal, high turnover respectively, F-test 0.2) and did not discriminate between groups (FIG. 7). Additionally, whether BSAP discriminated turnover-type was assessed. BSAP levels in high turnover differed from those in low and normal turnover ($p<0.05$ for both) (FIG. 8) and BSAP discriminated low and high turnover ROD (FIG. 7). These data are in contrast to the larger study by Malluche et al.[5], but similar to those of the KDIGO led consortium[20]. It will be tested if combining miRNA expression signatures with BSAP and/or other clinically used bone turnover markers improve diagnostic accuracy for turnover type, the findings for BSAP will be validated, and the diagnostic test characteristics of turnover-type for other bone turnover markers will be examined. In sum, these data support the scientific premise that novel ROD biomarkers for turnover are needed.

Figure 9:
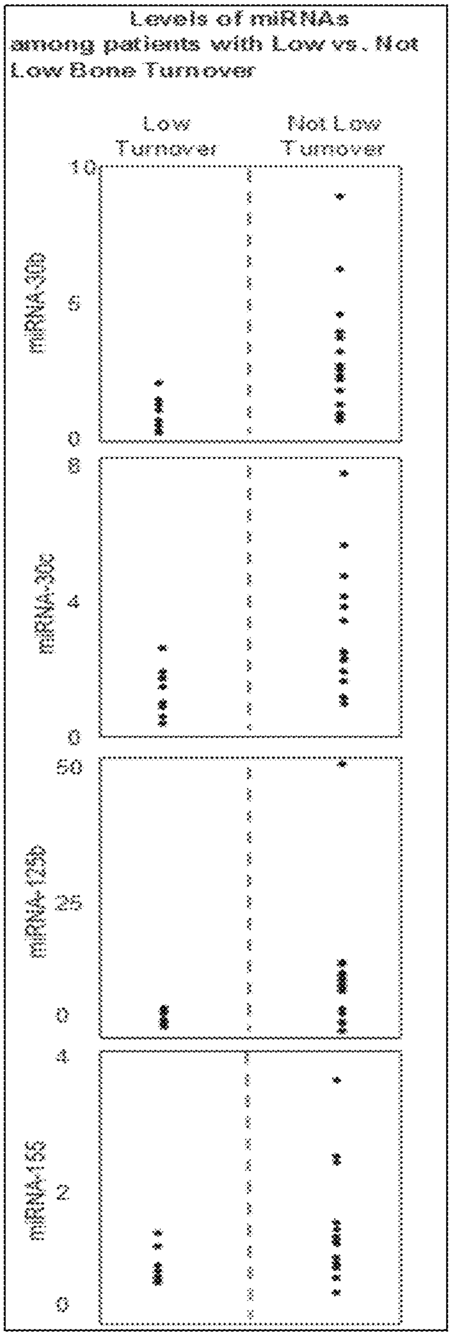
FIG. 9 shows levels of miRNAs among patients with low vs not low bone turnover.
Figure 13:
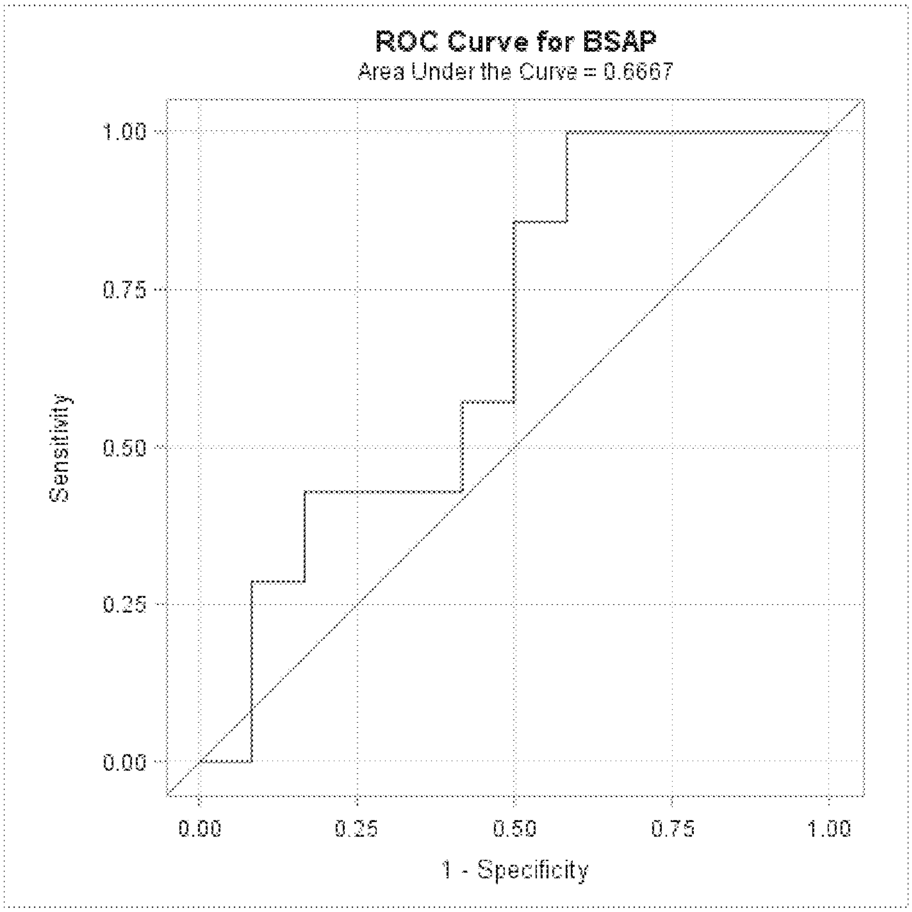
FIG. 13 shows receiver operating characteristic (ROC) curve for BSAP.
Figure 14:
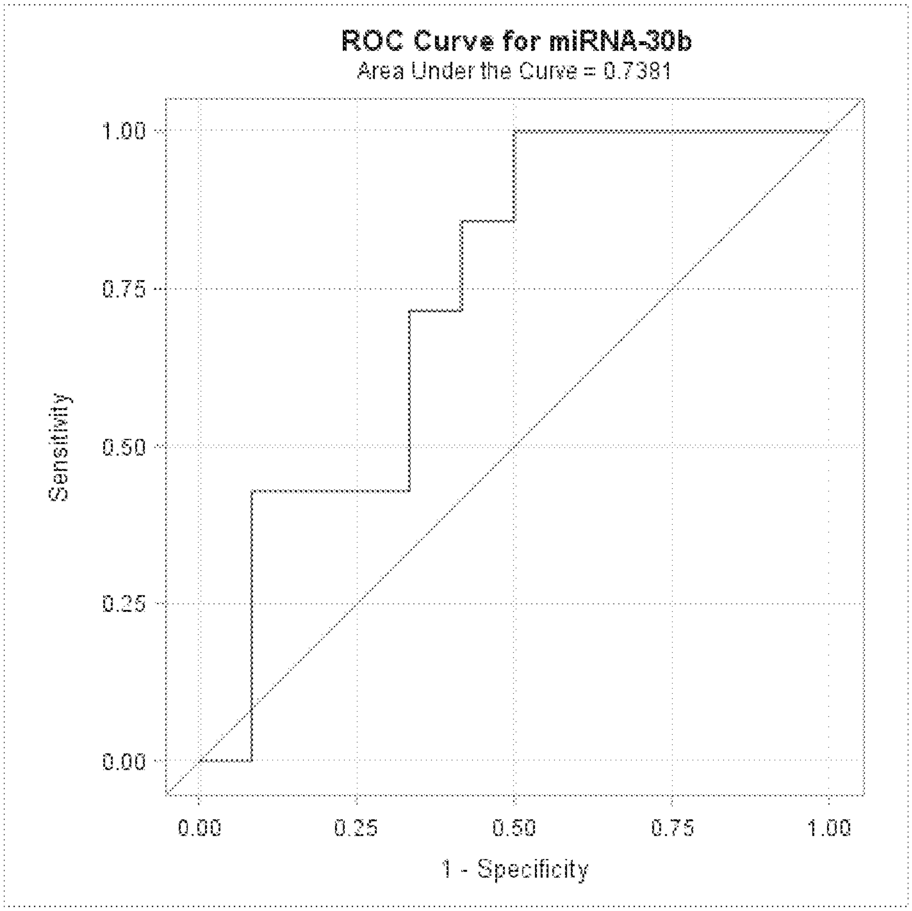
FIG. 14 shows receiver operating characteristic (ROC) curve for miRNA-30b.
Figure 15:
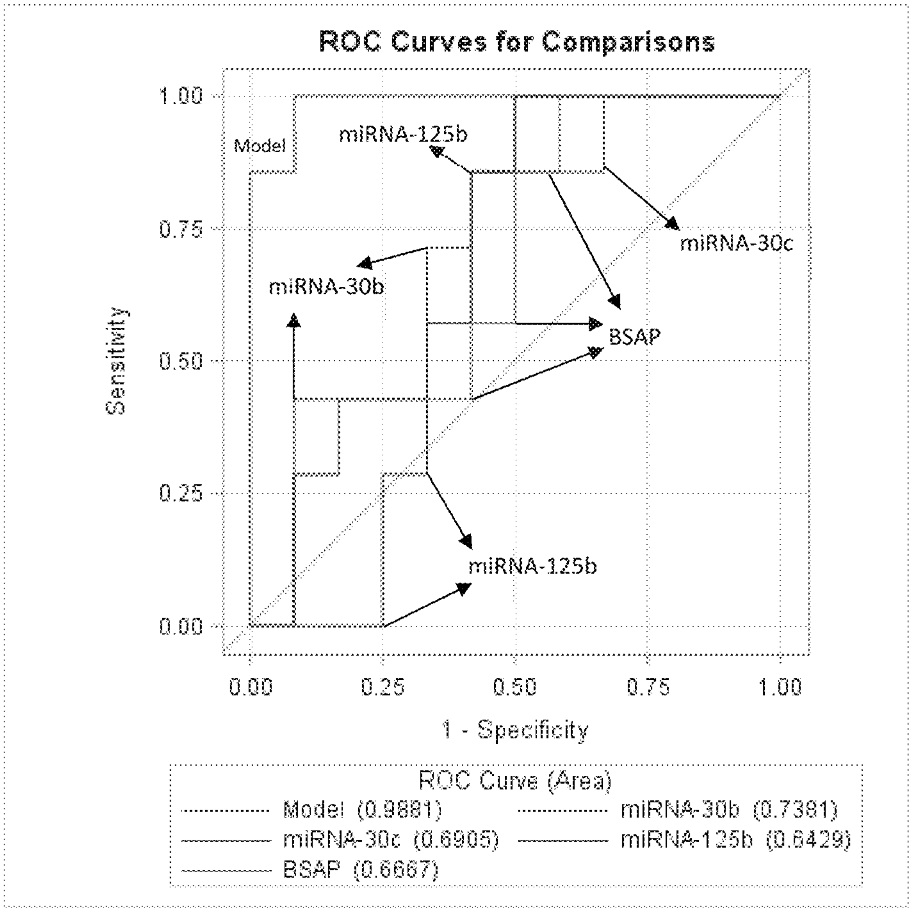
FIG. 15 shows receiver operating characteristic (ROC) curves for comparisons. To conform to the requirements for PCT patent applications, color lines have been marked up with arrows and labels.

Circulating miRNAs as novel biomarkers of bone disease. miRNAs are small noncoding sequences of ~22 nucleotides that bind to the 3'-untranslated regions of mRNAs to silence gene expression by inhibiting translation or promoting degradation of target mRNAs. miRNA expression during osteoblast and osteoclast development has been studied[21, 43, 44], bone cell phenotypic effects of miRNA substitutions and knockdowns have been described[45, 46], and the impact of hormones and RANK[47] on miRNA expression signatures have been reported. Dysregulation in levels of circulating miRNA expression has been noted in patients with osteoporosis[48-50] and fractures[51, 52]. In CKD patients, levels of miRNAs and PTH have been correlated[53] and in cell culture inorganic phosphate was shown to modulate osteoclastogenesis by miRNA-233[54], but miRNAs have not been validated as biomarkers of turnover against gold standard bone biopsy in CKD patients with ROD. In 24 CKD patients, it was assessed whether miRNAs that inhibit osteoblast (miRNA-30b, 30c,125b) and osteoclast (miRNA-155) development were associated with either high or low turnover (defined as the upper and lower tertile of BFR/BS and Adjusted Apposition Rate by histomorphometry respectively). While these miRNAs did not discriminate high turnover, they discriminated low turnover. Levels of the miRNAs (normalized to *C. elegans* miRNA-39) differed significantly between low and non-low turnover ROD turnover (FIG. 9; $p<0.05$ for all). Although it may seem paradoxical that miRNAs that inhibit bone cell development were higher in patients with non-low turnover ROD, this finding may represent a regulatory response that attempts to decrease BFR when BFR is high, or on the other hand may be consistent with low level cellular activity in low turnover. In FIG. 10 all miRNAs discriminated low from non-low turnover ROD, with miRNA-30b, 30c, and 125b having greater diagnostic accuracy than that reported for PTH and BSAP in the ROD biomarker study commissioned by KDIGO (0.701 and 0.757, respectively)[20]. These results can be validated and miRNA-seq can be used to determine if other miRNAs also enhance the diagnostic accuracy of low vs. non low turnover. miRNA expression signatures specific to high turnover ROD will also be identified. In sum, these data support the hypothesis that miRNAs diagnose turnover and they lay the groundwork for the proposal to identify circulating miRNA expression signatures specific to low and high turnover ROD.

Accurate non-invasive biomarker of bone turnover. The study described herein lays the groundwork to change the paradigm of ROD diagnosis and management from invasive bone biopsy to non-invasive serum analysis of miRNAs, in conjunction with bone turnover markers.

Non-invasive biomarker development overcomes noted limitations of invasive bone biopsy. It will improve patient care and enable development of efficient large scale clinical trials of ROD specific therapies.

Discovery of miRNA expression profiles of turnover. miRNA-seq identification of expression signatures that are related to and regulate turnover may elucidate potential novel targets for ROD treatment.

Precision medicine. miRNA profiling can permit individual patient level diagnosis of ROD-type. Thus, ROD treatment can be tailored to each patient's underlying bone disorder.

Circulating miRNA expression signatures that serve as better diagnostic biomarkers of bone turnover than those in current clinical use can be identified. Without being bound by theory, low and high turnover ROD have unique circulating miRNA expression signatures. Circulating miRNA expression signatures that discriminate low versus high turnover ROD can be identified.

Rationale. ROD treatment is based on the goal to lower turnover from high to normal, but not to low levels. The gold standard to diagnose turnover is bone biopsy, which is impractical for use in almost all CKD patients. The current non-invasive biomarker of turnover in ROD (PTH) does not have sufficient accuracy for turnover to confidently guide and safely treat ROD. miRNAs have cell regulatory functions and they have been associated with metabolic bone diseases and fractures. In the discovery cohort of 24 patients across the CKD spectrum, miRNAs associated with inhibition of osteoblast (miRNAs-30b, 30c, 125b) and osteoclast (miRNA-155) function were better biomarkers of low turnover than PTH. miRNA-seq can be used to identify additional expression signatures that are related to both low and high turnover ROD. miRNAs identified both in the data described herein and in miRNA-seq can be further validated.

Experimental Design. Data from 24 patients who participated in the bone biopsy sub-study can be leveraged. The cohort has been described in detail[7, 55, 56]. In brief, 180 patients were recruited from nephrology clinics between 2008 and 2012, 24 patients agreed to undergo transiliac crest bone biopsy with quantitative histomorphometry. Serum and plasma were collected and stored at −80° C. The biopsy cohort's characteristics stratified by tertile of bone formation rate are described in FIG. 11. miRNA analysis can be performed on all serum[57,58]. All measures of PTH, bone turnover markers, and bone histomorphometry were measured. Power considerations based on 24 patients are outlined in the Human Subjects section.

Total RNA isolation and quantification. Total RNA from patient serum can be isolated using miRNeasy Mini Kit (Qiagen) according to the manufacturer's instructions. Total RNA is eluted from the column in RNase-free water and stored at −80° C.

Ion Proton Semiconductor standard methods for small RNA sequencing. Total RNA and miRNA can be first evaluated for quantity, quality, and percent miRNA content in total RNA using Agilent Bioanalyzer. Starting amount of RNA will be 10-20 ng for miRNA library. For miRNA library preparation, 0.5% amount of miRNA in total RNA will be the cut-off in decision whether the sample should be enriched for miRNA. If needed, a step of enrichment can be conducted, following the small RNA library preparation procedure in the Ion Total RNA-Seq Kit v2 User Guide, Pub. No. 4476286 Rev. E (Life Technologies). Each resulting barcoded library can be quantified and its quality accessed by Agilent Bioanalyzer and multiple libraries pooled in equal molarity. Eight microliters of 100 pM pooled libraries will be applied to Ion Sphere Particles (ISP) template preparation and amplification using Ion OneTouch 2, followed by ISP loading onto PI chip and sequencing on Ion Proton semiconductor. Each PI chip could generate ~50 million usable reads of 21-22 bp miRNA fragments. Sequence mapping will be performed using Torrent Suit Software v4.6 (TSS 4.6), aligned to human genome hg19.

Analytical Approach. miRNA expression signatures will be pooled from across levels of kidney function since previous work suggests that total miRNA levels do not differ by kidney function or dialysis status[58]. For PCR, we previously identified that serum provides the greatest RNA yield, and that the use of added *C elegans* miRNA-39 offered superior reproducibility than U96 internal controls. Similar to the previous data, low and high turnover will be defined as BFR/BS and Adjusted Apposition Rate within the lower and upper tertile, respectively, of the population. Where low and high turnover are the objects of classification, a set of high priority signals will be defined using the positive false discovery rate (pFDR) approach; any signals with a q-value <0.05 will be prioritized for downstream analyses. However, if >100 signals exceed this criterion a more stringent q-value of 1% will be used. This set of miRNA profiles will then be iteratively submitted to principal components analysis (PCA), the lead signals that explain most of the variance in the dataset will be taken, and a receiver operating characteristic (ROC) analysis will be performed to calculate the discriminative capacity of the profiles using the ROC AUC index. This will be performed twice: once with and once without PTH and bone turnover markers (BSAP, procollagen type 1 N-terminal propeptide, C-telopeptide, Tartrate Resistant Acid Phosphatase-5b, Sclerostin, FGF-23). The next iteration will then limit the selected targets to 80% of the lead signals and repeat the analysis. On each iteration, the selection of lead signals will be further restricted, the ROC AUC will be calculated and the iteration will be ended when the iteration-to-iteration AUC incremental improvement becomes less than 0.02. The final selected signals, with or without PTH and bone turnover markers, whichever is better, will be submitted for validation.

The accuracy of miRNA expression signatures can be validated.

Rationale. The miRNAs that discriminated low and high turnover ROD described previously and any additional miRNA expression signatures discovered can be further validated. Validating the accuracy of the expression signatures is useful prior to their use as a biomarker of turnover in the future.

Experimental Design. Data from 36 bone biopsies and serum stored at −80° C. can be leveraged. Enrollment began in August 2016 and will continue until 2019. Currently, six patients have undergone bone biopsy. All specimens will undergo histomorphometry. miRNA analysis will be performed on serum. All measures of PTH and bone turnover markers will be measured. Power considerations based on 36 patients is outlined in the Human Subjects section.

Cohort Characteristics. Transiliac crest bone biopsies will be obtained from 36 patients with CKD (Stages 3-5; n=12 per stage (6 women and 6 men per stage). Inclusion criteria include: age >50, CKD stages 3-5 not on dialysis. All causes of CKD will be enrolled. All races and ethnicities will be included, and subjects will need to have been on a stable dose of vitamin D2/D3 or PTH lowering agents (e.g. calcitriol) over the last 3 months. Patients will be excluded due to amputations, malignancy or non-CKD causes of bone disease, significant co-morbidities that may alter bone (solid organ lung transplant, heart or lung disease, intestinal malabsorption); and those treated in the past year with prednisone of ≥90 days, or those ever treated with bisphosphonates, teriparatide, calcitonin, selective estrogen receptor modulators, estrogen, or dilantin.

Recruitment and Study Procedures. Subjects are recruited from nephrology clinics. More than 3500 patients with CKD are seen yearly. Subjects referred for both clinical biopsy and those only participating in this research are eligible. The main clinical indication for bone biopsy in CKD patients is to determine turnover before ROD treatment. Patients undergoing a biopsy for research purposes will be assured that while the biopsy is being obtained mainly for research purposes, the results will be given to their physician. Approximately 50% of subjects will be referred for clinical purposes. Those who agree to participate in the study will have a baseline visit, where historical, clinical, and laboratory information will be obtained. Serum will be stored at −80° C. for batch assay at study completion. Tetracycline dosing (Sumycin, 250 mg 4×/day for 3 days; 12-day holiday, 3 additional days) will be given to the patient prior to iliac crest bone biopsy being performed. Specimens are stored in ethanol and shipped overnight for analysis.

Histomorphometry can be performed according to KDIGO TMV classification[18].

Total RNA Isolation and Quantification can be performed and described above.

Confirmation of miRNA expression signatures by Real-Time PCR. Only those miRNAs from the data previously described and those found to have discriminatory capabilities between low vs. non-low and high vs. non-high will be assessed. Real-time PCR amplification will be performed on plasma miRNAs using TaqMan miRNA Assays (TaqMan MGP probes, FAM dye-labeled) using Applied Biosystems ViiA 7 Real-Time PCR systems (Applied Biosystems) as it has previously been published[58]. The $\Delta\Delta C_T$ method will be used to analyze relative changes in miRNA expression, normalized by spike of *C. elegans* miR-39.

Analytical Approach. Primary outcomes are low vs. non-low and high vs. non-high turnover ROD. Diagnostic test characteristics (AUC, specificity, sensitivity, positive and negative predictive values, and net reclassification index) for miRNA expression signatures for low vs. non-low and high vs. non-high turnover ROD will be assessed in the validation cohort, with and without PTH and bone turn-over markers. ROC curves will be compared between any additional signatures and from the data described herein (miRNA-30b, 30c, 125b and 155) using a non-parametric approach[59]. Although the ability of the miRNA profiles to identify low and high turnover is of interest, it will be also tested if the miRNA profiles are related to continuous states of skeletal dynamics. Thus, using dynamic histomorphometric indices as the phenotypic target, the same iterative approach described above for selection of the optimal expression signatures will be used, and use regression instead of logistic models and incremental $R^2$ instead of ROC AUC as the performance metric. Validated miRNAs will undergo in silico analysis to identify their gene targets using publicly available target gene prediction software and databases[60-62]. Detailed gene set enrichment analysis of predicted target genes with gene ontology (GO) terms will be performed and curated biological path-ways using GSEA[63, 64]. This analysis will provide important biological clues about the underlying mechanism of miRNA associations with bone turnover. Lastly, the final set of miRNAs will be examined in a longitudinal fashion for its ability to diagnose a temporal change in turnover as described above.

miRNA expression signatures specific to discriminating low vs. non-low and high vs. non-high turnover can be discovered. The signatures, additional panels of miRNAs discovered through miRNA-seq, may be able to describe additional variability in turnover than the four miRNAs described herein; thus, accuracy for turnover-type will be optimized. Combining expression signatures with PTH and/or bone turnover markers may provide the most accurate diagnostic information. miRNAs may also describe other aspects of ROD beyond turnover, including Mineralization and Volume. If that is the case, it will be assessed how the signatures are affected by levels of vitamin D metabolites and mineral ions and determine relationships to bone imaging collected. Although biopsies used for validation will be from non-diabetic patients, diabetic patients can also be enrolled in validation studies. Additional characterization of miRNA-30c, 30b, 125b and 155 as biomarkers of turnover with the bone turnover markers will also be continued. In silico functional analyses will be performed to determine pathways that differ in low and high turnover that may lead to discover or use of additional bone biomarkers (e.g., serum DKK1 if WNT pathway differentiates); pathways that are unidentifiable will be the subject of future investigations. Although the circulating expression signatures against miRNA expression in human bone tissue are not being validated, previous studies have found significant associations between circulating and tissue-level miRNA patterns in other populations[50]; these analyses can be performed in the future. Finally, if there is no sufficient heterogeneity in turnover to validate the expression signatures in the newly recruited cohort, how miRNA signatures are related to turnover on a continuous scale can be further pursued in the future and the baseline histomorphometric data can be combined to increase the numbers of subjects with higher levels of turnover and proceed to analyze the cohort as high vs. non-high turnover ROD since it is anticipated that the majority of patients will have high turnover ROD at baseline.

miRNA expression signatures that serve as biomarkers for bone turnover changes due to treatment interventions can be tested. Without being bound by theory, changes in bone turnover are reflected by changes in circulating miRNA expression signatures.

Rationale and Overview. ROD is not static over the course of a CKD patient's life, and can change from high to low turnover ROD and vice-versa depending on level of kidney function, patients' age, and treatment with therapies that alter bone[5, 36, 65-69]. Although a biomarker of turnover with cross-sectional utility is helpful, a biomarker that reflects changes in turnover is optimal as it could be used to guide management decisions (i.e., stop calcitriol or calcimimetic). The dynamics of the miRNA expression signatures discovered and validated can be examined after interventions that result in a dramatic change in turnover from high to low (parathyroidectomy[70], anti-resorptives). A quadruple label approach will be used to quantify changes in dynamic indices of histomorphometry in order to obtain prospective data on bone turnover with only a single biopsy procedure[71, 72]. In the quadruple labeling protocol, 2 sets of double tetracycline labels are administered: one set before intervention begins, and a second set 3 months after the intervention; a single biopsy is then performed after the second set of labels. Because two different tetracyclines are used that fluoresce in different colors, a single biopsy can be used to assess dynamic indices of bone before and after intervention[71, 72].

Experimental Design. Twenty-two patients with CKD Stage 3-5D regardless of kidney transplantation status undergoing parathyroidectomy for renal hyperparathyroidism or anti-resorptive treatment will undergo quadruple label transiliac crest bone biopsy to quantify dynamic indices of bone at baseline (pre-treatment) and 3 months after treatment. Bone turnover is uniformly high in patients with renal hyperparathyroidism who are candidates for parathyroidectomy[70]. For CKD patients treated with anti-resorptives, screening to rule out low bone turnover will occur by PTH[20, 73]. Sample Size Justification for 22 patients are outlined in the Human Subjects section. Inclusion criteria include: age ≥18; CKD stages 3-5D regardless of kidney transplantation status; both genders; all races/ethnicities. Patients with bilateral lower extremity amputations, malignancy, non-CKD causes of bone disease, co-morbidities that may alter bone (non-kidney solid organ, intestinal malabsorption), or patients in whom bone biopsy is not safe (unable to stop anti-coagulants) will be excluded.

Recruitment and Study Procedures. Subjects will be recruited from the nephrology, endocrine, and endocrine surgery clinics. Patients who agree to participate will have a baseline visit to obtain historical, clinical, and laboratory information. Serum will be stored at −80° C. for batch assay at study completion. Tetracycline Label 1 (Sumycin, 250 mg 4×/day for 3 days; 12-day holiday, 3 additional days) will be given prior to intervention and Tetracycline Label 2 (Demeclocycline 150 mg 4×/day for 3 days; 12-day holiday, 3 additional days) will be given 3 months after the intervention and prior to iliac crest bone biopsy. Specimens will be stored in ethanol and histomorphometry will be performed.

Histomorphometry can be performed according to published methods for the quadruple label method[71, 72]. For both time-points, ROD-type will be classified according to the KDIGO TMV system (low, normal, high turnover)[18]. Static indices are quantified only at the 3-month time-point with the quadruple label method.

miRNA analyses. For pre- and 3-month time-points, relative expression levels of miRNAs validated above will be performed as described above by Real-Time PCR.

Analytical Approach. Whether there is agreement between histomorphometry and miRNA expression signatures for high and low turnover ROD at baseline and 3-months respectively will be tested. Subjects will be classified as having high vs. non-high and low vs. non-low turnover ROD at baseline and 3-months respectively: once by dynamic indices of histomorphometry and once by the miRNA signatures. This dual classification can be collapsed into a 2×2 table where rows signify agreement between histomorphometric and miRNA classifiers at baseline and columns signify their agreement at 3-months. A Fisher's Exact Test of the agreement of miRNA and histomorphometric classification at baseline and after the treatment-induced change at 3-months will be used. Next, the miRNA score will be regressed on the change in dynamic indices from histomorphometry to determine the model $R^2$. Twenty-two patients provide 80% power, 5% alpha to detect an $R^2$ accounted for by biomarkers of 0.39 with no covariates, 0.41 with one covariate, and 0.54 with two covariates.

It is expected that candidates for parathyroidectomy will have high turnover ROD at baseline and that turnover will uniformly decrease after parathyroidectomy[70]. Screening to rule out low turnover ROD with PTH may result in false negatives for the anti-resorptive treated patients; in this case, those patients will be excluded from the primary analysis and their baseline turnover and miRNA data will be used to enhance cohort heterogeneity in turnover. It is expected that validated miRNA signatures will accurately reflect high turnover at baseline and low turnover at 3-months. It is expected that the change in miRNA score from baseline to 3-months will characterize the change in turnover confirmed by histomorphometry. It is assumed that low turnover from any cause (suppression of PTH after parathyroidectomy; suppression of osteoclast function after anti-resorptives) results in an unchanged miRNA expression signature. However, miRNA expression signatures for low turnover may differ by induction method; in this case, the analyses will be stratified according to induction method and additional RNA-seq will be conducted to identify other miRNA patterns that correspond to the 3-month turnover. A limitation of the approach disclosed herein is that a group of patients being treated with anabolic agents, which increase bone turnover rates, will not be included. However, the effect of these agents in patients with CKD on bone turnover is not as well studied, nor as commonly used in patients with CKD. This group can be assessed in the future.

Future Directions. These studies will allow the creation of a diagnostic biomarker (miRNA signature) that is superior to that used in clinical practice. This same biomarker could be used to assess changes in bone turnover. A multi-center study that tests the clinical utility of using these biomarkers to diagnose and manage ROD in CKD patients can be performed to examine improvement of clinical end-points such as bone histomorphometry, bone density, fractures, and mortality. In addition, miRNA may not be linked to gene changes in bone. However, the data collected would allow future studies to examine the gene and biologic effects of novel miRNAs identified by miRNA-seq. In addition, the miRNA signatures identified in response to parathyroidectomy and/or anti-resorptives may facilitate studies of novel targets for ROD treatment.

Human Subjects Involvement, Characteristics, and Design

Existing data from two cohorts of patients with transiliac crest bone biopsies will be leveraged. In a discovery cohort of 24 CKD Stage 3-5D patients with bone biopsies and serum and plasma stored at −80° C., miRNA-sequence (seq) with real time PCR confirmation will be used to discover miRNA expression signatures specific to low and high turnover ROD. In a validation cohort of 36 CKD Stage 3-5 patients with bone biopsies, both any additional the miRNA expression signatures discovered and the miRNAs described herein for low and high turnover ROD will be validated.

Twenty-two new patients can be enrolled for bone biopsy and blood. The patients will be given a unique identifier and the blood and bone biopsy samples sent for analyses. Whether miRNA expression signatures identified and validated change in relationship to bone turnover after parathyroidectomy or initiation of anti-resorptives will be determined. A quadruple label approach will be used to quantify changes in dynamic parameters of histomorphometry in order to obtain prospective data on bone turnover with only a single biopsy procedure. In the quadruple labeling protocol, 2 sets of double tetracycline labels are administered: one set before intervention begins, and a second set 3 months after the intervention; a single biopsy is then performed after the second set of labels. Because two different tetracyclines are used that fluoresce in different colors, a single biopsy can be used to assess dynamic indices of bone remodeling before and after intervention.

Justification of Sample Size

The discovery cohort leverages 24 bone biopsies with histomorphometry. Twenty-four biopsies will enable the estimation of specificity with a precision of ±14% under the assumption of 95% sensitivity and an expected specificity of 70%.[74]

The validation cohort leverages 36 bone biopsies with histomorphometry. This sample size will permit estimation of the specificity of the miRNA signatures in the validation cohort with a precision of ±11.5% under assumptions identical to those above. There will be 80% power and 5% alpha to detect an AUC difference between the validation and discovery cohorts larger than 0.15.[75] This is a "large" effect size consistent with the small numbers of samples collected under these previous studies.

The proposed research detailed herein involves twenty-two adult men and women with CKD Stages 3, 4, 5, 5D regardless of kidney transplantation status. Subjects will attend one study visit to obtain clinical information, blood specimens, and complete questionnaires. Eligible subjects will include men and women, all race/ethnicities, age ≥18 years, with CKD (defined as CKD-EPI GFR ≤60 ml/minute). The approximate demographic composition of Northern Manhattan is 63% Hispanic, 20% African-American, 15% Caucasian, and 2% other.

Therefore, a significant representation of minorities in this study is anticipated.

Population

Twenty-two patients with CKD stages 3, 4, 5 and 5D regardless of kidney transplantation status who are undergoing parathyroidectomy for renal hyperparathyroidism or are starting anti-resorptive treatment for treatment of osteoporosis and/or fragility fractures. Equal numbers of patients undergoing parathyroidectomy (n=11) and undergoing anti-resorptive treatment (n=11) will be included.

Justification for Inclusion and Exclusion Criteria

Special classes of subjects such as pregnant women, prisoners, institutionalized individuals or others who may be considered vulnerable populations will not be included. Inclusion and exclusion criteria were selected to limit heterogeneity, but to maintain the ability to assess links between bone quality and important clinical risk factors for fracture and its mechanisms. Patients who will not be able to undergo bone biopsy will be excluded. The complete inclusion/exclusion criteria are:

Inclusion Criteria (1) CKD stages 3, 4, 5 and 5D regardless of kidney transplantation status; (2) Age ≥18 years; (3) Both genders; (4) All races and ethnicities; (5) Stable doses of nutritional vitamin D or active vitamin D metabolites for at least 3 months before enrollment Exclusion Criteria (1) Non-kidney Solid organ transplantation; (2) Bilateral lower extremity amputations or non-ambulatory; (3) Malignancy requiring chemotherapy or metastatic to bone; (4) Non-renal metabolic bone disease (e.g., Paget's disease, primary HPTH, Osteogenesis Imperfecta); (5) Endocrinopathy: current hyperthyroidism or untreated hypothyroidism, Cushing's syndrome; (6) Medical diseases (end stage liver disease, heart or lung disease, intestinal malabsorption); (7) Ever treated with bisphosphonates, teriparatide, calcitonin, selective estrogen receptor modulators, estrogen, or dilantin; (8) patients unable to stop anticoagulants for 5-days.

Justification of Sample Size

For the analysis of the classification of high and low turnover at baseline and 3-months by the miRNA signatures compared to gold standard histomorphometry, a Fisher's Exact Test of the agreement of histomorphometry and miRNA classification at baseline and after the treatment-induced changes at 3-months will be used. Twenty-two patients provide 80% power, 5% alpha to detect a minimum between-method agreement of 0.82 (Kappa). For regression models, the miRNA score on the change in dynamic indices from histomorphometry will be regressed to determine the model $R^2$, twenty-two patients provide 80% power, 5% alpha to detect an $R^2$ accounted for by biomarkers of 0.39 with no covariates, 0.41 with one covariate, and 0.54 with two covariates.

Enrollment Strategy

Subjects will be recruited from the general nephrology, endocrine, and endocrine surgery clinics. More than 5000 patients with CKD regardless of kidney transplantation status are seen yearly. Eligible subjects will be referred to the study by their physician, who will first ascertain that they are willing to discuss the study with study personnel. Potential subjects will be approached for participation either during their clinic visit or by telephone interview. The protocol will be described in detail. Each patient will be counseled that all aspects of the study are separate from their management as a patient. They will be assured that participation is entirely voluntary and that refusal to participate in the study will not in any way influence their care. Statements to this effect will be included in all Informed Consent Forms. Bone biopsy will be discussed. Those who agree to participate in the study will be invited to attend a baseline visit (Visit 1) that will occur 1-month before their surgical or medical intervention (i.e., parathyroidectomy, anti-resorptive treatment) where historical, clinical, and laboratory information will be obtained and they will receive instructions on completion their first label (Sumycin). Visit 2 will occur 3-months after their intervention and historical, clinical, and laboratory information will be obtained and they will receive instructions on completion of their second label (Demeclocycline). The bone biopsy will be obtained at Visit 3. Blood from Visits 1 and 2 will be stored at −80° C. and batch assayed at study completion. The data collection scheme by visit number is presented in FIG. 12.

Sources of Materials

The sources of research materials obtained from individually identifiable living human subjects will include blood, medical records, and transiliac bone biopsy cores. All patients in will have 3 visits. Clinical and laboratory data will be collected as outlined in FIG. 12 and includes: (1) assessment of medical, dietary and fracture history and physical activity levels; (2) blood (serum) for miRNAs; and (3) transiliac crest bone biopsy. Although these tests will be obtained for research purposes, results of transiliac crest bone biopsy will be made available to the treating physicians. Data from the above tests will be recorded in a study chart for each participant, which will be stored in a locked file cabinet in the primary investigator's locked office. Subject data will be de-identified and entered into a password secured database that will reside on a Departmental server and will be available only to investigators and key personnel directly involved in this research. All electronic data will be analyzed on password-protected, encrypted workstations. Only investigators directly involved in this research study will have access to subject identities. In addition, such data will be available to both IRBs and the sponsoring NIH Institute.

For the bone biopsy procedures, patients will receive pre-medication with oral lorazepam and diazepam for anxiety and amnesia and the underlying bone will be anesthetized with a mixed solution of 0.25% Marcaine and 1% lidocaine.

Quadruple label transiliac crest bone biopsy[71, 72]. Tetracycline Label 1 (Sumycin, 250 mg 4×/day for 3 days; 12-day holiday, 3 additional days) will be given prior to intervention and Tetracycline Label 2 (Demeclocycline 150 mg 4×/day for 3 days; 12-day holiday, 3 additional days) will be given to the patient 3 months after the intervention and prior to iliac crest bone biopsy. Specimens will be fixed in ethanol and shipped overnight for analysis Potential Benefits of the Proposed Research to Human Subjects and Others The main benefit of this study is the discovery of new and more accurate biomarkers of bone turnover that can be used to diagnose and guide ROD treatment. Participants will benefit by having a detailed assessment of CKD-mineral and bone disease, including biochemical assessment (PTH, Vitamin D, Phosphorus) and bone biopsy, the results of which will be made available to them and their physicians and may inform their clinical management.

Importance

The incidence and prevalence of CKD is rapidly growing and has become a worldwide epidemic. ROD affects almost all CKD patients and it is associated with increased susceptibility to fragility fracture, which in CKD patients is associated with a much higher risk of morbidity and mortality than for that of the general population. Treatment of ROD is based on bone turnover. However, establishing bone turnover type is a clinical challenge. Bone biopsy, the gold standard, is not practical to use in the clinic, and circulating levels of PTH, the clinical standards, is not accurate enough to provide a trustworthy assessment of turnover. Thus, treatment of ROD and prevention of fractures is greatly impeded by the lack of an accurate and simple to obtain biomarker of turnover. The protocol disclosed herein hypothesizes that miRNA expression signatures are specific to turnover-type and can be used to diagnose and guide treatment of ROD. miRNA expression signatures as accurate biomarkers of turnover can be used in disease management and be studied further. This could change the paradigm of ROD care and greatly advance the field of renal osteodystrophy diagnostics, treatment and drug development. The knowledge gained from this study should advance understanding of the role of miRNAs in bone turnover in CKD, potentially identify novel therapeutic targets for ROD treatment, and the ability to diagnose turnover non-invasively may facilitate future clinical trials evaluating novel drug therapies for ROD.

REFERENCES FOR EXAMPLE 3

1. Coresh J, Selvin E, Stevens L A, Manzi J, Kusek J W, Eggers P, Van Lente F, Levey A S. Prevalence of chronic kidney disease in the United States. JAMA. 2007; 298 (17):2038-47. doi: 10.1001/jama.298.17.2038. PubMed PMID: 17986697.
2. Spasovski G B, Bervoets A R, Behets G J, Ivanovski N, Sikole A, Dams G, Couttenye M M, De Broe M E, D'Haese P C. Spectrum of renal bone disease in end-stage renal failure patients not yet on dialysis. Nephrol Dial Transplant. 2003; 18(6):1159-66. PubMed PMID: 12748350.
3. Hamdy N A, Kanis J A, Beneton M N, Brown C B, Juttmann J R, Jordans J G, Josse S, Meyrier A, Lins R L, Fairey I T. Effect of alfacalcidol on natural course of renal bone disease in mild to moderate renal failure. BMJ. 1995; 310(6976):358-63. PubMed PMID: 7677827; PMCID: PMC2548761.
4. Coen G, Mazzaferro S, Bonucci E, Taggi F, Ballanti P, Bianchi A R, Donato G, Massimetti C, Smacchi A, Cinotti G A. Bone GLA protein in predialysis chronic renal failure. Effects of 1,25(OH)2D3 administration in a long-term follow-up. Kidney Int. 1985; 28(5):783-90. PubMed PMID: 3878905.
5. Malluche H H, Mawad H W, Monier-Faugere M C. Renal osteodystrophy in the first decade of the new millennium: analysis of 630 bone biopsies in black and white patients. J Bone Miner Res. 2011; 26(6):1368-76. doi: 10.1002/jbmr.309. PubMed PMID: 21611975; PMCID: PMC3312761.
6. Behets G J, Spasovski G, Sterling L R, Goodman W G, Spiegel D M, De Broe M E, D'Haese P C. Bone histomorphometry before and after long-term treatment with cinacalcet in dialysis patients with secondary hyperparathyroidism. Kidney Int. 2015; 87(4):846-56. doi: 10.1038/ki.2014.349. PubMed PMID: 25337774; PMCID: PMC4382689.

7. Nickolas T L, Stein E M, Dworakowski E, Nishiyama K K, Komandah-Kosseh M, Zhang C A, McMahon D J, Liu X S, Boutroy S, Cremers S, Shane E. Rapid cortical bone loss in patients with chronic kidney disease. J Bone Miner Res. 2013; 28(8):1811-20. doi: 10.1002/jbmr.1916. PubMed PMID: 23456850; PMCID: PMC3720694.
8. Nickolas T L, McMahon D J, Shane E. Relationship between Moderate to Severe Kidney Disease and Hip Fracture in the United States. J Am Soc Nephrol. 2006; 17(11):3223-32. PubMed PMID: 17005938.
9. Fried L F, Biggs M L, Shlipak M G, Seliger S, Kestenbaum B, Stehman-Breen C, Sarnak M, Siscovick D, Harris T, Cauley J, Newman A B, Robbins J. Association of kidney function with incident hip fracture in older adults. J Am Soc Nephrol. 2007; 18(1):282-6. PubMed PMID: 17167115.
10. Ball A M, Gillen D L, Sherrard D, Weiss N S, Emerson S S, Seliger S L, Kestenbaum B R, Stehman-Breen C. Risk of Hip Fracture Among Dialysis and Renal Transplant Recipients. JAMA: The Journal of the American Medical Association. 2002; 288(23):3014-8. PubMed PMID: 12479766.
11. Dooley A C, Weiss N S, Kestenbaum B. Increased risk of hip fracture among men with CKD. Am J Kidney Dis. 2008; 51(1):38-44. PubMed PMID: 18155531.
12. Naylor K L, McArthur E, Leslie W D, Fraser L A, Jamal S A, Cadarette S M, Pouget J G, Lok C E, Hodsman A B, Adachi J D, Garg A X. The three-year incidence of fracture in chronic kidney disease. Kidney Int. 2014. doi: 10.1038/ki.2013.547. PubMed PMID: 24429401.
13. Isakova T, Craven T E, Scialla J J, Nickolas T L, Schnall A, Barzilay J, Schwartz A V, Action to Control Cardiovascular Risk in Diabetes T. Change in estimated glomerular filtration rate and fracture risk in the Action to Control Cardiovascular Risk in Diabetes Trial. Bone. 2015; 78:23-7. doi: 10.1016/j.bone.2015.04.037. PubMed PMID: 25937184; PMCID: PMC4466209.
14. Go A S, Chertow G M, Fan D, McCulloch C E, Hsu C Y. Chronic kidney disease and the risks of death, cardiovascular events, and hospitalization. N Engl J Med. 2004; 351(13):1296-305. doi: 10.1056/NEJMoa041031. PubMed PMID: 15385656.
15. London G M, Marchais S J, Guerin A P, Metivier F. Arteriosclerosis, vascular calcifications and cardiovascular disease in uremia. Curr Opin Nephrol Hypertens. 2005; 14(6):525-31. PubMed PMID: 16205470.
16. London G M, Marchais S J, Guerin A P, Boutouyrie P, Metivier F, de Vernejoul M C. Association of bone activity, calcium load, aortic stiffness, and calcifications in ESRD. J Am Soc Nephrol. 2008; 19(9):1827-35. Epub 2008/05/16. doi: 10.1681/asn.2007050622. PubMed PMID: 18480316; PMCID: PMC2518431.
17. Kim S M, Long J, Montez-Rath M, Leonard M, Chertow G M. Hip Fracture in Patients with Non-Dialysis-Requiring Chronic Kidney Disease. J Bone Miner Res. 2016. Epub 2016/05/05. doi: 10.1002/jbmr.2862. PubMed PMID: 27145189.
18. Moe S, Drueke T, Cunningham J, Goodman W, Martin K, Olgaard K, Ott S, Sprague S, Lameire N, Eknoyan G, Kidney Disease: Improving Global O. Definition, evaluation, and classification of renal osteodystrophy: a position statement from Kidney Disease: Improving Global Outcomes (KDIGO). Kidney Int. 2006; 69(11):1945-53. doi: 10.1038/sj.ki.5000414. PubMed PMID: 16641930.
19. Chapter 1: Introduction and definition of CKD-MBD and the development of the guideline statements. Kidney Int. 2009; 76(S113):S3-S8.
20. Sprague S M, Bellorin-Font E, Jorgetti V, Carvalho A B, Malluche H H, Ferreira A, D'Haese P C, Drueke T B, Du H, Manley T, Rojas E, Moe S M. Diagnostic Accuracy of Bone Turnover Markers and Bone Histology in Patients With CKD Treated by Dialysis. Am J Kidney Dis. 2015. doi: 10.1053/j.ajkd.2015.06.023. PubMed PMID: 26321176.
21. Eguchi T, Watanabe K, Hara E S, Ono M, Kuboki T, Calderwood S K. OstemiR: A Novel Panel of MicroRNA Biomarkers in Osteoblastic and Osteocytic Differentiation from Mesencymal Stem Cells. PLoS ONE. 2013; 8(3): e58796. doi: 10.1371/journal.pone.0058796. PubMed PMID: 23533592; PMCID: PMC3606401.
22. Balderman J A, Lee H Y, Mahoney C E, Handy D E, White K, Annis S, Lebeche D, Hajjar R J, LoscalzoJ, Leopold J A. Bone morphogenetic protein-2 decreases microRNA-30b and microRNA-30c to promote vascular smooth muscle cell calcification. Journal of the American Heart Association. 2012; 1(6):e003905. Epub 2013/01/15. doi: 10.1161/jaha.112.003905. PubMed PMID: 23316327; PMCID: PMC3540659.
23. Slatopolsky E, Delmez, J. Renal Osteodystrophy. In: Coe F L, and Favus, M. J., editor. Disorders of Bone and Mineral Metabolism. New York: Raven Press; 1992. p. 905-34.
24. Toussaint N D, Lau K K, Strauss B J, Polkinghorne K R, Kerr P G. Associations between vascular calcification, arterial stiffness and bone mineral density in chronic kidney disease. Nephrol Dial Transplant. 2008; 23(2): 586-93. doi: 10.1093/ndt/gfm660. PubMed PMID: 17933842.
25. London G M, Marty C, Marchais S J, Guerin A P, Metivier F, de Vernejoul M C. Arterial calcifications and bone histomorphometry in end-stage renal disease. J Am Soc Nephrol. 2004; 15(7):1943-51. PubMed PMID: 15213285.
26. Adragao T, Herberth J, Monier-Faugere M C, Branscum A J, Ferreira A, Frazao J M, Dias Curto J, Malluche H H. Low bone volume—a risk factor for coronary calcifications in hemodialysis patients. Clin J Am Soc Nephrol. 2009; 4(2):450-5. Epub 2009/01/23. doi: 10.2215/cjn.01870408. PubMed PMID: 19158372; PMCID: PMC2637600
27. Kurz P, Monier-Faugere M C, Bognar B, Werner E, Roth P, Vlachojannis J, Malluche H H. Evidence for abnormal calcium homeostasis in patients with adynamic bone disease. Kidney Int. 1994; 46(3):855-61. Epub 1994/09/01. PubMed PMID: 7996807.
28. Alem A M, Sherrard D J, Gillen D L, Weiss N S, Beresford S A, Heckbert S R, Wong C, Stehman-Breen C. Increased risk of hip fracture among patients with end-stage renal disease. Kidney Int. 2000; 58(1):396-9. doi: 10.1046/j.1523-1755.2000.00178.x. PubMed PMID: 10886587.
29. London G, Coyne D, Hruska K, Malluche H H, Martin K J. The new kidney disease: improving global outcomes (KDIGO) guidelines—expert clinical focus on bone and vascular calcification. Clin Nephrol. 2010; 74(6):423-32. PubMed PMID: 21084045; PMCID: PMC3770279.
30. Jamal S A, Ljunggren O, Stehman-Breen C, Cummings S R, McClung M R, Goemaere S, Ebeling P R, Franek E, Yang Y C, Egbuna O I, Boonen S, Miller P D. Effects of denosumab on fracture and bone mineral density by level of kidney function. J Bone Miner Res. 2011; 26(8):1829-35. Epub 2011/04/15. doi: 10.1002/jbmr.403. PubMed PMID: 21491487.

31. Ishani A, Blackwell T, Jamal S A, Cummings S R, Ensrud K E, Investigators M. The effect of raloxifene treatment in postmenopausal women with CKD. J Am Soc Nephrol. 2008; 19(7):1430-8. doi: 10.1681/ASN.2007050555. PubMed PMID: 18400939; PMCID: PMC2440292.
32. Jamal S A, Bauer D C, Ensrud K E, Cauley J A, Hochberg M, Ishani A, Cummings S R. Alendronate Treatment in Women with Normal to Severely Impaired Renal Function: An Analysis of the Fracture Intervention Trial*. J Bone Miner Res. 2007. PubMed PMID: 17243862.
33. Miller P D, Schwartz E N, Chen P, Misurski D A, Krege J H. Teriparatide in postmenopausal women with osteoporosis and mild or moderate renal impairment. Osteoporos Int. 2007; 18(1):59-68. PubMed PMID: 17013567.
34. Miller P D, Roux C, Boonen S, Barton I P, Dunlap L E, Burgio D E. Safety and efficacy of risedronate in patients with age-related reduced renal function as estimated by the cockcroft and gault method: a pooled analysis of nine clinical trials. J Bone Miner Res. 2005; 20(12):2105-15. PubMed PMID: 16294264.
35. Cejka D, Benesch T, Krestan C, Roschger P, Klaushofer K, Pietschmann P, Haas M. Effect of teriparatide on early bone loss after kidney transplantation. Am J Transplant. 2008; 8(9):1864-70. doi: 10.1111/j.1600-6143.2008.02327.x. PubMed PMID: 18786230.
36. Cejka D, Kodras K, Bader T, Haas M. Treatment of Hemodialysis-Associated Adynamic Bone Disease with Teriparatide (PTH1-34): A Pilot Study. Kidney & blood pressure research. 2010; 33(3):221-6. doi: 10.1159/000316708. PubMed PMID: 20588059.
37. Palcu P, Dion N, Ste-Marie L G, Goltzman D, Radziunas I, Miller P D, Jamal S A. Teriparatide and bone turnover and formation in a hemodialysis patient with low-turnover bone disease: a case report. Am J Kidney Dis. 2015; 65(6):933-6. doi: 10.1053/j.ajkd.2015.01.025. PubMed PMID: 25843705.
38. Sumida K, Ubara Y, Hoshino J, Mise K, Hayami N, Suwabe T, Kawada M, Imafuku A, Hiramatsu R, Hasegawa E, Yamanouchi M, Sawa N, Takaichi K. Once-weekly teriparatide in hemodialysis patients with hypoparathyroidism and low bone mass: a prospective study. Osteoporosis International. 2016; 27(4):1441-50. doi: 10.1007/s00198-015-3377-6. PubMed PMID: 26525045.
39. Block G A, Bone H G, Fang L, Lee E, Padhi D. A single-dose study of denosumab in patients with various degrees of renal impairment. J Bone Miner Res. 2012; 27(7):1471-9. doi: 10.1002/jbmr.1613. PubMed PMID: 22461041; PMCID: PMC3505375
40. Coco M, Rush H. Increased incidence of hip fractures in dialysis patients with low serumparathyroid hormone. Am J Kidney Dis. 2000; 36(6):1115-21. PubMed PMID: 11096034.
41. Davies M R, Lund R J, Mathew S, Hruska K A. Low turnover osteodystrophy and vascular calcification are amenable to skeletal anabolism in an animal model of chronic kidney disease and the metabolic syndrome. J Am Soc Nephrol. 2005; 16(4):917-28. doi: 10.1681/ASN.2004100835. PubMed PMID: 15743994.
42. Barreto D V, Barreto Fde C, Carvalho A B, Cuppari L, Draibe S A, Dalboni M A, Moyses R M, Neves K R, Jorgetti V, Miname M, Santos R D, Canziani M E. Association of changes in bone remodeling and coronary calcification in hemodialysis patients: a prospective study. Am J Kidney Dis. 2008; 52(6):1139-50. doi: 10.1053/j.ajkd.2008.06.024. PubMed PMID: 18824289.
43. Bakhshandeh B, Soleimani M, Hafizi M, Paylakhi S H, Ghaemi N. MicroRNA signature associated with osteogenic lineage commitment. Molecular Biology Reports. 2012; 39(7):7569-81. doi: 10.1007/s11033-012-1591-2. PubMed PMID: 22350160.
44. Hu R, Liu W, Li H, Yang L, Chen C, Xia Z-Y, Guo L-J, Xie H, Zhou H-D, Wu X-P, Luo X-H. A Runx2/miR-3960/miR-2861 Regulatory Feedback Loop during Mouse Osteoblast Differentiation. Journal of Biological Chemistry. 2011; 286(14):12328-39. doi: 10.1074/jbc.M110.176099.
45. Lian J B, Stein G S, van Wijnen A J, Stein J L, Hassan M Q, Gaur T, Zhang Y. MicroRNA control of bone formation and homeostasis. Nat Rev Endocrinol. 2012; 8(4):212-27. doi: 10.1038/nrendo.2011.234. PubMed PMID: 22290358; PMCID: PMC3589914.
46. van Wijnen A J, van de Peppel J, van Leeuwen J P, Lian J B, Stein G S, Westendorf J J, Oursler M-J, Im H-J, Taipaleenmaki H, Hesse E, Riester S, Kakar S. MicroRNA Functions in Osteogenesis and Dysfunctions in Osteoporosis. Current Osteoporosis Reports. 2013; 11(2):72-82. doi: 10.1007/s11914-013-0143-6. PubMed PMID: 23605904; PMCID: PMC3678273.
47. Kagiya T, Nakamura S. Expression profiling of microRNAs in RAW264.7 cells treated with a combination of tumor necrosis factor alpha and RANKL during osteoclast differentiation. J Periodontal Res. 2013; 48(3):373-85. doi: 10.1111/jre.12017. PubMed PMID: 23078176.
48. An J H, Ohn J H, Song J A, Yang J Y, Park H, Choi H J, Kim S W, Kim S Y, Park W Y, Shin C S. Changes of microRNA profile and microRNA-mRNA regulatory network in bones of ovariectomized mice. J Bone Miner Res. 2014; 29(3):644-56. doi: 10.1002/jbmr.2060. PubMed PMID: 23929739.
49. Garmilla-Ezquerra P, Sañudo C, Delgado-Calle J, Pérez-Nuñez M I, Sumillera M, Riancho J A. Analysis of the Bone MicroRNome in Osteoporotic Fractures. Calcified tissue international. 2015; 96(1):30-7. doi: 10.1007/s00223-014-9935-7. PubMed PMID: 25432767.
50. Seeliger C, Karpinski K, Haug A T, Vester H, Schmitt A, Bauer J S, van Griensven M. Five freely circulating miRNAs and bone tissue miRNAs are associated with osteoporotic fractures. J Bone Miner Res. 2014; 29(8):1718-28. Epub 2014/01/17. doi: 10.1002/jbmr.2175. PubMed PMID: 24431276.
51. Heilmeier U, Hackl M, Skalicky S, Weilner S, Schroeder F, Vierlinger K, Patsch J M, Baum T, Oberbauer E, Lobach I, Burghardt A J, Schwartz A V, Grillari J, Link T M. Serum miRNA Signatures Are Indicative of Skeletal Fractures in Postmenopausal Women With and Without Type 2 Diabetes and Influence Osteogenic and Adipogenic Differentiation of Adipose Tissue-Derived Mesenchymal Stem Cells In Vitro. J Bone Miner Res. 2016; 31(12):2173-92. Epub 2016/06/28. doi: 10.1002/jbmr.2897. PubMed PMID: 27345526.
52. Weilner S, Skalicky S, Salzer B, Keider V, Wagner M, Hildner F, Gabriel C, Dovjak P, Pietschmann P, Grillari-Voglauer R, Grillari J, Hackl M. Differentially circulating miRNAs after recent osteoporotic fractures can influence osteogenic differentiation. Bone. 2015; 79:43-51. Epub 2015/06/01. doi: 10.1016/j.bone.2015.05.027. PubMed PMID: 26026730.
53. Jeong S, Oh J M, Oh K H, Kim I W. Differentially expressed miR-3680-5p is associated with parathyroid hormone regulation in peritoneal dialysis patients. PLoS One. 2017; 12(2):e0170535. doi: 10.1371/journal.pone.0170535. PubMed PMID: 28152049.

54. M'Baya-Moutoula E, Louvet L, Metzinger-Le Meuth V, Massy Z A, Metzinger L. High inorganic phosphate concentration inhibits osteoclastogenesis by modulating miR-223. Biochimica et biophysica acta. 2015; 1852(10 Pt A):2202-12. doi: 10.1016/j.bbadis.2015.08.003. PubMed PMID: 26255635.
55. Nickolas T L, Cremers S, Zhang A, Thomas V, Stein E, Cohen A, Chauncey R, Nikkel L, Yin M T, Liu X S, Boutroy S, Staron R B, Leonard M B, McMahon D J, Dworakowski E, Shane E. Discriminants of prevalent fractures in chronic kidney disease. J Am Soc Nephrol. 2011; 22(8):1560-72. Epub 2011/07/26. doi: ASN.2010121275 [pii] 10.1681/ASN.2010121275. PubMed PMID: 21784896; PMCID: PMC3148711
56. Nickolas T L, Stein E, Cohen A, Thomas V, Staron R B, McMahon D J, Leonard M B, Shane E. Bone mass and microarchitecture in CKD patients with fracture. J Am Soc Nephrol. 2010; 21(8):1371-80. Epub 2010/04/17. doi: ASN.2009121208 [pii] 10.1681/ASN.2009121208. PubMed PMID: 20395370; PMCID: PMC2938588.
57. Chaturvedi P, Chen N X, O'Neill K, McClintick J N, Moe S M, Janga S C. Differential miRNA Expression in Cells and Matrix Vesicles in Vascular Smooth Muscle Cells from Rats with Kidney Disease. PLoS One. 2015; 10(6):e0131589. doi: 10.1371/journal.pone.0131589. PubMed PMID: 26115487; PMCID: PMC4482652.
58. Chen N X, Kiattisunthorn K, O'Neill K D, Chen X, Moorthi R N, Gattone V H, 2nd, Allen M R, Moe S M. Decreased microRNA is involved in the vascular remodeling abnormalities in chronic kidney disease (CKD). PLoS One. 2013; 8(5):e64558. doi: 10.1371/journal-.pone.0064558. PubMed PMID: 23717629; PMCID: PMC3661525.
59. DeLong E R, DeLong D M, Clarke-Pearson D L. Comparing the areas under two or more correlated receiver operating characteristic curves: a nonparametric approach. Biometrics. 1988; 44(3):837-45. PubMed PMID: 3203132.
60. Griffiths-Jones S, Saini H K, van Dongen S, Enright A J. miRBase: tools for microRNA genomics. Nucleic Acids Res. 2008; 36 (Database issue):D154-8. doi: 10.1093/nar/gkm952. PubMed PMID: 17991681; PMCID: PMC2238936.
61. Lewis B P, Shih I H, Jones-Rhoades M W, Bartel D P, Burge C B. Prediction of mammalian microRNA targets. Cell. 2003; 115(7):787-98. PubMed PMID: 14697198.
62. Sethupathy P, Corda B, Hatzigeorgiou A G. TarBase: A comprehensive database of experimentally supported animal microRNA targets. RNA. 2006; 12(2):192-7. doi: 10.1261/rna.2239606. PubMed PMID: 16373484; PMCID: PMC1370898.
63. Subramanian A, Tamayo P, Mootha V K, Mukherjee S, Ebert B L, Gillette M A, Paulovich A, Pomeroy S L, Golub T R, Lander E S, Mesirov J P. Gene set enrichment analysis: a knowledge-based approach for interpreting genome-wide expression profiles. Proc Natl Acad Sci USA. 2005; 102(43):15545-50. doi: 10.1073/pnas.0506580102. PubMed PMID: 16199517; PMCID: PMC1239896.
64. Subramanian A, Kuehn H, Gould J, Tamayo P, Mesirov J P. GSEA-P: a desktop application for Gene Set Enrichment Analysis. Bioinformatics. 2007; 23(23):3251-3. doi: 10.1093/bioinformatics/btm369. PubMed PMID: 17644558.
65. Ferreira A, Frazao J M, Monier-Faugere M C, Gil C, Galvao J, Oliveira C, Baldaia J, Rodrigues I, Santos C, Ribeiro S, Hoenger R M, Duggal A, Malluche H H. Effects of sevelamer hydrochloride and calcium carbonate on renal osteodystrophy in hemodialysis patients. J Am Soc Nephrol. 2008; 19(2):405-12. PubMed PMID: 18199805; PMCID: PMC2396748
66. Malluche H H, Monier-Faugere M C, Wang G, Fraza O J, Charytan C, Coburn J W, Coyne D W, Kaplan M R, Baker N, McCary L C, Turner S A, Goodman W G. An assessment of cinacalcet HCl effects on bone histology in dialysis patients with secondary hyperparathyroidism. Clin Nephrol. 2008; 69(4):269-78. PubMed PMID: 18397701.
67. Monier-Faugere M C, Mawad H, Qi Q, Friedler R M, Malluche H H. High prevalence of low bone turnover and occurrence of osteomalacia after kidney transplantation. J Am Soc Nephrol. 2000; 11(6):1093-9. Epub 2000/05/23. PubMed PMID: 10820173.
68. Coco M, Pullman J, Cohen H W, Lee S, Shapiro C, Solorzano C, Greenstein S, Glicklich D. Effect of risedronate on bone in renal transplant recipients. J Am Soc Nephrol. 2012; 23(8):1426-37. doi: 10.1681/ASN.2011060623. PubMed PMID: 22797188; PMCID: PMC3402282.
69. Coco M, Glicklich D, Faugere M C, Burris L, Bognar I, Durkin P, Tellis V, Greenstein S, Schechner R, Figueroa K, McDonough P, Wang G, Malluche H. Prevention of bone loss in renal transplant recipients: a prospective, randomized trial of intravenous pamidronate. J Am Soc Nephrol. 2003; 14(10):2669-76. Epub 2003/09/30. PubMed PMID: 14514747.
70. Chan H W, Chu K H, Fung S K, Tang H L, Lee W, Cheuk A, Yim K F, Tong M K, Lee K C. Prospective study on dialysis patients after total parathyroidectomy without autoimplant. Nephrology. 2010; 15(4):441-7. doi: 10.1111/j.1440-1797.2009.01257.x. PubMed PMID: 20609096.
71. Lindsay R, Cosman F, Zhou H, Bostrom M P, Shen V W, Cruz J D, Nieves J W, Dempster D W. Anovel tetracycline labeling schedule for longitudinal evaluation of the short-term effects of anabolic therapy with a single iliac crest bone biopsy: early actions of teriparatide. J Bone Miner Res. 2006; 21(3):366-73. doi: 10.1359/JBMR.051109. PubMed PMID: 16491283.
72. Rubin M, Dempster D, Sliney J, Zhou H, Nickolas T, Stein E, Dworakowski E, Dellabadia M, Ives R, McMahon D, Zhang C, Silverberg S, Shane E, Cremers S, Bilezikian J. PTH(1-84) administration reverses abnormal bone remodeling dynamics and structure in hypoparathyroidism. J Bone Miner Res. 2011. Epub 2011/07/08. doi: 10.1002/jbmr.452. PubMed PMID: 21735476; PMCID: PMC4019384.
73. Bervoets A R, Spasovski G B, Behets G J, Dams G, Polenakovic M H, Zafirovska K, Van H V, De Broe M E, D'Haese P C. Useful biochemical markers for diagnosing renal osteodystrophy in predialysis end-stage renal failure patients. Am J Kidney Dis. 2003; 41(5):997-1007. PubMed PMID: 12722034.
74. Schafer H. Efficient confidence bounds for ROC curves. Stat Med. 1994; 13(15):1551-61. PubMed PMID: 7973233.
75. Hajian-Tilaki K. Sample size estimation in diagnostic test studies of biomedical informatics. Journal of biomedical informatics. 2014; 48:193-204. doi: 10.1016/j.jbi.2014.02.013. PubMed PMID: 24582925.

Example 4—A microRNA Approach to Diagnosing Renal Osteodystrophy

CKD-Mineral and Bone Disease (CKD-MBD)

More than 1 in 10 Americans have chronic kidney disease. CKD-MBD affects nearly all CKD patients and encompasses disorders of:

Skeleton

Parathyroid—Vitamin D Axis

Calcium—Phosphate mineral metabolism

Soft tissue calcification

Compared to the general population, CKD-MBD is associated with up to 17-fold increased risk of fractures, 1.4-fold increased risk of cardiovascular (CV) disease, and 3- and 10-fold greater mortality risk after fractures and CV events.

Renal Osteodystrophy (ROD) is the skeletal component of CKD-MBD. It is defined by disorders in bone turnover, mineralization and volume. In ROD, bone turnover, mineralization and volume can be low, normal or high.

ROD management is based on Turnover and Mineralization. ROD management can include suppressing high turnover with vitamin D receptor analogs and/or calcimimetics. ROD management can also include avoiding the development of low turnover that can be induced by the same agents that treat high turnover.

Methods to diagnose turnover in ROD are sub-optimal. The gold standard is TCN double label iliac crest bone biopsy, which is invasive, expensive, time-consuming and available at only several centers worldwide. Parathyroid Hormone (PTH) and Bone Specific Alkaline Phosphatase (BSAP) are recommended by KDIGO but have moderate diagnostic accuracy:

AUC Low from Non-Low intact PTH 0.701 (0.653-0.750)

BSAP 0.757 (0.713-0.801)

AUC High from Non-High

Intact PTH 0.724 (0.663-0.786)

BSAP 0.711 (0.611-0.767)

New ROD diagnostic methods are needed such as microRNAs (miRs). miRs are small and non-coding, consisting of about 22 nucleotides. miRs bind the 3'-untranslated region of mRNAs, thus, they can inhibit gene translation and promote mRNA degradation. Single miRs can target up to 100 distinct mRNAs from different genes and can orchestrate expression of entire networks regulating systems biology. miRs are highly stable in blood due to complexes formed with proteins and lipids. There are clinical trials for liver disease and cancer involving Miravirsen, MRX34.

miRs are involved in bone regulation by affecting osteoblast and osteoclast development. 80 unique miRs have been found associated with BMD, fractures and osteoporosis in human studies. miR profiles change in response to osteoporosis treatments (i.e., teriparatide, denosumab). Associations with renal osteodystrophy have not been studied.

Without being bound by theory, it is described herein that miR expression levels would correlate with bone turnover and would be superior to clinically used protein biomarkers for discriminating low and high bone turnover.

Methods—Study Design and Histomorphometry. Cross sectional study of 24 patients with CKD: TCN double labeled transiliac crest bone biopsy and bio-banked blood at −80° C. Bone turnover status: Bone Formation Rate/Bone Surface (BFR/BS) and Adjusted Apposition Rate (Adj.A.R.), remodeling indices were tertiled to define low, normal or high turnover.

Methods—Assays. Four a priori selected miRs that regulate bone cell development:

Osteoblast Development: miR-30b, 30c, 125b;

Osteoclast Development: miR-155;

Total RNA from human serum were isolated using miRNeasy Mini Kit (Qiagen);

Levels of miRs determined by real time PCR using TaqMan miRNA Assays (Applied Biosystems);

$\Delta\Delta C_T$ method was used to analyze the relative changes in miR levels and normalized by U6, a non-human ubiquitous miR.

Serologic markers include:

CKD-MBD: Intact PTH and BSAP

Formation: Procollagen of type-1 N-terminal propeptide (P1NP), Osteocalcin

Resorption: C-terminal telopeptide of type 1 collagen (CTX), Tartrate resistant acid phosphatase 5b (Trab5b)

In some embodiments, the serologic markers were analyzed using Roche Elecsys 2010 analyzer (Roche Diagnostics, Indianapolis, IN).

Figure 16B:
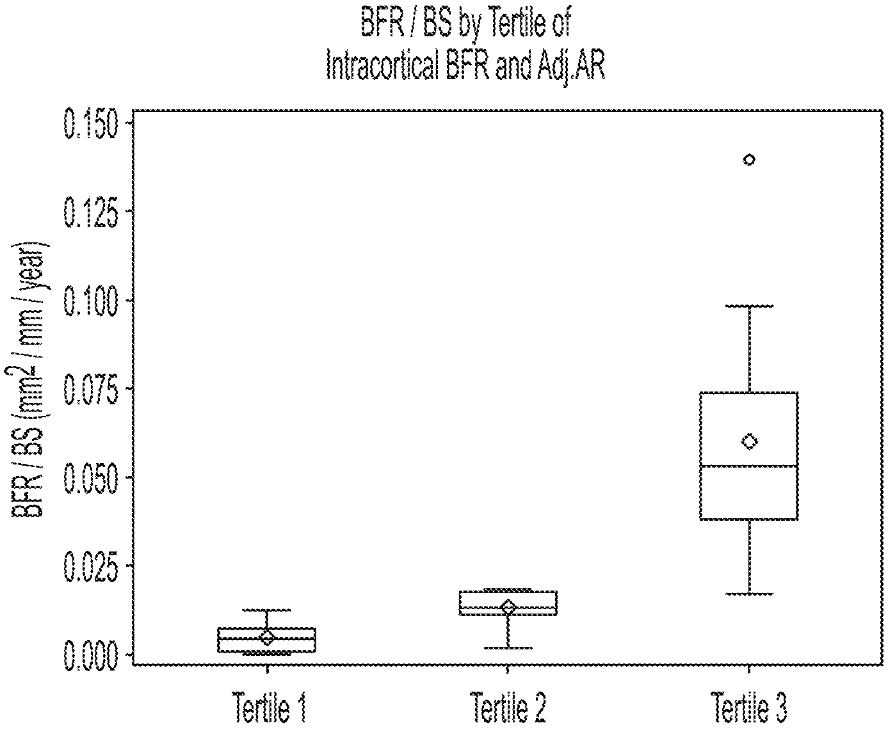

Cohort characteristics and bone turnover are described in FIGS. 16A-B. Cohort characteristics are described in FIG. 16A. Bone turnover is described in FIG. 16B.

Figure 17A:
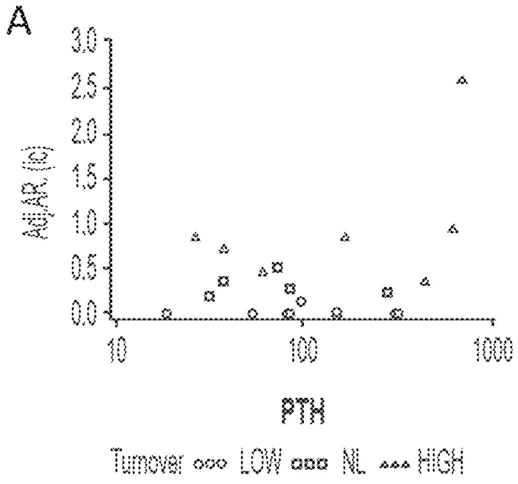
FIGS. 17A-B show scatter plots of Adj.A.R. and PTH, BSAP.
Figure 17B:
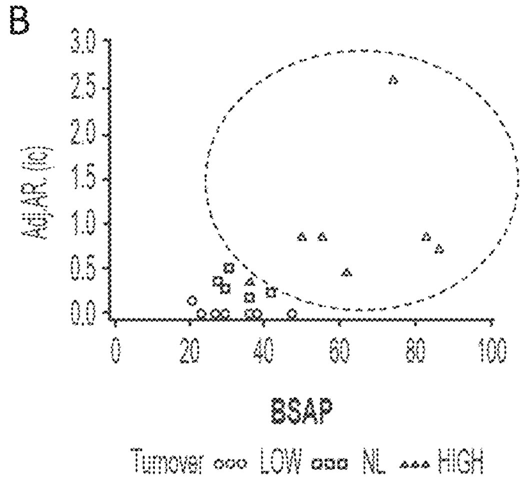

Scatter plots of Adj.A.R. and PTH, BSAP are shown in FIGS. 17A-B. FIG. 17A shows a scatter plot of Adj.A.R. and PTH. FIG. 17B shows a scatter plot of Adj.A.R. and BSAP. PTH levels neither correlated with nor differed by Adj.A.R. BSAP levels correlated with (p 0.52; $p<0.02$) and was higher with higher Adj.A.R. ($p<0.05$).

Figure 18A:
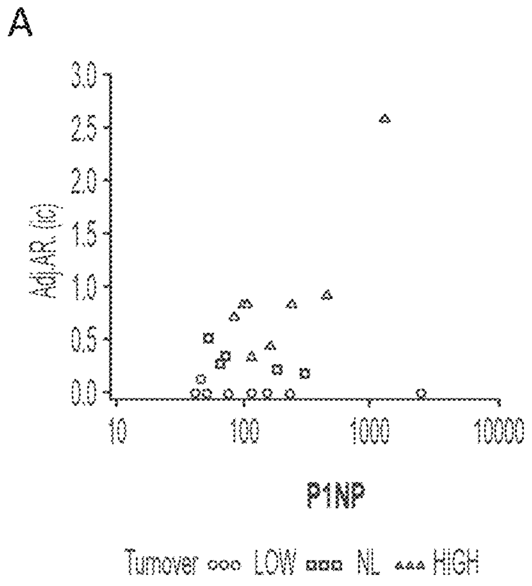
FIGS. 18A-B show scatter plots of Adj.A.R. and Bone Formation Markers.
Figure 18B:
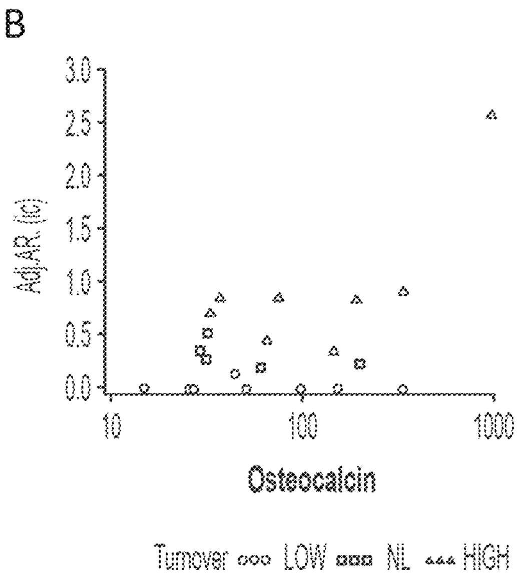

Scatter Plots of Adj.A.R. and bone formation markers are shown in FIGS. 18A-B. FIG. 18A shows a scatter plot of Adj.A.R. and P1NP. FIG. 18B shows a scatter plot of Adj.A.R. and osteocalcin. P1NP and osteocalcin levels neither correlated with nor differed by Adj.A.R.

Figure 19A:
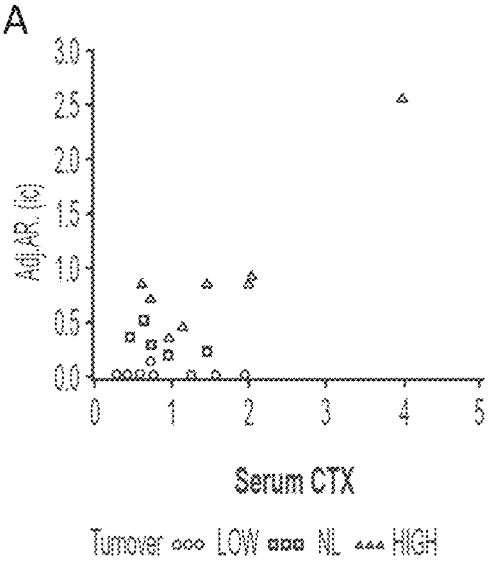
FIGS. 19A-B show scatter plots of Adj.A.R. and Bone Resorption Markers.
Figure 19B:
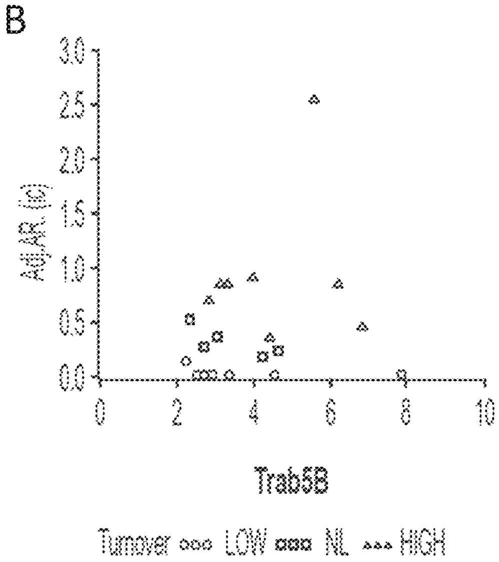

Scatter plots of Adj.A.R. and bone resorption markers are shown in FIGS. 19A-B. CTX and Trap-5b levels neither correlated with nor differed by Adj.A.R. FIG. 19A show a scatter plot of Adj.A.R. and serum CTX. FIG. 19B shows a scatter plot of Adj.A.R. and Trab5B.

Figure 20A:
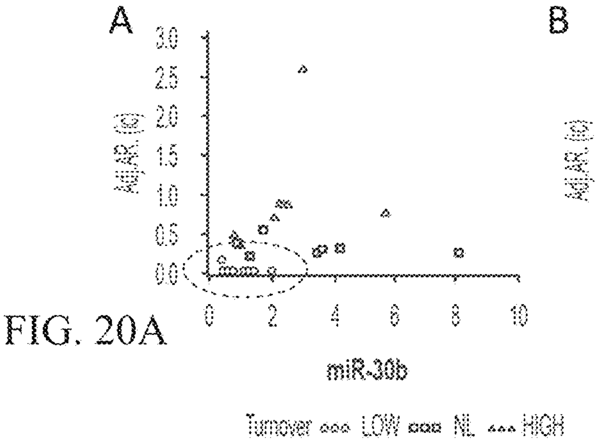
FIGS. 20A-C scatter plots of Adj.A.R. and miRs affecting osteoblast development.
Figure 20B:
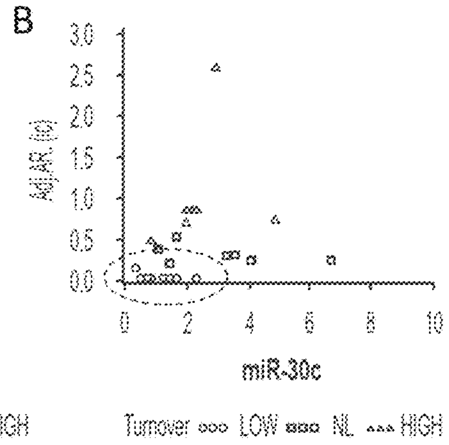
Figure 20C:
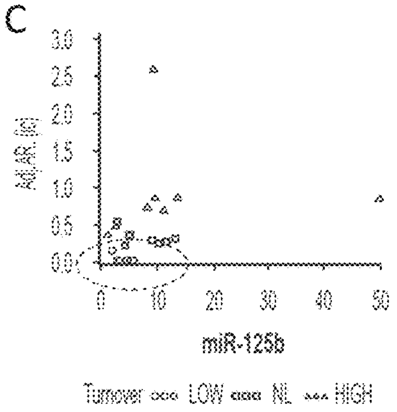

Scatter plots of Adj.A.R. and miRs affecting osteoblast development are shown in FIGS. 20A-C. miRs are correlated with Adj. A.R. (p 0.50, 0.42, 0.49; $p<0.05$ for all) and are lower in patients with the lowest compared to higher levels of Adj.A.R. ($p<0.05$ for all comparisons). FIG. 20A shows a scatter plot of Adj.A.R. and miR-30b. FIG. 20B shows a scatter plot of Adj.A.R. and miR-30c. FIG. 20C shows a scatter plot of Adj.A.R. and miR-125b.

Figure 21:
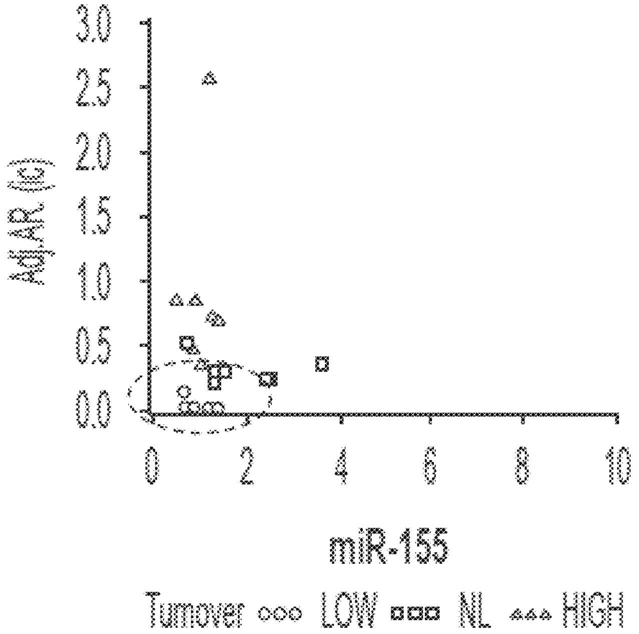
FIG. 21 shows a scatter plot of Adj.A.R. and miR affecting osteoclast development.

Scatter plot of Adj.A.R. and miR affecting osteoclast development is shown in FIG. 21. miR-155 did not correlate with Adj.A.R. mir-155 is significantly lower in patients with the lowest compared to higher levels of Adj.A.R. ($p<0.05$).

Figure 22A:
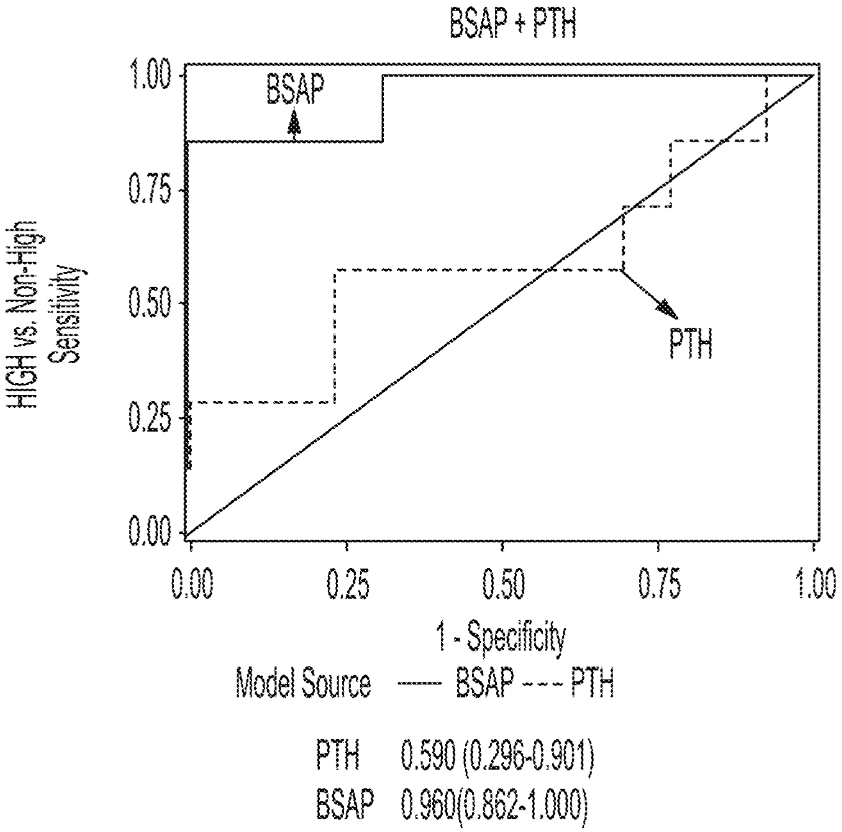
FIGS. 22A-C show discrimination of high vs. non-high turnover as defined by BFR/BS and Adj.A.R.
Figure 22B:
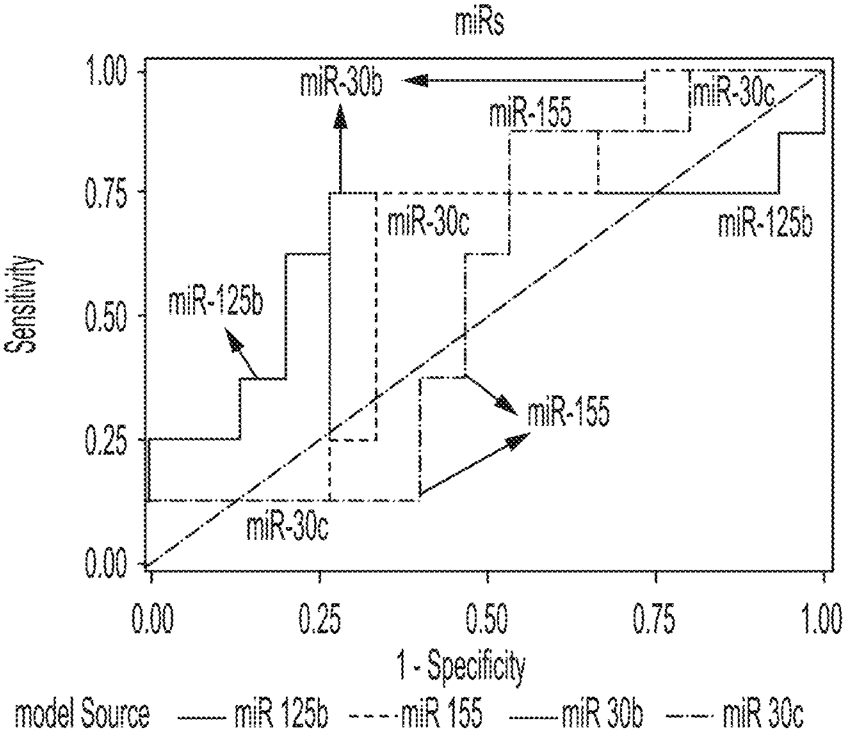
Figure 22C:
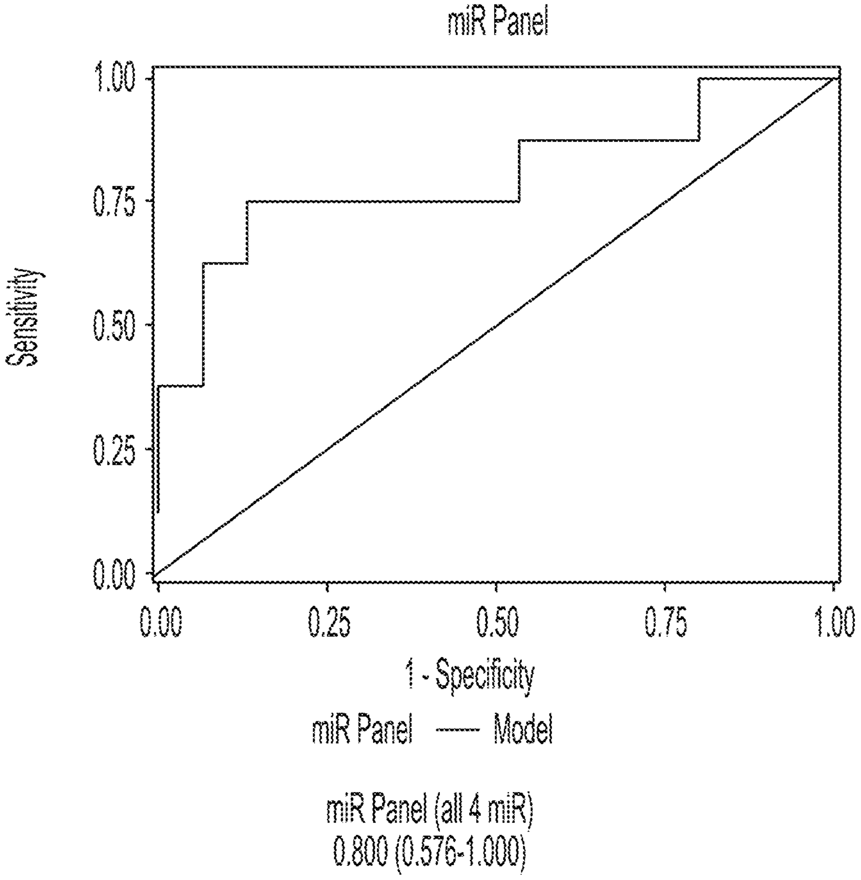

Discrimination of high vs. non-high turnover as defined by BFR/BS and Adj.A.R. is shown in FIGS. 22A-C. FIG. 22A shows BSAP and PTH. FIG. 22B shows different miRs. FIG. 22C shows a miR panel including all four miRs.

Figure 23A:
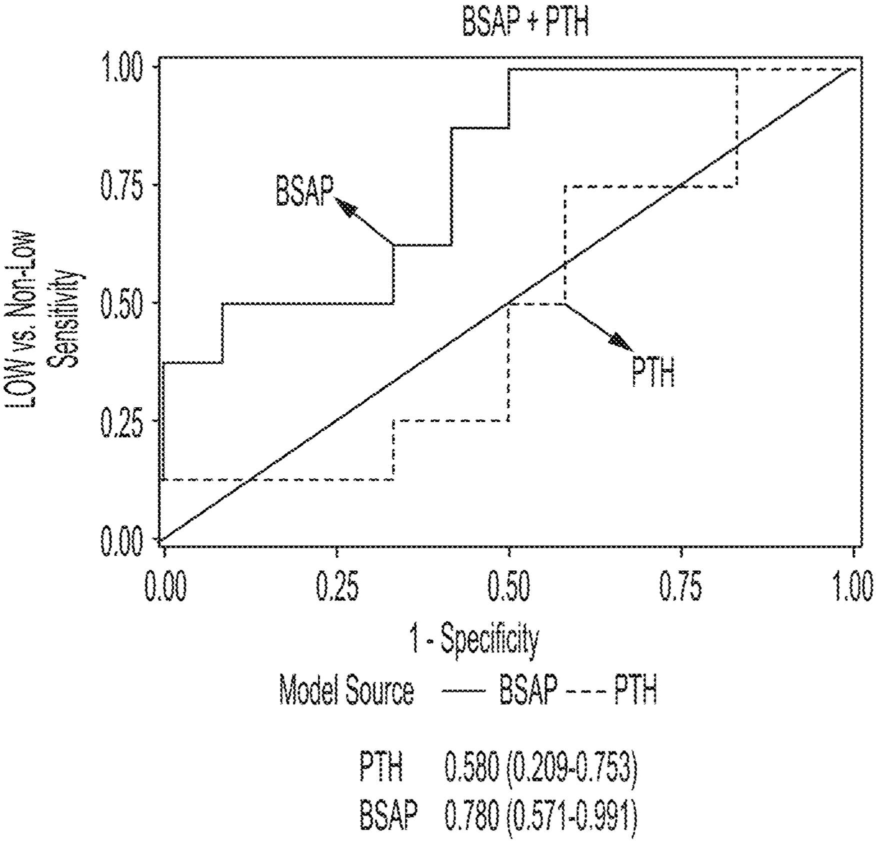
FIGS. 23A-C show a discrimination of low vs. non-low turnover as defined by BFR/BS and Adj.A.R.
Figure 23B:
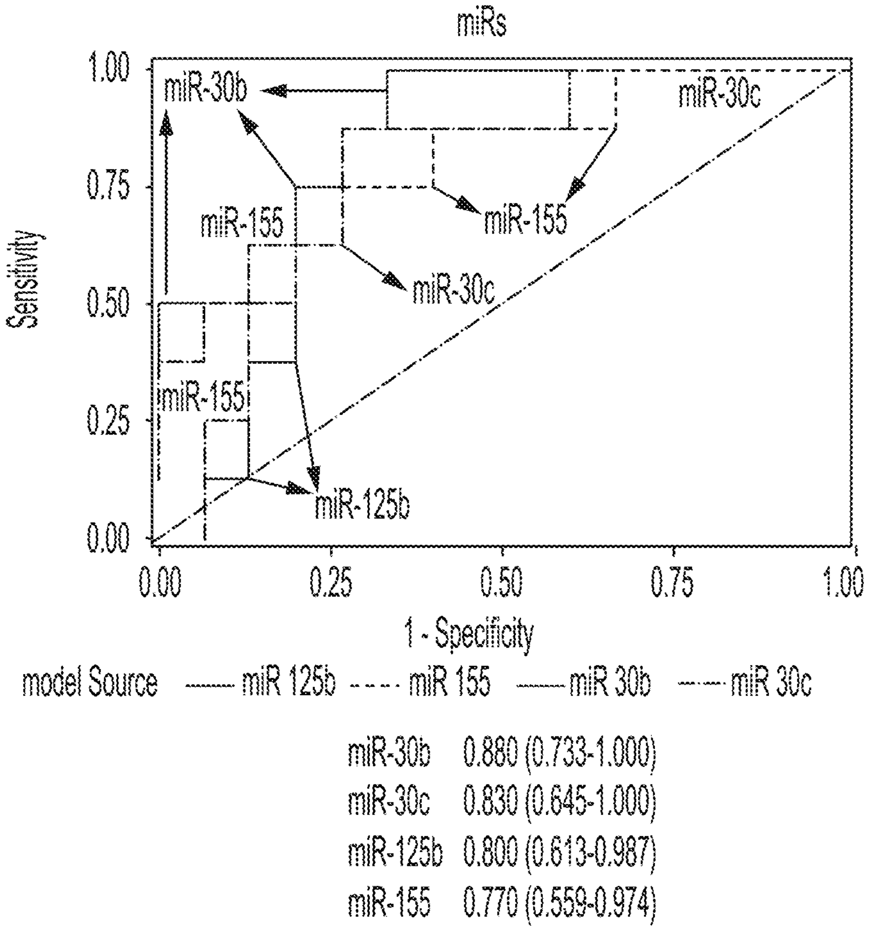
Figure 23C:
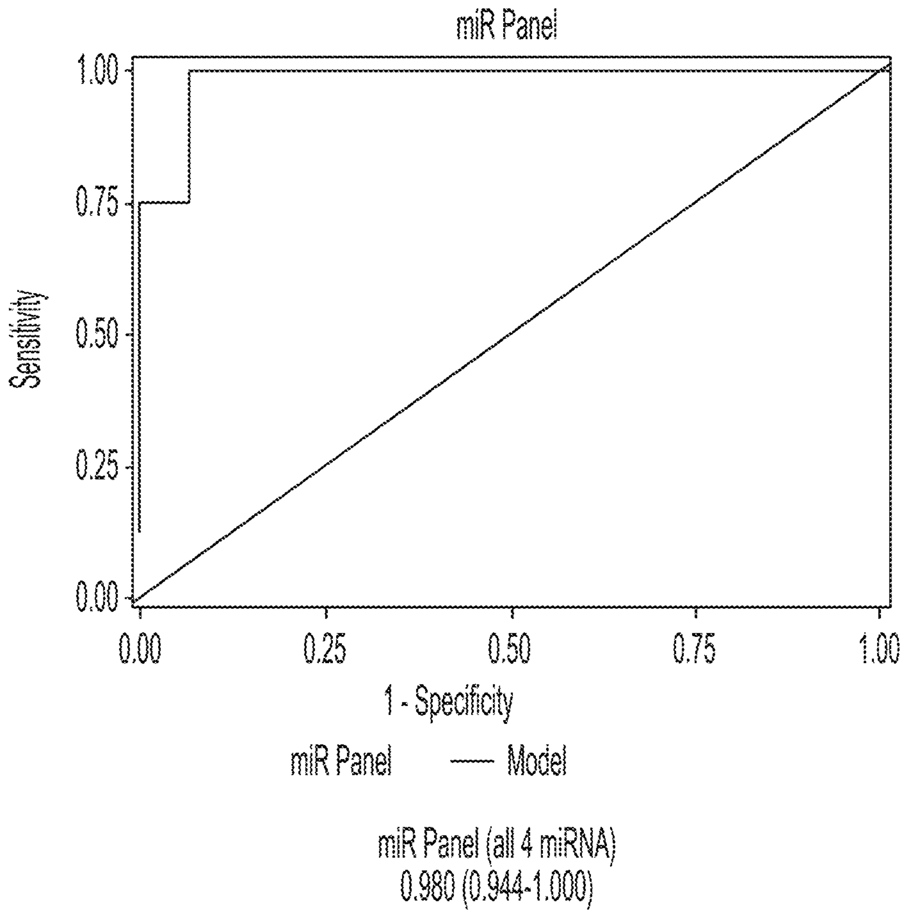

Discrimination of low vs. non-low turnover as defined by BFR/BS and Adj.A.R. is shown in FIGS. 23A-C. FIG. 23A shows BSAP and PTH. FIG. 23B shows different miRs. FIG. 23C shows a miR panel including all four miRs.

Figure 24:
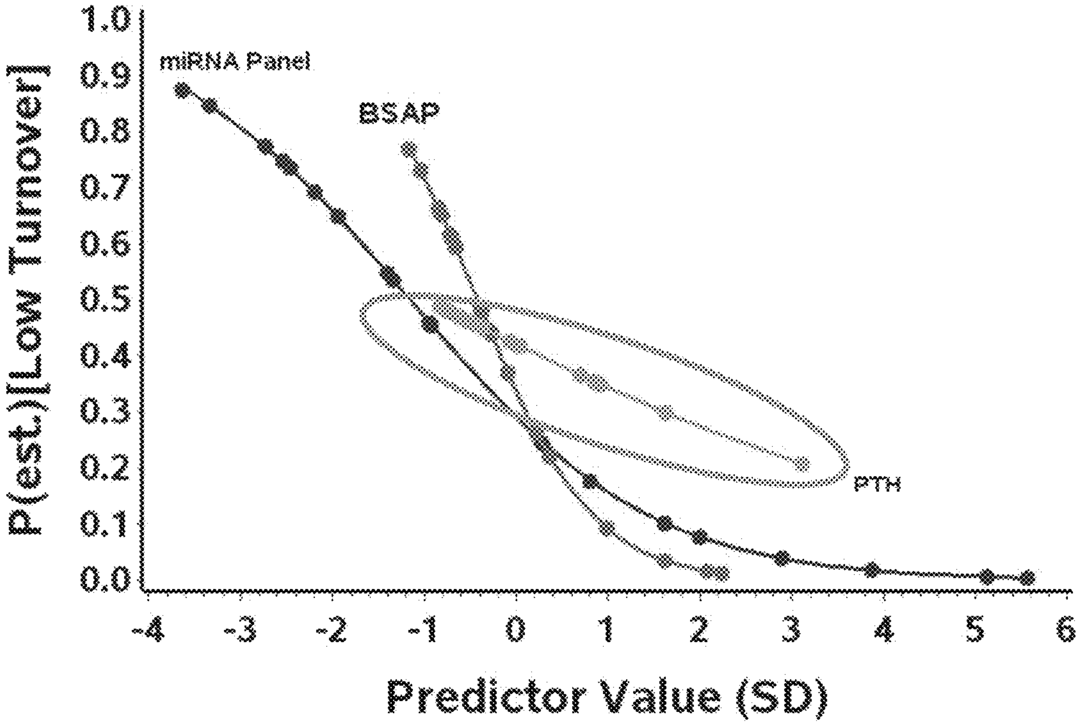
FIG. 24 shows the probability of identifying low turnover with the miR-Panel compared to PTH and BSAP.

FIG. 24 shows the probability of identifying low turnover with the miR-Panel compared to PTH and BSAP.

In summary, BSAP and miR-30b, 30c and 125b correlated with turnover. For high versus non-high turnover, BSAP provided excellent discrimination. PTH, other markers of formation and resorption, and miRs did not discriminate high versus non-high turnover. For low versus non-low turnover, miRs provided moderate to high discrimination individually. A miR-panel provided excellent discrimination and it was superior to BSAP. BSAP provided moderate discrimination. PTH and other markers of formation and resorption did not discriminate low versus non-low turnover.

In conclusion, miRs were associated with bone turnover determined by gold-standard TCN double labeled histomorphometry. miRs were superior to clinically used biomarkers in discriminating low from non-low turnover. Additional miR markers of both low and high turnover may be identified. Validation and qualification of miRs for turnover in large prospective cohorts may be performed. Determination of miR profiles in response to changes in turnover may be performed.

REFERENCES FOR EXAMPLE 4

1. Malluche et al JBMR 2011
2. Sprague et al AJKD 2015

Example 5

A. Specific Aims

Seventeen percent of Americans have chronic kidney disease (CKD)[1]. Renal osteodystrophy (ROD) is a complex disorder of bone metabolism that affects nearly all CKD patients over their lifetimes[2-6]. ROD is associated with adverse clinical outcomes including bone loss[7], fractures[8-13], cardiovascular events[14-16], and death[17]. ROD is defined by the Kidney Disease Improving Global Outcomes (KDIGO) classification of bone Turnover, Mineralization, and Volume (TMV)[18]. TMV class can change over time or the initial bone abnormality can worsen as kidney function declines. The main focus of treatment is Turnover, with the goal to reduce high turnover with active vitamin D and/or calcimimetics, while minimizing excessive use of these same agents to avoid the development of low turnover bone. The KDIGO best evidence guidelines recommend that clinical use (starting/stopping) of these agents is guided by the biomarkers parathyroid hormone (PTH) and bone specific alkaline phosphatase (BSAP)[19]. However, bone biopsy studies in CKD patients demonstrated that PTH is a poor guide to starting or stopping ROD treatment, with areas under the curve (AUC) of 0.724 and 0.701 for differentiating high and low turnover ROD respectively[20]. Therefore, KDIGO recommends tetracycline-labeled transiliac crest bone biopsy with histomorphometry to define turnover and guide treatment strategies[18]. A major limitation of bone biopsy is that it is invasive, expensive, not widely available, and requires ~3-months to obtain results. Thus, there is an unmet clinical need to identify biomarkers with better diagnostic accuracy for the identification of underlying bone turnover to guide treatment decisions and for use in future clinical trials.

Data from an a priori defined subset of circulating microRNAs (miRNA) that are associated with osteoblast (miRNA-30b, 30c, 125b) and osteoclast (miRNA-155) development suggest they may be accurate biomarkers of low turnover. In twenty-four CKD patients with bone biopsies, low turnover ROD was associated with lower levels of miRNAs ($p<0.05$) and areas under the curve (AUC) for discrimination from non-low turnover ROD was 0.866, 0.813, 0.813, and 0.723 for miRNA-30b, 30c, 125b, and 155 respectively. Importantly, in this cohort a circulating miRNA profile combining all 4 miRNAs had an AUC discrimination of 0.929, while PTH and BSAP did not discriminate. These findings were confirmed at the bone-tissue level in a rat model of ROD. Without being bound by theory, based on these data circulating miRNAs may discriminate low turnover in ROD. The proposal aims to expand findings in a large cohort of CKD patients with low, normal, and high turnover ROD (N=90; 30/group). Then, in patients and animals with CKD the effects of changes in turnover rate will be determined over time on circulating miRNA expression and prospective relationships between circulating and bone-tissue miRNA expression and measures of bone quality will be characterized. These results will determine if the circulating miRNA profile can serve as a biomarker for guiding ROD management. This high impact proposal has the potential to result in a paradigm shift in the non-invasive diagnosis and management of ROD.

Low Turnover Bone Disease has a Unique Circulating miRNA Profile.

In a large bone biopsy cohort, data will be expanded by measuring the circulating miRNA profile for low turnover ROD and determine if it is a better diagnostic biomarker of ROD than those in current clinical use. In a cross-sectional cohort of 90 patients with ROD (30/group low, normal, high turnover ROD), diagnostic test characteristics will be quantified for circulating miRNAs identified the data. Diagnostic test characteristics of circulating miRNA profiles will be analyzed and compared to those of PTH and BSAP and other clinically used biomarkers of bone formation, resorption, and metabolism.

Changes in Bone Turnover are Reflected by Changes in the Circulating miRNA Profile.

Test if the circulating miRNA profile changes when bone turnover changes in response to ROD treatment. In humans, transiliac crest bone biopsy will be obtained from 30 dialysis patients using a quadruple label single-biopsy protocol to measure turnover before and 9 months after administration of calcimimetics, which are medications that dramatically decrease PTH and bone turnover. In a rat model of ROD, treatments will be implemented to change turnover rates as measured by bone histomorphometry. In both humans and rats, it will be determined if the circulating miRNA profile previously studied undergoes a directional change when bone turnover goes from of high to low (humans and rats) or low to high (rats only).

Circulating miRNA Profile of ROD is Reflective of miRNA Expression at the Bone-Tissue Level and is Related to Bone Microarchitecture and Mechanical Properties.

Relationships between circulating miRNA and bone miRNA expression, microarchitecture, and biomechanical properties will be determined. In human and rat bone, relationships between circulating levels of, and bone (marrow vs bone-tissue) expression, of miRNAs will be quantified. In humans, prospective relationships between changes in the circulating miRNA profile and bone microarchitecture and estimated mechanics by high resolution pQCT will be determined with finite element analyses. In rat bone, relationships between circulating miRNAs and the same bone microarchitecture measures by microCT will be determined, but also mechanical tests to assess fragility will be conducted.

B. Significance

Renal osteodystrophy (ROD) is a significant disease. ROD is a complex heterogeneous disorder of bone that results from abnormal calcium/phosphate metabolism, decreased calcitriol synthesis, increased parathyroid hormone (PTH) levels, metabolic acidosis, and defective bone mineralization[21]. ROD is the bone component of CKD-Mineral and Bone Disease (CKD-MBD), a disorder of bone, mineral metabolism, and soft tissue calcifications. Seventeen percent of Americans have CKD[1] and CKD-MBD occurs in nearly 100% of CKD patients[2-6]. ROD results in bone loss[7] and fractures[8-13] and has been linked to increased risk of vascular calcifications and CV events[16,22-25]. For CKD patients, compared to the general population, fractures and cardiovascular (CV) risk are more than 17-[8,12,26] and 1.4-fold[14] greater respectively, and mortality rates after fracture and CV events are more than 3-[17] and 10-fold greater[14], respectively. In 2010, healthcare associated costs after fracture in CKD patients exceeded $600 million[17], and total Medicare spending for CKD patients in 2018 was $118 billion[27]. Thus improvements in the diagnosis and clinical management of ROD is a critical first step in the long-term goal of reducing morbidity, mortality and healthcare associated costs for patients with CKD[28].

ROD treatment is predicated on preventing and avoiding the development of low turnover. The 2005 KDIGO committee shifted the historical nomenclature of ROD-type (e.g., osteitis fibrosa cystica) to a unified classification system based on bone Turnover, Mineralization, and Volume (TMV)[18], and ROD is now classified as low, normal, or high turnover ROD. Despite this change, current ROD treatment remains focused on suppressing high turnover with active vitamin D receptor analogs (VDRA; calcitriol, paricalcitol, doxercalciferol) and/or calcimimetics (cinacalcet, etelcalcetide), while simultaneously avoiding the development of low turnover through excessive use of these same agents. In addition, emerging data and clinical experience suggest that ROD with bone loss or fractures may be safely managed with treatments for osteoporosis (anti-resorptives for high turnover; anabolics for low turnover)[29-38], as long as low turnover can be identified and avoided. The primary concern in identifying and preventing the development of low turnover is that it has been associated with risk of fractures[39] and vascular calcification that may increase CV risk[23,40,41] Guidelines and clinical experience recommend that diagnosis of turnover should be obtained prior to starting ROD treatment, and turnover should be monitored during therapy because turnover may change, thus requiring a change to treatment (discontinuing VDRA/calcimimetics for over suppression of turnover). The gold standard method to define turnover is double labeled tetracycline iliac crest bone biopsy with quantitative histomorphometry. However, bone biopsy is invasive, expensive, requires ~3-months for results, cannot be used for rapid decision making, is not easily used as a disease and treatment monitoring tool, and is available at only a few centers worldwide. In addition, it assumes that iliac crest remodeling is representative of systemic turnover. These limitations render bone biopsy impractical and in the vast majority of cases impossible to use for either diagnosis or treatment monitoring.

PTH and BSAP have poor accuracy for low turnover. KDIGO recommends that circulating levels of parathyroid hormone (PTH) and bone specific alkaline phosphatase (BSAP) can be used in the clinic to diagnose and guide management of ROD[19]. Two large bone biopsy studies recently characterized contemporary trends in ROD and diagnostic accuracy of PTH and BSAP for turnover type[5,20]. In 630 CKD-5D patients, Malluche et al.[5] reported that low turnover was prevalent in the majority of patients (58%) while only a minority (3%) had a defect in mineralization. PTH levels were lower in patients with low compared to high turnover ROD, but diagnostic accuracy of PTH for turnover was not assessed.

Figure 25:
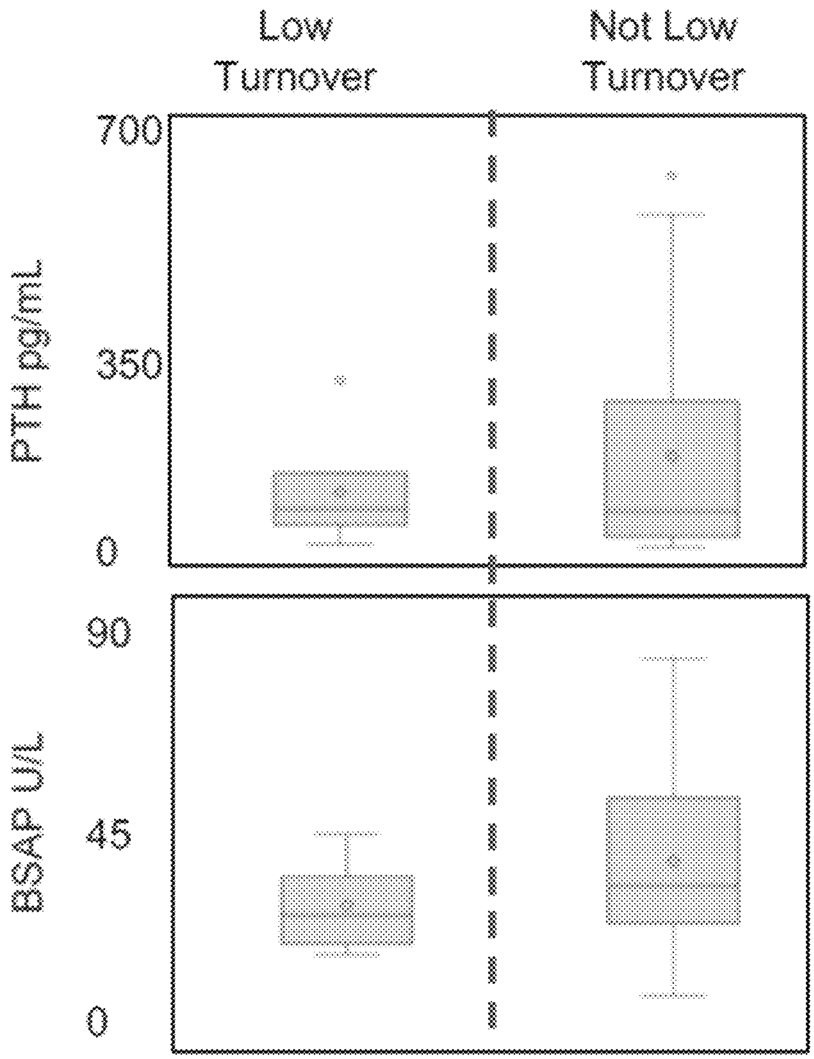
FIG. 25 shows that levels of PTH and BSAP in patients with low vs. non-low bone turnover did not differ between groups.

Total alkaline phosphatase, a formation marker that is commonly measured in dialysis patients, did not differ between turnover types. A second study was led through a KDIGO consortium. It included 492 CKD-5D patients from 4 countries and assessed the diagnostic accuracy of PTH and BSAP for turnover type[20]. Similar to Malluche et al.[5] the prevalence of low turnover predominated (59%). PTH and BSAP insufficiently identified low turnover to confidently guide ROD treatment, with areas under the curve (AUC) of 0.701 and 0.757 respectively; combining PTH with BSAP did not improve diagnostic accuracy for low turnover (AUC 0.743). For PTH, the sensitivity and specificity for discriminating low vs. non-low turnover were 65%, and 67% respectively. Local experience with PTH and BSAP also demonstrates that they poorly discriminate low from non-low turnover. 24 patients with CKD Stages 3-5D underwent bone biopsy. Low and non-low turnover was defined as the lowest vs. the upper two tertiles of the bone formation rate per bone surface (BFR/BS). FIG. 25 shows that PTH and BSAP levels did not differ by low or non-low turnover (PTH mean±SD pg/mL: 114±98 vs. 161±187; BSAP: 32±9 vs. 41±25 for low vs. non-low turnover respectively, $p>0.1$) and did not discriminate between groups as shown in FIG. 26. These data from two large cohorts of patients on dialysis and a local cohort of patients across the CKD spectrum confirm that accurate diagnostic markers for low turnover ROD are lacking. From a patient care perspective, the lack of low turnover biomarkers impedes ROD treatment, to the detriment of CKD patients.

Figure 27:
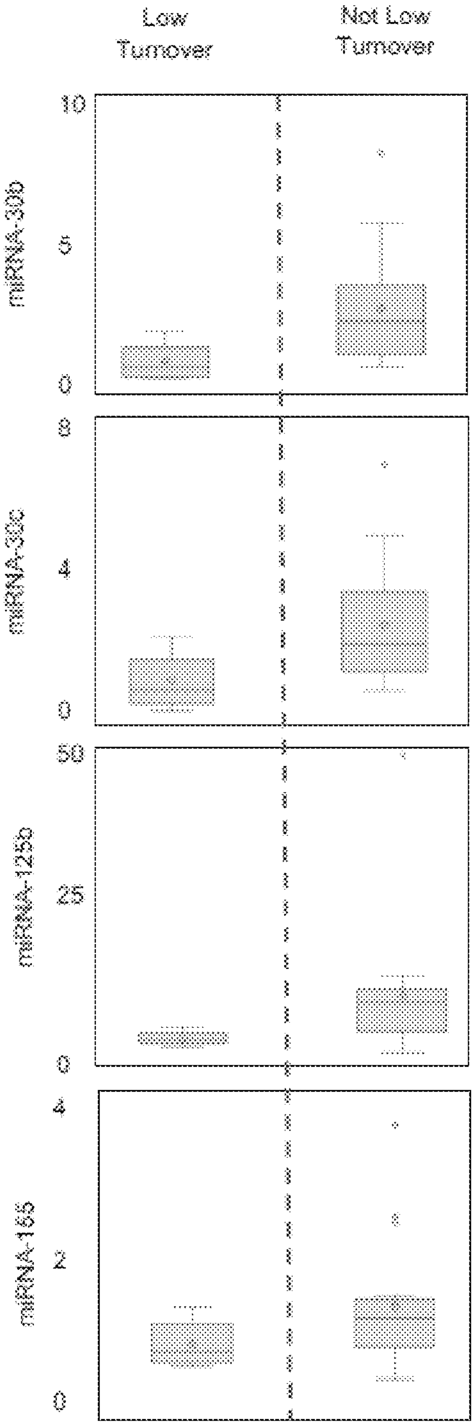
FIG. 27 shows levels of miRNAs among patients with low vs. not low bone turnover.

Circulating miRNAs are novel biomarkers of bone turnover and quality. miRNAs are small noncoding sequences of ~22 nucleotides that bind to the 3'-untranslated regions of mRNAs to silence gene expression by inhibiting translation or promoting degradation of target mRNAs. miRNA expression during osteoblast and osteoclast development has been studied[42-44], bone cell phenotypic effects of miRNA substitutions and knockdowns have been described[45,46], and the impact of hormones and RANK47 on miRNA expression signatures have been reported. Circulating miRNA can serve as biomarkers as they are resistant to degradation in blood. Dysregulation in levels of circulating miRNA expression has been noted in non-CKD patients with osteoporosis48-50 and fractures[51,52]. In CKD patients, levels of miRNAs and PTH have been correlated[53] and in cell culture inorganic phosphate was shown to modulate osteoclastogenesis by miRNA-23354. Circulating miRNAs have not been evaluated as biomarkers of turnover or bone quality in CKD. In 24 CKD patients it was assessed if miRNAs that inhibit osteoblast (miRNA-30b, 30c,125b[43,55-57]) and osteoclast (miRNA-155[58,59]) development were associated with low turnover (defined as the lower tertile of BFR/BS). Circulating levels of miRNA-30b, 30c, and 125b (normalized to *C. elegans* miRNA-39) were lower in patients with low compared to non-low turnover ROD as shown in FIG. 27 ($p<0.05$), while miRNA-155 trended lower in low turnover (p 0.06). Although it may seem paradoxical that miRNAs that inhibit bone cell development were higher in patients with non-low turnover ROD, this finding may represent a regulatory response that attempts to decrease BFR when BFR is high, or on the other hand may be consistent with low level cellular activity in low turnover. miRNA-30b, 30c, and 125b discriminated low turnover ROD as shown in FIG. 26. Importantly, the circulating miRNAs had greater diagnostic accuracy than that reported for PTH and BSAP in the KDIGO commissioned ROD biomarker study (0.701 and 0.757, respectively)[20]. Furthermore, combining all miRNAs into a Low Turnover Biomarker Panel, had diagnostic accuracy that was significantly better than PTH and BSAP as shown in FIG. 26. Finally, relationships between miRNAs and microarchitectural measures of bone quality were also quantified as assessed by histomorphometry: circulating miRNA-30b, 30c and 125b were moderately correlated with trabecular bone volume, number, and separation (p 0.3-0.4; $p<0.05$). These data in humans suggest that circulating miRNAs are accurate biomarkers of low turnover and bone quality. These human data will establish the circulating miRNA profile as a biomarker of low turnover and will inform their use in clinical trials as surrogate markers of low turnover ROD.

Figure 28:
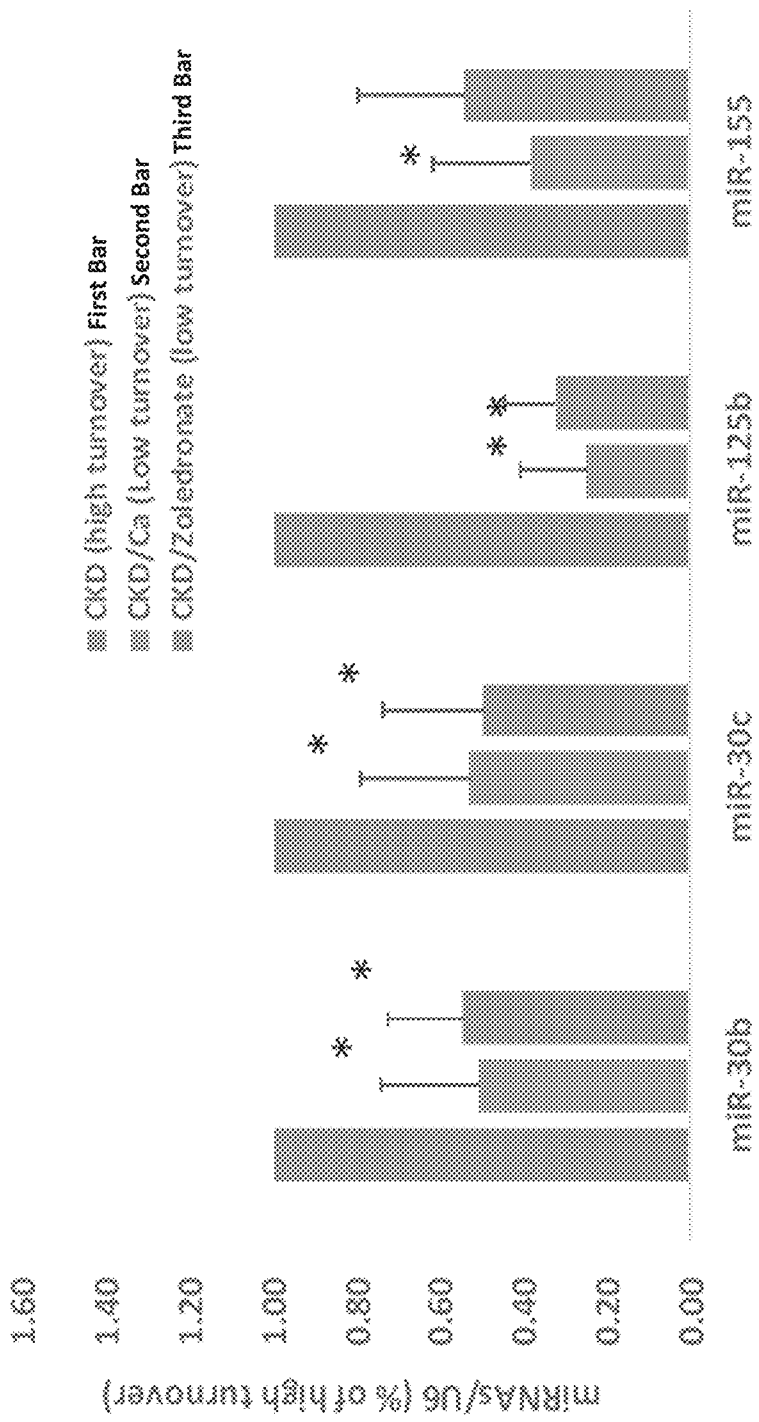
FIG. 28 demonstrates that CKD rats with low turnover have low expression of bone miR30b, 30c, 125b and 155, which reflect circulating miRNA in humans.
Figure 29B:
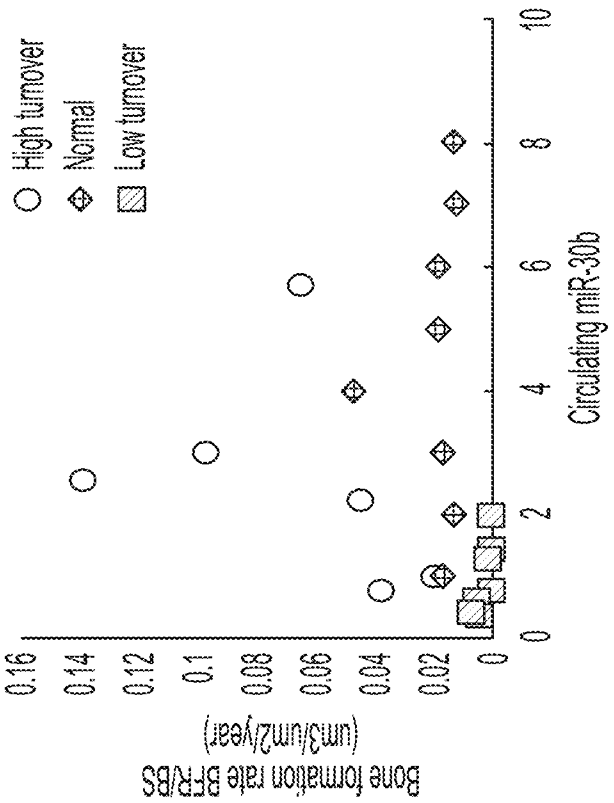
FIGS. 29A-B show correlations assessed between BFR/BS (bone turnover) and bone expression of miRNA in rats (FIG. 29A) and circulating miRNA in humans (FIG. 29B).
Figure 29A:
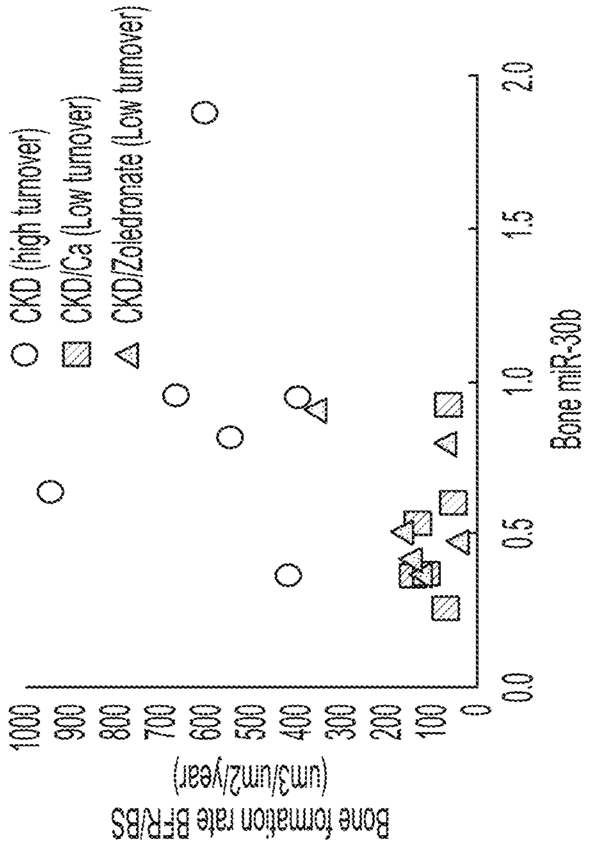

Bone expression of miRNAs in rats with low bone turnover are consistent with clinical findings. The Cy/+ rat model of CKD was used to assess bone expression of miRNAs. Cy/+ rats are characterized by an autosomal dominant progressive cystic kidney disease that is not allogenic with human ADPKD[60]. In this rat model, CKD-MBD develops spontaneously, with a much faster progression to end stage disease in male animals by 30 to 35 weeks of age, whereas female rats do not develop azotemia even as old as 21 months[61], or after oophorectomy. The Cy/$+_{IU}$ colony of rats has been bred for nearly 20 years. The model recapitulates CKD-MBD with progressive kidney disease, hyperphosphatemia, secondary hyperparathyroidism, elevated FGF-23, resulting in ROD and vascular calcification. Importantly, the slowly progressive nature of the model allows for examination of interventions that differentially affect bone remodeling. Specifically, low turnover bone remodeling has been induced with calcium in the drinking water (calcium binders) and zoledronic acid[62,63], calcimimetics[64] and anti-sclerostin antibody[65]. Data as shown in FIG. 28 demonstrates that CKD rats with low turnover, either due to calcium or bisphosphonate treatment, have low expression of bone miR30b, 30c, 125b and 155, which reflect circulating miRNA in humans. There are ongoing studies with KP-2326, a peptide that parallels etelcalcetide. FIGS. 29A-B show correlations, which were assessed between BFR/BS (bone turnover) and bone expression of miRNA in rats (FIG. 29A) and circulating miRNA in humans (FIG. 29B) and a nearly identical relationship in rat bone tissue and in human circulation was found.

Taken together, this work demonstrates that the circulating miRNA profile in humans: (a) differs in CKD patients with low vs. non-low turnover as shown in FIG. 27; (b) better discriminates low turnover ROD than the standard markers (PTH and BSAP; FIG. 26); and (c) is similar to that in the bone of rats with ROD as shown in FIG. 28, providing rationale to use this rat model to study the source of miRNA/mechanisms as shown in FIGS. 29A-B. These preliminary data provide rationale to examine the utility of measuring circulating miRNAs at a single timepoint for diagnosing turnover, to use serial circulating miRNA measures to assess changes in turnover in response to treatments, and to determine the bone expression of miRNA profile and its relationship to circulating miRNA and bone quality.

C. Innovation.

Innovations are conceptual and technical. Conceptual innovations may change the paradigm of ROD diagnostics and management. Technical innovations may advance clinical care and scientific discovery.

Accurate non-invasive biomarker of bone turnover. The subject matter disclosed herein lays the groundwork to change the paradigm of ROD diagnosis/management from invasive bone biopsy to non-invasive analysis of circulating miRNAs, which will overcome the noted limitations of invasive bone biopsy, improve patient care, and enable development of efficient large-scale clinical trials of ROD specific therapies.

Novel miRNA profiles of low turnover in the setting of ROD. Determination of miRNA profiles of turnover and their bone cell origin may elucidate potential novel targets for ROD treatment.

Precision medicine. miRNA profiling can be used to develop a diagnostic test that will permit individual patient level diagnosis of ROD-type. Thus, ROD treatment can be tailored to each patient's underlying bone disorder.

D. Research Design

In a Large Bone Biopsy Cohort, the Data Will be Expanded by Measuring the Circulating miRNA Profile for Low Turnover ROD and Determine if it is a Better Diagnostic Biomarker of ROD than Those in Current Clinical Use.

Low Turnover Bone Disease has a Unique Circulating miRNA Profile.

Rationale and Goal. ROD treatment is focused on lowering turnover from high to normal, while avoiding either the development of, or initiating treatment in, pre-existing low turnover ROD. The gold standard method to diagnose turnover-type is tetracycline double labeled bone biopsy, which is impractical for use in almost all CKD patients. The current non-invasive biomarkers of turnover in ROD (PTH, BSAP) have poor diagnostic accuracy for turnover-type to confidently and safely guide ROD treatment. miRNAs are stable in blood, have cell regulatory functions, and have been associated with metabolic bone diseases and fractures. In the discovery cohort of 24 patients across the CKD spectrum, it is found that circulating miRNAs associated with inhibition of osteoblast (miRNAs-30b, 30c, 125b) and osteoclast (miRNA-155) development were better biomarkers of low turnover than PTH and BSAP. Findings will be expanded by leveraging data from two large cohorts of patients across the CKD spectrum with bone biopsy proven low, normal, and high turnover ROD.

Experimental Design. Cross-sectional study in 90 patients with CKD stages 3-5D. Diagnostic test characteristics of circulating miRNAs for low turnover ROD will be compared to: (1) bone biomarkers recommended by KDIGO (PTH, BSAP); (2) bone formation (osteocalcin, P1NP) and resorption (C-telopeptide, TRAP-5b) markers in clinical use; (3) bone biomarkers associated with CKD-MBD (FGF-23, Calcium, Phosphorus) and (4) bone hormones that regulate bone metabolism (IGF-1, DKK-1, sclerostin).

Population as shown in FIG. 30. This study leverages pre-existing data from 90 patients with CKD 3-5D who underwent bone biopsy for clinical and research purposes. A cohort of 90 CKD patients was selected to cover the spectrum of bone turnover (low, normal, high) with 30/group and would approximate low turnover prevalence in clinical settings (~30% of CKD 3-5D patients have low turnover ROD[2,5,20,66,67]).

Demographic and Clinical Data. Demographic characteristics and medical history, including medication usage and fracture, social and family history, were collected at the time of biopsy.

Biochemical data. All subjects have plasma and serum stored at −80° C. Assays will be obtained as shown in FIG. 31.

Histomorphometry. Tetracycline double labeled bone samples underwent standard 2-dimensional analysis for dynamic and static indices of histomorphometry according to American Society of Bone and Mineral Research guidelines[68]. ROD-type was classified according to the KDIGO TMV system (low, normal, high turnover)[18].

RNA Isolation and Quantification and Confirmation of miRNA Expression Profiles. All serum will be sent for miRNA analysis[69,70]. For PCR, serum provides the greatest RNA yield and thus serum will be utilized in the subject matter described herein. For all analyses, miRNA profiles will be pooled from across levels of kidney function since previous work suggests that total miRNA levels are minimally affect by kidney function and levels in patients with CKD 3b-4 was similar to those on hemodialysis[70].

Total RNA isolation and quantification. Total RNA from patient serum will be isolated. Total RNA from patient serum may be isolated using miRNeasy Mini Kit (Qiagen) according to the manufacturer's instructions. Total RNA is eluted from the column in RNase-free water and stored at −80° C.

Confirmation of miRNA expression profiles by Real-Time PCR. miRNA 30b, 30c, 125b, and 155 will be quantified from RNA isolated from the stored serum samples of the 90 CKD patients. Real-time PCR amplification will be performed. Real-time PCR amplification may be performed on serum miRNAs using TaqMan miRNA Assays (TaqMan MGP probes, FAM dye-labeled) using Applied Biosystems ViiA 7 Real-Time PCR systems (Applied Biosystems)[70]. The $\Delta\Delta C_T$ method will be used to analyze relative changes in miRNA expression, normalized by spike of *C. elegans* miR-39 which we have found to provide a better internal control than U6.

Analysis Plan and Statistical Approach. The primary outcome will compare the 4 miRNAs individually and as a group/profile with the KDIGO recommended PTH and BSAP tests to the reference standard BFR/BS from transiliac crest histomorphometry in a representative sample of the target population on the outcome of low bone turnover. The secondary outcome will determine relationships between the miRNA profiles and the TMV classification system and continuous states of skeletal dynamics from histomorphometry.

Primary Analysis. Possible directions of miRNAs for the different bone states are summarized in FIG. 32. ROD turnover type will be based on gold standard histomorphometric analysis of tetracycline double labeled bone samples. Sensitivity and specificity pairs, positive and negative predictive values, likelihood ratio of positive and negative result pairs and ROC (AUC) analyses with confidence intervals will be estimated; and classifications of the miRNAs and KDIGO biochemical tests will be compared to gold standard histomorphometric assessment of turnover[71-73].

Secondary Analysis. The relationship of circulating miRNA profile to TMV classification and continuous measures of skeletal dynamics will also be examined. Thus, using histomorphometric measures, the diagnostic characteristics of the miRNA profile to distinguish TMV classification of mineralization and volume as phenotypic targets, will be assessed via the ROC analysis and regression and incremental $R^2$ as the performance metric for the continuous outcomes of bone formation, volume and mineralization.

Sample Size and Justification (including Power Analysis). The cohort of the present subject matter leverages 90 bone biopsies (n=30/group with low, normal, high turnover) with histomorphometry performed for both clinical and research indications. Since the miRNAs are chosen, by design, to have high sensitivity for identification of low bone turnover, there is concern with the confidence in the specificity achieved with the miRNA signatures. Ninety biopsies will enable to estimate specificity with a precision of +7.3% under the assumption of 95% sensitivity and an expected specificity of 75%[74]. A normal approximation for two correlated binomial proportions has 80% power with two-sided 5% alpha to detect a difference between KDIGO specificity of 0.65 against a miRNA profile specificity of 0.85. The proposed sample size and inclusion/exclusion criteria ensure the spectrum of bone turnover is covered.

It may be demonstrated that the circulating miRNA expression profiles discovered in the data will remain robust diagnostic markers of low turnover ROD in the expanded cohort. The miRNAs may have superior performance compared to PTH, BSAP and other clinically used markers of bone turnover/metabolism. The miRNA panel is expected to describe more variability in turnover than any individual miRNA, PTH, BSAP and other markers of bone turnover/metabolism. Therefore, the miRNAs will have optimal accuracy for turnover-type. It may be found that combining the miRNA profile with PTH and/or bone turnover/metabolism markers provides the most accurate diagnostic information. It may be found that miRNAs also describe other aspects of ROD beyond turnover, including mineralization and volume (i.e., TMV) which would be of added benefit.

miRNAseq can also be performed as an alternative approach to identify other miRNA markers of low turnover ROD. These miRNAs identified in the alternative approach will be used subsequently. Data was conducted on stored (−80° C.) serum and plasma from dialysis patients and miRNAseq was run using Illumina NextSeq 500. The results showed good RNA yield and quality despite from frozen sample. The miRNAseq analysis identified 500-1000 UMI (Unique Molecular Index) miRNAs reads, including the miRNAs 30b, 30c, 125b, and 155. To use miRNAseq, low to non-low turnover samples would be compared. Serum and plasma gave nearly equivalent results.

Cross-sectional design. Explore whether changes in miRNA levels reflect changes in turnover and whether medications that alter turnover affect levels of miRNAs.

Protection of miRNA discovery work and ability to translate results into a widely available clinical test. There is a precedent for PCR based testing, for example HCV, C. Diff and HIV. Furthermore, with the advent of precision medicine a widespread application of this diagnostic method is anticipated in the future. Rationale for innovative biomarker methods for ROD diagnostics is supported by the disappointing history of protein diagnostics (PTH, BSAP) in ROD.

To Test if the Circulating miRNA Profile Changes when Bone Turnover Changes in Response to ROD Treatment.

Changes in Bone Turnover are Reflected by Changes in the Circulating miRNA Profile.

Rationale and Overview. ROD is not static over the course of a CKD patient's life, and can change from high to low turnover ROD and vice-versa depending on level of kidney function, patient's age, and treatment with therapies that alter bone turnover[5,35,75-79]. Although a biomarker of turnover with cross-sectional utility is helpful, a biomarker that reflects changes in turnover is better as it could be used not only to start treatment (i.e., whether or not to start VDRA/calcimimetic), but also to guide management decisions (i.e., stop VDRA/calcimimetic). The dynamics of the miRNA profile will be examined after interventions which result in a dramatic change in turnover from high to low due to suppression of PTH (calcimimetics). An ongoing study (humans) that uses a quadruple label approach to obtain prospective data will be leveraged on, and quantify changes in, dynamic indices of histomorphometry with a single bone biopsy[80,81]: 20 patients on hemodialysis being treated with 9 months of etelcalcetide. Patients in this study have blood stored at −80° C. and undergo quadruple label transiliac crest bone biopsy and HR-pQCT of the radius and tibia to assess bone density, geometry and microarchitecture. In addition to these 20 patients, an additional 10 patients will be enrolled who are also undergoing treatment with a calcimimetic and perform quadruple label bone biopsy. To further explore change in levels of miRNAs due to treatment, the Cy/+ rat model of progressive CKD will be used to assess changes in levels of miRNAs from high to low turnover and low to high turnover.

Experimental Design. Ten-month prospective quadruple label bone biopsy study (Human Study) in 30 patients with CKD-5D, who are undergoing a clinically indicated treatment that will change bone turnover from high to low. 3 study visits are included to obtain information pertaining to clinical history, skeletal imaging, and blood and bone biopsy samples as shown in FIG. 33.

Clinically indicated calcimimetic to lower PTH and that change turnover from high to low in CKD.

Quadruple label transiliac crest bone biopsy to quantify dynamic indices of bone at baseline (pre-treatment) and 9 months after treatment. This technique allows the assessment of change with only an end point biopsy.

Screening procedures to ensure that participants have high bone turnover.

High Resolution Peripheral Quantitative Computed Tomography (HR-pQCT) will be used in analyses.

Recruitment, Informed Consent, Screening, Bone Biopsy Recruitment. Subjects in will primarily come from ISS (AMGEN 20177411; n=20), and secondarily from new recruitment (n=10). Eligibility criteria will be harmonized to AMGEN 20177411 to limit potential bias from divergent eligibility criteria that are itemized in the Human Subjects Section.

Subjects from etelcalcetide study. CKD-5D on hemodialysis for ≥3 months; age ≥18 years. Informed consent procedures for AMGEN 2017411 permit the use of data for other purposes, in addition to the parent study.

New Recruitment. Potential participants will be identified from the nephrology and endocrine clinics, based on eligibility criteria that are harmonized to AMGEN 20177411 and itemized in the Human Subjects Section. After permission to approach the patient is provided by the patient's physician, the study will be explained. If they agree to further screening to determine if they adhere to the full eligibility criteria, informed consent (IFC) will be obtained.

Screening will occur to confirm the presence of high turnover: PTH >the KDIGO target for CKD-5D82 and total alkaline phosphatase ≥the upper tertile of the reference range[20,83,84]. Quadruple Bone Labeling and Bone Biopsy and Histomorphometry. Recruited subjects who pass screening will start bone biopsy labeling one-month prior to their clinical treatment. In the quadruple labeling protocol, two sets of double tetracycline labels are administered: one set before intervention begins, and a second set 9 months after the intervention. A single biopsy is then performed after the second set of labels. Because two different tetracyclines are used that fluoresce in different colors, a single biopsy can be used to assess dynamic indices of bone before and after intervention[80,81]. The quadruple label procedure is as follows[80,81]:

Tetracycline Label #1 (Sumycin, 250 mg 4×/day for 3 days; 12-day holiday, 3 additional days) given one month prior to intervention.

Tetracycline Label #2 (Demeclocycline 150 mg 4×/day for 3 days; 12-day holiday, 3 additional days) given 9 months after the intervention.

Transiliac Crest Bone Biopsy and Histomorphometry obtained 5-days after completion of label #2, at the non-dominant side. Two iliac crest bone cores will be obtained: (1) A 7.5 mm bone core obtained with a 7.5 mm Rochester Trephine to be used for analyses; and (2) A 3 mm bone core obtained with a Jamshidi trephine to be used for analyses. The 7.5 mm bone biopsy specimen will be stored in ethanol for histomorphometry and bone tissue protein and gene expression. The 3 mm bone core will be flash frozen and stored in −80° C. for miRNA analyses. Histomorphometric analysis will be performed according to published methods for the quadruple label method[80,81]. For both time-points, ROD-type will be classified as low, normal, or high turnover based on TMV[18]. Static indices are quantified only at the 9-month time-point with the quadruple label method.

Biochemical assays will be obtained as per FIG. 31.

Circulating miRNA analyses. For pre-, 3- and 10-month time-points, the levels of miRNAs will be determined by RT-PCR.

Analysis Plan and Statistical Approach (FIG. 34). The agreement in pre-, post-, and pre-to-post-treatment changes will be tested in histomorphometry and miRNA expression profiles for low turnover ROD both before and after 9-months of treatment with calcimimetics that alter bone turnover from high to low. Histomorphometry indices and miRNA results will be analyzed as continuous measures. Intra-class correlation coefficients, correlation and partial correlation will be used for the cross-sectional analysis at the pre- and post-treatment timepoints and to assess agreement of the pre-to-post treatment change scores. The influence of covariates on the association will be assessed with multiple regression and quantile regression.

Sample Size and Justification (including Power Analysis). Thirty patients provide 80% power, 5% alpha to have a 0.18% desired error margin surrounding the estimate of the intraclass correlation. For regression models, the change in miRNA score will be regressed on the change in dynamic indices from histomorphometry to determine the model $R^2$, thirty patients provide 80% power, 5% alpha to detect an R2 accounted for by the biomarkers of 0.28 with no covariates and 0.30 with two covariates.

Animal Study. In order to examine circulating miRNA in rats with different bone turnover states, the Cy/+(CKD) rat will be used[62,63,65]. These animals develop spontaneous CKD-MBD and progressive hyperparathyroidism with high turnover bone by 22-24 weeks of age that worsens without intervention. For the present study, male Cy/+IU rats (14/group; hereafter called CKD) will be placed on an autoclaved grain diet until 17 weeks of age, and then changed to a casein diet (Purina AIN-76A; 0.7% Pi, 0.6% Ca) in order to produce a more consistent CKD phenotype[85]. Treatment begins at 18 weeks of age (~50% normal GFR), and terminal euthanasia at either 23 weeks of age (~25% normal GFR) or 28 weeks of age (~15% normal GFR). Animals are anesthetized with isoflurane and undergo cardiac puncture for blood collection followed by exsanguination and bilateral pneumothorax to ensure death. The blood will be used to quantify circulating miRNA as shown in the preliminary data for humans with some saved for the possibility of miRNAseq. In order to obtain ample blood quantity for RNA isolation, terminal exsanguination collection must be used. Bone turnover will be suppressed with either 3% calcium gluconate in the drinking water, to simulate high dose calcium binders, or KP-2326 (0.6 mg/kg i.p. three times per week), a pre-clinical analogue of etelcalcetide. Blood will be collected at baseline, week 18, week 23, and week 28. The rationale to use calcium or KP-2326 to suppress bone turnover is to separate a potential effect of blood calcium levels on miRNA expression. The goal is to create a diagnostic test that could be used to monitor turnover with any treatment of ROD (i.e., calcium or calcimimetic). Dose response studies have been performed in the rats with the KP-2326 and have shown >50% suppression of PTH without profound hypocalcemia. Study drug will be provided. Calcitriol will not be used as it is shown that this drug is not effective at suppressing bone turnover in this model[86]. FIG. 35 itemizes the experimental groups.

Analysis Plan and Statistical Approach. Animals will be classified into low vs non-low turnover based on comparisons to normal animals in related publications[62-65]. Based on these studies, turnover may be suppressed in response to either calcium or the calcimimetic KP2326.

The Following Comparisons Will be Made:

1) To test that there are differences in circulating miRNA profiles between moderate and severe HPT, groups 1 and 2 will be compared.

2) To test that the miRNA profile is similar regardless of treatment producing low turnover, groups 2, 3 and 4 will be compared.

3) To test that conversion from low to high turnover alters circulating miRNA profile regardless of treatment, the change in miRNA profiles from 23 weeks to 28 weeks in groups 5 and 6 will be compared.

Between groups comparison of miRNA profiles (Groups 1 and 2), across group comparisons (Groups 2, 3 and 4), and miRNA change scores (Groups 5 and 6) will be estimated with Wilcoxon linear rank tests with Hodges-Lehmann confidence limits for the location shift for the two-group comparisons and one-way ANOVA of Wilcoxon scores for the multi-group comparison. If Group 5 and 6 change scores are tested to be normally distributed, parametric tests will be performed.

Sample Size and Justification (including Power Analysis). 14 rats are proposed to be grouped per group, as, on average, 1 to 2 per group are lost due to unrelated illness, cardiac sudden death or other problem; the goal is to have an n of 12 with all end points for analyses. The rationale for this is based on the most variable of measures, intact PTH, and it has been found that the n of 12 provides 80% power to detect the effect sizes published[62,63,65,87-90]: a 1.2-SD difference between groups when an underlying lognormal distribution is assumed.

The primary end point of the current study is circulating miRNA profile. In the data of stored bone (n=6 to 8) a SD of 0.31, 0.51, 0.92 and 1.79 for bone miRNA 125b, 30b, 30c, and 155, respectively, was observed. Similar SD are anticipated for rat circulating miRNA. Thus, the proposed sample size provides for the detection of effect sizes comparable to the low-versus high turnover results shown in FIG. 28.

For humans, it is expected that validated miRNA profiles will accurately reflect low turnover at 9-months. It is expected that the change in miRNA score from baseline to 9-months will predict the change in bone turnover confirmed by histomorphometry. In rats, it is expected that the miRNA profiles will also reflect bone histomorphometry low turnover. It is expected that the changes in bone turnover due to treatments itemized as shown in FIG. 35 will result in changes to circulating miRNA expression. Furthermore, it is expected that changes in miRNA expression in rats would parallel changes in humans similar to the data shown in FIGS. 29A-B.

Lack of bone biopsy confirmation of high turnover may occur as part of recruitment screening. Patient screening to rule in high turnover ROD at recruitment with PTH and total alkaline phosphatase may result in false positives (i.e., inclusion of subjects with normal or low turnover). However, it is expected that the relative reduction of turnover from baseline (regardless of the baseline turnover rate) by suppression of PTH with a calcimimetic will result in the same miRNA profile regardless of baseline turnover (i.e., normal to low and high to low).

Determining Relationships Between Circulating miRNA and Bone miRNA Expression, Microarchitecture, and Biomechanical Properties.

Without being bound by theory, the circulating miRNA profile of ROD is reflective of miRNA expression at the bone-tissue level.

Without being bound by theory, the circulating miRNA profile of ROD is reflective of bone microarchitecture and mechanical properties.

Rationale and Overview. Bone samples obtained will be utilized to determine: (1) if the miRNA profile in circulation reflects that in bone-tissue; and (2) to quantify relationships between the circulating miRNA profile and bone microarchitecture and mechanical properties (biomechanical competence). The goal is to utilize the circulating miRNA profile to optimally assess bone in ROD, and the long-term goal is to utilize the circulating miRNA profile to make more accurate prediction of fracture risk. There is focus on relationships between circulating miRNAs and bone turnover measured by gold standard histomorphometry. Relationships between miRNAs and microarchitectural aspects of bone quality and bone mechanical properties will be examined. Bone quality encompasses bone turnover, but also geometry, microarchitecture, crystallinity, mineralization, collagen properties, and microdamage; bone quality is directly related to bone strength. Bone strength will be estimated by finite element analysis (FEA) of HR-pQCT and then measured directly in rodent bone. Prospectively collected human biopsies and rat bones will be used to measure levels of, and relationships between, circulating and bone-tissue miRNAs to understand the bone cell contributions to circulating miRNA. Relationships between treatment induced changes in the circulating miRNA profile and changes in bone microarchitecture and FiniteElement Analyses (FEA) estimates of mechanics assessed by HR-pQCT of the radius and tibia will be determined. Relationships between rat circulating miRNAs and the same bone microarchitecture measures assessed in humans will be determined by microCT in the rat, but also bone mechanical properties ex vivo will be directly measured to assess mechanical competence (fragility).

Primary Outcomes.

Humans and rats. Relationship between the miRNA profile in circulation and in bone marrow and bone tissue.

In humans, pre- and post-treatment changes in the circulating miRNA profile will be compared to changes in cortical and trabecular tissue and bone mineral density and microarchitecture by HR-pQCT and whole bone stiffness and failure load estimated by FEA as published[91-93].

In rats, pre- and post-treatment changes in the circulating miRNA profile will be compared with cortical and trabecular tissue bone mineral density and microarchitecture by microCT and bone mechanics.

Experimental Design and Methods

A) Human studies. Patient characteristics, bone biopsy and prospective measures of the circulating miRNA profile. At baseline (pre-treatment) and endpoint (9-months of treatment), patients will undergo HR-pQCT. Quadruple label bone biopsy occurs at end of treatment.

HR-pQCT (microarchitecture of cortical and trabecular bone) and estimated bone mechanical competence (FEA).

Imaging will be done on the Scanco XtremeCT, XCT II (nominal resolution 60 μm3). Previously described methods will be used to perform bone imaging[93-96]. In brief, scans of the non-dominant radius and tibia will be obtained. Three scans will be obtained per limb to image the standard sites and the more cortical proximal sites, that permit extensive analysis of effects of PTH and its changes at cortical bone. The cortical and trabecular compartments will be segmented using a fully automatic contouring procedure, while the fine structure is segmented using a simple threshold process.

Finite element analysis (FEA). Axial stiffness, estimated failure load, and the load fraction between corticalc and trabecular bone will be determined using linear FEA[97,98]. To account for variability in material properties, which may be impacted by mineralization defects related to CKD, the models will incorporate material properties that are scaled by the local tissue mineral density (scaled tissue properties)[97,99]. This will provide insight into the variable contribution of mineralization defects and microstructural deficits.

HR-pQCT Quality Control. HR-pQCT image acquisition, quality assurance and control, and analyses will be performed. Daily scans of a phantom containing rods of hydroxyapatite (HA) with calibrated densities (i.e. 0, 100, 200, 400, and 800 mg HA/cm3; QRM, Moehrendorf, Germany). Images will be scored for movement at acquisition (score 1-5 with 1 indicating best quality)100 and repeated for scores >2. If images are scored >3 at the time of analysis they will be excluded.

Bone Biopsy Methods

Quadruple Label Histomorphometry. Methods are described above.

Acquisition of bone RNA. A 7.5 mm core for histomorphometry and a 3 mm core for miRNA analyses will be obtained. The 7.5 mm core will be flushed to collect bone marrow and then processed for histomorphometry and bone tissue property testing. The 3 mm core will be flushed with saline to collect marrow and then snap frozen. The snap frozen sample will undergo ex vivo microCT followed by isolation of RNA from the bone.

B) Rat studies. Treatment groups are detailed above. At sacrifice, right and left tibia and femora will be collected as shown in FIG. 36. The marrow will be flushed with α-MEM media, centrifuged, and the pellet stored in Quizol for future RNA isolation.

Figure 37A:
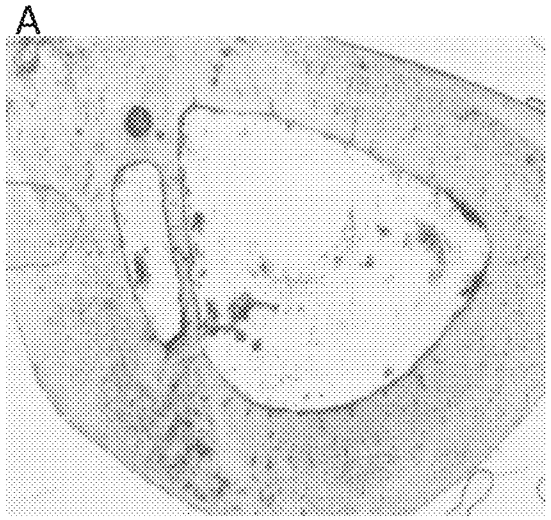
FIGS. 37A-B shows an initial flush of bone marrow.
Figure 37B:
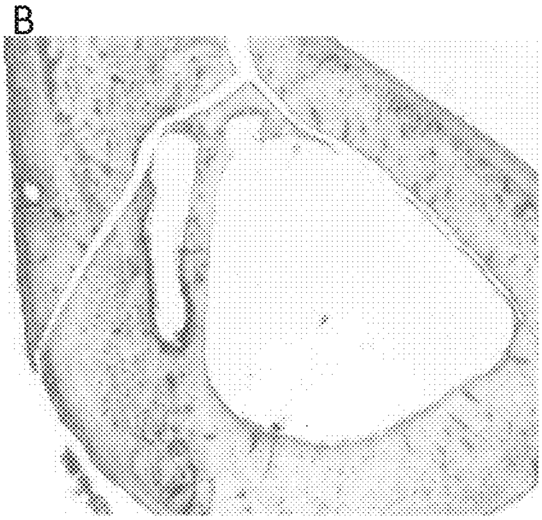
Figure 38B:
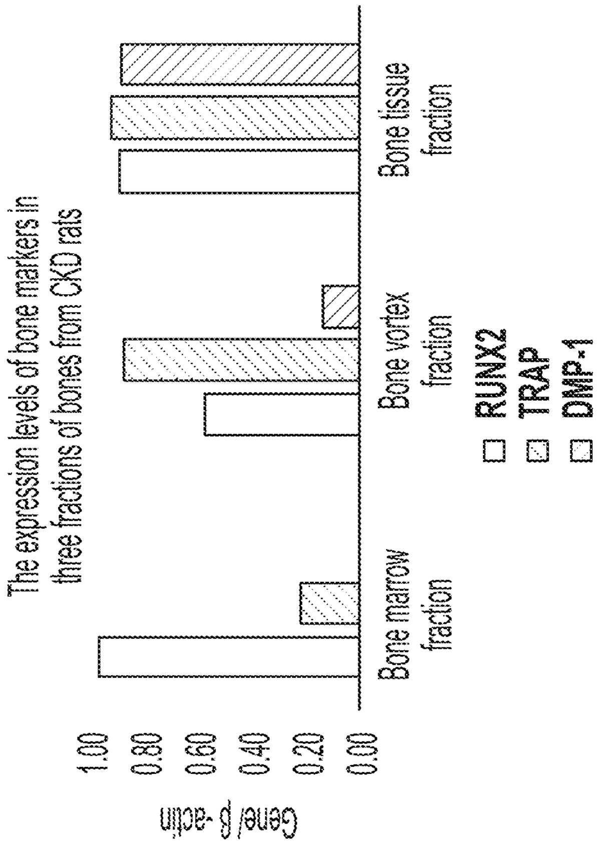
FIGS. 38A-B show differential bone compartmental expression of miRNAs and bone makers in bone marrow vs. vortex (surface cells) vs. tissue from CKD animals with high turnover.
Figure 38A:
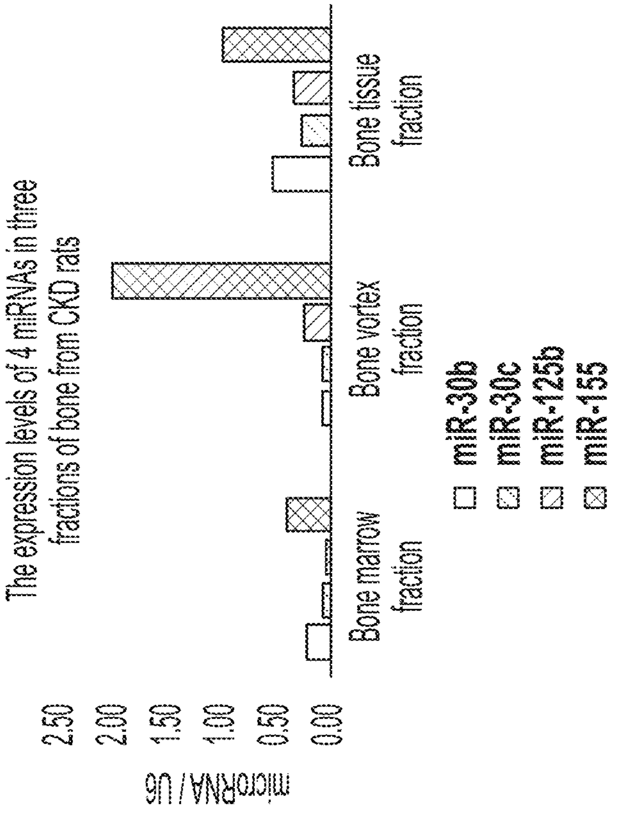

Bone miRNA/Preliminary Data. The purpose of measuring the circulating miRNA is to reflect underlying bone histomorphometry. To further identify the bone source of the circulating miRNA, the technique for collecting marrow will be modified. As shown in FIGS. 37A-B, an initial flush of bone marrow was performed (as above and as published[90]) which would include all mesenchymal and blood cells (FIG. 37A), but then added a second, high speed vortex to collect remaining marrow stuck to the surface of bone and bone surface cells (activated osteoblasts and osteoclasts; =vortex fraction); the remaining sample reflected bone, mostly the osteocyte fraction (=bone-tissue fraction; FIG. 37B). FIGS. 38A-B show that there is differential bone compartmental expression of miRNAs and bone makers in bone marrow vs. vortex (surface cells) vs. tissue from CKD animals with high turnover. FIG. 38A shows the expression levels of 4 miRNAs in three fractions of bone from CKD rats. FIG. 38B shows the expression levels of bone markers in three fractions of bones from CKD rats. The bone marrow fraction had high expression of RUNX2 but low expression of miR-30b and 30c (consistent with the effect of these miRNA to inhibit BMP-2 mediated osteoblast differentiation[21,55,56]). The bone vortex (surface cell) fraction had increased expression of TRAP (osteoclast marker) and miRNA-155 (regulator of osteoclast differentiation[58,59]) compared to the bone marrow fraction. The bone-tissue fraction had increased expression of DMP-1 (osteocyte marker) and miRNA-125b (known to negatively inhibit osteoblast differentiation[101] and is present in osteocyte secreted exosomes[102]) compared to the bone marrow and vortex fractions. These data demonstrate that miRNA can be measured in bone, and importantly, miRNA expression can be correlated with cell markers to determine the likely cell source of the miRNA. For the present study, human bone will have bone marrow and tissue collected for miRNA, while all 3 compartments will be collected for rats.

Bone Mechanical Testing. Mechanical properties of femora will be determined by four-point bending as published[63,65]. The posterior surface will be placed on two metal supports located +/−9 mm from the mid-diaphysis testing site, the upper supports will be 6 mm apart centered on the bone. Lumbar vertebra will be tested in compression. Specimens are loaded to failure at a rate of 0.5 mm/min, producing a force-displacement curve for each sample. Structural mechanical properties (ultimate load, stiffness, pre, post, total displacement and energy to failure) will be obtained directly from the curves, while apparent material properties (ultimate stress, elastic modulus, pre, post, total toughness) will be derived from force-displacement curves, cross-sectional moment of inertia, and the distance from the centroid to the tensile surface using standard beam-bending equations for four-point bending.

Analysis Plan and Statistical Approach (Human and Animal Studies; FIG. 39). Humans: assess agreement between levels of miRNA in circulation and in bone-marrow vs bone-tissue. Rats: assess agreement between miRNA in circulation and in bone marrow vs. vortex/surface bone cells vs. bone tissue. Correlation/partial correlation and intraclass correlation coefficients will be used. Assess relationships between changes in circulating levels of the miRNA profile and in bone quality and strength measured by HR-pQCT with application of FEA by correlation/partial correlation and intra-class correlation coefficients for agreement and by regression for changes in miRNA on changes in bone quality. Assess relationships between changes in circulating miRNA and identical microarchitectural parameters in humans by microCT. In addition, perform gold standard mechanical property studies with the primary end point being work to failure (energy under curve, an integration of failure load and stiffness).

Sample Size and Justification (including Power Analysis). Humans. With a desired intraclass correlation=0.90 between circulating and tissue-level miRNA in at least one compartment, 80% power and 5% alpha requires 30 subjects to detect an intraclass correlation coefficient with a lower confidence limit >0.77 which would be accepted as agreement between circulating and tissue-level miRNA to suggest a plausible causal association. Thirty subjects provide similar power and alpha to detect a correlation between measures with r-value >0.48 and $R^2$ of 0.23, 0.27 and 0.29 for the unique variance in change in bone quality accounted for by the change in circulating miRNA after adjusting 1, 2, or 3 covariates, respectively. Animals. In publications, an n of 14 per group allowed for comparison of PTH levels, the most variable of the biochemical measures[63,65].

Based on preliminary work, it is expected that levels of miRNA in circulation will reflect those in the bone-tissue compartment in both humans and rats and will be reflected by ρ2 (correlation) and $R^2$ (regression); this finding will reflect that bone cells, rather than marrow cells, produce the miRNA profile. It is anticipated that miRNA expression in the three rat and two human bone compartments will not correlate with each other based on rat data. It is expected that the change in miRNA will reflect improvements in bone quality (increases in cortical density; decreases in cortical porosity), and this effect will be independent of the PTH lowering effect of calcimimetics (humans) and calcimimetics+calcium (rats). Based on data difficulty with measurement of miRNA in rats, is not anticipated and it is assumed that the same techniques will work in humans (although the tissue will not be large enough to conduct the vortex step).

Bone or bone marrow miRNA profiles may not correspond to circulating miRNA profiles. That may reflect timing of collection of bone vs. blood. Alternatively, some of the circulating miRNA may not arise from bone and instead be from another organ involved in ROD pathogenesis. For example miRNA-30b is known to be involved in the regulation of parathyroid gland malignancy[103]. One study identified down-regulation of miRNA-125 in the parathyroid glands of rats with secondary hyperparathyroidism induced by ⅚th nephrectomy compared to normal rats[104]. In the rats, parathyroid glands will be collected at the time of sacrifice.

Smaller trephine may alter the ability to detect adequate quantity of miRNAs. For data in rats, only tibia or femur was used, and the bone compartment RNA yield was fairly low. Thus, combining more bones in rats will allow the investigation of additional and/or use miRNAseq. In humans, it has been shown that the 3 mm core yields 294 mcg RNA (mean, range 20 to 1600 ng) and only 3 samples were less than 50 ng. For miRNA, only need 40 ng are needed to run all 4 miRNAs proposed herein.

The data in humans suggest that the miRNA profile is related to trabecular bone quality based on histomorphometry. However, it is possible that the miRNAs are more reflective of changes in the composition of bone collagen rather than microarchitecture or strength. Collagen properties can be assessed using Raman spectroscopy, as it has been done in rats[88], and can analyze human bone sections via this method.

Arteries in the rats will be collected to also determine if miRNAs explain the link between bone and arterial calcification, as it is shown that at least miR-155 was linked to arterial calcification in the Cy/+ rats[70]. In humans, upper and lower extremity arterial calcification will be measured by HR-pQCT and it will be tested whether miRNAs explain the presence and severity of arterial calcifications[105,106].

Sex as a biological factor. Although only male rats are used for this study due to the lack of CKD and skeletal disease in female Cy/+IU rats, the human studies will include both men and women. Depending on results, the analyses can be repeated in female adenine mice or rats.

REFERENCES FOR EXAMPLE 5

1. Office G A. Kidney Disease Research Funding and Priority Setting Report2016.
2. Spasovski G B, Bervoets A R, Behets G J, et al. Spectrum of renal bone disease in end-stage renal failure patients not yet on dialysis. Nephrol Dial Transplant 2003; 18:1159-66.
3. Hamdy N A, Kanis J A, Beneton M N, et al. Effect of alfacalcidol on natural course of renal bone disease in mild to moderate renal failure. BMJ 1995; 310:358-63.
4. Coen G, Mazzaferro S, Bonucci E, et al. Bone GLA protein in predialysis chronic renal failure. Effects of 1,25(OH)2D3 administration in a long-term follow-up. Kidney Int 1985; 28:783-90.
5. Malluche H H, Mawad H W, Monier-Faugere M C. Renal osteodystrophy in the first decade of the new millennium: analysis of 630 bone biopsies in black and white patients. J Bone Miner Res 2011; 26:1368-76.
6. Behets G J, Spasovski G, Sterling L R, et al. Bone histomorphometry before and after long-term treatment with cinacalcet in dialysis patients with secondary hyperparathyroidism. Kidney Int 2015; 87:846-56.
7. Nickolas T L, Stein E M, Dworakowski E, et al. Rapid cortical bone loss in patients with chronic kidney disease. J Bone Miner Res 2013; 28:1811-20.
8. Nickolas T L, McMahon D J, Shane E. Relationship between Moderate to Severe Kidney Disease and Hip Fracture in the United States. J Am Soc Nephrol 2006; 17:3223-32.
9. Fried L F, Biggs M L, Shlipak M G, et al. Association of kidney function with incident hip fracture in older adults. J Am Soc Nephrol 2007; 18:282-6.
10. Ball A M, Gillen D L, Sherrard D, et al. Risk of Hip Fracture Among Dialysis and Renal Transplant Recipients. JAMA: The Journal of the American Medical Association 2002; 288:3014-8.
11. Dooley A C, Weiss N S, Kestenbaum B. Increased risk of hip fracture among men with CKD. Am J Kidney Dis 2008; 51:38-44.
12. Naylor K L, McArthur E, Leslie W D, et al. The three-year incidence of fracture in chronic kidney disease. Kidney Int 2014.
13. Isakova T, Craven T E, Scialla J J, et al. Change in estimated glomerular filtration rate and fracture risk in the Action to Control Cardiovascular Risk in Diabetes Trial. Bone 2015; 78:23-7.
14. Go A S, Chertow G M, Fan D, McCulloch C E, Hsu C Y. Chronic kidney disease and the risks of death, cardiovascular events, and hospitalization. N Engl J Med 2004; 351:1296-305.
15. London G M, Marchais S J, Guerin A P, Metivier F. Arteriosclerosis, vascular calcifications and cardiovascular disease in uremia. Curr Opin Nephrol Hypertens 2005; 14:525-31.
16. London G M, Marchais S J, Guerin A P, Boutouyrie P, Metivier F, de Vemejoul M C. Association of bone activity, calcium load, aortic stiffness, and calcifications in ESRD. J Am Soc Nephrol 2008; 19:1827-35.
17. Kim S M, Long J, Montez-Rath M, Leonard M, Chertow G M. Hip Fracture in Patients with Non-Dialysis-Requiring Chronic Kidney Disease. J Bone Miner Res 2016.
18. Moe S, Drueke T, Cunningham J, et al. Definition, evaluation, and classification of renal osteodystrophy: a position statement from Kidney Disease: Improving Global Outcomes (KDIGO). Kidney Int 2006; 69:1945-53.
19. Chapter 1: Introduction and definition of CKD-MBD and the development of the guideline statements. Kidney Int 2009; 76:S3-S8.
20. Sprague S M, Bellorin-Font E, Jorgetti V, et al. Diagnostic Accuracy of Bone Turnover Markers and Bone Histology in Patients With CKD Treated by Dialysis. Am J Kidney Dis 2015.
21. Slatopolsky E, Delmez, J. Renal Osteodystrophy. In: Coe F L, and Favus, M. J., ed. Disorders of Bone and Mineral Metabolism. New York: Raven Press; 1992:905-34.
22. Toussaint N D, Lau K K, Strauss B J, Polkinghorne K R, Kerr P G. Associations between vascular calcification, arterial stiffness and bone mineral density in chronic kidney disease. Nephrol Dial Transplant 2008; 23:586-93.
23. London G M, Marty C, Marchais S J, Guerin A P, Metivier F, de Vernejoul M C. Arterial calcifications and bone histomorphometry in end-stage renal disease. J Am Soc Nephrol 2004; 15:1943-51.
24. Adragao T, Herberth J, Monier-Faugere M C, et al. Low bone volume—a risk factor for coronary calcifications in hemodialysis patients. Clin J Am Soc Nephrol 2009; 4:450-5.
25. Kurz P, Monier-Faugere M C, Bognar B, et al. Evidence for abnormal calcium homeostasis in patients with adynamic bone disease. Kidney Int 1994; 46:855-61.
26. Alem A M, Sherrard D J, Gillen D L, et al. Increased risk of hip fracture among patients with end-stage renal disease. Kidney Int 2000; 58:396-9.
27. United States Renal Data System Annual Data Report 2018.
28. London G, Coyne D, Hruska K, Malluche H H, Martin K J. The new kidney disease: improving global outcomes (KDIGO) guidelines—expert clinical focus on bone and vascular calcification. Clin Nephrol 2010; 74:423-32.
29. Jamal S A, Ljunggren O, Stehman-Breen C, et al. Effects of denosumab on fracture and bone mineral density by level of kidney function. J Bone Miner Res 2011; 26:1829-35.
30. Ishani A, Blackwell T, Jamal S A, Cummings S R, Ensrud K E, Investigators M. The effect of raloxifene treatment in postmenopausal women with CKD. J Am Soc Nephrol 2008; 19:1430-8.
31. Jamal S A, Bauer D C, Ensrud K E, et al. Alendronate Treatment in Women with Normal to Severely Impaired Renal Function: An Analysis of the Fracture Intervention Trial*. J Bone Miner Res 2007.
32. Miller P D, Schwartz E N, Chen P, Misurski D A, Krege J H. Teriparatide in postmenopausal women with osteoporosis and mild or moderate renal impairment. Osteoporos Int 2007; 18:59-68.
33. Miller P D, Roux C, Boonen S, Barton I P, Dunlap L E, Burgio D E. Safety and efficacy of risedronate in patients with age-related reduced renal function as estimated by the cockcroft and gault method: a pooled analysis of nine clinical trials. J Bone Miner Res 2005; 20:2105-15.
34. Cejka D, Benesch T, Krestan C, et al. Effect of teriparatide on early bone loss after kidney transplantation. Am J Transplant 2008; 8:1864-70.
35. Cejka D, Kodras K, Bader T, Haas M. Treatment of Hemodialysis-Associated Adynamic Bone Disease with Teriparatide (PTH1-34): A Pilot Study. Kidney & blood pressure research 2010; 33:221-6.
36. Palcu P, Dion N, Ste-Marie L G, et al. Teriparatide and bone turnover and formation in a hemodialysis patient with low-turnover bone disease: a case report. Am J Kidney Dis 2015; 65:933-6.
37. Sumida K, Ubara Y, Hoshino J, et al. Once-weekly teriparatide in hemodialysis patients with hypoparathyroidism and low bone mass: a prospective study. Osteoporosis International 2016; 27:1441-50.
38. Block G A, Bone H G, Fang L, Lee E, Padhi D. A single-dose study of denosumab in patients with various degrees of renal impairment. J Bone Miner Res 2012; 27:1471-9.
39. Coco M, Rush H. Increased incidence of hip fractures in dialysis patients with low serum parathyroid hormone. Am J Kidney Dis 2000; 36:1115-21.
40. Davies M R, Lund R J, Mathew S, Hruska K A. Low turnover osteodystrophy and vascular calcification are amenable to skeletal anabolism in an animal model of chronic kidney disease and the metabolic syndrome. J Am Soc Nephrol 2005; 16:917-28.
41. Barreto D V, Barreto Fde C, Carvalho A B, et al. Association of changes in bone remodeling and coronary calcification in hemodialysis patients: a prospective study. Am J Kidney Dis 2008; 52:1139-50.
42. Bakhshandeh B, Soleimani M, Hafizi M, Paylakhi S H, Ghaemi N. MicroRNA signature associated with osteogenic lineage commitment. Molecular Biology Reports 2012; 39:7569-81.
43. Eguchi T, Watanabe K, Hara E S, Ono M, Kuboki T, Calderwood S K. OstemiR: A Novel Panel of MicroRNA Biomarkers in Osteoblastic and Osteocytic Differentiation from Mesencymal Stem Cells. PLoS ONE 2013; 8:e58796.
44. Hu R, Liu W, Li H, et al. A Runx2/miR-3960/miR-2861 Regulatory Feedback Loop during Mouse Osteoblast Differentiation. Journal of Biological Chemistry 2011; 286: 12328-39.
45. Lian J B, Stein G S, van Wijnen A J, et al. MicroRNA control of bone formation and homeostasis. Nat Rev Endocrinol 2012; 8:212-27.
46. van Wijnen A J, van de Peppel J, van Leeuwen J P, et al. MicroRNA Functions in Osteogenesis and Dysfunctions in Osteoporosis. Current Osteoporosis Reports 2013; 11:72-82.
47. Kagiya T, Nakamura S. Expression profiling of microRNAs in RAW264.7 cells treated with a combination of tumor necrosis factor alpha and RANKL during osteoclast differentiation. J Periodontal Res 2013; 48:373-85.
48. An J H, Ohn J I-I, Song J A, et al. Changes of microRNA profile and microRNA-mRNA regulatory network in bones of ovariectomized mice. J Bone Miner Res 2014; 29:644-56.
49. Garmilla-Ezquerra P, Sañudo C, Delgado-Calle J, Pérez-Nuñez M I, Sumillera M, Riancho J A. Analysis of the Bone MicroRNome in Osteoporotic Fractures. Calcified tissue international 2015; 96:30-7.
50. Seeliger C, Karpinski K, Haug A T, et al. Five freely circulating miRNAs and bone tissue miRNAs are associated with osteoporotic fractures. J Bone Miner Res 2014; 29:1718-28.
51. Heilmeier U, Hackl M, Skalicky S, et al. Serum miRNA Signatures Are Indicative of Skeletal Fractures in Postmenopausal Women With and Without Type 2 Diabetes and Influence Osteogenic and Adipogenic Differentiation of Adipose Tissue-Derived Mesenchymal Stem Cells In Vitro. J Bone Miner Res 2016; 31:2173-92.
52. Weilner S, Skalicky S, Salzer B, et al. Differentially circulating miRNAs after recent osteoporotic fractures can influence osteogenic differentiation. Bone 2015; 79:43-51.
53. Jeong S, Oh J M, Oh K H, Kim I W. Differentially expressed miR-3680-5p is associated with parathyroid hormone regulation in peritoneal dialysis patients. PLoS One 2017; 12:e0170535.
54. M'Baya-Moutoula E, Louvet L, Metzinger-Le Meuth V, Massy Z A, Metzinger L. High inorganic phosphate concentration inhibits osteoclastogenesis by modulating miR-223. Biochimica et biophysica acta 2015; 1852: 2202-12.
55. Balderman J A, Lee H Y, Mahoney C E, et al. Bone morphogenetic protein-2 decreases microRNA-30b and microRNA-30c to promote vascular smooth muscle cell calcification. Journal of the American Heart Association 2012; 1:e003905.

56. Zhang Y, Xie R L, Croce C M, et al. A program of microRNAs controls osteogenic lineage progression by targeting transcription factor Runx2. Proc Natl Acad Sci USA 2011; 108:9863-8.
57. Wang H, Xie Z, Hou T, et al. MiR-125b Regulates the Osteogenic Differentiation of Human Mesenchymal Stem Cells by Targeting BMPR1b. Cell Physiol Biochem 2017; 41:530-42.
58. Zhao H, Zhang J, Shao H, et al. Transforming Growth Factor beta1/Smad4 Signaling Affects Osteoclast Differentiation via Regulation of miR-155 Expression. Molecules and cells 2017; 40:211-21.
59. Zhang J, Zhao H, Chen J, et al. Interferon-beta-induced miR-155 inhibits osteoclast differentiation by targeting SOCS1 and MITF. FEBS Lett 2012; 586:3255-62.
60. Moe S M, Chen N X, Seifert M F, et al. A rat model of chronic kidney disease-mineral bone disorder. Kidney Int 2009; 75:176-84.
61. Cowley B D, Jr., Gudapaty S, Kraybill A L, et al. Autosomal-dominant polycystic kidney disease in the rat. Kidney Int 1993; 43:522-34.
62. Allen M R, Chen N X, Gattone V H, 2nd, et al. Skeletal effects of zoledronic acid in an animal model of chronic kidney disease. Osteoporos Int 2013; 24:1471-81.
63. Moe S M, Chen N X, Newman C L, et al. A comparison of calcium to zoledronic acid for improvement of cortical bone in an animal model of CKD. J Bone Miner Res 2014; 29:902-10.
64. Moe S M, Seifert M F, Chen N X, et al. R-568 reduces ectopic calcification in a rat model of chronic kidney disease-mineral bone disorder (CKD-MBD). Nephrol Dial Transplant 2009; 24:2371-7.
65. Moe S M, Chen N X, Newman C L, et al. Anti-sclerostin antibody treatment in a rat model of progressive renal osteodystrophy. J Bone Miner Res 2015; 30:499-509.
66. Lehmann G, Ott U, Kaemmerer D, Schuetze J, Wolf G. Bone histomorphometry and biochemical markers of bone turnover in patients with chronic kidney disease Stages 3-5. Clin Nephrol 2008; 70:296-305.
67. Lehmann G, Stein G, Huller M, Schemer R, Ramakrishnan K, Goodman W G. Specific measurement of PTH (1-84) in various forms of renal osteodystrophy (ROD) as assessed by bone histomorphometry. Kidney Int 2005; 68:1206-14.
68. Dempster D W, Compston J E, Drezner M K, et al. Standardized nomenclature, symbols, and units for bone histomorphometry: a 2012 update of the report of the ASBMR Histomorphometry Nomenclature Committee. J Bone Miner Res 2013; 28:2-17.
69. Chaturvedi P, Chen N X, O'Neill K, McClintick J N, Moe S M, Janga S C. Differential miRNA Expression in Cells and Matrix Vesicles in Vascular Smooth Muscle Cells from Rats with Kidney Disease. PLoS One 2015; 10:e0131589.
70. Chen N X, Kiattisunthorn K, O'Neill K D, et al. Decreased microRNA is involved in the vascular remodeling abnormalities in chronic kidney disease (CKD). PLoS One 2013; 8:e64558.
71. Bloch D A. Comparing two diagnostic tests against the same "gold standard" in the same sample. Biometrics 1997; 53:73-85.
72. Biggerstaff B J. Comparing diagnostic tests: a simple graphic using likelihood ratios. Stat Med 2000; 19:649-63.
73. Tekindal M A, Ateş C, Kaymaz Ö G, Yavuz Y. THE PERFORMANCES OF TWO DIAGNOSTICS TESTS: MCNEMAR AND NEWCOMBE GRAPHICAL APPROACH. Pakistan Journal of Statistics 2017; 33:301-14.
74. Schafer H. Efficient confidence bounds for ROC curves. Stat Med 1994; 13:1551-61.
75. Ferreira A, Frazao J M, Monier-Faugere M C, et al. Effects of sevelamer hydrochloride and calcium carbonate on renal osteodystrophy in hemodialysis patients. J Am Soc Nephrol 2008; 19:405-12.
76. Malluche H H, Monier-Faugere M C, Wang G, et al. An assessment of cinacalcet HCl effects on bone histology in dialysis patients with secondary hyperparathyroidism. Clin Nephrol 2008; 69:269-78.
77. Monier-Faugere M C, Mawad H, Qi Q, Friedler R M, Malluche H H. High prevalence of low bone turnover and occurrence of osteomalacia after kidney transplantation. J Am Soc Nephrol 2000; 11:1093-9.
78. Coco M, Pullman J, Cohen H W, et al. Effect of risedronate on bone in renal transplant recipients. J Am Soc Nephrol 2012; 23:1426-37.
79. Coco M, Glicklich D, Faugere M C, et al. Prevention of bone loss in renal transplant recipients: a prospective, randomized trial of intravenous pamidronate. J Am Soc Nephrol 2003; 14:2669-76.
80. Lindsay R, Cosman F, Zhou H, et al. A novel tetracycline labeling schedule for longitudinal evaluation of the short-term effects of anabolic therapy with a single iliac crest bone biopsy: early actions of teriparatide. J Bone Miner Res 2006; 21:366-73.
81. Rubin M, Dempster D, Sliney J, et al. PTH(1-84) administration reverses abnormal bone remodeling dynamics and structure in hypoparathyroidism. J Bone Miner Res 2011.
82. Ketteler M, Block G A, Evenepoel P, et al. Executive summary of the 2017 KDIGO Chronic Kidney Disease-Mineral and Bone Disorder (CKD-MBD) Guideline Update: what's changed and why it matters. Kidney Int 2017; 92:26-36.
83. Bervoets A R, Spasovski G B, Behets G J, et al. Useful biochemical markers for diagnosing renal osteodystrophy in predialysis end-stage renal failure patients. Am J Kidney Dis 2003; 41:997-1007.
84. Khairallah P, Nickolas T L. Management of Osteoporosis in CKD. Clin J Am Soc Nephrol 2018; 13:962-9.
85. Moe S M, Radcliffe J S, White K E, et al. The pathophysiology of early-stage chronic kidney diseasemineral bone disorder (CKD-MBD) and response to phosphate binders in the rat. J Bone Miner Res 2011; 26:2672-81.
86. Newman C L, Tian N, Hammond M A, et al. Calcitriol Suppression of Parathyroid Hormone Fails to Improve Skeletal Properties in an Animal Model of Chronic Kidney Disease. American journal of nephrology 2016; 43:20-31.
87. Allen M R, Chen N X, Gattone Ii V H, Moe S M. Adverse Mandibular Bone Effects Associated with Kidney Disease Are Only Partially Corrected with Bisphosphonate and/or Calcium Treatment. Am J Nephrol 2013; 38:458-64.
88. Newman C L, Moe S M, Chen N X, et al. Cortical bone mechanical properties are altered in an animal model of progressive chronic kidney disease. PLoS One 2014; 9:e99262.
89. Allen M R, Newman C L, Chen N, Granke M, Nyman J S, Moe S M. Changes in skeletal collagen crosslinks and matrix hydration in high- and low-turnover chronic kidney disease. Osteoporos Int 2015; 26:977-85.

90. Chen N X, O'Neill K D, Allen M R, Newman C L, Moe S M. Low Bone Turnover in Chronic Kidney Disease Is Associated with Decreased VEGF-A Expression and Osteoblast Differentiation. American journal of nephrology 2015; 41:464-73.
91. Iyer S P, Nikkel L E, Nishiyama K K, et al. Kidney transplantation with early corticosteroid withdrawal: paradoxical effects at the central and peripheral skeleton. J Am Soc Nephrol 2014; 25:1331-41.
92. Luckman M, Hans D, Cortez N, et al. Spine Trabecular Bone Score as an Indicator of Bone Microarchitecture at the Peripheral Skeleton in Kidney Transplant Recipients. Clin J Am Soc Nephrol 2017; 12:644-52.
93. Nishiyama K K, Pauchard Y, Nikkel L E, et al. Longitudinal HR-pQCT and Image Registration Detects Endocortical Bone Loss in Kidney Transplantation Patients. J Bone Miner Res 2014.
94. Iyer S N L, Nishiyama K, Dworakowski E, Cremers S, Zhang A, McMahon D J, Boutroy S, Liu X S, Ratner L, Cohen D, Guo X E, Shane E, Nickolas T L. Kidney transplantation with early corticosteroid withdrawal: paradoxical effects at the central and peripheral skeleton. J Am Soc Nephrol: in press 2014.
95. Nickolas T L, Cremers S, Zhang A, et al. Discriminants of prevalent fractures in chronic kidney disease. J Am Soc Nephrol 2011; 22:1560-72.
96. Kent K, Whalen J, Strickland A, Leonard M B, Burghardt A J. Feasibility and reproducibility using HRpQCTII in children and adolescents (Abstract). American Society for Bone and Mineral Research Annual Meeting, Atlanta, GA 2016.
97. Macneil J A, Boyd S K. Bone strength at the distal radius can be estimated from high-resolution peripheral quantitative computed tomography and the finite element method. Bone 2008; 42:1203-13.
98. Mueller T L, Christen D, Sandercott S, et al. Computational finite element bone mechanics accurately predicts mechanical competence in the human radius of an elderly population. Bone 2011; 48:1232-8.
99. Zhou B, Wang J, Yu Y E, et al. High-resolution peripheral quantitative computed tomography (HRpQCT) can assess microstructural and biomechanical properties of both human distal radius and tibia: Ex vivo computational and experimental validations. Bone 2016; 86:58-67.
100. Pialat J B, Burghardt A J, Sode M, Link T M, Majumdar S. Visual grading of motion induced image degradation in high resolution peripheral computed tomography: Impact of image quality on measures of bone density and microarchitecture. Bone 2012; 50:111-8.
101. Mizuno Y, Yagi K, Tokuzawa Y, et al. miR-125b inhibits osteoblastic differentiation by down-regulation of cell proliferation. Biochem Biophys Res Commun 2008; 368:267-72.
102. Sato M, Suzuki T, Kawano M, Tamura M. Circulating osteocyte-derived exosomes contain miRNAs which are enriched in exosomes from MLO-Y4 cells. Biomed Rep 2017; 6:223-31.
103. Vaira V, Verdelli C, Forno I, Corbetta S. MicroRNAs in parathyroid physiopathology. Molecular and cellular endocrinology 2017; 456:9-15.
104. Shilo V, Mor-Yosef Levi I, Abel R, et al. Let-7 and MicroRNA-148 Regulate Parathyroid Hormone Levels in Secondary Hyperparathyroidism. J Am Soc Nephrol 2017; 28:2353-63.
105. Patsch J M, Zulliger M A, Vilayphou N, et al. Quantification of lower leg arterial calcifications by highresolution peripheral quantitative computed tomography. Bone 2014; 58:42-7.
106. Paccou J, Edwards M H, Patsch J M, et al. Lower leg arterial calcification assessed by high-resolution peripheral quantitative computed tomography is associated with bone microstructure abnormalities in women. Osteoporos Int 2016.

Example 6—A microRNA Approach to Diagnose Renal Osteodystrophy Abstract

Background: A main obstacle to diagnosis and manage renal osteodystrophy (ROD) is the identification of bone turnover-type (low, normal, high). The gold standard, tetracycline double-labeled transiliac crest bone biopsy, is impractical to obtain in most patients. The Kidney Disease Improving Global Outcomes Guidelines recommend parathyroid hormone (PTH) and bone specific alkaline phosphatase (BSAP) for the diagnosis of turnover-type. However, PTH and BSAP have insufficient diagnostic accuracy to differentiate low from non-low turnover, an important criterion to guide ROD treatment. Without being bound by theory, the subject matter disclosed herein provides that four circulating microRNAs (miRNAs) that regulate osteoblast (miRNA-30b, 30c, 125b) and osteoclast development (miRNA-155) would provide superior discrimination of low from non-low turnover than biomarkers in clinical use.

Methods: In twenty-three patients with CKD 3-5D, tetracycline double-labeled transiliac crest bone biopsy was obtained and circulating levels of intact PTH, BSAP, and miRNA-30b, 30c, 125b and 155 were measured. Spearman correlations assessed relationships between miRNAs and dynamic parameters of histomorphometry and PTH and BSAP. Diagnostic test characteristics for discriminating low from non-low turnover were determined by receiver operator curve analysis; areas under curve (AUC) were compared by $\chi 2$-test. In CKD rat models of low and high turnover ROD, histomorphometry was performed and the expression of bone-tissue miRNAs was determined.

Results: Circulating miRNAs moderately correlated with bone formation rate/bone surface and adjusted apposition rate at the endo- and intra-cortical envelops ($\rho$ 0.43-0.51; $p<0.05$). Discrimination of low vs. non-low turnover was 0.866, 0.813, 0.813 and 0.723 for miRNA-30b, 30c, 125b and 155 respectively, and 0.509 and 0.589 for PTH and BSAP respectively. For all four miRNAs combined, the AUC was 0.929, which was superior to that of PTH and BSAP alone ($p<0.05$). In CKD rats, bone tissue levels of the four miRNAs reflected the findings in human serum.

Conclusions: These data suggest that circulating miRNAs provide accurate non-invasive identification of bone turnover.

INTRODUCTION

Renal osteodystrophy (ROD) is a complex disorder of bone metabolism that affects nearly all patients with CKD (1-5). ROD results in bone loss(6) and fractures(7-12) and has been linked to increased risk of vascular calcification, cardiovascular (CV) events(13-17) and increased healthcare costs(18). For CKD patients, compared to the general population, fractures and CV risk are more than 17-(7,11,19) and 1.4-fold(20) greater respectively. Mortality rates after fracture and CV events are more than 3-(18) and 10-fold greater(20), respectively, and in 2010 healthcare associated costs in patients with CKD after fracture exceeded $600 million(18).

ROD is defined by the Kidney Disease Improving Global Outcomes (KDIGO) classification of bone Turnover, Mineralization and Volume (TMV)(21). ROD TMV class can change over time or the initial bone abnormality can worsen as kidney function declines. The primary goal of ROD treatment is reducing high bone turnover with calcitriol and its analogues and/or calcimimetics, at the same time as avoiding the development of low turnover through excessive use of these same agents. In addition, emerging data and clinical experience suggest that ROD with bone loss or fractures may be safely managed with treatments that are used for osteoporosis (anti-resorptives for high turnover ROD; anabolics for low turnover ROD)(22-32), as long as low turnover ROD can be identified. The primary concern in identifying and preventing the development of low turnover ROD is the association with risk of fractures(33) and the development and progression of vascular calcifications that are linked to increased CV risk(14,34,35). Guidelines and clinical experience recommend that diagnosis of turnover should be obtained prior to starting ROD treatment, and turnover should be monitored during the course of therapy because turnover may change, thus requiring treatment adjustments. Tetracycline double-labeled transiliac crest bone biopsy with histomorphometry is the gold standard method to define turnover; however, its widespread use in the clinic for either diagnosis or treatment monitoring is impractical. Therefore, the KDIGO best evidence guidelines recommend that clinical use (i.e., starting/stopping) of these agents is guided by the biomarkers parathyroid hormone (PTH) and bone specific alkaline phosphatase (BSAP)(36). However, bone biopsy studies in CKD patients demonstrated that PTH and BSAP are suboptimal guides for ROD treatment due to their weak discrimination for low turnover ROD (0.701 and 0.757, respectively)(37). Thus, there is an unmet clinical need to identify non-invasive biomarkers with strong diagnostic accuracy for low turnover ROD that can be used to guide ROD treatment decisions and for use in clinical trials.

MicroRNAs (miRNA) are small noncoding sequences of ~22 nucleotides that bind to the 3'-untranslated regions of mRNAs to alter gene expression by inhibiting translation or promoting degradation of target mRNAs. Experimental studies have examined miRNA expression during osteoblast and osteoclast development (38-40), bone cell phenotypic effects of miRNA substitutions and knockdowns have been described(41,42) and the impact of hormones and RANK (43) on miRNA expression signatures. In non-CKD patients with osteoporosis, relationships between miRNAs and histomorphometry have been reported(44), and dysregulation in levels of circulating miRNA expression has been associated with osteoporosis(45-47) and fractures(48,49). In CKD patients, levels of miRNAs and PTH have been correlated (50) and in cell culture inorganic phosphate was shown to modulate osteoclastogenesis by miRNA-233(51). miRNAs have not been tested as biomarkers of turnover in CKD. Without being bound by theory, the subject matter described herein provides that circulating miRNAs reported in previous investigations to regulate osteoblast (miRNA-30b, 30c, 125b(39,52-54)) and osteoclast (miRNA-155(55,56)) development would be associated with low turnover. Furthermore, without being bound by theory, the subject matter described herein provides that that the circulating miRNA profile of low turnover ROD detected in humans would be reflected at the bone-tissue level in a rat model of CKD with low turnover ROD.

Methods

Cohort

The study design has been previously described (6,57,58). In brief, twenty-four patients with CKD stages 3-5D were recruited from the general nephrology clinics of CUIMC. eGFR was determined by the MDRD short formula for CKD patients not on dialysis(59). Patients were excluded if they had a history of malignancy, bilateral lower extremity amputations, non-ambulatory, institutionalized, or used bisphosphonates, Teriparatide, gonadal steroids, aromatase inhibitors or anticonvulsants that induce cytochrome-P450. All CKD etiologies were eligible.

Laboratory Measurements and Circulating microRNA Isolation and Analysis

Fasting blood samples were obtained in the morning. Routine laboratories were measured by Quest diagnostics. PTH and BSAP were measured in a research laboratory. Calciotropic hormones and BTMs were measured in a specialized research laboratory. Intact PTH, serum total 25-hydroxyvitmain D (25-OHD), bone specific alkaline phosphatase (BSAP), N-Mid osteocalcin, procollagen of type-1 N-terminal propeptide (P1NP), tartrate resistant acid phosphatase 5b (TrapSb), and C-terminal telopeptides of type I collagen (CTX) were measured by Roche Elecsys 2010 analyzer (Roche Diagnostics, Indianapolis, IN). Intra- and inter-assay precisions are: intact PTH 1.0% and 4.4%; BSAP 6.0% and 8.0%; osteocalcin 0.8% and 2.9%; P1NP 1.1% and 5.5%; and CTX 1.1% and 5.5%. For 25-OHD the normal range is >30 ng/mL and the inter-assay precision is 2.6-4.4%. miRNA was measured: total RNA were isolated from serum and miRNA expression determined by real time PCR using TaqMan miRNA assay (Applied Biosystem, Foster City, CA) normalized by spiking with *C. elegans* miRNA-39(60).

Transiliac Bone Biopsy and Histomorphometry

After double-labeling with tetracycline in a 3:12:3-day sequence, transiliac bone biopsy was performed using a 7.5 mm Bordier-type trephine. Specimens were fixed in 70% ethanol, processed without decalcification and embedded in Methylmethacrylate. Histomorphometry was performed on Goldner's Trichrome stained or unstained sections with a morphometric program (OsteoMeasure, Version 4.000, OsteoMetrics, Inc., Atlanta, GA, USA). All variables were expressed and calculated according to the recommendations of the American Society for Bone and Mineral Research(61). Classification of ROD was assessed by interpreting of histology and histomorphometry indexes according to the TMV system(62). The lowest tertile of the bone formation rate/bone surface (BFR/BS) at the intracortical envelop was used to define low turnover.

Animal Models

The Cy/+ rat model of CKD was used to assess bone expression of miRNAs. Cy/+ rats are characterized by an autosomal dominant progressive cystic kidney disease that is not allogenic with human ADPKD(63). In this rat model, CKD-MBD develops spontaneously, with a much faster progression to end stage disease in male animals by 30 to 35 weeks of age, whereas female rats do not develop azotemia even as old as 21 months(64), or after oophorectomy. The Cy/+IU colony of rats has been bred for nearly 20 years. The model recapitulates CKD-MBD with progressive kidney disease, hyperphosphatemia, secondary hyperparathyroidism, elevated FGF-23, resulting in ROD and vascular calcification. Importantly, the slowly progressive nature of the model allows for examination of interventions that differentially affect bone remodeling. Specifically, low turnover bone remodeling has been induced with calcium in the drinking water (calcium binders) and zoledronic acid(65, 66). In brief, CKD animals (n=8-10 each group) began treatment at 25 weeks for a total of 10 weeks and received 1) no treatment (control CKD=high PTH/high turnover, 2) 3% calcium in the drinking water (CKD/Ca group=low PTH/low turnover), or 3) a single injection of zoledronic acid (CKD/Zol group=high PTH/low turnover). At 35 weeks of age, animals were euthanized and bone tissue were collected. Bone histomorphometry as previously reported (67). RNA was isolated from tibia and bone miRNA expression determined by real time PCR using TaqMan miRNA assay as above.

Statistical Methods

For human subjects, statistical analyses were conducted using SAS (version 9.4, SAS Institute, Cary, NC). Continuous data were evaluated for normality before statistical testing and log-transformed when appropriate. The cohort was stratified into patients with low and non-low turnover based on the BFR/BS, with the lowest tertile of BFR/BS being defined as low turnover. Group differences for continuous parameters between patients with low vs. non-low turnover were determined by Wilcoxon Rank Sum. Relationships between miRNAs, PTH and BSAP and histomorphometry were determined by Spearman correlation. Standard receiver operator characteristic (ROC) curve analysis was performed to determine the ability of miRNAs to discriminate low and high turnover. Rat bone RNA expression were analyzed using One-Way ANOVA and within group comparisons by Fisher's post hoc analysis. The results are expressed as means±SD, with $p<0.05$ considered significant (GraphPad Prizm Software, La Jolla, CA).

Results

Cohort Characteristics and Levels of Circulating Bone Biomarkers

Cohort characteristics stratified by low and non-low turnover-type are presented in FIG. 40. Bone turnover groups did not differ by demographics, kidney function, or comorbid status. Biochemical markers of CKD-MBD (calcium, phosphorus, 25(OH)D, PTH and FGF-23), bone formation (BSAP. osteocalcin, P1NP) and resorption (C-telopeptide and Trap-5B) markers, and sclerostin did not differ between low and non-low turnover. In contrast, circulating levels of miRNA-30b, 30c and 125b were lower in subjects with low compared to non-low turnover.

Relationships Between miRNAs, Biochemical Makers of CKD-MBD and Bone Turnover

Spearman correlations were used to evaluate relationships between miRNAs and markers of CKD-MBD and bone turnover and histomorphometry (FIG. 41 and FIG. 42). miRNA-30b, 30c and 125b were directly and strongly related to each other and were positively and moderately related to miRNA-155. miRNA-30b, 30c and 125b were indirectly related to phosphorus levels and miRNA-30b and 30c were indirectly related to calcium. None of the miRNAs were related to circulating biomarkers of CKD-MBD or bone turnover. Relationships between miRNAs and the main dynamic parameters of bone formation and mineralization (BFR/BS, Aj.A.R. and MLT) were quantified at the trabecular, endocortical and intracortical regions of the iliac crest specimen (FIG. 42). miRNA-30b and 30c were moderately and directly related to BFR/BS and AjAR at the cortical and endocortical envelops and inversely related to mineralization lag time at the endocortical envelope. 25(OH)D and markers of bone formation and resorption were moderately related to BFR/BS at trabecular, endocortical and intracortical bone regions. PTH was directly related to BFR/BS only in trabecular bone and BSAP was inversely related to mineralization in cortical bone. Sclerostin and FGF-23 were not related to any histomorphometric parameter.

Discrimination analysis was used to determine the diagnostic test characteristics of miRNAs and markers of CKD-MBD and bone turnover to differentiate low from non-low (FIG. 43). For low vs. non-low turnover ROD, all miRNAs had moderate discrimination. When the four miRNAs were included into a single diagnostic panel, they had high discrimination for low vs. non-low turnover ROD (AUC 0.929; 95% CI 0.821-1.000), which was significantly greater than for PTH and BSAP. Neither the other markers CKD-MBD and bone turnover nor sclerostin discriminated low from non-low turnover ROD.

Bone Tissue miRNA Expression in CKD Rats with Low and High Turnover ROD

Figure 44A:
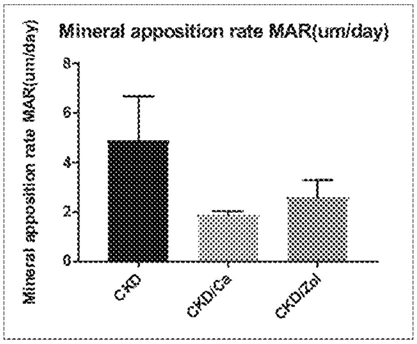
FIGS. 44A-C show that histomorphometric analysis of bone tissue confirmed the type of turnover induced by each intervention.
Figure 44B:
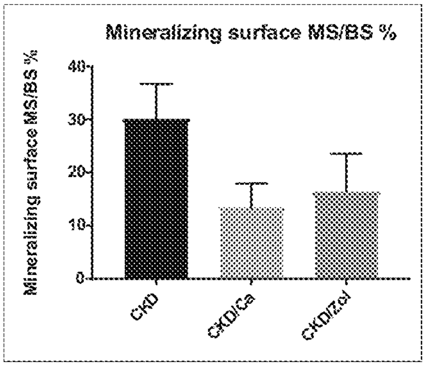
Figure 44C:
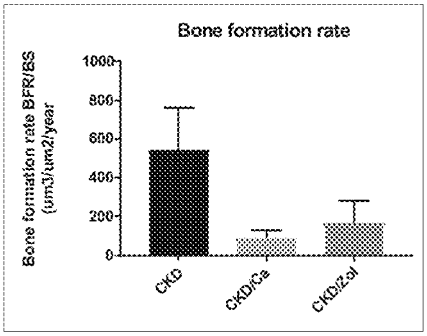
Figure 45:
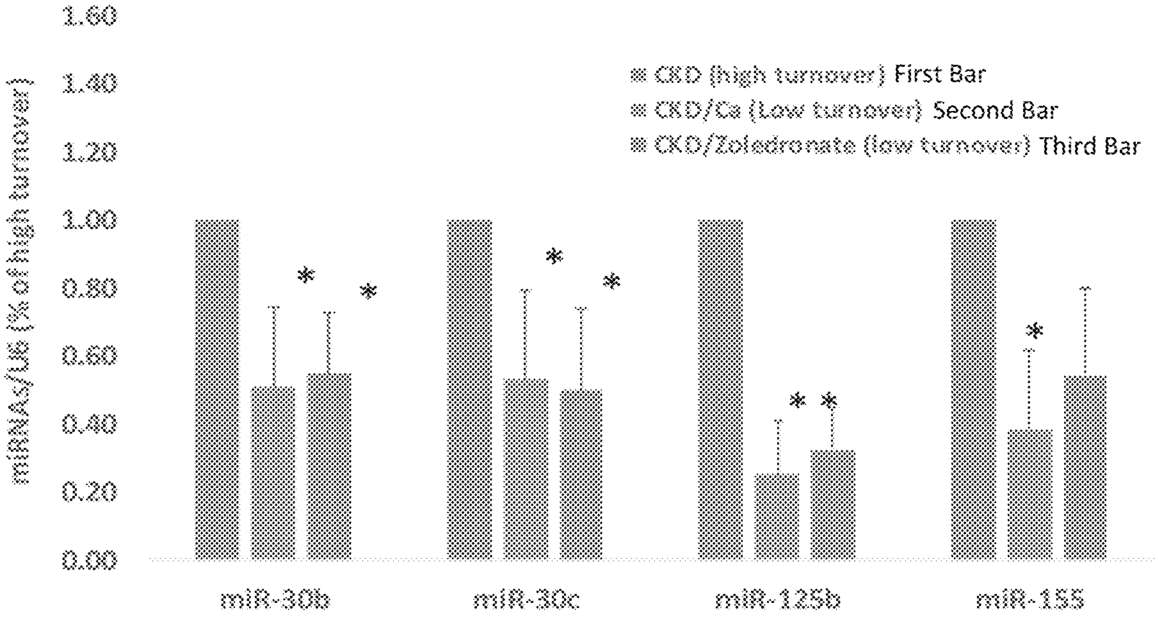
FIG. 45 shows quantified bone-tissue expression of the miRNA 30b, 30c, 125b and 155 in the CKD rats was quantified.
Figure 50:
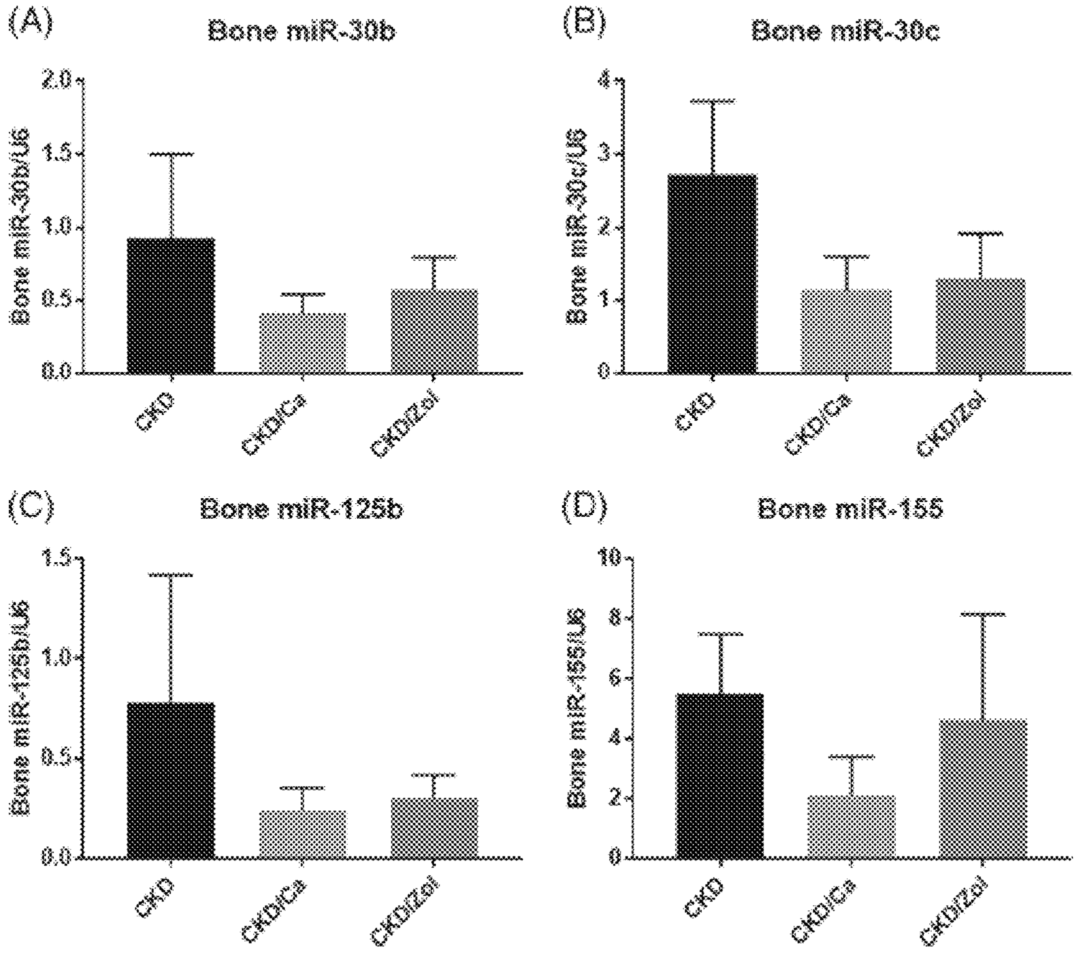
FIGS. 50A-D show quantification of miRNA-30b (FIG. 50A), 30c (FIG. 50B), 125b (FIG. 50C), and 155 (FIG. 50D) expression in bone tissue from rats with high and low turnover renal osteodystrophy. Data are shown as mean±SD (n=8 to 10 rats each group). *p<0.05 CKD versus CKD/Ca or CKD/Zol.

Low turnover was induced in CKD rats by 3% calcium in the drinking water t (low turnover, low PTH) or by administration of a single dose of zoledronic acid (low turnover, high PTH), whereas CKD rats without treatment had high turnover and high PTH. Histomorphometric analysis of bone tissue confirmed the type of turnover induced by each intervention as shown in FIGS. 44A-C. FIG. 44A shows mineral apposition rate. FIG. 44B shows mineralizing surface. FIG. 44C shows bone formation rate. Bone-tissue expression of the miRNA 30b, 30c, 125b and 155 in the CKD rats was quantified as shown in FIG. 45. Levels of all four miRNAs were lower in rats with low turnover and low PTH compared to rats with high turnover. In rats with low bone turnover and high PTH, levels of miRNA-30b, 30c and 125b but not 155 were lower compared to rats with high turnover as shown in FIG. 45. Calcium feeding or Zoledronic acid induced low turnover. The miRNA is expressed as % of the untreated or high turnover results. Low turnover was associated with statistically lower levels of miRNA expression at the bone-tissue level, regardless of how the turnover was induced.

DISCUSSION

These novel data suggest that circulating miRNAs provide accurate non-invasive diagnosis of low turnover type. The goal was to test whether a priori defined miRNAs that regulate osteoblast and osteoclast development are associated with low bone turnover. It was determined that the KDIGO recommended biomarkers of turnover, PTH and BSAP, along with 25(OH)D and other clinically used markers of bone turnover did not discriminate low turnover. In contrast, individually, circulating miR-30b, 30c, 125b, and 155 had moderate diagnostic accuracy for low turnover and a panel of all four miRNAs had high diagnostic accuracy for low turnover that was significantly better than that of PTH and BSAP. Furthermore, it was demonstrated that the circulating miRNA profile for low turnover ROD in humans was mimicked at the bone-tissue level in two rat models of low bone turnover: PTH lowering therapy with calcium or by an anti-resorptive agent.

Tetracycline double-labeled iliac crest bone biopsy is the gold standard method to determine ROD turnover-type. However, bone biopsy is not practical to obtain in the vast majority of CKD patients around the world. Therefore, KDIGO recommends using PTH and BSAP both to define turnover-type and to inform the treatment of ROD. Defining turnover-type, especially discriminating low from non-low turnover, is critical to managing ROD (68). Currently accepted treatment strategies for ROD include the use of vitamin D analogs and/or calcimimetics to suppress or mitigate the increase in PTH that occur with declining kidney function. Another critical reason to define turnover-type in ROD is to avoid treatment-induced over-suppression of remodeling, as low turnover ROD has been associated with increased risk of fractures and cardiovascular events. Furthermore, recent updates to the 2017 KDIGO Guidelines on the treatment of osteoporosis in patients with CKD recommend defining turnover-type before starting anti-osteoporosis medications so that these agents are not given to patients with low turnover(68). A major limitation of this approach is the insufficient adequacy of PTH and BSAP to discriminate turnover-type.

Two large bone biopsy studies characterized contemporary trends in prevalence rates of ROD turnover types and the diagnostic accuracy of PTH and BSAP for turnover(4, 37). In 630 dialysis patients, Malluche et al. (4) reported that low turnover was prevalent in the majority of patients (58%). Levels of PTH were lower in patients with low compared to high turnover and total alkaline phosphatase did not differ between turnover-types. A second study of 492 patients on hemodialysis was led by a KDIGO consortium and assessed the diagnostic accuracy of PTH and BSAP for turnover-type(37). Similar to Malluche et al. (4) the prevalence of low turnover predominated (59%). PTH and BSAP insufficiently identified low or high turnover to guide confidently ROD treatment: for PTH and BSAP the AUC for discriminating low vs. non-low turnover was 0.701 and 0.757 respectively and for discriminating high vs. non-high turnover ROD was 0.724 and 0.711 respectively. Combining PTH with BSAP did not improve accuracy for identifying either low or high turnover ROD. Sprague et al (37) also assessed diagnostic test characteristics for P1NP, which did not differ from those of PTH or BSAP. Among non-dialysis CKD patients, diagnostic test characteristics of PTH, BSAP, P1NP, osteocalcin and Trap-5b for turnover-type were similar to those reported for patients on dialysis (1,5,69,70). Our investigation assessed diagnostic test characteristics for markers of CKD-MBD (PTH, 25(OH)D, BSAP, FGF-23), of bone formation (P1NP, osteocalcin) and resorption (C-telopeptide, Trap-5b) and of WNT signaling (sclerostin) for discrimination of turnover-type. None of the biochemical markers discriminated low turnover. The body of literature on the use of circulating biomarkers of bone to discriminate ROD turnover-type and our findings support the need for the development and study of non-invasive biomarkers with greater accuracy for ROD turnover-type. Therefore, it is encouraging to note that all miRNAs tested in our study discriminated low turnover ROD with greater diagnostic accuracy than that reported for PTH and BSAP in the largest ROD biomarker studies to date (0.701 and 0.757, respectively)(4,37).

These data are the first to use a miRNA approach to identify non-invasive biomarkers of ROD turnover-type. There is a growing body of literature on relationships between miRNAs and diseases of the skeleton. miRNA expression during osteoblast and osteoclast development has been studied(38-40), bone cell phenotypic effects of miRNA substitutions and knockdowns have been described(41,42), and the impact of hormones and RANK(43) on miRNA expression signatures have been reported. Dysregulation in levels of circulating miRNA expression has been noted in patients with osteoporosis(45-47) and fractures(48,49). In CKD patients, levels of miRNAs and PTH have been correlated(50) and in cell culture inorganic phosphate was shown to modulate osteoclastogenesis by miRNA-233(51), but miRNAs have not been tested as biomarkers of turnover against gold standard bone biopsy in CKD patients with ROD. miRNAs did not correlated with PTH, 25(OH)D, BSAP or other markers of CKD-MBD or bone turnover. This may reflect differences in their relationships with cellular processes and gene networks occurring at the bone-tissue level. Indeed, the animal models suggest that levels of circulating miRNAs reflect miRNA expression in bone-tissue and may represent a direct non-invasive marker of bone cell activity. In contrast, levels of calciotropic hormones, such as PTH, are regulated by phosphorus and calcium rather than bone cellular activity. Bone turnover makers reflect osteoblast and osteoclast activity, but osteocalcin, P1NP monomer and C-telopeptide are cleared by the kidney and circulating levels may not accurately reflect bone cell activity. A panel of miRNAs more accurately discriminated low turnover than a single miRNA; a finding that is consistent with data in other diseases such as hepatocellular cancer(71). These data need to be confirmed in future studies with large cohorts of patients, with human bone-tissue level confirmation of miRNA expression patterns, and with studies demonstrating that the miRNA profile changes in response to bone-tissue level changes in turnover.

Studies were conducted to quantify bone-tissue expression levels of miRNAs in a rat model of ROD to confirm bone as a source of these miRNA. The mechanism of developing low turnover was either treatment of calcium in drinking water to reduce levels of PTH or the administration of zoledronic acid. Similar to circulating miRNA profiles in humans bone tissue expression of the four miRNAs were lower in rats with low turnover induced by low PTH, and miRNA-30c and 125 were lower in rats with low turnover induced with high PTH by zoledronic acid compared to bone from rats with high turnover. These results suggest that lower bone miRNA expression is reflecting the low turnover in CKD regardless of PTH levels.

Future work in larger prospective cohorts can be used to validate these data, our reported AUCs for PTH and BSAP are consistent with those reported in other studies of patients with CKD. Furthermore, further data is needed regarding the miRNA profile changes in response to changes in turnover-type, whether due to the natural history of renal osteodystrophy or due to treatment effects. The miRNA panel that was identified had accurate discrimination for low turnover versus non-low turnover, an important differentiation for when to stop, or when not to start, treatments. While the animal data suggest that bone-tissue miRNA expression is reflected by bone turnover status, studies are needed to determine circulating miRNA in animals, the cell origin of these miRNAs (e.g., osteoblast, osteocyte, osteoclast), and human bone tissue miRNA expression levels.

In conclusion, four circulating miRNA biomarkers were identified in the present subject matter that discriminated low bone turnover ROD. Further validation of their diagnostic test characteristics can be performed, additionally, other miRNA biomarkers of low and high turnover can be identifed, and and further studies on the use of the panel of miRNA to inform clinical management can be performed.

REFERENCES FOR EXAMPLE 6

1. Spasovski G B, Bervoets A R, Behets G J, Ivanovski N, Sikole A, Dams G, et al. Spectrum of renal bone disease in end-stage renal failure patients not yet on dialysis. Nephrol Dial Transplant. 2003; 18(6):1159-66.
2. Hamdy N A, Kanis J A, Beneton M N, Brown C B, Juttmann J R, Jordans J G, et al. Effect of alfacalcidol on natural course of renal bone disease in mild to moderate renal failure. BMJ. 1995; 310(6976):358-63.
3. Coen G, Mazzaferro S, Bonucci E, Taggi F, Ballanti P, Bianchi A R, et al. Bone GLA protein in predialysis chronic renal failure. Effects of 1,25(OH)2D3 administration in a long-term follow-up. Kidney Int. 1985; 28(5):783-90.
4. Malluche H H, Mawad H W, Monier-Faugere M C. Renal osteodystrophy in the first decade of the new millennium: analysis of 630 bone biopsies in black and white patients. J Bone Miner Res. June 2011; 26(6):1368-76.
5. Behets G J, Spasovski G, Sterling L R, Goodman W G, Spiegel D M, De Broe M E, et al. Bone histomorphometry before and after long-term treatment with cinacalcet in dialysis patients with secondary hyperparathyroidism. Kidney Int. April 2015; 87(4):846-56.
6. Nickolas T L, Stein E M, Dworakowski E, Nishiyama K K, Komandah-Kosseh M, Zhang C A, et al. Rapid cortical bone loss in patients with chronic kidney disease. J Bone Miner Res. August 2013; 28(8):1811-20.
7. Nickolas T L, McMahon D J, Shane E. Relationship between Moderate to Severe Kidney Disease and Hip Fracture in the United States. J Am Soc Nephrol. 2006; 17(11):3223-32.
8. Fried L F, Biggs M L, Shlipak M G, Seliger S, Kestenbaum B, Stehman-Breen C, et al. Association of kidney function with incident hip fracture in older adults. J Am Soc Nephrol. 2007; 18(1):282-6.
9. Ball A M, Gillen D L, Sherrard D, Weiss N S, Emerson S S, Seliger S L, et al. Risk of Hip Fracture Among Dialysis and Renal Transplant Recipients. JAMA: The Journal of the American Medical Association. 2002; 288 (23):3014-8.
10. Dooley A C, Weiss N S, Kestenbaum B. Increased risk of hip fracture among men with CKD. Am J Kidney Dis. January 2008; 51(1):38-44.
11. Naylor K L, McArthur E, Leslie W D, Fraser L A, Jamal S A, Cadarette S M, et al. The three-year incidence of fracture in chronic kidney disease. Kidney Int. Jan. 15, 2014.
12. Isakova T, Craven T E, Scialla J J, Nickolas T L, Schnall A, Barzilay J, et al. Change in estimated glomerular filtration rate and fracture risk in the Action to Control Cardiovascular Risk in Diabetes Trial. Bone. September 2015; 78:23-7.
13. Toussaint N D, Lau K K, Strauss B J, Polkinghorne K R, Kerr P G. Associations between vascular calcification, arterial stiffness and bone mineral density in chronic kidney disease. Nephrol Dial Transplant. February 2008; 23(2):586-93.
14. London G M, Marty C, Marchais S J, Guerin A P, Metivier F, de Vernejoul M C. Arterial calcifications and bone histomorphometry in end-stage renal disease. J Am Soc Nephrol. July 2004; 15(7):1943-51.
15. London G M, Marchais S J, Guerin A P, Boutouyrie P, Metivier F, de Vernejoul M C. Association of bone activity, calcium load, aortic stiffness, and calcifications in ESRD. J Am Soc Nephrol. September 2008; 19(9):1827-35. Epub 2008/05/16.
16. Adragao T, Herberth J, Monier-Faugere M C, Branscum A J, Ferreira A, Frazao J M, et al. Low bone volume—a risk factor for coronary calcifications in hemodialysis patients. Clin J Am Soc Nephrol. February 2009; 4(2):450-5. Epub 2009/01/23.
17. Kurz P, Monier-Faugere M C, Bognar B, Werner E, Roth P, Vlachojannis J, et al. Evidence for abnormal calcium homeostasis in patients with adynamic bone disease. Kidney Int. September 1994; 46(3):855-61. Epub 1994/09/01.
18. Kim S M, Long J, Montez-Rath M, Leonard M, Chertow G M. Hip Fracture in Patients with Non-Dialysis-Requiring Chronic Kidney Disease. J Bone Miner Res. May 4 2016. Epub 2016/05/05.
19. Alem A M, Sherrard D J, Gillen D L, Weiss N S, Beresford S A, Heckbert S R, et al. Increased risk of hip fracture among patients with end-stage renal disease. Kidney Int. July 2000; 58(1):396-9.
20. Go A S, Chertow G M, Fan D, McCulloch C E, Hsu C Y. Chronic kidney disease and the risks of death, cardiovascular events, and hospitalization. N Engl J Med. Sep. 23, 2004; 351(13):1296-305.
21. Moe S, Drueke T, Cunningham J, Goodman W, Martin K, Olgaard K, et al. Definition, evaluation, and classification of renal osteodystrophy: a position statement from Kidney Disease: Improving Global Outcomes (KDIGO). Kidney Int. June 2006; 69(11):1945-53.
22. Jamal S A, Ljunggren O, Stehman-Breen C, Cummings S R, McClung M R, Goemaere S, et al. Effects of denosumab on fracture and bone mineral density by level of kidney function. J Bone Miner Res. August 2011; 26(8):1829-35. Epub 2011/04/15.
23. Ishani A, Blackwell T, Jamal S A, Cummings S R, Ensrud K E, Investigators M. The effect of raloxifene treatment in postmenopausal women with CKD. J Am Soc Nephrol. July 2008; 19(7):1430-8.
24. Jamal S A, Bauer D C, Ensrud K E, Cauley J A, Hochberg M, Ishani A, et al. Alendronate Treatment in Women with Normal to Severely Impaired Renal Function: An Analysis of the Fracture Intervention Trial*. J Bone Miner Res. 2007.
25. Miller P D, Schwartz E N, Chen P, Misurski D A, Krege J H. Teriparatide in postmenopausal women with osteoporosis and mild or moderate renal impairment. Osteoporos Int. January 2007; 18(1):59-68.
26. Miller P D, Roux C, Boonen S, Barton I P, Dunlap L E, Burgio D E. Safety and efficacy of risedronate in patients with age-related reduced renal function as estimated by the cockcroft and gault method: a pooled analysis of nine clinical trials. J Bone Miner Res. 2005; 20(12):2105-15.
27. Cejka D, Benesch T, Krestan C, Roschger P, Klaushofer K, Pietschmann P, et al. Effect of teriparatide on early bone loss after kidney transplantation. Am J Transplant. September 2008; 8(9):1864-70.
28. Cejka D, Kodras K, Bader T, Haas M. Treatment of Hemodialysis-Associated Adynamic Bone Disease with Teriparatide (PTH1-34): A Pilot Study. Kidney & blood pressure research. 2010; 33(3):221-6.
29. Palcu P, Dion N, Ste-Marie L G, Goltzman D, Radziunas I, Miller P D, et al. Teriparatide and bone turnover and formation in a hemodialysis patient with low-turnover bone disease: a case report. Am J Kidney Dis. June 2015; 65(6):933-6.
30. Sumida K, Ubara Y, Hoshino J, Mise K, Hayami N, Suwabe T, et al. Once-weekly teriparatide in hemodialysis patients with hypoparathyroidism and low bone mass: a prospective study. Osteoporosis International. journal article 2016; 27(4):1441-50.
31. Block G A, Bone H G, Fang L, Lee E, Padhi D. A single-dose study of denosumab in patients with various degrees of renal impairment. J Bone Miner Res. July 2012; 27(7):1471-9.
32. Khairallah P, Nickolas T L. Management of Osteoporosis in CKD. Clin J Am Soc Nephrol. Feb. 27, 2018.

33. Coco M, Rush H. Increased incidence of hip fractures in dialysis patients with low serum parathyroid hormone. Am J Kidney Dis. 2000; 36(6):1115-21.
34. Davies M R, Lund R J, Mathew S, Hruska K A. Low turnover osteodystrophy and vascular calcification are amenable to skeletal anabolism in an animal model of chronic kidney disease and the metabolic syndrome. J Am Soc Nephrol. April 2005; 16(4):917-28.
35. Barreto D V, Barreto Fde C, Carvalho A B, Cuppari L, Draibe S A, Dalboni M A, et al. Association of changes in bone remodeling and coronary calcification in hemodialysis patients: a prospective study. Am J Kidney Dis. December 2008; 52(6):1139-50. Epub 2008/10/01.
36. Chapter 1: Introduction and definition of CKD-MBD and the development of the guideline statements. Kidney Int.//print 2009; 76(5113):53-58.
37. Sprague S M, Bellorin-Font E, Jorgetti V, Carvalho A B, Malluche H H, Ferreira A, et al. Diagnostic Accuracy of Bone Turnover Markers and Bone Histology in Patients With CKD Treated by Dialysis. Am J Kidney Dis. Aug. 25, 2015.
38. Bakhshandeh B, Soleimani M, Hafizi M, Paylakhi S H, Ghaemi N. MicroRNA signature associated with osteogenic lineage commitment. Molecular Biology Reports. journal article 2012; 39(7):7569-81.
39. Eguchi T, Watanabe K, Hara E S, Ono M, Kuboki T, Calderwood S K. OstemiR: A Novel Panel of MicroRNA Biomarkers in Osteoblastic and Osteocytic Differentiation from Mesencymal Stem Cells. PLoS ONE. 2013; 8(3): e58796.
40. Hu R, Liu W, Li H, Yang L, Chen C, Xia Z-Y, et al. A Runx2/miR-3960/miR-2861 Regulatory Feedback Loop during Mouse Osteoblast Differentiation. Journal of Biological Chemistry. Apr. 8, 2011 2011; 286(14):12328-39.
41. Lian J B, Stein G S, van Wijnen A J, Stein J L, Hassan M Q, Gaur T, et al. MicroRNA control of bone formation and homeostasis. Nat Rev Endocrinol. Jan. 31, 2012; 8(4):212-27.
42. van Wijnen A J, van de Peppel J, van Leeuwen J P, Lian J B, Stein G S, Westendorf J J, et al. MicroRNA Functions in Osteogenesis and Dysfunctions in Osteoporosis. Current Osteoporosis Reports. journal article 2013; 11(2):72-82.
43. Kagiya T, Nakamura S. Expression profiling of microRNAs in RAW264.7 cells treated with a combination of tumor necrosis factor alpha and RANKL during osteoclast differentiation. J Periodontal Res. June 2013; 48(3):373-85.
44. Feichtinger X, Muschitz C, Heimel P, Baierl A, Fahrleitner-Pammer A, Redl H, et al. Bone-related Circulating MicroRNAs miR-29b-3p, miR-550a-3p, and miR-324-3p and their Association to Bone Microstructure and Histomorphometry. Scientific reports. Mar. 20, 2018; 8(1): 4867.
45. An J H, Ohn J H, Song J A, Yang J Y, Park H, Choi H J, et al. Changes of microRNA profile and microRNA-mRNA regulatory network in bones of ovariectomized mice. J Bone Miner Res. March 2014; 29(3):644-56.
46. Garmilla-Ezquerra P, Sañudo C, Delgado-Calle J, Pérez-Nuñez M I, Sumillera M, Riancho J A. Analysis of the Bone MicroRNome in Osteoporotic Fractures. Calcified tissue international. journal article 2015; 96(1):30-7.
47. Seeliger C, Karpinski K, Haug A T, Vester H, Schmitt A, Bauer J S, et al. Five freely circulating miRNAs and bone tissue miRNAs are associated with osteoporotic fractures. J Bone Miner Res. August 2014; 29(8):1718-28. Epub 2014/01/17.
48. Heilmeier U, Hackl M, Skalicky S, Weilner S, Schroeder F, Vierlinger K, et al. Serum miRNA Signatures Are Indicative of Skeletal Fractures in Postmenopausal Women With and Without Type 2 Diabetes and Influence Osteogenic and Adipogenic Differentiation of Adipose Tissue-Derived Mesenchymal Stem Cells In Vitro. J Bone Miner Res. December 2016; 31(12):2173-92. Epub 2016/06/28.
49. Weilner S, Skalicky S, Salzer B, Keider V, Wagner M, Hildner F, et al. Differentially circulating miRNAs after recent osteoporotic fractures can influence osteogenic differentiation. Bone. October 2015; 79:43-51. Epub 2015/06/01.
50. Jeong S, Oh J M, Oh K H, Kim I W. Differentially expressed miR-3680-5p is associated with parathyroid hormone regulation in peritoneal dialysis patients. PLoS One. 2017; 12(2): e0170535.
51. M'Baya-Moutoula E, Louvet L, Metzinger-Le Meuth V, Massy Z A, Metzinger L. High inorganic phosphate concentration inhibits osteoclastogenesis by modulating miR-223. Biochimica et biophysica acta. October 2015; 1852(10 Pt A):2202-12.
52. Balderman J A, Lee H Y, Mahoney C E, Handy D E, White K, Annis S, et al. Bone morphogenetic protein-2 decreases microRNA-30b and microRNA-30c to promote vascular smooth muscle cell calcification. Journal of the American Heart Association. December 2012; 1(6): e003905. Epub 2013/01/15.
53. Zhang Y, Xie R L, Croce C M, Stein J L, Lian J B, van Wijnen A J, et al. A program of microRNAs controls osteogenic lineage progression by targeting transcription factor Runx2. Proc Natl Acad Sci USA. Jun. 14, 2011; 108(24):9863-8.
54. Wang H, Xie Z, Hou T, Li Z, Huang K, Gong J, et al. MiR-125b Regulates the Osteogenic Differentiation of Human Mesenchymal Stem Cells by Targeting BMPR1b. Cell Physiol Biochem. 2017; 41(2):530-42.
55. Zhao H, Zhang J, Shao H, Liu J, Jin M, Chen J, et al. Transforming Growth Factor beta1/Smad4 Signaling Affects Osteoclast Differentiation via Regulation of miR-155 Expression. Molecules and cells. March 2017; 40(3): 211-21. Epub 2017/04/01.
56. Zhang J, Zhao H, Chen J, Xia B, Jin Y, Wei W, et al. Interferon-beta-induced miR-155 inhibits osteoclast differentiation by targeting SOCS1 and MITF. FEBS Lett. Sep. 21, 2012; 586(19):3255-62. Epub 2012/07/10.
57. Nickolas T L, Cremers S, Zhang A, Thomas V, Stein E, Cohen A, et al. Discriminants of prevalent fractures in chronic kidney disease. J Am Soc Nephrol. August 2011; 22(8):1560-72. Epub 2011/07/26.
58. Nickolas T L, Stein E, Cohen A, Thomas V, Staron R B, McMahon D J, et al. Bone mass and microarchitecture in CKD patients with fracture. J Am Soc Nephrol. August 2010; 21(8):1371-80. Epub 2010/04/17.
59. Coresh J, Astor B, McQuillan G, Kusek J, Greene T, Van Lente F, et al. Calibration and random variation of the serum creatinine assay as critical elements of using equations to estimate glomerular filtration rate. American Journal of Kidney Diseases. 2002; 39(5):920-9.
60. Chen N X, Kiattisunthorn K, O'Neill K D, Chen X, Moorthi R N, Gattone V H, 2nd, et al. Decreased microRNA is involved in the vascular remodeling abnormalities in chronic kidney disease (CKD). PLoS One. 2013; 8(5):e64558.
61. Dempster D W, Compston J E, Drezner M K, Glorieux F H, Kanis J A, Malluche H, et al. Standardized nomenclature, symbols, and units for bone histomorphometry: a 2012 update of the report of the ASBMR Histomorphometry Nomenclature Committee. J Bone Miner Res. January 2013; 28(1):2-17.

62. KDIGO clinical practice guideline for the diagnosis, evaluation, prevention, and treatment of Chronic Kidney Disease-Mineral and Bone Disorder (CKD-MBD). Kidney Int Suppl. August 2009(113):S1-130. Epub 2009/08/01.

63. Moe S M, Chen N X, Seifert M F, Sinders R M, Duan D, Chen X, et al. A rat model of chronic kidney disease-mineral bone disorder. Kidney Int. January 2009; 75(2):176-84. Epub 2008/09/19.

64. Cowley B D, Jr., Gudapaty S, Kraybill A L, Barash B D, Harding M A, Calvet J P, et al. Autosomal-dominant polycystic kidney disease in the rat. Kidney Int. March 1993; 43(3):522-34.

65. Allen M R, Chen N X, Gattone V H, 2nd, Chen X, Carr A J, LeBlanc P, et al. Skeletal effects of zoledronic acid in an animal model of chronic kidney disease. Osteoporos Int. April 2013; 24(4):1471-81.

66. Moe S M, Chen N X, Newman C L, Gattone V H, 2nd, Organ J M, Chen X, et al. A comparison of calcium to zoledronic acid for improvement of cortical bone in an animal model of CKD. J Bone Miner Res. April 2014; 29(4):902-10. Epub 2013/09/17.

67. Moe S M, Chen N X, Newman C L, Organ J M, Kneissel M, Kramer I, et al. Anti-sclerostin antibody treatment in a rat model of progressive renal osteodystrophy. J Bone Miner Res. March 2015; 30(3):499-509.

68. Ketteler M, Block G A, Evenepoel P, Fukagawa M, Herzog C A, McCann L, et al. Executive summary of the 2017 KDIGO Chronic Kidney Disease-Mineral and Bone Disorder (CKD-MBD) Guideline Update: what's changed and why it matters. Kidney Int. July 2017; 92(1):26-36. Epub 2017/06/26.

69. Bervoets A R, Spasovski G B, Behets G J, Dams G, Polenakovic M H, Zafirovska K, et al. Useful biochemical markers for diagnosing renal osteodystrophy in predialysis end-stage renal failure patients. Am J Kidney Dis. May 2003; 41(5):997-1007.

70. Lehmann G, Ott U, Kaemmerer D, Schuetze J, Wolf G. Bone histomorphometry and biochemical markers of bone turnover in patients with chronic kidney disease Stages 3-5. Clin Nephrol. October 2008; 70(4):296-305.

71. Lin X J, Chong Y, Guo Z W, Xie C, Yang X J, Zhang Q, et al. A serum microRNA classifier for early detection of hepatocellular carcinoma: a multicentre, retrospective, longitudinal biomarker identification study with a nested case-control study. Lancet Oncol. July 2015; 16(7):804-15. Epub 2015/06/20.

Example 7—A microRNA Approach to Discriminate Cortical Low Bone Turnover in Renal Osteodystrophy Abstract A main obstacle to diagnose and manage renal osteodystrophy (ROD) is the identification of intracortical bone turnover type (low, normal, high). The gold standard, tetracycline-labeled transiliac crest bone biopsy, is impractical to obtain in most patients. The Kidney Disease Improving Global Outcomes Guidelines recommend PTH and bone-specific alkaline phosphatase (BSAP) for the diagnosis of turnover type. However, PTH and BSAP have insufficient diagnostic accuracy to differentiate low from non-low turnover and were validated for trabecular turnover. Without being bound by theory, four circulating microRNAs (miRNAs) that regulate osteoblast (miRNA-30b, 30c, 125b) and osteoclast development (miRNA-155) would provide superior discrimination of low from non-low turnover than biomarkers in clinical use. In 23 patients with CKD 3-5D, tetracycline-labeled transiliac crest bone biopsy was obtained and circulating levels of intact PTH, BSAP, and miRNA-30b, 30c, 125b, and 155 were measured. Spearman correlations assessed relationships between miRNAs and histomorphometry and PTH and BSAP. Diagnostic test characteristics for discriminating low from non-low intracortical turnover were determined by receiver operator curve analysis; areas under the curve (AUC) were compared by $\chi 2$ test. In CKD rat models of low and high turnover ROD, histomorphometry was performed and the expression of bone tissue miRNAs was determined. Circulating miRNAs moderately correlated with bone formation rate and adjusted apposition rate at the endo- and intracortical envelopes ($\rho=0.43$ to $0.51$; $p<0.05$). Discrimination of low versus non-low turnover was 0.866, 0.813, 0.813, and 0.723 for miRNA-30b, 30c, 125b, and 155, respectively, and 0.509 and 0.589 for PTH and BSAP, respectively. For all four miRNAs combined, the AUC was 0.929, which was superior to that of PTH and BSAP alone and together ($p<0.05$). In CKD rats, bone tissue levels of the four miRNAs reflected the findings in human serum. These data suggest that a panel of circulating miRNAs provide accurate noninvasive identification of bone turnover in ROD.

INTRODUCTION

Renal osteodystrophy (ROD) is a progressive disease of cortical bone.[1, 2, 3, 4, 5] In ROD, cortical density, geometry, microarchitecture, and strength undergo progressive deterioration caused by the combined actions of high circulating levels of PTH and elevated bone remodeling rates.[1, 2, 6] In contrast, ROD is associated with trabecular hypertrophy rather than the trabecular dropout and disconnectivity that is associated with postmenopausal and glucocorticoid-induced osteoporosis.[2] Therefore, CKD patients are at increased risk of cortical-type bone fractures; since 1992 there has been a doubling of peripheral fracture incidence in patients with end-stage kidney disease on dialysis.[7,8]

Although cortical bone is critical to the pathogenesis of ROD, trabecular rather than cortical remodeling rates are used to determine ROD type and to inform ROD treatment decisions.[3, 9, 10, 11, 12] Indeed, the Kidney Disease Improving Global Outcomes (KDIGO) Guidelines defined ROD by bone turnover, mineralization, and volume in trabecular bone based on quantitative histomorphometry of tetracycline double-labeled transiliac crest bone biopsy.[9] Furthermore, the primary goal of ROD treatment is to reduce high bone turnover with calcitriol and its analogues and/or calcimimetics, at the same time as avoiding the development of low turnover through excessive use of these same agents. Because widespread use of bone biopsy in the clinic for either diagnosis or treatment monitoring of ROD is impractical, KDIGO recommended that clinical use (ie, starting/stopping) of agents used to treat ROD are guided by the biomarkers PTH and bone-specific alkaline phosphatase (BSAP) based on their ability to discriminate low turnover in trabecular bone.[13] However, large-scale multinational bone biopsy studies in dialysis patients demonstrated that PTH and BSAP were poor guides for ROD treatment because of their suboptimal discrimination for low turnover ROD (areas under the curve [AUCs] 0.701 and 0.757, respectively).[3, 10] Although we assume that relationships between the cortical, endocortical, and trabecular bone compartments and bone turnover, bone turnover markers (BTMs), and ROD treatments are similar, there are no comparative studies of these relationships. Thus, there is an unmet clinical need to identify noninvasive biomarkers with strong diagnostic accuracy allowing differentiation between low from non-low turnover ROD; it is not clear whether the development and study of novel biomarkers of turnover should measure cortical rather than trabecular turnover.

MicroRNAs (miRNAs) are small noncoding sequences of approximately 22 nucleotides that bind to the 3'-untranslated regions of mRNAs to alter gene expression by inhibiting translation or promoting degradation of target mRNAs. Experimental studies have examined miRNA expression during osteoblast and osteoclast development[14, 15, 16]: Bone cell phenotypic effects of miRNA substitutions and knockdowns have been described[17, 18] and the impact of hormones and RANK[19] on miRNA expression signatures. In non-CKD patients with osteoporosis, relationships between miRNAs and histomorphometry have been reported,[20] and dysregulation in levels of circulating miRNA expression has been associated with osteoporosis[21, 22, 23] and fractures.[24, 25] In CKD patients, levels of miRNAs and PTH have been correlated[26]; in cell culture, inorganic phosphate was shown to modulate osteoclastogenesis by miRNA-233.[27] miRNAs have not been tested as biomarkers of turnover in CKD. We hypothesized that (i) circulating miRNAs reported in previous investigations to regulate osteoblast (miRNA-30b, 30c, 125b[15, 28, 29, 30]) and osteoclast (miRNA-155[31, 32]) development are associated with low turnover in all bone compartments; (ii) PTH, BSAP, and circulating BTMs used in clinical practice reflect turnover within cortical and endocortical bone; and (iii) the turnover within all three bone compartments are highly correlated. Without being bound by theory circulating miRNA profile of low turnover ROD detected in humans will be reflected at the bone tissue level in a rat model of CKD with low turnover ROD.

Subjects and Methods

Cohort

The Institutional Review Board of Columbia University Irving Medical Center (CUIMC) approved this cross-sectional study; all subjects provided written informed consent. The study design has been previously described.[1, 33, 34] In brief, 23 patients with CKD stages 3 to 5D were recruited from the general nephrology clinics of CUIMC. The estimated glomerular filtration rate (eGFR) was determined by the Modification of Diet in Renal Disease short formula for CKD patients not on dialysis.[35] Patients were excluded if they had a history of malignancy or bilateral lower extremity amputations; were nonambulatory; were institutionalized; or used bisphosphonates, teriparatide, gonadal steroids, aromatase inhibitors, or anticonvulsants that induce cytochrome-P450. All CKD etiologies were eligible. Thirteen participants had a history of fracture: five participants had vertebral fractures (occult and clinical); four participants had an ankle or metatarsal fracture; four participants had a radius fracture; one patient had a hip, clavicle, rib, or pelvic fracture; and eight participants had multiple fractures. One participant had two fractures that occurred within 12 months of bone biopsy and measurement of miRNAs and BTMs. In sensitivity analysis, removal of this participant from analysis did not materially change the results; thus, this participant was included in this research.

Laboratory Measurements and Circulating microRNA Isolation and Analysis

Fasting blood samples were obtained in the morning. Routine laboratories were measured by Quest Diagnostics (Secaucus, NJ, USA). PTH and BSAP were measured at CUIMC in a research laboratory. Calciotropic hormones and BTMs were measured at CUIMC in a specialized research laboratory. Intact PTH, serum total 25-hydroxyvitamin D (25-OHD), BSAP, N-Mid osteocalcin (OCN), P1NP, tartrate-resistant acid phosphatase 5b (TRAP-5b), and CTx were measured by Roche Elecsys 2010 Analyzer (Roche Diagnostics, Indianapolis, IN, USA). C-terminal fibroblast growth factor 23 (FGF-23) and sclerostin (SOST) were measured by ELISA (Immunotopics, San Clemente, CA, USA) and TECOmedical (Sissach, Switzerland), respectively. Intra- and interassay precisions are intact PTH 1.0% and 4.4%; BSAP 6.0% and 8.0%; OCN 0.8% and 2.9%; P1NP 1.1% and 5.5%; CTx 1.1% and 5.5%, FGF-23 2.40% and 4.70%, and SOST 3.1% and 3.5%, respectively. For 25-OHD the normal range is >30 ng/mL and the interassay precision is 2.6% to 4.4%. miRNA was measured at Indiana University School of Medicine: total RNA was isolated from serum and miRNA expression determined by real-time PCR using TaqMan miRNA assay (Applied Biosystem, Foster City, CA, USA) normalized by spiking with *C. elegans* miRNA-39.[36]

Transiliac Bone Biopsy and Histomorphometry

Figure 51:
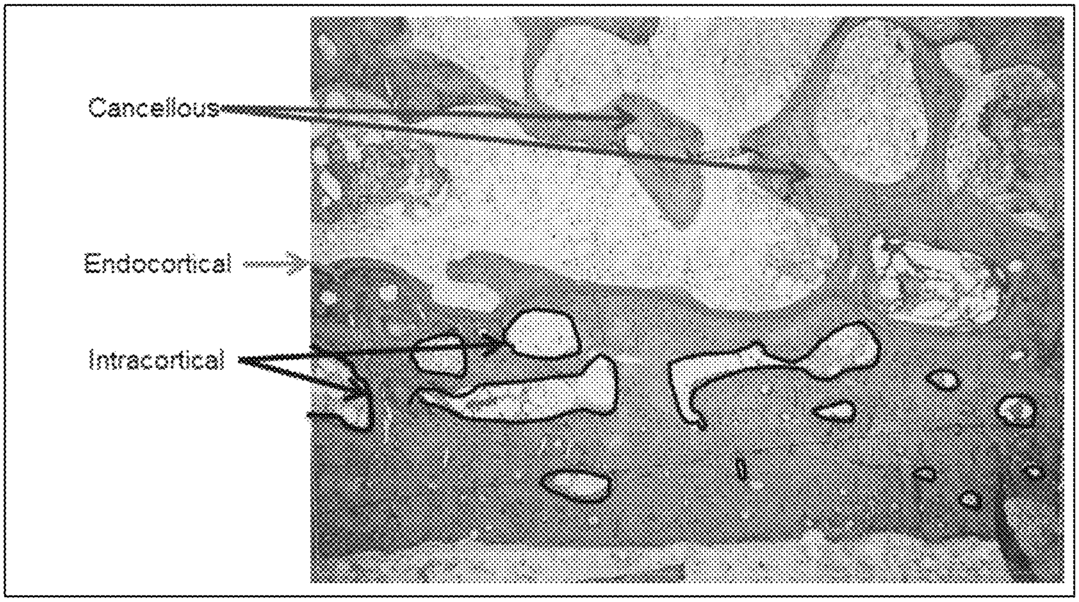
FIG. 51 shows a diagram of trabecular, endocortical and intracortical bone compartment segmentation. The trabecular and endocortical envelopes include all interior bone surfaces in contact with the bone marrow space; the endocortical envelop is then defined as the bone surface lining the cortex. If segmentation of the inner boundary of cortex includes or straddles an open space, it is considered to be a bone marrow extension if the thickness of the trabecula separating the open space from the bone marrow cavity is ≤radius of the open space; therefore, the open space is excluded from the inner boundary of the cortex and included as part of the trabecular envelope. The intracortical bone surface is referred to as the Haversian or osteonal canal surface and defined as the surface of cortical porosity where there are enlarged Haversian or osteonal canals ≥50 μm in diameter.

After double-labeling with tetracycline in a 3-:12-:3-day sequence, transiliac bone biopsy was performed using a 7.5-mm Bordier-type trephine. Specimens were fixed in 70% ethanol, processed without decalcification, and embedded in methylmethacrylate. Histomorphometry was performed on Goldner's trichrome stained or unstained sections with a morphometric program (OsteoMeasure, Version 4.000; OsteoMetrics, Inc., Atlanta, GA, USA). The trabecular, endocortical, and cortical bone compartments were delineated manually prior to measurement of histomorphometric parameters (FIG. 51). All variables were expressed and calculated according to the recommendations of the ASBMR for the trabecular, endocortical, and cortical bone compartments.[37] Classification of ROD was assessed by interpreting histology and histomorphometry indices according to the Turnover, Mineralization, and Volume (TMV) system.[38]

Animal Models

The Cy/+ rat model of CKD was used to assess bone expression of miRNAs. Cy/+ rats are characterized by an autosomal dominant progressive cystic kidney disease that is not allogenic with human ADPKD.[39] In this rat model, chronic kidney disease-mineral and bone disorder (CKD-MBD) develops spontaneously, with a much faster progression to end-stage disease in male animals by 30 to 35 weeks of age, whereas female rats do not develop azotemia even as old as 21 months,[40] or after oophorectomy (unpublished data). The Cy/$+_{IU}$ colony of rats has been bred at Indiana University for nearly 20 years. The model recapitulates CKD-MBD with progressive kidney disease, hyperphosphatemia, secondary hyperparathyroidism, elevated FGF-23, resulting in ROD and vascular calcification. Importantly, the slowly progressive nature of the model allows for examination of interventions that differentially affect bone remodeling. Specifically, we have induced low turnover bone remodeling by two methods: with calcium in the drinking water (calcium binders) and zoledronic acid.[41, 42] In brief, CKD animals (n=8 to 10 each group) began treatment at 25 weeks for a total of 10 weeks and received: (i) no treatment (control CKD=high PTH/high turnover; (ii) 3% calcium in the drinking water (CKD/Ca group=low PTH/low turnover); or (iii) a single injection of 20 μg/kg of zoledronic acid (CKD/Zol group=high PTH/low turnover). At 35 weeks of age, animals were euthanized and bone tissue was collected. Bone histomorphometry was performed as previously reported.[43] RNA was isolated from tibia, and bone miRNA expression was determined by real-time PCR using TaqMan miRNA assay as described above. All procedures were reviewed and approved by the Indiana University School of Medicine Institutional Animal Care and Use Committee.

Statistical Methods

For human subjects, statistical analyses were conducted using SAS (version 9.4; SAS Institute, Cary, NC, USA). Continuous data were evaluated for normality before statistical testing and log-transformed when appropriate. Relationships between miRNAs, PTH, BSAP, BTMs, and histomorphometric parameters (bone formation rate/bone surface [BFR/BS]; adjusted apposition rate [AjAR]; mineralization lag time [MLT]) were determined by Spearman correlations at the trabecular, endocortical, and intracortical bone compartments. The cohort was stratified into patients with low and non-low turnover based on the BFR/BS at the intracortical envelope because of the known importance of cortical bone in the pathogenesis of impaired bone quality in patients with CKD.[1] The lowest tertile of intracortical BFR/BS defined low turnover because there are no normative reference data for cortical bone. Group differences for continuous parameters between patients with low versus non-low turnover were determined by Wilcoxon rank sum. Standard receiver operator characteristic (ROC) curve analysis was performed to determine the ability of biomarkers to discriminate between low and non-low turnover. We also created two biomarker panels for ROC analyses: (i) an miRNA panel including all four miRNAs; and (ii) a CKD-MBD panel including BSAP and CTX. Rat bone miRNA expression was analyzed using one-way ANOVA and within group comparisons by Fisher's post hoc analysis. The results are expressed as means±SD, with $p<0.05$ considered significant (GraphPad Prism Software; GraphPad, La Jolla, CA, USA).

Results

Cohort Characteristics, Levels of Circulating Biomarkers, and Relationships with Kidney Function Cohort characteristics stratified by low and non-low turnover in intracortical bone are presented in FIG. 46. In patients with low intracortical turnover, intracortical BFR/BS and mineral apposition rate were lower whereas MLT was higher. In contrast, among patients with low turnover based on intracortical remodeling, only BFR/BS was significantly lower in the trabecular and endocortical compartments. Bone turnover groups did not differ by demographics, kidney function, or comorbid status. Biochemical markers of CKD-MBD (calcium, phosphorus, 25(OH)D, PTH, and FGF-23), bone formation (BSAP, OCN, P1NP) and resorption (C-telopeptide, TRAPSB) markers, and SOST did not differ between low and non-low turnover. In contrast, circulating levels of miRNA-30b, 30c, and 125b were significantly lower in subjects with low compared with non-low turnover. Levels of BSAP, P1NP, and TRAP-5b, and circulating miRNAs were not affected by eGFR or dialysis status (FIG. 47 and FIG. 52A-D). In contrast, levels of PTH, vitamin D, OCN, CTx, SOST, and FGF-23 were related to kidney function.

Relationships Between Histomorphometry, miRNAs, Biochemical Makers of CKD-MBD, and Bone Turnover Spearman correlations were used to evaluate relationships between histomorphometric parameters in the trabecular, endocortical, and intracortical compartments and miRNAs and biomarkers of CKD-MBD and BTMs (FIGS. 47 and 48). BFR/BS was correlated moderately to strongly between compartments: Although trabecular BFR/BS described 72% of the heterogeneity in endocortical BFR/BS, it described only 59% of the heterogeneity in intracortical BFR/BS. CKD-MBD biomarkers, BTMs, and miRNAs were moderately related to formation and mineralization measures at the trabecular, endocortical, and intracortical regions. For CKD-MBD biomarkers, PTH and 25(OH)D were directly related to BFR/BS in trabecular bone and BSAP was directly related to BFR/BS in trabecular and intracortical bone. For BTMs, OCN and CTx were directly related to BFR/BS in all bone compartments. For the miRNAs, miRNA-30b, 30c, and 125b were directly and strongly related to each other and were positively and moderately related to miRNA-155. miRNA-30b, 30c, and 125b were inversely related to phosphorus levels; miRNA-30b and 30c were inversely related to calcium. None of the miRNAs were related to CKD-MBD biomarkers or BTMs. miRNA-30b, 30c, and 125b were moderately and directly related to the AjAR in intracortical bone and 125b was inversely related to MLT in intracortical bone.

We used discrimination analysis to determine and compare diagnostic test characteristics of miRNAs, markers of CKD-MBD (PTH, BSAP), and BTMs to differentiate low from non-low turnover in all bone compartments (FIG. 49). In trabecular bone, markers of CKD-MBD and BTMs moderately discriminated low turnover. A CKD-MBD biomarker panel, including BSAP and CTx, had good discrimination for low turnover (AUC 0.882; 95% CI, 0.731 to 1.000) that was superior to the individual miRNAs, but not to the miRNA panel. In endocortical bone, none of the individual biomarkers discriminated low turnover; however, the miRNA panel of all four miRNAs had excellent discrimination (AUC 0.982; 95% CI, 0.940 to 1.000) that was superior to the other individual BTM and the CKD-MBD panel. In intracortical bone, none of the markers of CKD-MBD or BTM discriminated, but all miRNAs moderately discriminated low turnover. The miRNA panel highly discriminated low turnover (AUC 0.929; 95% CI, 0.821 to 1.000), which was superior to other biomarkers.

Bone Tissue miRNA Expression in CKD Rats with Low and High Turnover ROD

Figure 53C:
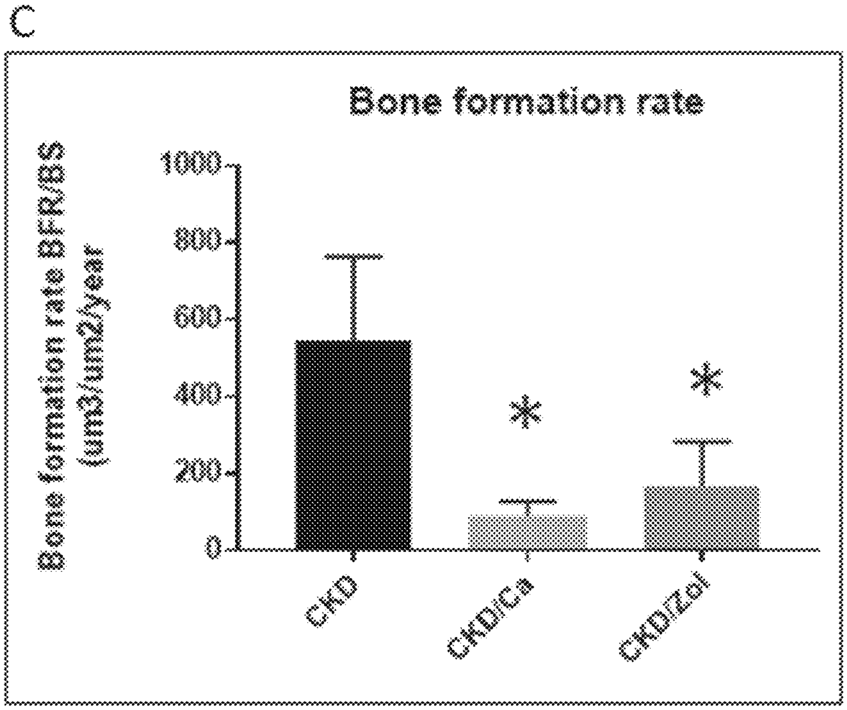

We induced low bone turnover in CKD rats by either adding calcium (3%) in the drinking water (low turnover, low PTH) or administration of a single dose of zoledronic acid (low turnover, high PTH), whereas CKD rats without treatment had high turnover and high PTH. Histomorphometric analysis of bone tissue confirmed the type of turnover induced by each intervention (FIGS. 53A-C). We also quantified bone tissue expression of the miRNA 30b, 30c, 125b, and 155 in the CKD rats (FIGS. 50A-D). Levels of all four miRNAs were lower in rats with low turnover and low PTH compared with rats with high turnover. In rats with low bone turnover and high PTH, levels of miRNA-30b, 30c, and 125b, but not 155 were lower compared with rats with high turnover. Levels of miRNAs did not differ between rats with low bone turnover induced by dietary calcium or zoledronic acid.

DISCUSSION

We report relationships between bone turnover in the trabecular, endocortical, and intracortical compartments and both traditional and novel circulating markers of bone turnover. Differences in bone turnover rates were present between the bone compartments, and turnover in the trabecular and intracortical compartments was similar only 60% of the time. Although it was thought that discrimination of low turnover by markers of CKD-MBD, BTMs, and miR- NAs would be similar within the three bone compartments, differences were found: Markers of CKD-MBD and BTMs discriminated low turnover only in trabecular bone and miRNAs discriminated low turnover only in cortical bone. We used combinations of biomarkers to determine if discrimination could be significantly enhanced in comparison to the individual biomarkers; we found that a CKD-MBD panel (BSAP, CTx) had highest discrimination in trabecular bone and that a miRNA panel had highest discrimination in endocortical and intracortical bone. Furthermore, we demonstrated that the circulating miRNA profile for low turnover ROD in humans was mimicked at the bone tissue level in two rat models of low bone turnover: PTH lowering therapy with calcium or by an antiresorptive agent.

Cortical bone is critically important to the pathogenesis of ROD and CKD-associated fractures. Cortical bone comprises more than 75% of the skeleton and is a critical component of bone strength. Indeed, reductions in cortical thickness were shown to have a greater negative impact on whole bone strength than reductions in either trabecular number or thickness,[44] and small increases in cortical porosity disproportionately affect bone strength and may contribute substantially to the risk of fractures.[45, 46] ROD impairs cortical density, geometry, and microarchitecture based on the actions of hyperparathyroidism and elevated bone remodeling rates.[1, 2, 3, 4, 5] In a longitudinal study of 53 patients with CKD 2-5D, Nickolas and colleagues[1] used HR-pQCT to assess the effects of kidney disease on the skeleton. They reported that (i) cortical density and thickness decreased by 1.3% and 2.8% per year, respectively; (ii) cortical porosity increased by 4.2% per year; and (iii) trabecular microarchitecture was unchanged. They also reported that the cortical changes were driven by both elevated levels of PTH and bone turnover as measured by BTMs. Sharma and colleagues[6] performed transiliac crest bone biopsy in 14 patients with CKD 5-5D and quantified defects in the trabecular and cortical compartments by μCT. Although trabecular microarchitecture was relatively preserved, cortices were thinned and porous in all patients. Cortical defects were related to higher levels of PTH. The clinical relevance of cortical defects in ROD is manifested by the higher incidence of peripheral compared with central fractures.[7] Whereas evidence for the importance of cortical bone in the pathophysiology of ROD and CKD-associated fractures is well-established, the assessment of ROD-type by markers of CKD-MBD and BTMs is based on relationships within trabecular bone, under the assumption that turnover in all bone compartments are highly correlated and because trabecular bone is assumed to be the most metabolically active bone compartment. For the first time in CKD patients, we report on comparisons between bone-biopsy-derived compartmental turnover and markers of CKD-MBD, BTMs, and novel miRNA panel. Our findings highlight differences in turnover between compartments that may be relevant to ROD diagnosis and management.

Tetracycline double-labeled iliac crest bone biopsy is the gold standard method to determine ROD turnover type. However, bone biopsy is not practical to obtain in the vast majority of CKD patients. Therefore, KDIGO recommended using PTH and BSAP both to define turnover-type and to inform the treatment of ROD. Defining turnover type, especially discriminating low from non-low turnover, is critical to managing ROD.[47] Currently accepted treatment strategies for ROD include the use of vitamin D analogs and/or calcimimetics to suppress or mitigate the increase in PTH that occurs with declining kidney function. Another critical reason to define turnover type in ROD is to avoid treatment-induced oversuppression of bone remodeling, as low turnover ROD has been associated with increased risk of fractures and vascular calcifications.[48, 49, 50] Furthermore, recent updates to the 2017 KDIGO Guidelines on the treatment of osteoporosis in patients with CKD recommend defining turnover type before starting antiosteoporosis medications so that these agents are not given to patients with low turnover.[47] A major limitation of this approach is the insufficient adequacy of PTH and BSAP to discriminate between low and non-low turnover type. Two large bone biopsy studies characterized contemporary trends in prevalence rates of ROD turnover types and the diagnostic accuracy of PTH and BSAP for turnover.[3, 10] In 630 dialysis patients, Malluche and colleagues[3] reported that low turnover ROD was prevalent in the majority of patients (58%). Levels of PTH were lower in patients with low compared with high turnover, and total alkaline phosphatase did not differ between ROD turnover types. A second study of 492 patients on hemodialysis was led by a KDIGO consortium and assessed the diagnostic accuracy of PTH and BSAP for turnover type.[10] Similar to Malluche and colleagues[3] the prevalence of low turnover predominated (59%). PTH and BSAP insufficiently differentiated between low or high turnover to guide ROD treatment confidently: For PTH and BSAP, the AUC for discriminating low versus non-low turnover was 0.701 and 0.757, respectively, and for discriminating high versus non-high turnover ROD was 0.724 and 0.711, respectively. Combining PTH with BSAP did not improve accuracy for identifying either low or high turnover ROD. Sprague and colleagues[(10)] also assessed diagnostic test characteristics for P1NP, which did not differ from those of PTH or BSAP. Among nondialysis CKD patients, diagnostic test characteristics of PTH, BSAP, P1NP, OCN, and TRAP-5b for turnover type were similar to those reported for patients on dialysis.[11, 12, 51, 52] Our investigation assessed diagnostic test characteristics for markers of CKD-MBD [PTH, 25(OH)D, BSAP, FGF-23], of bone formation (P1NP, OCN), and resorption (C-telopeptide, TRAP-5b) and of WNT signaling (SOST) for discrimination of ROD turnover type within the three bone compartments. We found differential discrimination of low turnover within trabecular, endocortical, and intracortical bone. Within trabecular bone, markers of CKD-MBD and BTMs had moderate discrimination, and a biomarker panel including BSAP and CTx had excellent discrimination. Individually, these circulating markers had discrimination that was consistent with those of PTH and BSAP from the largest bone biopsy study to date (0.701 and 0.757, respectively).[3, 10] However, it is noteworthy that the markers did not discriminate low turnover within cortical bone. In contrast, the miRNAs discriminated in cortical (both the endo- and intracortical compartments) bone. These findings may be consistent with the known differential effects of PTH on trabecular and cortical bone remodeling. Although the underlying mechanisms of anabolic and catabolic effects of PTH on trabecular and cortical bone, respectively, are unclear, the differences in discrimination of low turnover between compartments for the various biomarkers may be explained by these same molecular mechanisms.[53, 54] Further research is needed to determine the mechanisms by which PTH modulates turnover in the bone compartments and miRNA expression.

Our data are the first to use a novel miRNA approach to identify novel noninvasive biomarkers of ROD turnover type. There is a growing body of literature on relationships between miRNAs and the skeleton.[14, 15, 16, 17, 18, 19, 21, 22, 23, 24, 25, 55, 56] Dysregulation in levels of circulating miRNA expression has been noted in patients with osteoporosis[21, 22, 23] and fractures.[24, 25] Changes in levels of circulating miRNA caused by treatment with teriparatide and denosumab have been reported to correlate with changes in BTMs and BMD.[56] However, Feurer and colleagues[55] recently reported on relationships between 32 a priori selected miRNAs and fracture, BMD, and microarchitecture and BTMs in women with osteoporosis and healthy kidney function. They reported that miRNAs did not correlate with circulating BTMs and relationships between miRNAs and bone outcomes were negated by age.[55] In CKD patients, levels of miRNAs and PTH have been correlated[26]; in cell culture, inorganic phosphate was shown to modulate osteoclastogenesis by miRNA-233,[27] but miRNAs have not been tested as biomarkers of turnover against the gold standard bone biopsy. We found that circulating miRNAs were not affected by kidney function, which is highly relevant to their utility across CKD grades. Similar to Feurer and colleagues,[55] we did not find that miRNAs correlated with PTH, 25(OH)D, BSAP, or other markers of CKD-MBD or bone turnover. This may reflect differences in their relationships with cellular processes and gene networks occurring at the bone tissue level. Indeed, our animal models suggest that levels of circulating miRNAs reflect miRNA expression in bone tissue and may represent a direct noninvasive marker of bone cell activity. In contrast, levels of calciotropic hormones, such as PTH, are regulated by phosphorus and calcium rather than bone cellular activity. Bone turnover markers reflect osteoblast and osteoclast activity, but OCN, P1NP monomer, and C-telopeptide are cleared by the kidney and circulating levels may not accurately reflect bone cell activity, in particular, when renal function is impaired. We found that a panel of miRNAs more accurately discriminated low versus non-low turnover ROD than a single miRNA: a finding that is consistent with data in other diseases such as hepatocellular cancer.[57] These data need to be confirmed in future studies with larger cohorts of patients, with human bone tissue level confirmation of miRNA expression patterns, and with studies demonstrating that the miRNA profile changes in response to bone tissue level changes in turnover.

We conducted studies to quantify bone tissue expression levels of miRNAs in a rat model of ROD to confirm bone as a source of these miRNA. The mechanism of developing low turnover was either treatment of calcium in drinking water to reduce levels of PTH or the administration of zoledronic acid. Similar to circulating miRNA profiles in humans, bone tissue expression of the four miRNAs was lower in rats with low turnover induced by low PTH, and bone tissue expression of miRNA-30c and 125 was lower in rats with low turnover, in the setting of high PTH, induced by zoledronic acid compared with bone from rats with high turnover. These results suggest that lower bone miRNA expression is reflecting the low turnover in CKD regardless of PTH levels.

Our investigation has limitations. This was a small cross-sectional study of patients recruited at a single center. Although future work is needed in larger prospective cohorts to validate these data, our reported AUCs for PTH and BSAP are consistent with those reported in other studies of patients with CKD. Furthermore, data are needed to demonstrate that the miRNA profile changes in response to changes in turnover type, whether based on the natural history of ROD or caused by treatment effects. The miRNA panel that we identified had accurate discrimination for low versus non-low turnover in cortical bone, which has been shown to be a critical bone compartment affected by ROD. This panel of miRNAs did not relate to turnover in trabecular bone and relationships between other miRNAs and turnover in trabecular bone need to be explored. Although our animal data suggest that bone tissue miRNA expression is reflected by bone turnover status, studies are needed to determine circulating miRNA in animals, the cell origin of these miRNAs (eg, osteoblast, osteocyte, osteoclast), and human bone tissue miRNA expression levels are needed.

In conclusion, we identified four circulating miRNA biomarkers that discriminated low from non-low bone turnover ROD in cortical bone. Further research is needed to validate their diagnostic test characteristics, determine their responsiveness to the dynamic and complex clinical presentations of bone disease in patients with CKD, and identify other putative miRNA biomarkers of low and high turnover ROD and demonstrate that they inform clinical management.

REFERENCES FOR EXAMPLE 7

1. Nickolas T L, Stein E M, Dworakowski E, et al. Rapid cortical bone loss in patients with chronic kidney disease. J Bone Miner Res. 2013; 28:1811-20.
2. Parfitt A M. A structural approach to renal bone disease. J Bone Miner Res. 1998; 13:1213-20.
3. Malluche H H, Mawad H W, Monier-Faugere M C. Renal osteodystrophy in the first decade of the new millennium: analysis of 630 bone biopsies in black and white patients. J Bone Miner Res. 2011; 26:1368-76.
4. Carvalho C, Magalhaes J, Neto R, et al. Cortical bone analysis in a predialysis population: a comparison with a dialysis population. J Bone Miner Metab. 2017; 35(5): 513-21.
5. Adragao T, Herberth J, Monier-Faugere M C, et al. Femoral bone mineral density reflects histologically determined cortical bone volume in hemodialysis patients. Osteoporos Int. 2010; 21:619-25.
6. Sharma A K, Toussaint N D, Masterson R, et al. Deterioration of cortical bone microarchitecture: critical component of renal osteodystrophy evaluation. Am J Nephrol. 2018; 47:376-84.
7. Wagner J, Jhaveri K D, Rosen L, Sunday S, Mathew A T, Fishbane S. Increased bone fractures among elderly United States hemodialysis patients. Nephrol Dial Transplant. 2014; 29:146-51.
8. Denburg M, Nickolas T L. Declining hip fracture rates in dialysis patients: is this winning the war? Am J Kidney Dis. 2018; 71:154-6.
9. Moe S, Drueke T, Cunningham J, et al. Definition, evaluation, and classification of renal osteodystrophy: a position statement from kidney disease: improving global outcomes (KDIGO). Kidney Int. 2006; 69:1945-53.
10. Sprague S M, Bellorin-Font E, Jorgetti V, et al. Diagnostic accuracy of bone turnover markers and bone histology in patients with CKD treated by dialysis. Am J Kidney Dis. 2016; 67(4):559-66.
11. Bervoets A R, Spasovski G B, Behets G J, et al. Useful biochemical markers for diagnosing renal osteodystrophy in predialysis end-stage renal failure patients. Am J Kidney Dis. 2003; 41:997-1007.
12. Spasovski G B, Bervoets A R, Behets G J, et al. Spectrum of renal bone disease in end-stage renal failure patients not yet on dialysis. Nephrol Dial Transplant. 2003; 18:1159-66.
13. Chapter 1: introduction and definition of CKD-MBD and the development of the guideline statements. Kidney Int. 2009; 76:53-8.

14. Bakhshandeh B, Soleimani M, Hafizi M, Paylakhi S H, Ghaemi N. MicroRNA signature associated with osteogenic lineage commitment. Mol Biol Rep. 2012; 39:7569-81.
15. Eguchi T, Watanabe K, Hara E S, Ono M, Kuboki T, Calderwood S K. OstemiR: a novel panel of microRNA biomarkers in osteoblastic and osteocytic differentiation from mesencymal stem cells. PLoS One. 2013; 8:e58796.
16. Hu R, Liu W, Li H, et al. A Runx2/miR-3960/miR-2861 regulatory feedback loop during mouse osteoblast differentiation. J Biol Chem. 2011; 286:12328-39.
17. Lian J B, Stein G S, van Wijnen A J, et al. MicroRNA control of bone formation and homeostasis. Nat Rev Endocrinol. 2012; 8:212-27.
18. van Wijnen A J, van de Peppel J, van Leeuwen J P, et al. MicroRNA functions in osteogenesis and dysfunctions in osteoporosis. Curr Osteoporos Rep. 2013; 11:72-82.
19. Kagiya T, Nakamura S. Expression profiling of microRNAs in RAW264.7 cells treated with a combination of tumor necrosis factor alpha and RANKL during osteoclast differentiation. J Periodontal Res. 2013; 48:373-85.
20. Feichtinger X, Muschitz C, Heimel P, et al. Bone-related circulating microRNAs miR-29b-3p, miR-550a-3p, and miR-324-3p and their association to bone microstructure and histomorphometry. Sci Rep. 2018; 8:4867.
21. An J H, Ohn J H, Song J A, et al. Changes of microRNA profile and microRNA-mRNA regulatory network in bones of ovariectomized mice. J Bone Miner Res. 2014; 29:644-56.
22. Garmilla-Ezquerra P, Sañudo C, Delgado-Calle J, Pérez-Nuñez M I, Sumillera M, Riancho J A. Analysis of the bone microRNome in osteoporotic fractures. Calcif Tissue Int. 2015; 96:30-7.
23. Seeliger C, Karpinski K, Haug A T, et al. Five freely circulating miRNAs and bone tissue miRNAs are associated with osteoporotic fractures. J Bone Miner Res. 2014; 29:1718-28.
24. Heilmeier U, Hackl M, Skalicky S, et al. Serum miRNA signatures are indicative of skeletal fractures in postmenopausal women with and without type 2 diabetes and influence osteogenic and adipogenic differentiation of adipose tissue-derived mesenchymal stem cells in vitro. J Bone Miner Res. 2016; 31:2173-92.
25. Weilner S, Skalicky S, Salzer B, et al. Differentially circulating miRNAs after recent osteoporotic fractures can influence osteogenic differentiation. Bone. 2015; 79:43-51.
26. Jeong S, Oh J M, Oh K H, Kim I W. Differentially expressed miR-3680-5p is associated with parathyroid hormone regulation in peritoneal dialysis patients. PLoS One. 2017; 12:e0170535.
27. M'Baya-Moutoula E, Louvet L, Metzinger-Le Meuth V, Massy Z A, Metzinger L. High inorganic phosphate concentration inhibits osteoclastogenesis by modulating miR-223. Biochim Biophys Acta. 1852; 2015:2202-12.
28. Balderman J A, Lee H Y, Mahoney C E, et al. Bone morphogenetic protein-2 decreases microRNA-30b and microRNA-30c to promote vascular smooth muscle cell calcification. J Am Heart Assoc. 2012; 1:e003905.
29. Zhang Y, Xie R L, Croce C M, et al. A program of microRNAs controls osteogenic lineage progression by targeting transcription factor Runx2. Proc Natl Acad Sci USA. 2011; 108:9863-8.
30. Wang H, Xie Z, Hou T, et al. MiR-125b regulates the osteogenic differentiation of human mesenchymal stem cells by targeting BMPR1b. Cell Physiol Biochem. 2017; 41:530-42.
31. Zhao H, Zhang J, Shao H, et al. Transforming growth factor beta1/Smad4 signaling affects osteoclast differentiation via regulation of miR-155 expression. Mol Cells. 2017; 40:211-21.
32. Zhang J, Zhao H, Chen J, et al. Interferon-beta-induced miR-155 inhibits osteoclast differentiation by targeting SOCS1 and MITF. FEBS Lett. 2012; 586:3255-62.
33. Nickolas T L, Cremers S, Zhang A, et al. Discriminants of prevalent fractures in chronic kidney disease. J Am Soc Nephrol. 2011; 22:1560-72.
34. Nickolas T L, Stein E, Cohen A, et al. Bone mass and microarchitecture in CKD patients with fracture. J Am Soc Nephrol. 2010; 21:1371-80.
35. Coresh J, Astor B, McQuillan G, et al. Calibration and random variation of the serum creatinine assay as critical elements of using equations to estimate glomerular filtration rate. Am J Kidney Dis. 2002; 39:920-9.
36. Chen N X, Kiattisunthorn K, O'Neill K D, et al. Decreased microRNA is involved in the vascular remodeling abnormalities in chronic kidney disease (CKD). PLoS One. 2013; 8:e64558.
37. Dempster D W, Compston J E, Drezner M K, et al. Standardized nomenclature, symbols, and units for bone histomorphometry: a 2012 update of the report of the ASBMR Histomorphometry Nomenclature Committee. J Bone Miner Res. 2013; 28:2-17.
38. KDIGO clinical practice guideline for the diagnosis, evaluation, prevention, and treatment of chronic kidney disease-mineral and bone disorder (CKD-MBD). Kidney Int. 2009; 113(Suppl):S1-130.
39. Moe S M, Chen N X, Seifert M F, et al. A rat model of chronic kidney disease-mineral bone disorder. Kidney Int. 2009; 75:176-84.
40. Cowley B D Jr, Gudapaty S, Kraybill A L, et al. Autosomal-dominant polycystic kidney disease in the rat. Kidney Int. 1993; 43:522-34.
41. Allen M R, Chen N X, Gattone V H 2nd, et al. Skeletal effects of zoledronic acid in an animal model of chronic kidney disease. Osteoporos Int. 2013; 24:1471-81.
42. Moe S M, Chen N X, Newman C L, et al. A comparison of calcium to zoledronic acid for improvement of cortical bone in an animal model of CKD. J Bone Miner Res. 2014; 29:902-10.
43. Moe S M, Chen N X, Newman C L, et al. Anti-sclerostin antibody treatment in a rat model of progressive renal osteodystrophy. J Bone Miner Res. 2015; 30:499-509.
44. Pistoia W, van Rietbergen B, Ruegsegger P. Mechanical consequences of different scenarios for simulated bone atrophy and recovery in the distal radius. Bone. 2003; 33:937-45.
45. Bala Y, Zebaze R, Seeman E. Role of cortical bone in bone fragility. Curr Opin Rheumatol. 2015; 27:406-13.
46. Cooper D M, Kawalilak C E, Harrison K, Johnston B D, Johnston J D. Cortical bone porosity: what is it, why is it important, and how can we detect it? Curr Osteoporos Rep. 2016; 14:187-98.
47. Ketteler M, Block G A, Evenepoel P, et al. Executive summary of the 2017 KDIGO chronic kidney disease-mineral and bone disorder (CKD-MBD) guideline update: what's changed and why it matters. Kidney Int. 2017; 92:26-36.
48. Coco M, Rush H. Increased incidence of hip fractures in dialysis patients with low serum parathyroid hormone. Am J Kidney Dis. 2000; 36:1115-21.
49. London G M, Marchais S J, Guerin A P, Boutouyrie P, Metivier F, de Vernejoul M C. Association of bone activity, calcium load, aortic stiffness, and calcifications in ESRD. J Am Soc Nephrol. 2008; 19:1827-35.

50. Fusaro M, Tripepi G, Noale M, et al. High prevalence of vertebral fractures assessed by quantitative morphometry in hemodialysis patients, strongly associated with vascular calcifications. Calcif Tissue Int. 2013; 93:39-47.

51. Behets G J, Spasovski G, Sterling L R, et al. Bone histomorphometry before and after long-term treatment with cinacalcet in dialysis patients with secondary hyperparathyroidism. Kidney Int. 2015; 87:846-56.

52. Lehmann G, Ott U, Kaemmerer D, Schuetze J, Wolf G. Bone histomorphometry and biochemical markers of bone turnover in patients with chronic kidney disease stages 3-5. Clin Nephrol. 2008; 70:296-305.

53. Silva B C, Bilezikian J P. Parathyroid hormone: anabolic and catabolic actions on the skeleton. Curr Opin Pharmacol. 2015; 22:41-50.

54. Rhee Y, Allen M R, Condon K, et al. PTH receptor signaling in osteocytes governs periosteal bone formation and intracortical remodeling. J Bone Miner Res. 2011; 26:1035-46.

55. Feurer E, Kan C, Croset M, Sornay-Rendu E, Chapurlat R. Lack of association between select circulating miRNAs and bone mass, turnover, and fractures: data from the OFELY cohort. J Bone Miner Res. 2019; 34:1074-85.

56. Anastasilakis A D, Makras P, Pikilidou M, et al. Changes of circulating microRNAs in response to treatment with teriparatide or denosumab in postmenopausal osteoporosis. J Clin Endocrinol Metab. 2018; 103:1206-13.

57. Lin X J, Chong Y, Guo Z W, et al. A serum microRNA classifier for early detection of hepatocellular carcinoma: a multicentre, retrospective, longitudinal biomarker identification study with a nested case-control study. Lancet Oncol. 2015; 16:804-15.

What is claimed is:

1. A method of treating low turnover renal osteodystrophy in a human subject, the method comprising:

i) administering an anabolic agent to the human subject if a level of miRNA-30b, miRNA-30c, miRNA-125b, miRNA-155, or any combination thereof in a blood sample from the human subject is lower than a mean level of miRNA-30b, miRNA-30c, miRNA-125b, miRNA-155, or any combination thereof measured in a cohort of subjects having chronic kidney disease and normal or high turnover renal osteodystrophy; or ii) administering to the human subject an agent that reduces bone turnover if a level of miRNA-30b, miRNA-30c, miRNA-125b, miRNA-155, or any combination thereof in a blood sample from the human subject is equal to or higher than a mean level of miRNA-30b, miRNA-30c, miRNA-125b, miRNA-155, or any combination thereof measured in a cohort of subjects having chronic kidney disease and normal or high turnover renal osteodystrophy, wherein the agent that reduces bone turnover is a vitamin D analog, calcitrol or analogs thereof, a calcimimetic, or an anti-resorptive agent;

wherein the anti-resorptive agent is alendronate, risedronate, or denosumab.

2. The method of claim 1, wherein the human subject has chronic kidney disease.

3. The method of claim 2, wherein the human subject has stage 3 to 5D chronic kidney disease.

4. The method of claim 1, further comprising measuring a level of parathyroid hormone (PTH), and/or bone specific alkaline phosphatase (BSAP) in a blood sample from the human subject.

5. The method of claim 1, wherein the anabolic agent is teriparatide or abaloparatide.

6. The method of claim 1, wherein the human subject is administered an anabolic agent if the level of miRNA-30b, miRNA-30c, miRNA-125b, miRNA-155, or any combination thereof in a blood sample from the human subject is at least 3-fold lower than a mean level of miRNA-30b, miRNA-30c, miRNA-125b, miRNA-155, or any combination thereof measured in a cohort of subjects having chronic kidney disease and normal or high turnover renal osteodystrophy.

7. The method of claim 6, wherein the anabolic agent is teriparatide or abaloparatide.

8. The method of claim 1, wherein the level of the miRNA-30b, miRNA-30c, miRNA-125b, miRNA-155, or any combination thereof is measured by real time PCR.

9. The method of claim 1, wherein the level of the miRNA-30b, miRNA-30c, miRNA-125b, miRNA-155, or any combination thereof is measured periodically.

10. The method of claim 9, wherein the measuring of the level of the miRNA-30b, miRNA-30c, miRNA-125b, miRNA-155, or any combination thereof is periodically repeated about every 3, 4, 5, 6, 7, 8, 9, 10, 11, or 12 months.

11. A method of reducing the risk of fractures associated with low turnover renal osteodystrophy in a human subject in need thereof, the method comprising:

i) administering an anabolic agent to the human subject if a level of miRNA-30b, miRNA-30c, miRNA-125b, miRNA-155, or any combination thereof in a blood sample from the human subject is lower than a mean level of miRNA-30b, miRNA-30c, miRNA-125b, miRNA-155, or any combination thereof measured in a cohort of subjects having chronic kidney disease and normal or high turnover renal osteodystrophy; or ii) administering to the human subject an agent that reduces bone turnover if a level of miRNA-30b, miRNA-30c, miRNA-125b, miRNA-155, or any combination thereof in a blood sample from the human subject equal to or higher than a mean level of miRNA-30b, miRNA-30c, miRNA-125b, miRNA-155, or any combination thereof measured in a cohort of subjects having chronic kidney disease and normal or high turnover renal osteodystrophy, wherein the agent that reduces bone turnover is a vitamin D analog, calcitrol or analogs thereof, a calcimimetic, or an anti-resorptive agent;

wherein the anti-resorptive agent is alendronate, risedronate, or denosumab.

* * * * *

```
                         SEQUENCE LISTING


<160> NUMBER OF SEQ ID NOS: 4

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 1

uguaaacauc cuacacucag cu                                            22


<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 2

uguaaacauc cuacacucuc agc                                           23


<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 3

ucccugagac ccuaacuugu ga                                            22


<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 4

uuaaugcuaa ucgugauagg ggu                                           23
```